(12) United States Patent
Trowell et al.

(10) Patent No.: US 10,473,665 B2
(45) Date of Patent: Nov. 12, 2019

(54) METHODS AND SYSTEMS FOR DETECTING AN ANALYTE OR CLASSIFYING A SAMPLE

(71) Applicant: Commonwealth Scientific and Industrial Research Organisation, Campbell, Australian Capital Territory (AU)

(72) Inventors: Stephen Charles Trowell, Oxley (AU); Helen Dacres, Monash (AU); Nam Cao Hoai Le, Thanh pho Bao Loc (VN); Murat Gel, Armadale (AU); Yonggang Zhu, Mentone (AU); Nan Wu, Shenyan (CN)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 1314 days.

(21) Appl. No.: 14/387,197

(22) PCT Filed: Apr. 15, 2013

(86) PCT No.: PCT/AU2013/000378
§ 371 (c)(1),
(2) Date: Sep. 22, 2014

(87) PCT Pub. No.: WO2013/155553
PCT Pub. Date: Oct. 24, 2013

(65) Prior Publication Data
US 2015/0094219 A1  Apr. 2, 2015

Related U.S. Application Data

(60) Provisional application No. 61/624,899, filed on Apr. 16, 2012.

(30) Foreign Application Priority Data

Apr. 12, 2013 (AU) ................................ 2013204332

(51) Int. Cl.
*B01L 3/00* (2006.01)
*G01N 33/58* (2006.01)
(Continued)

(52) U.S. Cl.
CPC ...... *G01N 33/581* (2013.01); *B01L 3/502715* (2013.01); *C12Q 1/66* (2013.01);
(Continued)

(58) Field of Classification Search
None
See application file for complete search history.

(56) References Cited

U.S. PATENT DOCUMENTS 4,891,120 A    1/1990 Sethi et al.
4,908,112 A    3/1990 Pace
(Continued)

FOREIGN PATENT DOCUMENTS

EP      2221606         8/2010
WO   WO 1999/049019    9/1999
(Continued)

OTHER PUBLICATIONS

Aloni et al. (2006) "Ancient genomic architecture for mammalian olfactory receptor clusters," Genome Biol. 7:R88.
(Continued)

*Primary Examiner* — Rebecca L Martinez
(74) *Attorney, Agent, or Firm* — Carol L. Francis; Bozicevic, Field & Francis LLP

(57) ABSTRACT

The present invention relates to methods and systems for detecting one or more analytes in a sample and/or for classifying a sample. In particular, the present invention relates to methods and systems which can be used to detect the analytes in real time and which rely on flowing through a microfluidic device one or more types of sensor molecule each comprising a domain that binds one or more analytes, (Continued)

Figure 1:
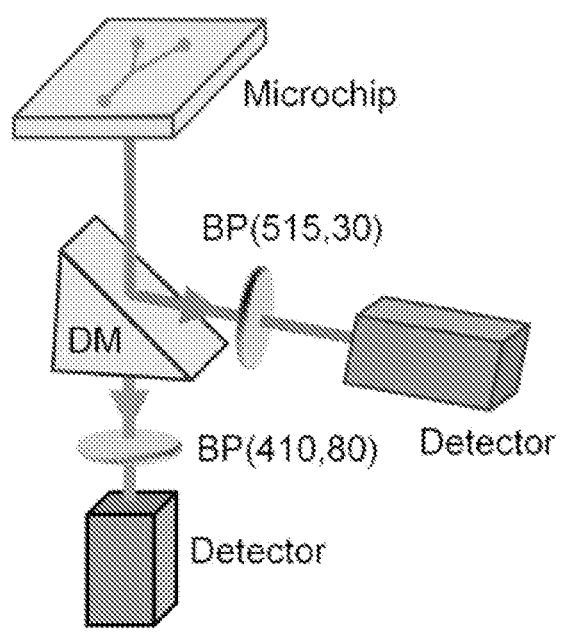

a chemiluminescent donor domain and an acceptor domain, wherein the separation and relative orientation of the chemiluminescent donor domain and the acceptor domain, in the presence and/or the absence of analyte, is within +50% of the Forster distance.

19 Claims, 52 Drawing Sheets

Specification includes a Sequence Listing.

(51) Int. Cl.
    *C12Q 1/66*     (2006.01)
    *G01N 33/53*     (2006.01)
    *G01N 33/542*     (2006.01)
    *G01N 21/76*     (2006.01)

(52) U.S. Cl.
    CPC .......... *G01N 21/76* (2013.01); *G01N 21/763* (2013.01); *G01N 33/5308* (2013.01); *G01N 33/542* (2013.01); *B01L 2300/0636* (2013.01); *B01L 2300/0654* (2013.01); *B01L 2300/0816* (2013.01); *B01L 2300/0867* (2013.01); *B01L 2300/1822* (2013.01); *B01L 2300/1827* (2013.01); *B01L 2400/0487* (2013.01); *G01N 2333/726* (2013.01); *G01N 2333/90241* (2013.01)

(56) References Cited

U.S. PATENT DOCUMENTS

| | | |
|---|---|---|
| 5,126,022 A | 6/1992 | Soane et al. |
| 5,196,524 A | 3/1993 | Gustafson et al. |
| 5,219,737 A | 6/1993 | Kajiyama et al. |
| 5,229,285 A | 7/1993 | Kajiyama et al. |
| 5,571,410 A | 11/1996 | Swedberg et al. |
| 5,580,523 A | 12/1996 | Bard |
| 5,670,356 A | 9/1997 | Sherf et al. |
| 5,750,015 A | 5/1998 | Soane et al. |
| 5,843,746 A | 12/1998 | Tatsumi et al. |
| 5,858,195 A | 1/1999 | Ramsey |
| 5,885,470 A | 3/1999 | Parce et al. |
| 6,793,753 B2 | 9/2004 | Unger et al. |
| 6,949,377 B2 | 9/2005 | Ho |
| 2002/0123059 A1 | 9/2002 | Ho |
| 2003/0170915 A1 | 9/2003 | Singh et al. |
| 2008/0085552 A1 | 4/2008 | Larson et al. |
| 2011/0037077 A1 | 2/2011 | Ichimura et al. |
| 2011/0071045 A1 | 3/2011 | Patterson |
| 2012/0077210 A1 | 3/2012 | Trowell et al. |

FOREIGN PATENT DOCUMENTS

| | | |
|---|---|---|
| WO | WO 2000/024878 | 5/2000 |
| WO | WO 2001/001025 | 1/2001 |
| WO | WO 2001/046691 | 6/2001 |
| WO | WO 2003/015923 | 2/2003 |
| WO | 2003035229 | 5/2003 |
| WO | WO 2006/105616 | 10/2006 |
| WO | WO 2007/019634 | 2/2007 |
| WO | WO 2007/033385 | 3/2007 |
| WO | WO 2009/018467 | 2/2009 |
| WO | WO 2009/020479 | 2/2009 |
| WO | WO 2009/044088 | 4/2009 |
| WO | WO 2010/085844 | 8/2010 |
| WO | WO 2011/091037 | 7/2011 |

OTHER PUBLICATIONS

Buck and Axel Cell (1991) "A novel multigene family may encode odorant receptors: A molecular basis for odor recognition," 65:175-187.

Dacres et al. (2009) "Direct comparison of bioluminescence-based resonance energy transfer methods for monitoring of proteolytic cleavage," Anal. Biochem. 385(2):194-202.

Dacres et al. (2009) "Direct comparison of fluorescence- and bioluminescence-based resonance energy transfer methods for real-time monitoring of thrombin-catalysed proteolytic cleavage," Biosensors and Bioelectronics 24(5):1164-1170.

Dacres et al. (2010) "Experimental Determination of the Förster Distance for Two Commonly Used Bioluminescent Resonance Energy Transfer Pairs," Anal. Chem. 82:432-435.

Dacres et al. (2011) "Greatly enhanced detection of a volatile ligand at femtomolar levels using bioluminescence resonance energy transfer (BRET)," Biosens. and Bioelectron. 29:119-124.

Dacres et al. (2012) "Effect of enhanced Renilla luciferase and fluorescent protein variants on the Förster distance of Bioluminescence resonance energy transfer (BRET)," Biochem. Biophys. Res. Commun. 425(3):625-629.

Day et al. (2004) "Evolution of beetle bioluminescence: the origin of beetle luciferin," Luminescence 19:8-20.

De et al. (2007) "An Improved Bioluminescence Resonance Energy Transfer Strategy for Imaging Intracellular Events in Single Cells and Living Subjects," Cancer Res. 67:7175-7183.

De et al. (2009) "BRET3: a red-shifted bioluminescence resonance energy transfer (BRET)-based integrated platform for imaging protein-protein interactions from single live cells and living animals," FASEB Journal 23(8):2702-2709.

De Wet et al. (1987) "Firefly luciferase gene: structure and expression in mammalian cells," Mol. Cell. Biol. 2987:725-737.

Doty, Richard L., (2012) "Gustation", WOREs Cognitive Science 3:29-46.

Esch et al. (2011) "The Role of Body-on-a-Chip Devices in Drug and Toxicity Studies," Annu. Rev. Biomed. Eng. 13:55-72.

Fang et al. (2005) "Determination of Ribonuclease H Surface Enzyme Kinetics by Surface Plasmon Resonance Imaging and Surface Plasmon Fluorescence Spectroscopy," Anal. Chem. 77(20):6528-6534.

Fehr et al. (2002) "Visualization of maltose uptake in living yeast cells by fluorescent nanosensors," PNAS 99(15):9846-9851.

Feldmesser et al. (2006) "Widespread ectopic expression of olfactory receptor genes," BMC Genomics 7:121.

Fredriksson and Schioth (2005) "The Repertoire of G-Protein-Coupled Receptors in Fully Sequenced Genomes," Mol. Pharmacol. 67(5):1414-1425.

Frishman and Argos (1997) "Seventy-Five Percent Accuracy in Protein Secondary Structure Prediction," Proteins 27:329-335.

Fuchs et al. (2001) "The human olfactory subgenome: from sequence to structure and evolution," Human Genetics 108:1-13.

Gill and von Hippel (1989) "Calculation of protein extinction coefficients from amino acid sequence data," Anal. Biochem. 182(2):319-326.

Glusman et al. (2000) "The olfactory receptor gene superfamily: data mining, classification, and nomenclature," Mammalian Genome 11(11):1016-1023.

Glusman et al. (2000) "Sequence, Structure, and Evolution of a Complete Human Olfactory Receptor Gene Cluster," Genomics 63(2):227-245.

Glusman et al. (2001) "The Complete Human Olfactory Subgenome," Genome Res. 11:685-702.

Godin et al. (2008) "Microfluidics and photonics for Bio-System-on-a-Chip: A review of advancements in technology towards a microfluidic flow cytometry chip," J. Biophotonics 1(5):355-376.

Greer and Szalay (2002) "Imaging of light emission from the expression of luciferases in living cells and organisms: a review," Luminescence 17:43-74.

Hall et al. (1997) "Two Modes of Ligand Binding in Maltose-binding Protein of *Escherichia coli* Functional Significance in Active Transport," J. Biol. Chem. 272:17615-17622.

Hastings (1996) "Chemistries and colors of bioluminescent reactions: a review," Gene 173:5-11.

Hofmann and Stoffel (1993) "MF C-35 a Database of Membrane Spanning Protein Segments," Biol. Chem. 374:166.

(56) References Cited

OTHER PUBLICATIONS

Holden and Cremer (2005) "Microfluidic Tools for Studying the Specific Binding, Adsorption, and Displacement of Proteins at Interfaces," Annu. Rev. Phys. Chem. 56:369-387.
Hushpulian et al. (2007) "Biocatalytic properties of recombinant tobacco peroxidase in chemiluminescent reaction," Biotransformation 25:2-4.
Inouye and Shimomura (1997) "The Use of Renilla Luciferase, Oplophorus Luciferase, and Apoaequorin as Bioluminescent Reporter Protein in the Presence of Coelenterazine Analogues as Substrate," Biochem. J. 233(2):349-353.
Klein et al. (1984) "Prediction of protein function from sequence properties: Discriminant analysis of a data base," Biochim. Biophys. Acta 787(3):221-226.
Kocan et al (2008) "Demonstration of Improvements to the Bioluminescence Resonance Energy Transfer (BRET) Technology for the Monitoring of G Protein-Coupled Receptors in Live Cells", Journal of Biomolecular Screening, 13(9):888-898.
Kocan et al (2011) "Enhanced BRET technology for the monitoring of agonist-induced and agonist-independent interactions between GPCRs and β-arrestins", Frontiers in Endocrinology, Cellular Endocrinology, 1(12):1-9.
Lander et al. (2001) "Initial sequencing and analysis of the human genome," Nature 409:860-921.
Li and Lin (2008) "Applications of microfluidic systems in environmental analysis," Anal Bioanl. Chem. 393(2):555-567.
Loening et al. (2006) "Consensus guided mutagenesis of Renilla luciferase yields enhanced stability and light output," Protein Eng. Des. Sel. 19(9):391-400.
Loening et al. (2007) "Red-shifted Renilla reniformis luciferase variants for imaging in living subjects." Nature Methods 4(8):641-643.
Lorenz et al. (1991) "Isolation and expression of a cDNA encoding Renilla reniformis luciferase." Proc. Natl. Acad. Sci. USA 88(10):4438-4442.
Mark et al. (2010) "Microfluidic lab-on-a-chip platforms: requirements, characteristics and applications," Chem. Soc. Rev. 39:1153-1182.
Medintz and Deschamps (2006) "Maltose-binding protein: a versatile platform for prototyping biosensing," Curr. Opin. Biotech. 17:17-27.
Mohammed and Desmulliez (2011) "Lab-on-a-chip based immunosensor principles and technologies for the detection of cardiac biomarkers: a review," Lab. Chip. 11:569-595.
Morin and Hastings (1971) "Energy transfer in a bioluminescent system," J. Cell. Physiol. 77(3):313-318.
Niimura and Nei (2003) "Evolution of olfactory receptor genes in the human genome," Proc. Natl. Acad. Sci. USA. 100(21):12235-12240.
Noh et al. (2011) "Biosensors in Microfluidic Chips," Top. Curr. Chem. 304:117-152.
Olender et al. (2004) "The olfactory receptor universe—from whole genome analysis to structure and evolution," Genet. Mol. Res. 3(4):545-553.
Olender et al. (2004) "The canine olfactory subgenome," Genomics. 83(3):361-372.
Park et al. (2009) "Detection of conformationally changed MBP using intramolecular FRET," Biochem. Biophys. Res. Commun. 388(3):560-564.
Persson and Argos (1994) "Prediction of Transmembrane Segments in Proteins Utilising Multiple Sequence Alignments," J. Mol. Biol. 237(2):182-192.
Pfleger and Eidne (2006) "Illuminating insights into protein-protein interactions using bioluminescence resonance energy transfer (BRET)," Nature Methods 3:165-174.
Pilpel and Lancet (1999) "The variable and conserved interfaces of modeled olfactory receptor proteins," Protein Science 8(5):969-977.
Remedios and Moens (1995) "Fluorescence Resonance Energy Transfer Spectroscopy Is a Reliable "Ruler" for Measuring Structural Changes in Proteins: Dispelling the Problem of the Unknown Orientation Factor," J. Structural Biol. 115(2):175-185.
Robertson (1998) "Two Large Families of Chemoreceptor Genes in the Nematodes Caenorhabditis elegans and Caenorhabditis briggsae Reveal Extensive Gene Duplication, Diversification, Movement, and Intron Loss," Genome Research 8:449-463.
Robertson (2001) "Updating the str and srj (stl) Families of Chemoreceptors in Caenorhabditis Nematodes Reveals Frequent Gene Movement Within and Between Chromosomes," Chem Senses 26(2):151-159.
Sengupta et al. (1996) "odr-10 Encodes a Seven Transmembrane Domain Olfactory Receptor Required for Responses to the Odorant Diacetyl," Cell 84(6):899-909.
Sharff et al. (1992) "Crystallographic evidence of a large ligand-induced hinge-twist motion between the two domains of the maltodextrin binding protein involved in active transport and chemotaxis," Biochemistry 31(44):10657-10663.
Sharff et al. (1993) "Refined 1.8-.ANG. structure reveals the mode of binding of .beta.-cyclodextrin to the maltodextrin binding protein," Biochemistry 32(40):10553-10559.
Sharon et al. (1998) "Genome Dynamics, Evolution, and Protein Modeling in the Olfactory Receptor Gene Superfamily," Ann. N Y Acad. Sci. 855:182-193.
Spurlino et al. (1991) "The 2.3-A resolution structure of the maltose- or maltodextrin-binding protein, a primary receptor of bacterial active transport and chemotaxis.," J. Biol. Chem. 266: 5202-5219.
Theberge et al. (2010) "Microdroplets in Microfluidics: An Evolving Platform for Discoveries in Chemistry and Biology," Angew. Chem Int. Ed 49(34):5846-5868.
Tsien (1998) "The Green Fluorescent Protein," Ann. Rev. Biochem. 67:509-544.
Unger et al. (2000) "Monolithic Microfabricated Valves and Pumps by Multilayer Soft Lithography," Science 288(5463):113-116.
Verhaegen and Christopoulos (2002) "Recombinant Gaussia Luciferase. Overexpression, Purification, and Analytical Application of a Bioluminescent Reporter for DNA Hybridization," Anal. Chem. 74(17):4378-4385.
Viviani (2002) "The origin, diversity, and structure function relationships of insect luciferases," Cell. Mol. Life Sci. 59(11):1833-1850.
Von Heijne (1992) "Membrane protein structure prediction : Hydrophobicity analysis and the positive-inside rule," J. Mol. Biol. 225(2):487-494.
Xu et al. (1999) "A bioluminescence resonance energy transfer (BRET) system: Application to interacting circadian clock proteins," Proc. Natl. Acad. Sci. USA. 96:151-156.
Yeo et al. (2011) "Microfluidic Devices for Bioapplications," Small 7:12-48.
Young et al. (2002) "Different evolutionary processes shaped the mouse and human olfactory receptor gene families," J. Human Mol. Genet. 11(5):535-546.
Zhang and Firestein (2002) "The olfactory receptor gene superfamily of the mouse," Nat. Neurosci. 5:124-133.
Zozulya et al. (2001) "The human olfactory receptor repertoire," Genome Biol. 2(6):0018.1-0018.12.

a b

30/44 a.

b.

METHODS AND SYSTEMS FOR DETECTING AN ANALYTE OR CLASSIFYING A SAMPLE

FIELD OF THE INVENTION

The present invention relates to methods and systems for detecting one or more analytes in a sample and/or for classifying a sample. In particular, the present invention relates to methods and systems which can be used to detect the analytes in real time and which rely on flowing through a microfluidic device one or more types of sensor molecule each comprising a domain that binds one or more analytes, a chemiluminescent donor domain and an acceptor domain, wherein the separation and relative orientation of the chemiluminescent donor domain and the acceptor domain, in the presence and/or the absence of analyte, is within ±50% of the Forster distance.

BACKGROUND OF THE INVENTION

Bioluminescence resonance energy transfer (BRET) occurs naturally in marine organisms such as *Aequorea victoria* and *Renilla reniformis* (Morin and Hastings, 1971). BRET is a form of Förster resonance energy transfer (RET), which is the non-radiative transfer of energy from an excited state donor to a ground state acceptor. There are two commonly used forms of the BRET principle, i.e., $BRET^1$ and $BRET^2$. Both use *Renilla luciferase* (RLuc) as the energy donor. In $BRET^1$, the substrate is native coelenterazine (CLZ) or coelenterazine h (CLZh). RLuc and a yellow fluorescent protein (YFP) are the energy donor and acceptor, respectively, giving peak donor emission at 475 nm and peak acceptor emission at 535 nm. In $BRET^2$, YFP is replaced with $GFP^2$ and a modified CLZ substrate, i.e. coelenterazine-400a or (CLZ400a) is used. The peak donor emission and acceptor emission are shifted to 395 nm and 515 nm, respectively (Dacres et al., 2009a, b; Pfleger and Eidne, 2006). A third form of BRET, i.e., $BRET^3$, has recently been developed. It used CLZh as the substrate and RLuc8 as the energy donor and mOrange as the acceptor, resulting in improved spectral resolution (De et al., 2009).

RET is a ratiometric technique which can eliminate data variability caused by fluctuations in light output due to variations in assay volume, assay conditions and signal decay across different wells in a plate. RET-based reactions are homogeneous, generally occurring in solution without solid-phase attachment. This allows for detection of analytes in different forms such as liquid, gas and even particulates without separation. The avoidance of solid-phase attachment eliminates the process of surface regeneration used in many surface-based techniques such as Surface Plasmon Resonance (SPR) (Fang et al., 2005) and, in conjunction with the fast reaction rate, allows it to be used for on-line monitoring.

So far, however, uses of BRET have been restricted to research laboratories using sophisticated detection equipment. Microfluidic technologies are attracting interest in many fields, including chemistry, biology, medicine, sensing and materials. Their advantages over conventional technologies include reduced reagent consumption, fast reaction rate, short analysis time, and amenability to automation and mass production (Holden and Cremer, 2005).

There have been substantial research and development in microfluidic technologies. Examples include an integrated biochip design with fluorescence light collection (EP 2221606), on-chip biosensing using Raman spectroscopy (WO 2009/020479), a biosensing device (WO 2009/018467) for detecting GPCR-ligand binding using surface plasmon resonance techniques, a light detection chip (US 2011/0037077 and US 2008085552) with mirrors as light reflectors, an assay device with a cartridge format (WO 2009/044088), a chemiluminescence-based microfluidic biochip (US 2002/0123059) and so on. Many of these device have the disadvantages of high cost per chip due to integration of multiple components, inability to perform real-time monitoring due to the requirement for surface regeneration and slow reaction of reagents, limited detection sensitivity, or signal drift.

Furthermore, there is considerable background art in the fields of electronic noses and electronic tongues, which contact a gaseous or liquid sample with an array of solid state sensors in order to detect analytes and/or classify the samples. Electronic noses and tongues have been bedevilled by poor performance due to limited selectivity of the sensors, poor sensitivity, sensor saturation and slow regeneration and sensor drift over time.

There is therefore a need for further methods of detecting analytes and classifying samples based on the analytes they contain, particularly methods that can be performed in real time and with increased sensitivity and that do not suffer from downtime due to the need to regenerate the sensing surface and that resist the confounding effects of sensor drift. Multiple channel microfluidic systems deploying an array of biologically derived sensors electro-optically coupled to a detection system offer a novel solution to these problems.

SUMMARY OF THE INVENTION

The present inventors have identified an improved method of detecting an analyte in a sample.

In one aspect, the present invention provides a method of detecting an analyte in a sample, the method comprising
i) flowing through a microfluidic device comprising one or more microchannels,
 a) the sample,
 b) a sensor molecule comprising a domain that binds the analyte, a chemiluminescent donor domain and an acceptor domain, wherein the separation and relative orientation of the chemiluminescent donor domain and the acceptor domain, in the presence and/or the absence of analyte, is within ±50% of the Forster distance,
 c) a substrate of the chemiluminescent donor,
ii) mixing the sensor molecule, sample and substrate in the device, and
iii) detecting modification of the substrate by the chemiluminescent donor using an electro-optical sensing device,
wherein the spatial location and/or dipole orientation of the chemiluminescent donor domain relative to the acceptor domain is altered when the analyte binds the sensor molecule.

In a preferred embodiment, the sensor molecule is not fixed to the device.

In a further preferred embodiment, the method can be used to detect the analyte in real time.

In another preferred embodiment, the sensor molecule and substrate enter the device through different microchannels. In an alternate embodiment, the sensor molecule and substrate enter the device through the same microchannel, however, in this embodiment it is preferred that the sensor molecule and substrate are mixed shortly before (for example 10 seconds, more preferably 1 second, or less) before entering the microchannel.

In a preferred embodiment, the Förster distance of the chemiluminescent donor domain and the acceptor domain is at least 5.6 nm, or at least 6 nm. In another preferred embodiment, the Förster distance of the chemiluminescent donor domain and the acceptor domain is between about 5.6 nm and about 10 nm, or is between about 6 nm and about 10 nm.

In a further preferred embodiment, the analyte binding or releasing from the sensor molecule results in a change in BRET ratio which is ≥15%, ≥20%, ≥30%, ≥35%, about 15% to about 50%, or about 15% to about 40%, of the maximum observed BRET ratio. A change in the BRET ratio of 15% or more increases the signal to noise ratio of analyte detection. This results in a superior limit of detection for any given sampling time and more precise coding of the level of concentration of analyte. Alternatively, at a fixed limit of detection, the greater change in BRET ratio facilitates shorter signal integration times and therefore more rapid detection.

In a further preferred embodiment, the quantum yield detected by the electro-optical sensing device is less than about 8%, or less than about 5%, or less than about 2%.

In another preferred embodiment, the acceptor domain has a Stokes Shift of between about 50 nm and about 150 nm. In an embodiment, the acceptor domain has a Stokes Shift of about 100 nm.

An advantage of the method of the present invention is that it is highly time resolved. Thus, in a preferred embodiment, the method is performed within about 1 s to about 100 s.

The sample can be in any form that is capable of being flowed through a microfluidic device. Examples include, but are not necessarily limited to, a liquid, gas, emulsion or suspension. In an embodiment, the sample is a liquid which has been pre-equilibrated with a gas.

In one embodiment, the suspension is, or comprises, a cell-free composition. In an alternate embodiment, the suspension comprises cells.

In an embodiment, the flow rate through the microfluidic device is between about 1 µl/hour to about 10 ml/hour, or 1 µl/hour to about 1 ml/hour, or 1 µl/hour to about 1.5 ml/hour, or about 20 µl/hour to about 0.5 ml/hour, and the preferred flow rate is between about 200 µl/hour to about 1 ml/hour.

In a preferred embodiment, the flow rate and length of the section of the microchannel comprising the sample, sensor molecule and substrate is such that the sample, sensor molecule and substrate are in the section for at least about 5 sec, at least about 10 sec, at least about 15 sec, at least about 20 sec, about 5 sec to about 50 sec, or about 10 sec to about 30 sec.

In one embodiment, for instance when the sensor molecule comprises a protein receptor such as a G coupled protein receptor, the concentration of the sensor molecule following step ii) is between about 1 nM to about 10 µM or between about 1 nM to about 1 µM. In another embodiment, for instance when the sensor molecule comprises a cleavable peptide-derived or periplasmic binding protein, the concentration of the sensor molecule following step ii) is between about 0.1 µM to about 10 µM.

In an embodiment, the flow through the microfluidic device is continuous flow, batch flow or stop flow.

The sample, sensor molecule and substrate may be actively mixed using mechanical, electrokinetic, acoustical or other suitable means. In a preferred embodiment, the mixing is achieved by diffusion over dimensions perpendicular to the direction of flow through a microchannel comprising the sample, sensor molecule and substrate. For example, efficient mixing (≥20%) of sample, sensor molecule and substrate can be conveniently achieved by predominantly passive diffusional (non-turbulent) processes.

The typical conditions include, flow rates of approximately no more than 1,000 microliters per hour, common microchannel lengths of approximately 10 mm or more and that the summed height of the stacked inputs when they are flowing in contact with each other in the common channel is approximately 200 micrometers or less (measured perpendicular to the direction of flow).

The sample, sensor molecule and substrate can be flowed through the microfluidic device by any suitable means such as, but are not necessarily limited to, one or more of pumping, vacuum, hydraulics, suction, electrokinesis, chemiosmosis, capillary force, acoustics, electromagnetics, piezoelectrics. Pumping mechanisms can be realised in compact, miniaturised and micron-size pumps. In a preferred embodiment, the sample, sensor molecule and substrate is flowed through the microfluidic device by suction (negative pressure), for example using a syringe pump in withdrawal mode.

In an embodiment, each microchannel has a cross-sectional area of about 1 µm$^2$ to about 1 mm$^2$.

In a further embodiment, the microchannel for the sample, sensor molecule and substrate each have a width of ≥300 µm and height ≥60 µm, width of ≥600 µm and height ≥30 µm or width of ≥1200 µm and height ≥15 µm. In an embodiment, the height is no greater than about 1 mm or about 0.5 mm. In another embodiment, the height is about 15 µm to about 1 mm or about 15 µm to about 0.5 mm. In a further embodiment, the width is no greater than about 1.5 mm. In yet a further embodiment, the width is about 300 µm to about 1.5 mm or about 300 µm to about 1.2 mm.

The lengths of the input microchannels for substrate, sensor molecule and sample are as short as possible, preferably less than 10 mm, and more preferably less than 5 mm.

The length of the common microchannel where the substrate, sensor molecule and sample are allowed to mix and react may be between 5 mm and 100 mm, or between 10 mm and 100 mm, preferably between 20 mm and 50 mm and may be linear, serpentine or any suitable combination of straight curved geometries. In an alternate embodiment, the common microchannel may be dispensed with entirely and the sensor molecule, substrate and sample may be introduced directly into the reaction chamber with or without active mixing.

In a further embodiment, step is performed in a reaction chamber with a volume of about 1 pl (i.e. picoliter or a trillionth of a liter) to about 200 µl and the preferred volume is 0.5 µl to about 8 µl, or 0.5 µl to about 2 µl.

In yet another embodiment, step iii) comprises processing at least one signal from the electro-optical sensing device to determine whether the analyte is absent or present in the sample, and if present optionally determining the concentration of the analyte in the sample.

In an embodiment, the domain that binds the analyte is a protein (which may be a peptide) or a nucleic acid. In a preferred embodiment, the domain is a protein. In an embodiment, the protein is a naturally occurring protein, which binds one or more analytes (ligand), or a variant of the protein which retains analyte (ligand) binding activity. Examples include, but are not necessarily limited to, a receptor, odorant binding protein, pheromone-binding protein, enzyme, ligand carrier or bacterial periplasmic binding protein. In an embodiment, the receptor is a G protein coupled receptor such as an odorant receptor or a taste receptor. In a further embodiment, the odorant receptor or taste receptor is from a nematode or vertebrate or is a mutant thereof.

In an embodiment, the chemiluminescent donor domain is a bioluminescent protein. Examples include, but are not necessarily limited to, a luciferase, a β-galactosidase, a lactamase, a horseradish peroxidase, an alkaline phosphatase, a β-glucuronidase or a β-glucosidase. Examples of luciferases include, but are not necessarily limited to, a *Renilla* luciferase, a Firefly luciferase, a Coelenterate luciferase, a North American glow worm luciferase, a click beetle luciferase, a railroad worm luciferase, a bacterial luciferase, a *Gaussia* luciferase, Aequorin, an *Arachnocampa* luciferase, or a biologically active variant or fragment of any one, or chimera of two or more, thereof. In a preferred embodiment, the *Renilla* luciferase variant is RLuc2 or RLuc8.

In an embodiment, the substrate is luciferin (such as a beetle luciferin), calcium, coelenterazine, or a derivative or analogue of coelenterazine.

In a preferred embodiment, the acceptor domain is a fluorescent acceptor domain.

In a further embodiment, the fluorescent acceptor domain is a protein. Examples include, but are not necessarily limited to, green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, Kaede protein or a Phycobiliprotein, or a biologically active variant or fragment of any one thereof.

In an alternate embodiment, the fluorescent acceptor domain is a non-protein. Examples include, but are not necessarily limited to, an Alexa Fluor dye, Bodipy dye, Cy dye, fluorescein, dansyl, umbelliferone, fluorescent microsphere, luminescent microsphere, fluorescent nanocrystal, Marina Blue, Cascade Blue, Cascade Yellow, Pacific Blue, Oregon Green, Tetramethylrhodamine, Rhodamine, Texas Red, rare earth element chelates, or any combination or derivatives thereof.

In an embodiment, the method further comprises providing a co-factor of the bioluminescent protein. Examples of co-factors include, but are not necessarily limited to, ATP, magnesium, oxygen, $FMNH_2$, calcium, or a combination of any two or more thereof.

In a preferred embodiment,
i) the bioluminescent protein is a luciferase or a biologically active variant or fragment, and/or
ii) the substrate is luciferin, coelenterazine, or a derivative or analogue of coelenterazine, and/or
iii) the acceptor domain is green fluorescent protein (GFP), Venus, mOrange, or a biologically active variant or fragment of any one thereof.

In a further preferred embodiment,
i) the luciferase is a *Renilla* luciferase, the acceptor domain is $GFP^2$, and the substrate is coelenterazine 400a,
ii) the luciferase is a *Renilla* luciferase 2, the acceptor domain is $GFP^2$, and the substrate is coelenterazine 400a,
iii) the luciferase is a *Renilla* luciferase 8, the acceptor domain is $GFP^2$, and the substrate is coelenterazine 400a,
iv) the luciferase is a *Renilla* luciferase 2, the acceptor domain is Venus, and the substrate is coelenterazine,
v) the luciferase is a *Renilla* luciferase 8, the acceptor domain is Venus, and the substrate is coelenterazine,
vi) the luciferase is a *Renilla* luciferase 8.6-535, the acceptor domain is mOrange, and the substrate is coelenterazine, or
vii) the luciferase is a *Renilla* luciferase 8, the acceptor domain is mOrange, and the substrate is coelenterazine.

More preferably,
i) the luciferase is a *Renilla* luciferase, the acceptor domain is $GFP^2$, and the substrate is Coelenterazine 400a,
ii) the luciferase is a *Renilla* luciferase 2, the acceptor domain is $GFP^2$, and the substrate is Coelenterazine 400a,
iii) the luciferase is a *Renilla* luciferase 8, the acceptor domain is $GFP^2$, and the substrate is Coelenterazine 400a,
iv) the luciferase is a *Renilla* luciferase 8.6-535, the acceptor domain is mOrange, and the substrate is Coelenterazine, or
v) the luciferase is a *Renilla* luciferase 8, the acceptor domain is mOrange, and the substrate is Coelenterazine.

Even more preferably,
i) the luciferase is a *Renilla* luciferase, the acceptor domain is $GFP^2$, and the substrate is Coelenterazine 400a,
ii) the luciferase is a *Renilla* luciferase 2, the acceptor domain is $GFP^2$, and the substrate is Coelenterazine 400a, or
iii) the luciferase is a *Renilla* luciferase 8, the acceptor domain is $GFP^2$, and the substrate is Coelenterazine 400a.

In an embodiment, the method comprises simultaneously or sequentially detecting two or more different analytes using the same microfluidic device, for example using a device as shown in FIGS. 14b and 14c.

In an embodiment, the microfluidic device comprises one or more sets of
a) three input microchannels, one each for the sensor molecule, substrate and sample, or
b) two input microchannels, one for the substrate and the other for a pre-mixture of the sensor molecule and sample, or
c) two input microchannels, one for the sensor molecule and the other for a pre-mixture of the substrate and sample.

In a further embodiment, at least one microchannel comprises a reaction chamber which has a different volume to at least one other microchannel.

In another embodiment, at least one microchannel comprises two or more reaction chambers of the same or different volume.

In a preferred embodiment, the electro-optical sensing device has at least two different wavelength channels, which may detect overlapping or non-overlapping wavelengths. In an alternate embodiment, the electro-optical sensing device has a single wavelength channel, wherein in this embodiment the donor quenches emission from the acceptor.

In an embodiment, the electro-optical sensing device comprises fibre bundle or liquid light guides. In an embodiment, diameter of the fibre bundle or liquid light guide is between about 1 mm and about 10 mm, or about 1 mm and about 6 mm. In an embodiment, the electro-optical sensing device further comprises a shutter box.

In an embodiment, the electro-optical sensing device comprises a bifurcated light guide, and no dichroic block.

In a preferred embodiment, the sensor molecule is present in a cell-free extract. In an alternate embodiment, the sensor molecule is expressed by cells (for example present on the surface of the cells or secreted by the cells) and provided as a cell suspension where the cells are intact.

The method can be used to sort cells. Thus, in an embodiment, the analyte is exposed on the surface of a cell and the method further comprises diverting cells comprising the analyte through a different microchannel than cells in the sample lacking the analyte, and collecting the cells comprising the analyte and/or collecting the cells lacking the analyte, wherein if both cell types are collected they are collected in separate containers.

In another aspect, the present invention provides a microfluidic system for detecting an analyte in a sample, the system comprising i) at least one reservoir suitable for containing (or comprising) a sensor molecule comprising a domain that binds the analyte, a chemiluminescent donor domain and an acceptor domain, wherein the separation and relative orientation of the chemiluminescent donor domain and the acceptor domain, in the presence and/or the absence of analyte, is within ±50% of the Forster distance, ii) a microfluidic device comprising one or more microchannels, iii) means for mixing the sensor molecule, the sample and a substrate of the chemiluminescent donor domain in the device, iv) a reaction chamber for detecting binding of the analyte to the sensor molecule, and v) an electro-optical sensing device, wherein the spatial location and/or dipole orientation of the chemiluminescent donor domain relative to the acceptor domain is altered when the analyte binds the sensor molecule.

In a preferred embodiment, the sensor molecule is not fixed to the microfluidic device.

In a further preferred embodiment, the system can be used to detect the analyte in real time.

In another preferred embodiment, the sensor molecule and substrate enter the device through different microchannels.

In a further preferred embodiment, the microfluidic device comprises at least two input microchannels, wherein one of the input microchannels is for flowing the sensor molecule into the device.

As the skilled addressee will appreciate, each of the preferred embodiments relating to the method of the invention also relate to the system of the invention and/or how the system can operate.

In an embodiment, the electro-optical sensing device comprises at least two different wavelength channels.

In a particularly preferred embodiment, the electro-optical sensing device is capable of simultaneously, or in rapid succession, detecting two different wavelength channels. For example, the electro-optical sensing device is capable of detecting two different wavelength channels in less than 1 second.

In a further embodiment, the microfluidic device is designed to enable the detection of two or more analytes. In an embodiment, the device comprises a separate microchannel for flowing each different sensor molecule into the device.

In an embodiment, the mixing occurs in the reaction chamber.

The present invention can also be used to classify a sample. For this purpose it is not essential that it already be known which analyte(s) in a sample actually bind(s) one or more sensor molecules. Thus, in another aspect the present invention provides a method of classifying a sample, the method comprising i) flowing through a microfluidic device comprising one or more microchannels,
   a) the sample,
   b) a sensor molecule comprising a domain that binds one or more analytes, a chemiluminescent donor domain and an acceptor domain, wherein the separation and relative orientation of the chemiluminescent donor domain and the acceptor domain, in the presence and/or the absence of analyte(s), is within ±50% of the Forster distance,
   c) a substrate of the chemiluminescent donor, ii) mixing the sensor molecule, sample and substrate in the device, iii) detecting modification of the substrate by the chemiluminescent donor using an electro-optical sensing device, iv) processing at least one signal from the electro-optical sensing device and correlating the pattern of electro-optical responses with one or more pre-determined characteristics of one or more samples of interest, and v) classifying the sample based on the correlation of the pattern of responses, wherein the spatial location and/or dipole orientation of the chemiluminescent donor domain relative to the acceptor domain is altered when the one or more analytes binds the sensor molecule.

In a preferred embodiment, the above method comprises two or more different sensor molecules each of which binds a different analyte (which may be a different set of analytes) or range of analytes, and step v) comprises classifying the sample based on the presence, absence or concentration of each of the analytes or range of analytes.

In an embodiment, one or more of the analytes are unknown.

In a further embodiment, the method can be used to classify the sample in real time.

In another embodiment, the sensor molecule is not fixed to the device.

In yet a further embodiment, the sensor molecule and substrate enter the device through different microchannels.

Also provided is a microfluidic system for classifying a sample, the system comprising i) at least one reservoir suitable for containing (or comprising) a sensor molecule comprising a domain that binds one or more analytes, a chemiluminescent donor domain and an acceptor domain, wherein the separation and relative orientation of the chemiluminescent donor domain and the acceptor domain, in the presence and/or the absence of analyte, is within ±50% of the Forster distance, ii) a microfluidic device comprising one or more microchannels, iii) means for mixing the sensor molecule, the sample and a substrate of the chemiluminescent donor domain in the device, iv) a reaction chamber for detecting binding of the analyte to the sensor molecule, and v) an electro-optical sensing device, wherein the spatial location and/or dipole orientation of the chemiluminescent donor domain relative to the acceptor domain is altered when the one or more analytes binds the sensor molecule.

In an embodiment, the system comprises two or more different sensor molecules each of which binds a different analyte, which may be a different set of analytes, or range of analytes.

In an embodiment, the system comprises two or more different sensor molecules each of which binds the same analyte at a different site and/or with a different level of affinity.

In another embodiment, one or more of the analytes, or range of analytes, are unknown.

In a further embodiment, the system can be used to classify samples in real time.

In an embodiment, the sensor molecule is not fixed to the device.

In a further embodiment, the sensor molecule and substrate enter the device through different microchannels.

In another embodiment, the microfluidic device comprises at least two input microchannels, wherein one of the input microchannels is for flowing the sensor molecule into the device.

In a further aspect, the present invention provides a method of screening for a compound that binds a molecule of interest, the method comprising i) flowing through a microfluidic device comprising one or more microchannels, a) a candidate compound, b) a sensor molecule comprising the molecule of interest, a chemiluminescent donor domain and an acceptor domain, wherein the separation and relative orientation of the chemiluminescent donor domain and the acceptor domain, in the presence and/or the absence the candidate compound, is within ±50% of the Forster distance, c) a substrate of the chemiluminescent donor, ii) mixing the sensor molecule, the candidate compound and substrate in the device, iv) detecting modification of the substrate by the chemiluminescent donor using an electro-optical sensing device, v) processing at least one signal from the electro-optical sensing device to determine whether the candidate compound binds the sensor molecule, and vi) selecting the compound if it binds the sensor molecule, wherein the spatial location and/or dipole orientation of the chemiluminescent donor domain relative to the acceptor domain is altered when the candidate compound binds the sensor molecule.

In a preferred embodiment, the method can be used to detect binding of the candidate compound to the sensor molecule in real time.

In a further preferred embodiment, the sensor molecule is not fixed to the device.

In another preferred embodiment, the sensor molecule and substrate enter the device through different microchannels.

In a preferred embodiment, the method further comprises confirming that the candidate compound binds the binding domain of the molecule of interest and not other domains of the sensor molecule. As the skilled person would appreciate, this can be performed using any one of a wide variety of techniques in the art such as using the molecule of interest on a column to capture the candidate compound, competitive binding assays, determining whether following incubation of the candidate compound with the molecule of interest modifies of the migration of the molecule of interest using gel chromatography and so on.

The candidate compound and the molecule of interest can be the same type of substance, for example, both could be nucleic acids, proteins (including peptides) or small molecules. In one embodiment, the molecule of interest is a protein such as, but not limited to, a receptor, odorant binding protein, pheromone-binding protein, enzyme, ligand carrier or bacterial periplasmic binding protein. The molecule of interest may be naturally occurring or a mutant/variant thereof.

In a further aspect, the present invention provides a microfluidic system for screening for a compound that binds a molecule of interest, the system comprising i) at least one reservoir suitable for containing (or comprising) a sensor molecule comprising the molecule of interest, a chemiluminescent donor domain and an acceptor domain, wherein the separation and relative orientation of the chemiluminescent donor domain and the acceptor domain, in the presence and/or the absence of a candidate compound, is within ±50% of the Forster distance, ii) a microfluidic device comprising one or more microchannels, iii) means for mixing the sensor molecule, the candidate compound, and a substrate of the chemiluminescent donor domain in the device, iv) a reaction chamber for detecting binding of the candidate compound to the sensor molecule, and v) an electro-optical sensing device, wherein the spatial location and/or dipole orientation of the chemiluminescent donor domain relative to the acceptor domain is altered when the candidate compound binds the sensor molecule.

In a preferred embodiment, the system can be used to detect binding of the candidate compound to the sensor molecule in real time.

In a further preferred embodiment, the sensor molecule is not fixed to the device.

In another preferred embodiment, the sensor molecule and substrate enter the device through different microchannels.

In a further embodiment, the microfluidic device comprises at least two input microchannels, wherein one of the input microchannels is for flowing the sensor molecule into the device The present inventors have also identified a hybrid BRET ($BRET^H$) detection system that does not suffer from the low luminescence trait of BRET2. Thus, in a further aspect, the present invention provides a method of detecting an analyte in a sample, the method comprising i) contacting the sample, in the presence of coelenterazine, with a sensor molecule comprising a) a domain that binds the analyte, b) *Renilla* luciferase, and c) green fluorescent protein 2, and determining whether bioluminescent resonance energy transfer (BRET) between the bioluminescent protein and the acceptor molecule is modified, wherein the spatial location and/or dipole orientation of the bioluminescent protein relative to the acceptor molecule is altered when the analyte binds the domain.

Naturally, the above method can readily be used in a method of the invention using a microfluidic device.

In a further aspect, the present invention provides an isolated sensor molecule comprising a domain that binds one or more analytes, *Renilla* luciferase, and green fluorescent protein 2.

The present inventors have identified polypeptides which bind 2-pentanone, and hence these polypeptides can be used to detect this compound.

Accordingly, in a further aspect the present invention provides a method of detecting 2-pentanone in a sample, the method comprising i) contacting the sample with a polypeptide which is *C. elegans* str-112 (SEQ ID 41) or str-113 (SEQ ID NO:42), or a variant thereof which binds 2-pentanone, and ii) detecting whether any of the polypeptide is bound to 2-pentanone.

As the skilled person would appreciate, there is an enormous array of different assays that can be configured once a new ligand/polypeptide binding pair has been identified. In one embodiment, the methods of the invention are used to detect 2-pentanone in a sample.

In an embodiment, the variant of str-113 is a str-114/str-113 fusion (SEQ ID NO:43).

In an embodiment, the polypeptide is detectably labelled. Examples of such detectably labelled polypeptides include, but are not limited to, those provided as SEQ ID NOs 13, 14, 18, 27, 28 and 30.

2-pentanone is produced by bacteria, and hence the above method can be used to detect, for example, bacterial infections or contaminations.

Thus, is a further aspect the present invention provides a method of detecting bacteria in a sample comprising detecting 2-pentanone using the method of the invention.

In an embodiment, the bacteria is *Escherichia* sp. such as *E. coli*.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1—Generic arrangement for performing the claimed method, showing the microfluidic chip (microchip) and a BRET detection system. DM=dichroic mirror, BP=band pass filter (wavelength centre in nm, width in nm).

Figure 2:
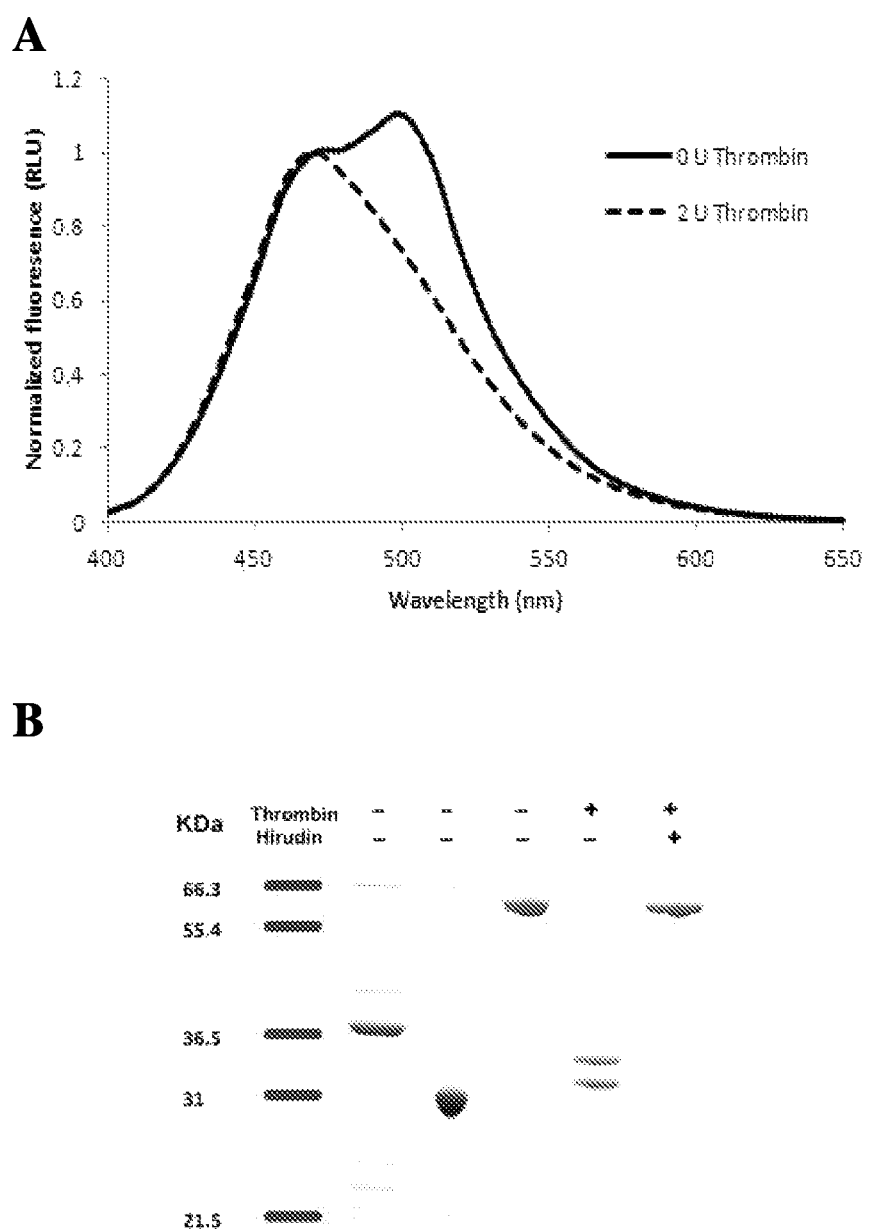

FIG. 2—Thrombin cleavage of $GFP^2$-RG-RLuc fusion protein sensor molecule monitored by (A) Spectral change of the hybrid BRET system upon addition 5 μM of native coelenterazine to $GFP^2$-RG-RLuc fusion protein with and without the addition of 2 units of thrombin and (B) SDS-PAGE analysis of purified His-tagged BRET proteins. 2.5 μg protein loaded per lane. From left to right; Molecular markers (KDa), RLuc, $GFP^2$, $GFP^2$-RG-RLuc, $GFP^2$-RG-RLuc following incubation with 54 nM thrombin for 90 minutes at 30° C.; $GFP^2$-RG-RLuc same conditions as previous lane except that thrombin has been pre-incubated with 2 units of hirudin for 10 minutes at room temp.

Figure 3:
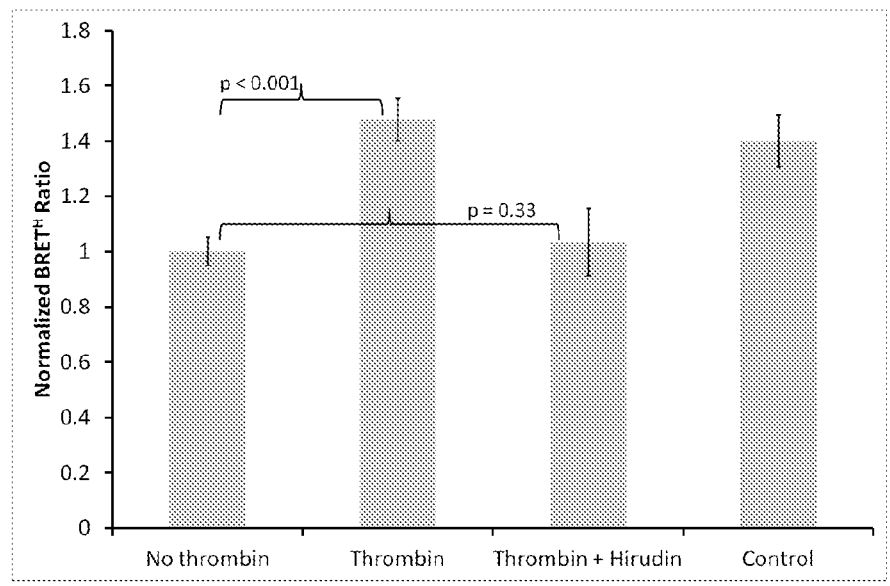

FIG. 3—Change in normalised $BRET^H$ ratio following thrombin cleavage (mean±S.D., n=3) of 1 μM of fusion proteins upon addition of 5 μM of native coelenterazine; $GFP^2$-RG-RLuc following treatment (90 minutes, 30° C.) with 54 nM thrombin or 54 nM of thrombin following pre-treatment (10 minutes, room temperature) with 2 units of hirudin. Controls consist of 1 μM of RLuc and $GFP^2$ proteins. p≤0.001 indicates a highly significant difference, p=0.33 indicates the changes are not significant.

Figure 4:
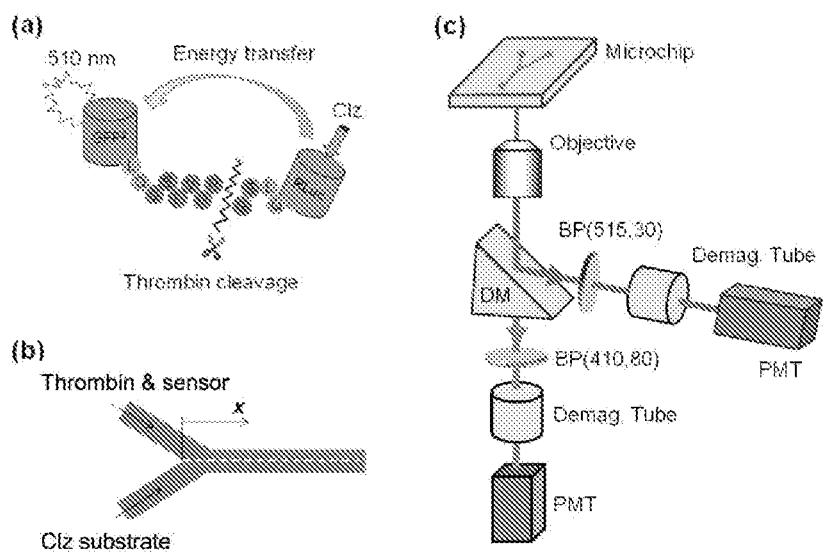

FIG. 4—Experimental set-up for on-chip detection. (a) A schematic drawing of the hybrid BRET reaction, and (b and c) the microfluidic chip system for BRET signal detection (Clz=Native coelenterazine, DM=dichroic mirror, BP=band pass, PMT=photomultiplier tube).

Figure 5:
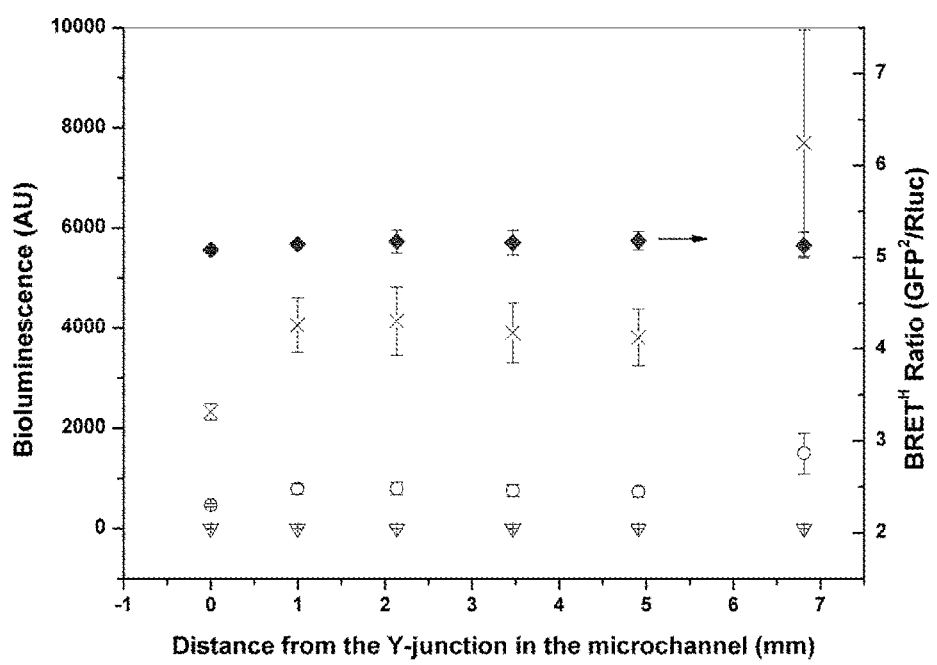

FIG. 5—Bioluminescence intensity (AU) of $GFP^2$-RG-RLuc thrombin sensor protein upon the addition of coelenterazine substrate and the $BRET^H$ ratio as a function of distance x from the Y-junction as labelled in FIG. 4b. The symbols + and ∇ represent bioluminescence background of RLuc and $GFP^2$ channel, respectively. ○ and X represent bioluminescence intensity of RLuc and $GFP^2$ channel, respectively. ♦ represents the BRET ratio. The fusion protein concentration was 3.0 μM. Native coelenterazine concentration was 58.6 μM; each aqueous flow rate was 20 μl/h; a 20× objective was used; filter band pass for $GFP^2$ and RLuc channel are 515 nm-555 nm and 430 nm-455 nm respectively; an internal gate time of 200 ms was used for data acquisition.

Figure 6:
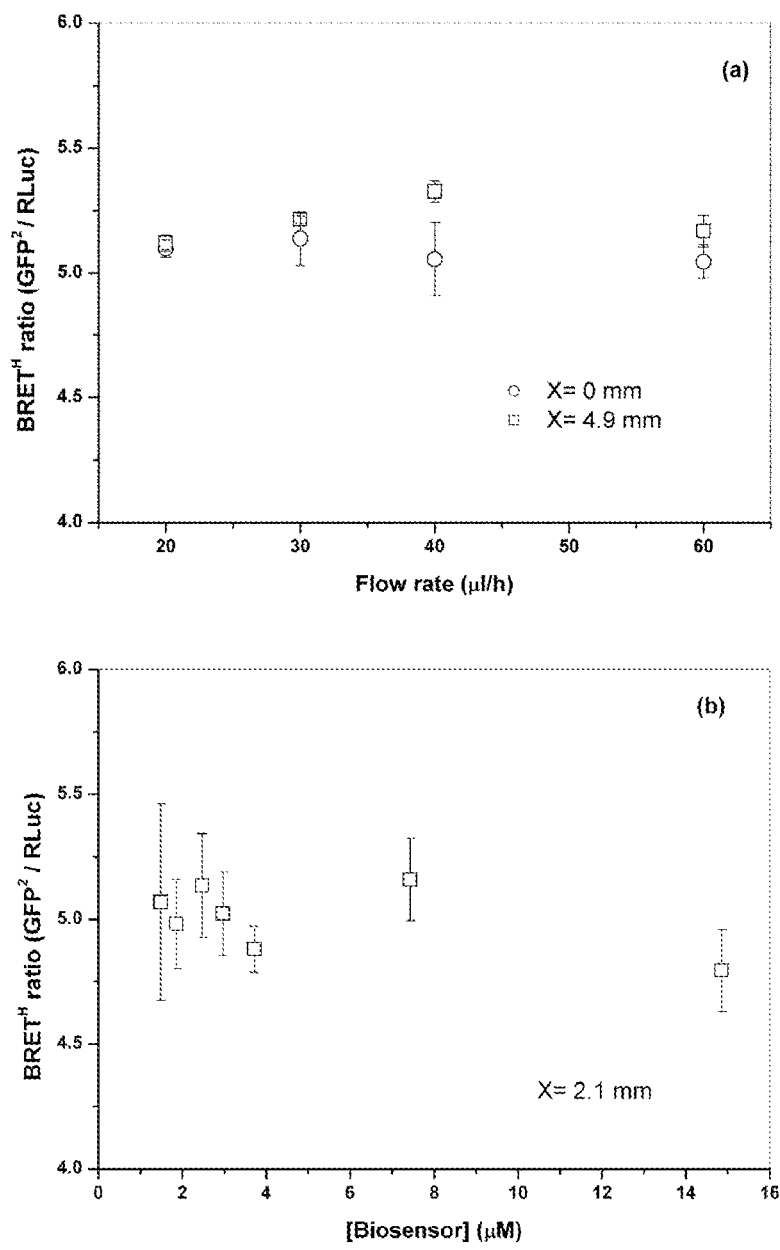

FIG. 6—$BRET^H$ ratios as a function of total flow rate of the aqueous streams (a) and the thrombin sensor concentration (b). (a) Thrombin sensor protein concentration was 3.0 μM and native coelenterazine concentration was 58.6 μM; (b) Native coelenterazine concentration was 58.6 μM; each aqueous flow rate was 20 μl/h; a 20× objective was used; filter band pass for $GFP^2$ and RLuc channel are 515 nm-555 nm and 430 nm-455 nm respectively; an internal gate time of 200 ms was used for data acquisition.

Figure 7:
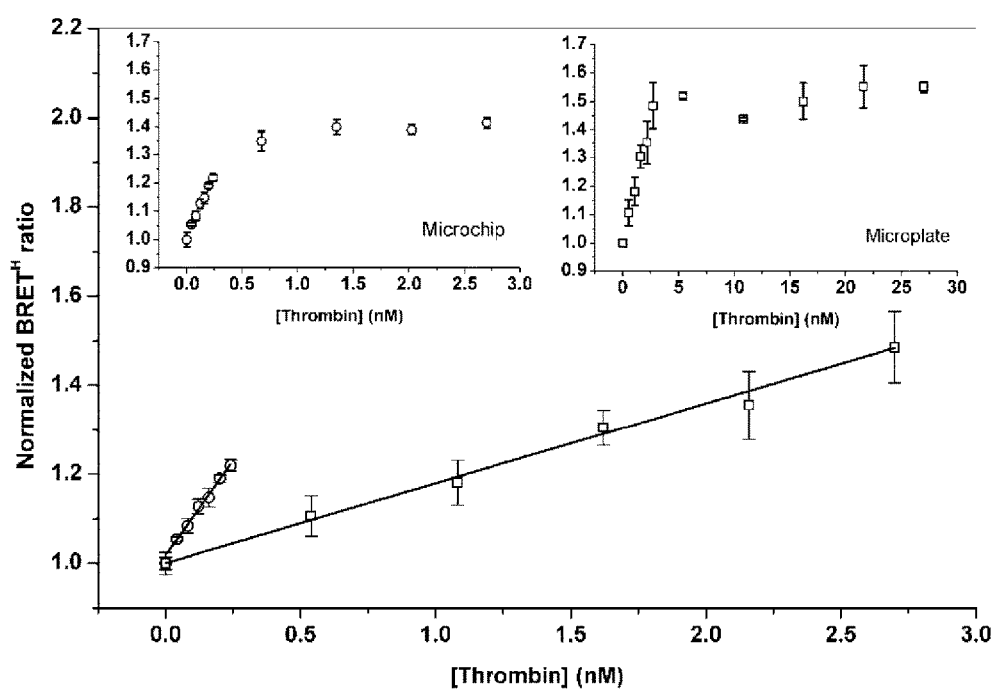
Figure 8:
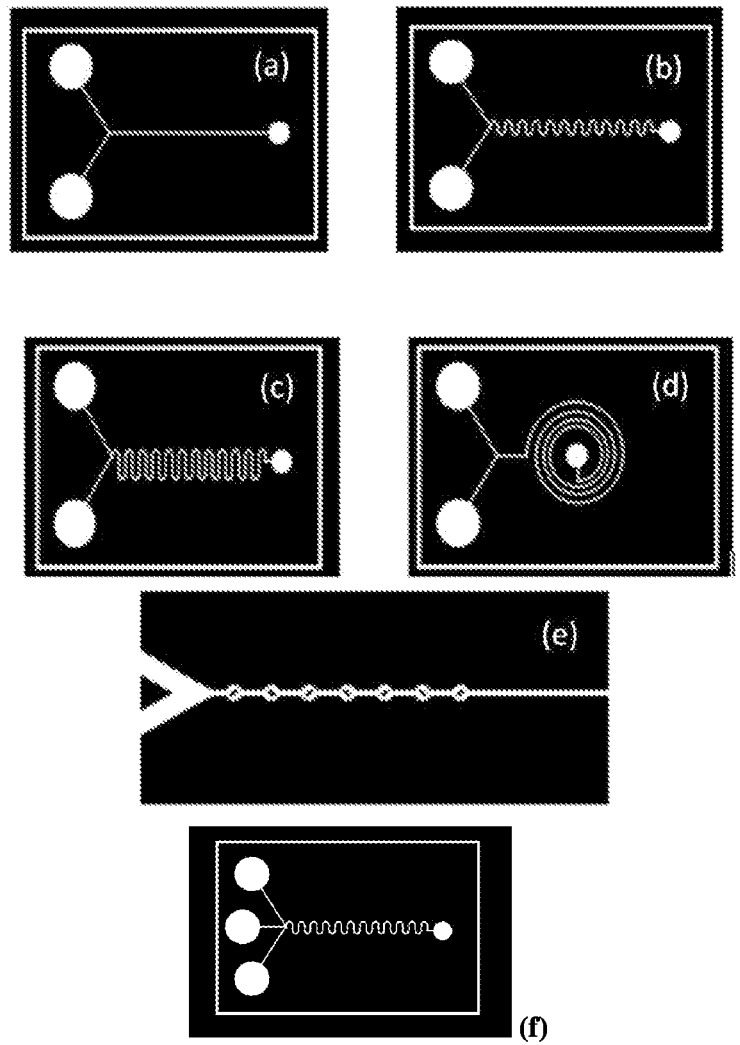

FIG. 7—Calibration curves for the $BRET^H$ thrombin sensors in microfluidic and microplate formats (mean±SD, n=5). All microfluidic measurements were obtained at x=2.1 mm. ○ and □ represent data for microchip and microplate measurements, respectively. The main graph shows the data at low thrombin concentrations while the insets show the corresponding full-range measurements. The lines are the linear regressions, which are y=0.835x+1.019 ($R^2$=0.996) for the microchip data and y=0.1797x+1.001 ($R^2$=0.995) for the microplate data. For the microchip method, the fusion protein concentration was 3.0 μM and native coelenterazine concentration was 58.6 μM, each aqueous flow rate was 20 μl/h. For the microplate method, the fusion protein and native coelenterazine concentrations were 1 μM and 5 μM, respectively FIG. 8—Examples of passive mixing designs (a) Y-shape with linear contact region (b) narrow serpentine, (c) wide serpentine, (d) spiral, (e) Y-shape channel with size variations and baffles, and (f) three inlet with narrow serpentine contact region.

Figure 9:
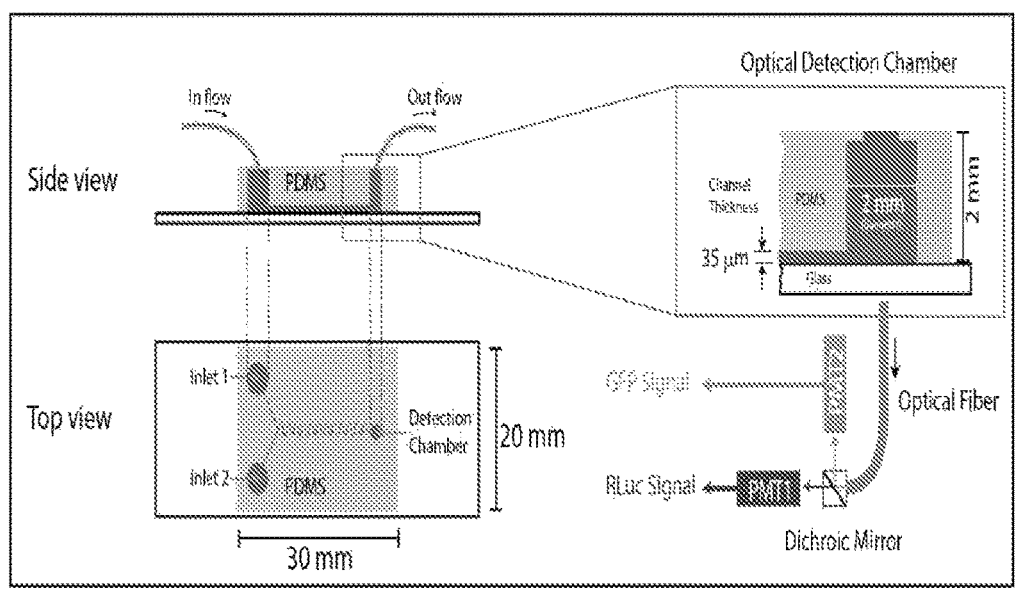

FIG. 9—Schematics of a particular example of a chip and on-chip optical detection system of the invention. PMT—photomultiplier tube. PDMS—polydimethylsiloxane chip matrix.

Figure 10:
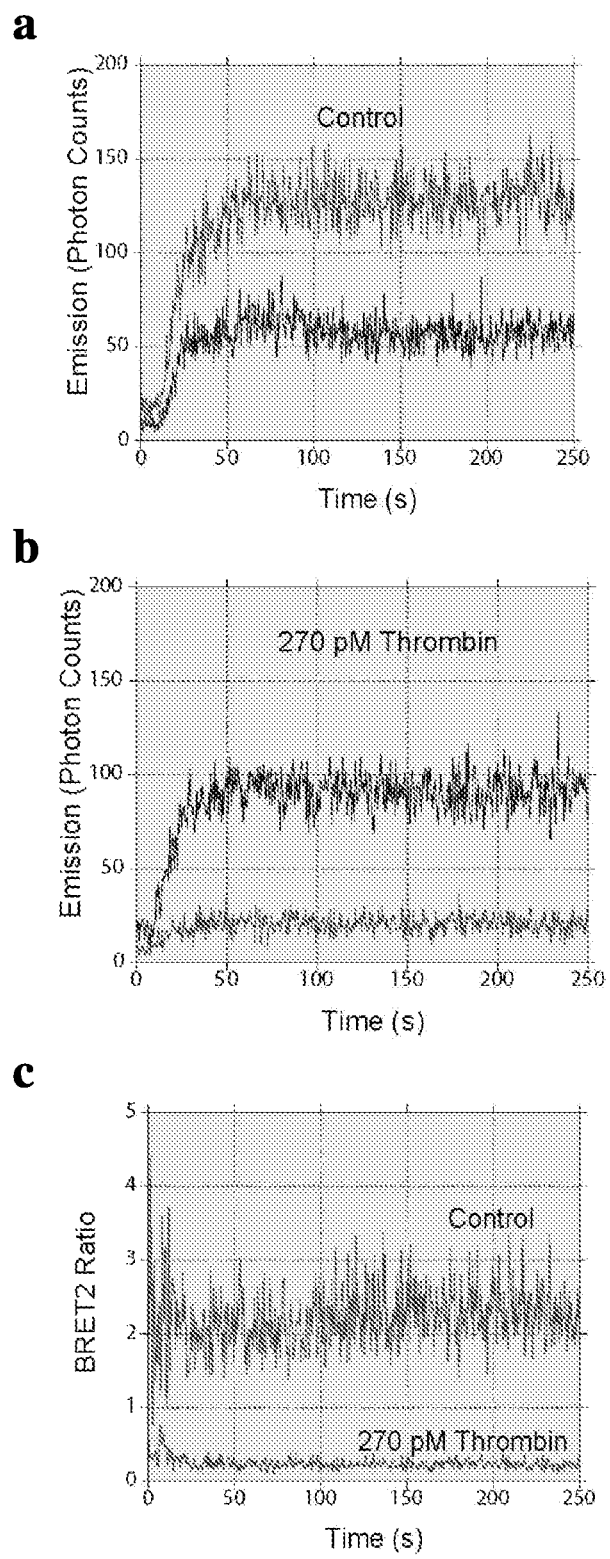

FIG. 10—Sample data indicates detection of thrombin by the change in $BRET^2$ ratio of a $GFP^2$-RG-RLuc thrombin sensor. a. GFP (green—top) and *Renilla* luciferase (blue—bottom) channel emission intensities with no thrombin present. b. GFP (green—bottom) and *Renilla* luciferase (blue—top) channel emission intensities following incubation of the sensor with 270 pM thrombin. c. $BRET^2$ ratio for the no thrombin and 270 pM thrombin conditions.

Figure 11:
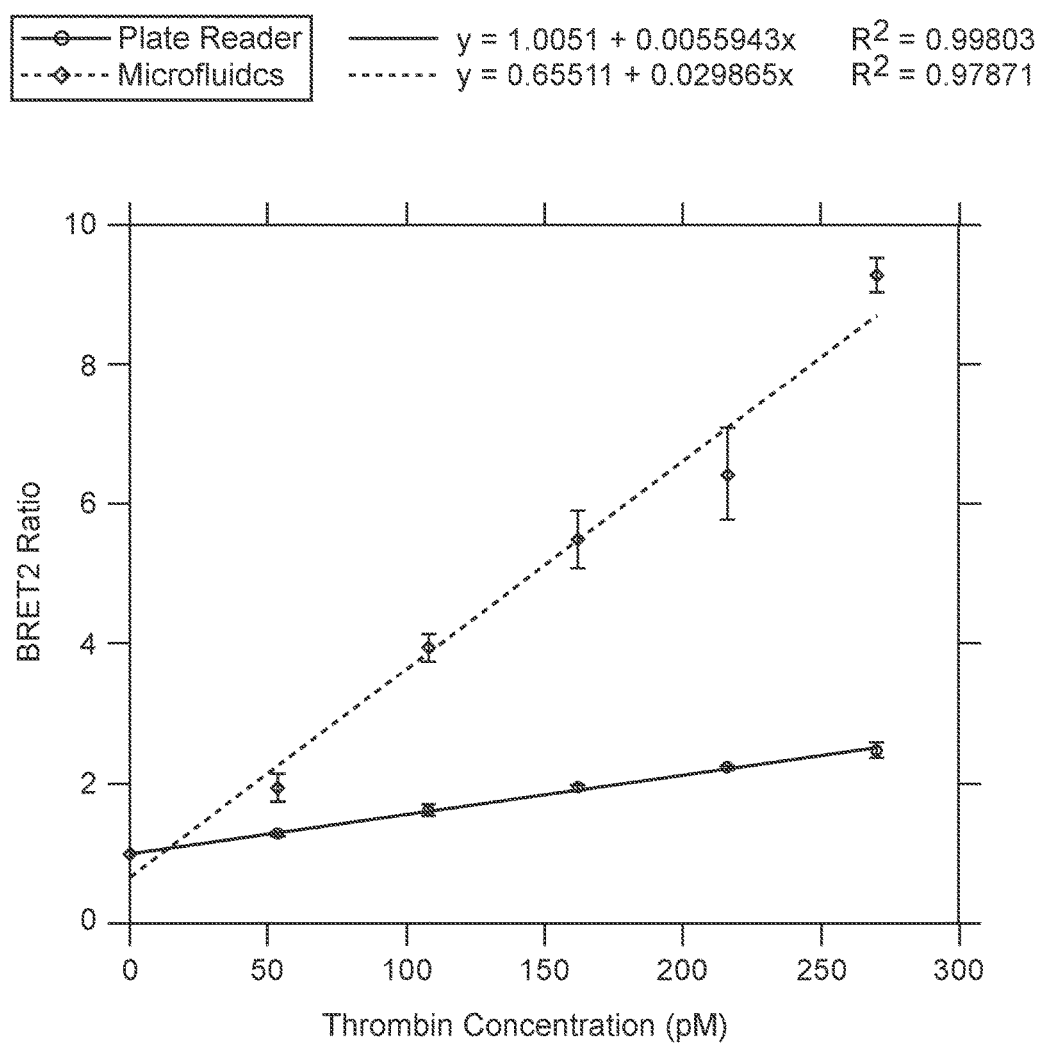

FIG. 11—Direct comparison of the sensitivity of thrombin detection by $BRET^2$ measurement, using a $GFP^2$-RG-RLuc thrombin sensor in the microfluidic device of FIG. 9 (blue line) compared with the results from a commercially available plate reader instrument (red line).

Figure 12:
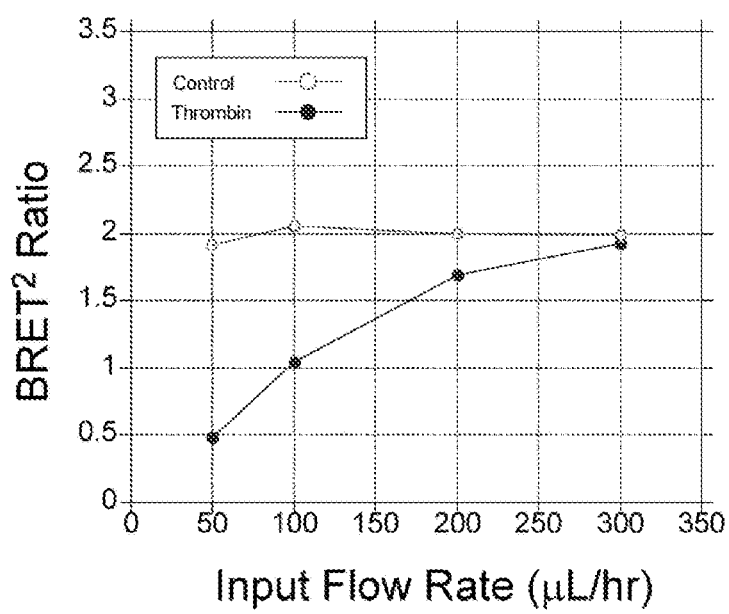

FIG. 12—$BRET^2$ ratio measured with a two inlet microfluidic device upon mixing thrombin biosensor (1 μM) with a preparation containing thrombin (540 nM) and coelenterazine 400a substrate (12.5 μM).

Figure 13:
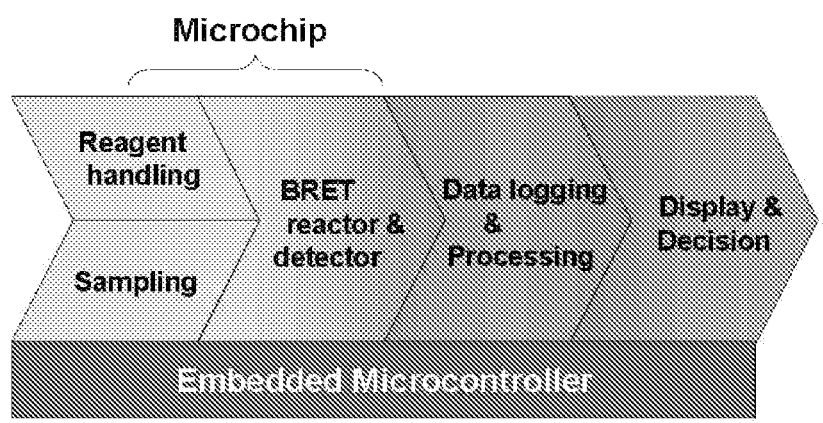

FIG. 13—Example of the subsystems of a system of the invention.

Figure 14:
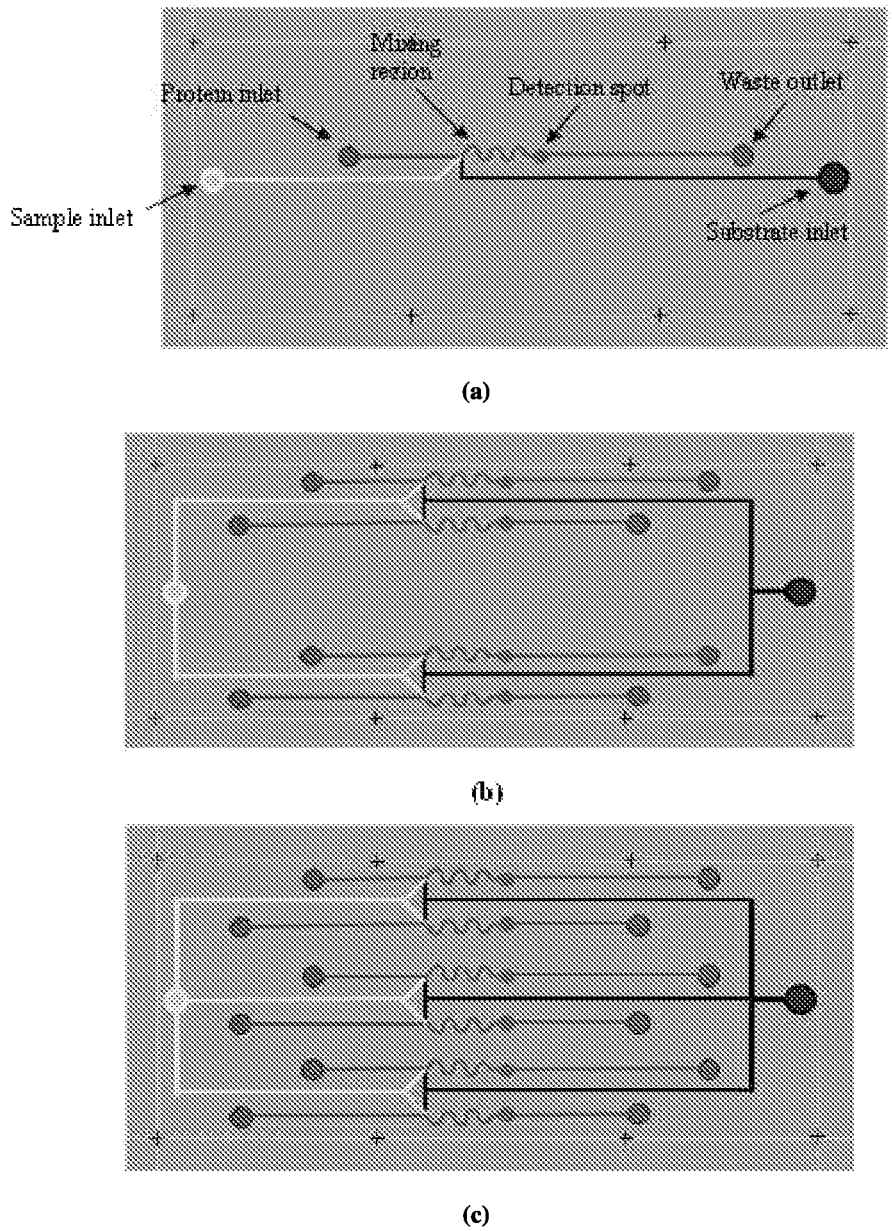

FIG. 14—Example of single and multiple sensor sensor chip designs.

Figure 15:
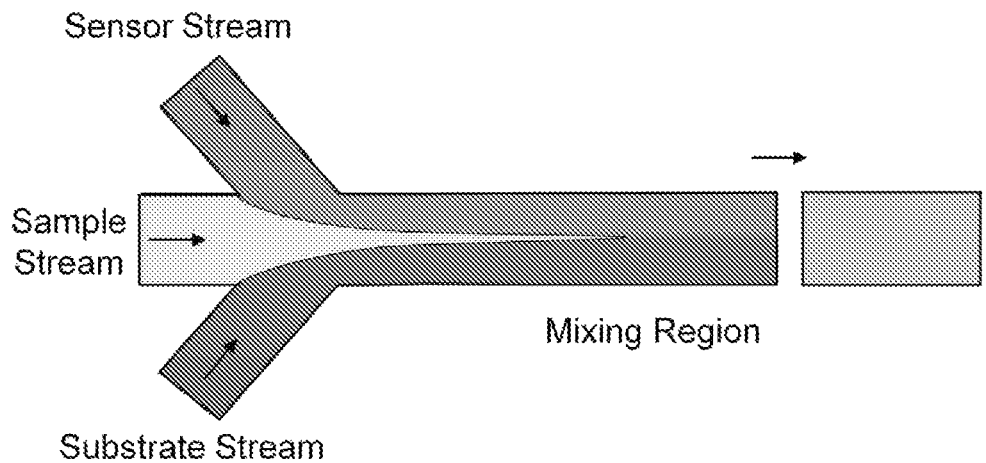

FIG. 15—Example of the zone of passive or diffusion-based reagent mixing when three microfluidic flows come into contact.

Figure 16:
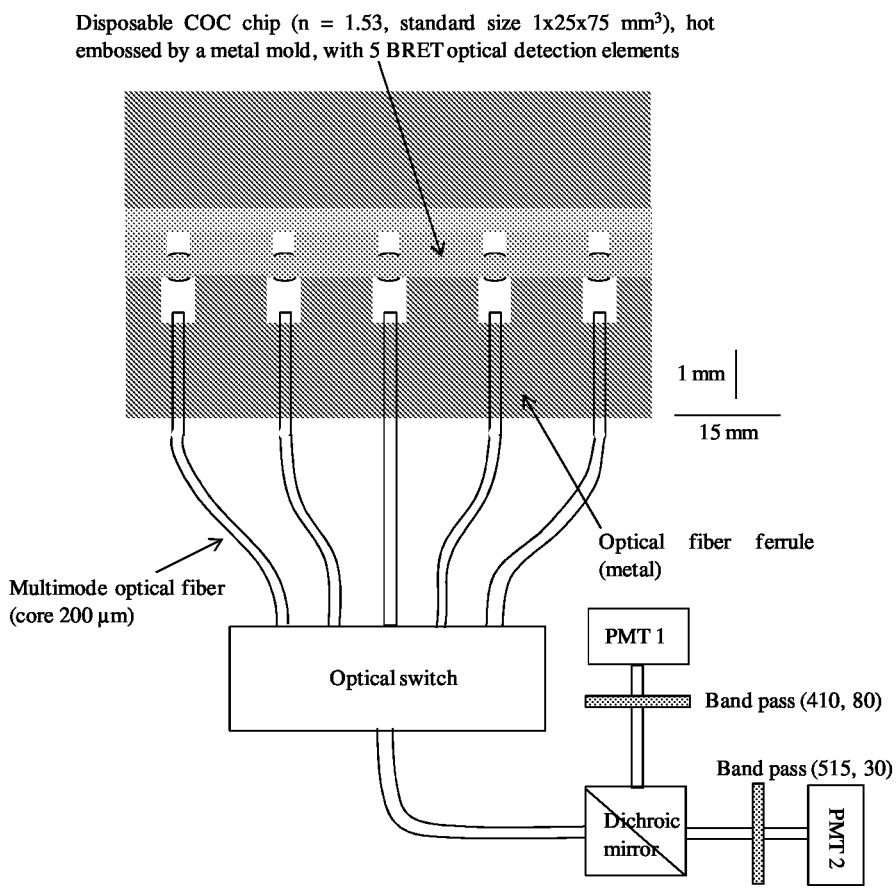

FIG. 16—Example of electro-optical detection system.

Figure 17:
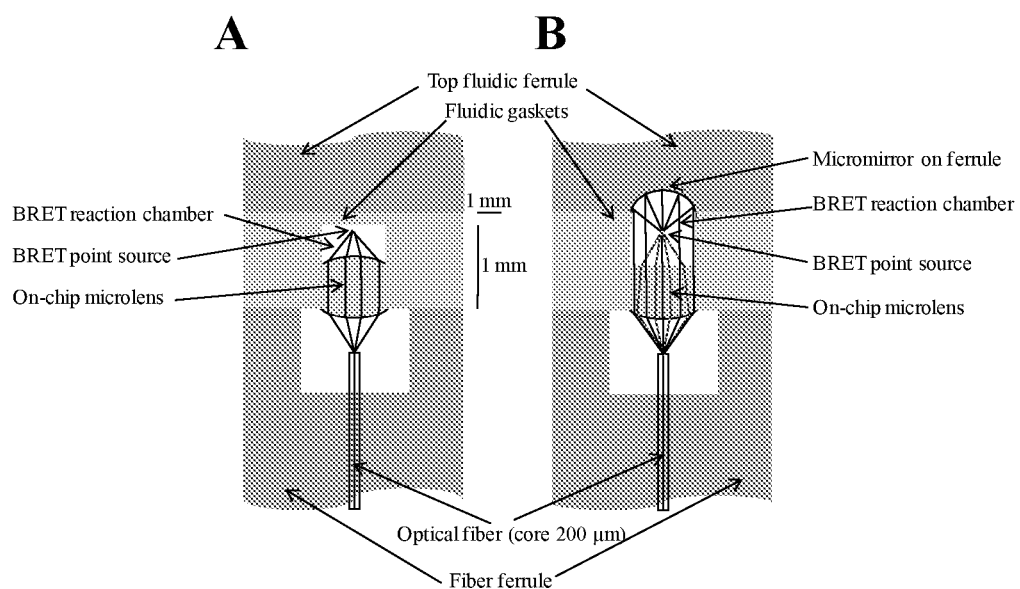

FIG. 17—Designs of two BRET optical detection elements (a) a double-convex microlens serves at the bottom of the reaction chamber to collect fluorescence from many BRET point sources inside the reaction chamber and focus onto a multimode optical fiber (core 200 µm) (b) a plano-convex microlens also serve as the bottom of the reaction chamber. However an aspherical micro mirror on top (micro-machined on the ferrule) will collect fluorescence from the top of the BRET point sources and collimate onto the microlens. Similar to (a), the plano-convex microlens will then focus the fluorescence into the core of the optical fiber.

Figure 18:
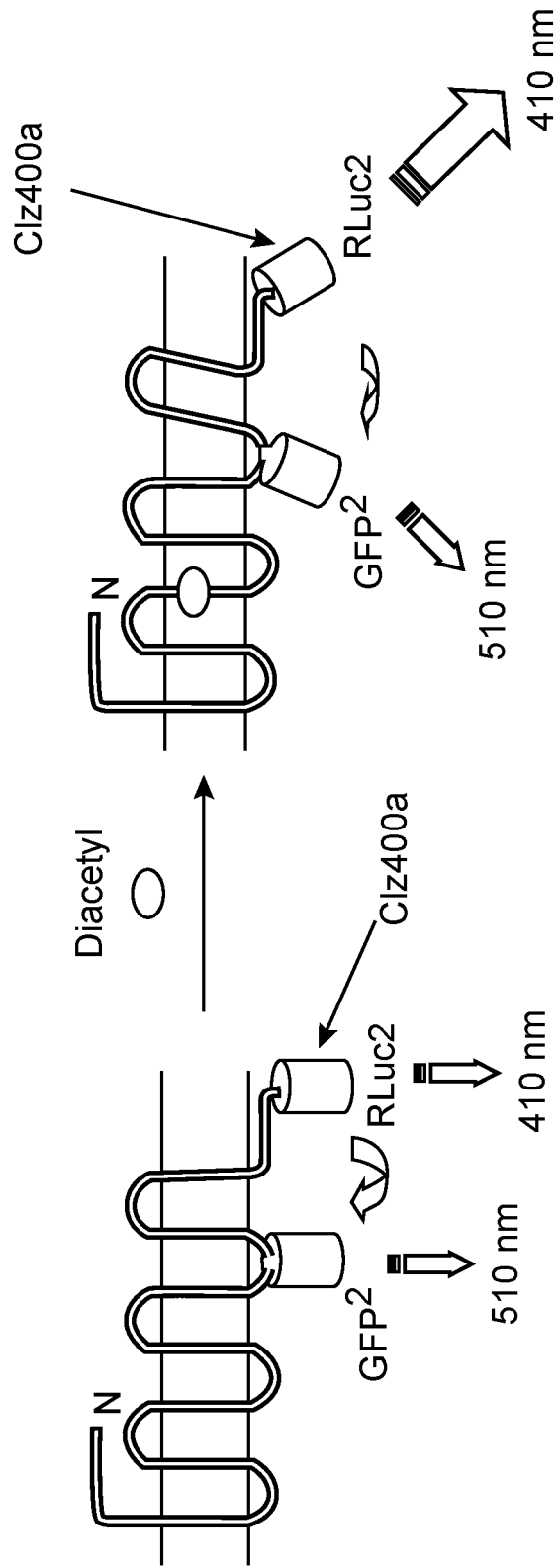

FIG. 18—Principle of resonance energy transfer in ODR-10 receptor constructs fused to RLuc2 and GFP$^2$. GFP$^2$ is inserted in the third intracellular loop of ODR-10 and RLuc2 at the C-terminus (OGOR2). Diacetyl binding causes a conformational change in the OGOR2 biosensor resulting in an increase in distance, or a change in the orientation of dipole moments, between the BRET$^2$ components. Clz400a=Coelenterazine 400a substrate.

Figure 19:
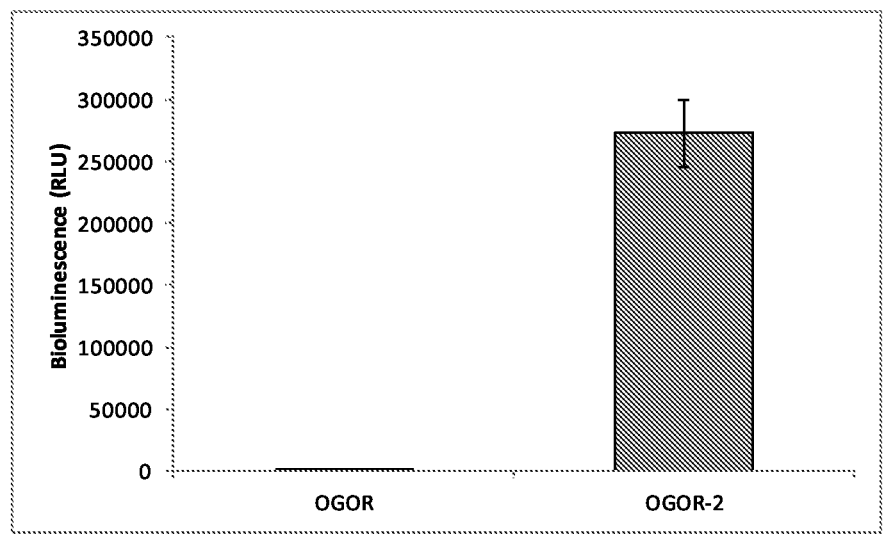

FIG. 19—Bioluminescence intensity of OGOR and OGOR2 sensors upon addition of 5 µM Clz400a to 20 nM of the sensor.

Figure 20:
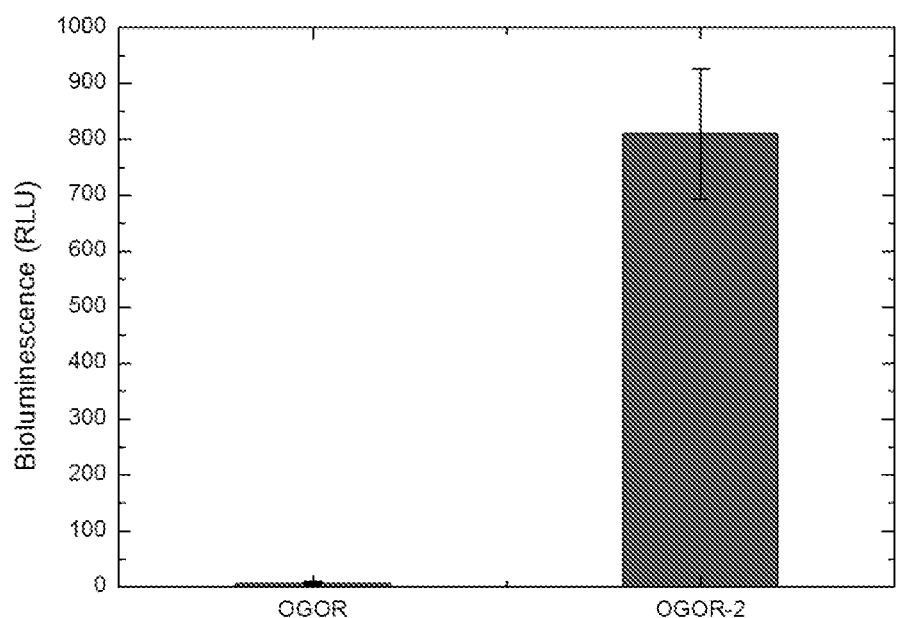

FIG. 20—Bioluminescence intensity of OGOR and OGOR2 sensors upon on-chip mixing of 12.5 µM Clz400a to 1 µM of the sensor.

Figure 21:
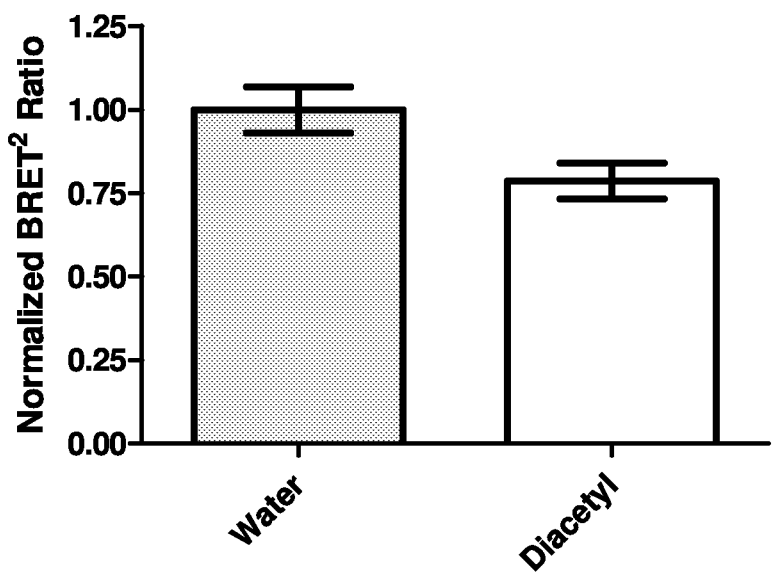

FIG. 21—BRET$^2$ signal from OGOR2 in the wells of a 96-well plate following incubation with 1 µM diacetyl in water, or a water only control (mean±SD, n=3).

Figure 22:
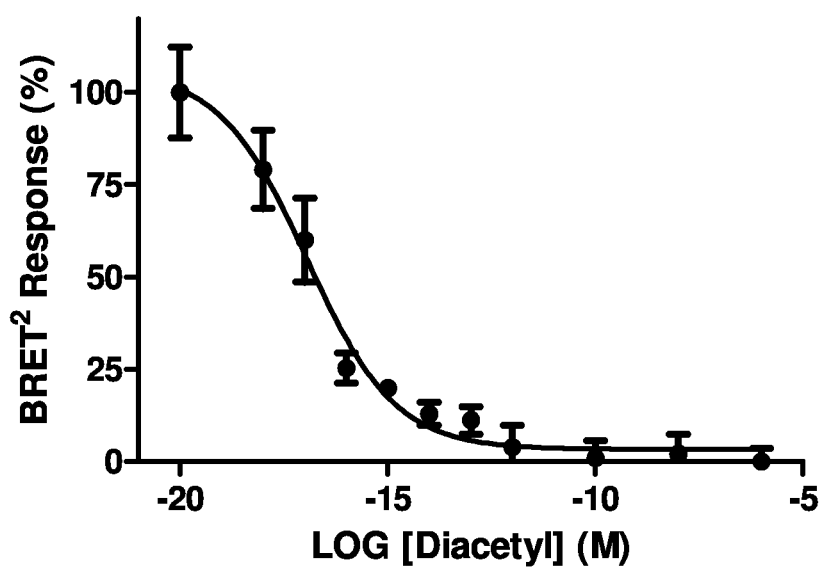

FIG. 22—Diacetyl concentration response curve for BRET$^2$ signal of OGOR2 in a microwell plate format.

Figure 23:
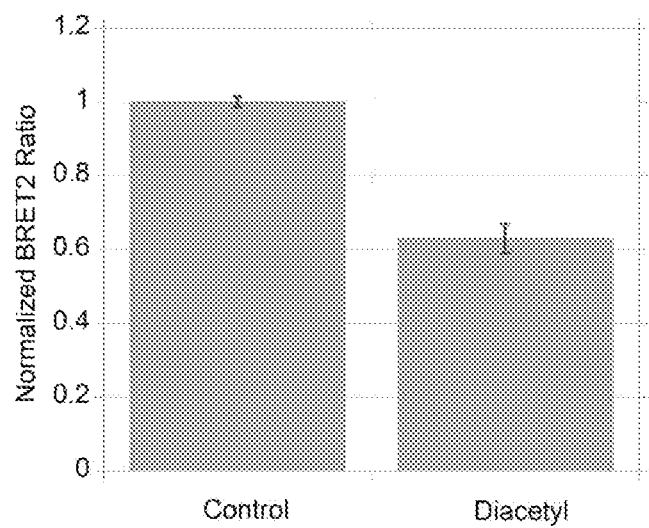

FIG. 23—Change in BRET$^2$ signal detected with on-chip microfluidic assay of OGOR2 signal following incubation with 10 fM diacetyl in PBS or a PBS only as control (mean±SD, n=3).

Figure 24:
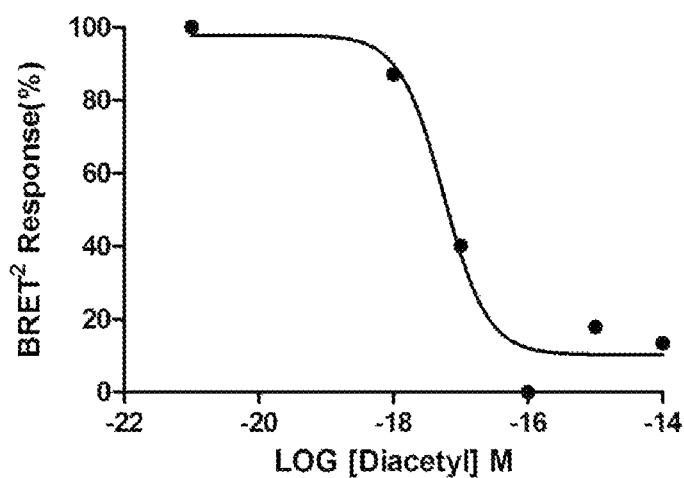

FIG. 24—Dose response of OGOR2 with on-chip (microfluidic) assay measurements.

Figure 25:
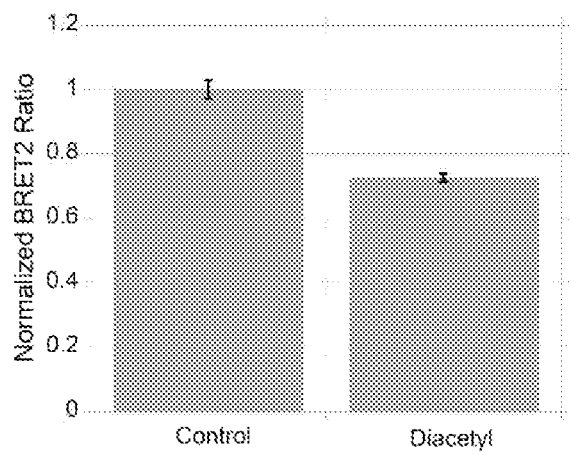

FIG. 25—Averaged change in BRET$^2$ signal detected using real-time microfluidic measurement upon on-chip contact of OGOR2 over a range of flow rates. 1 fM diacetyl in PBS or PBS only and 12.5 µM Clz400a substrate (mean±SD of BRET$^2$ ratio at four different flow rates).

Figure 26:
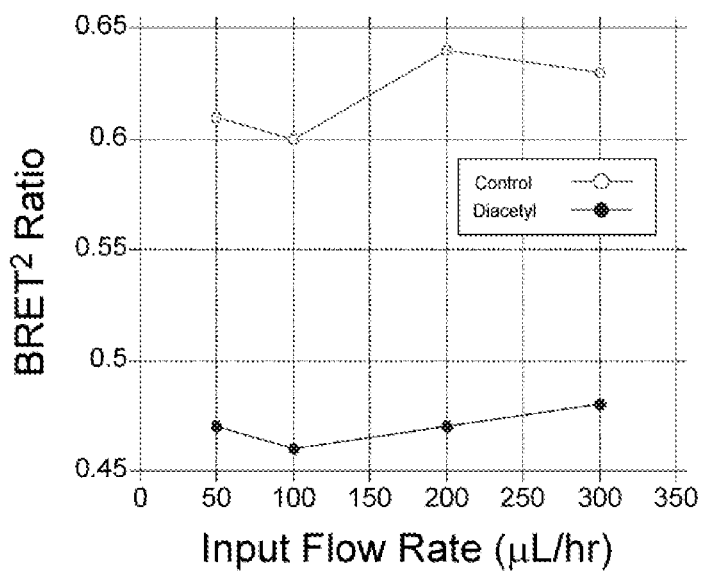

FIG. 26—BRET$^2$ ratio measured at different common flow rates with a three-inlet microfluidic device upon contacting OGOR2 (290 nM) with 1 femtomolar diacetyl solution in PBS and with 12.5 µM coelenterazine 400a.

Figure 27:
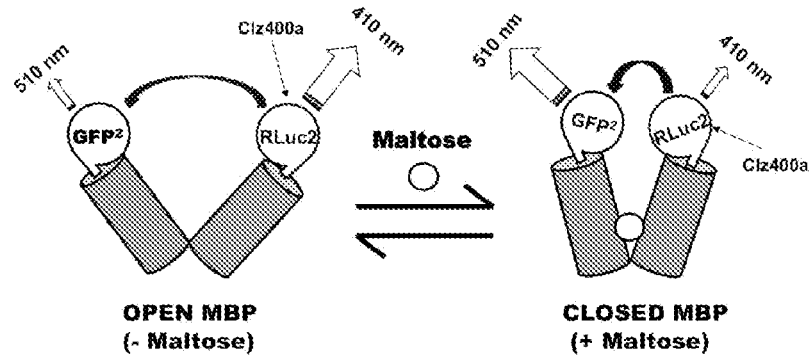

FIG. 27—Principle of BRET in MBP receptor constructs fused to BRET$^2$ components GFP$^2$ and RLuc2. Maltose binding causes a conformational change in the BRET$^2$ tagged MBP receptor bringing the BRET$^2$ components in closer proximity causing an increase in the efficiency of energy transfer from RLuc2 to GFP$^2$. Clz400a= Coelenterazine 400a substrate.

Figure 28:
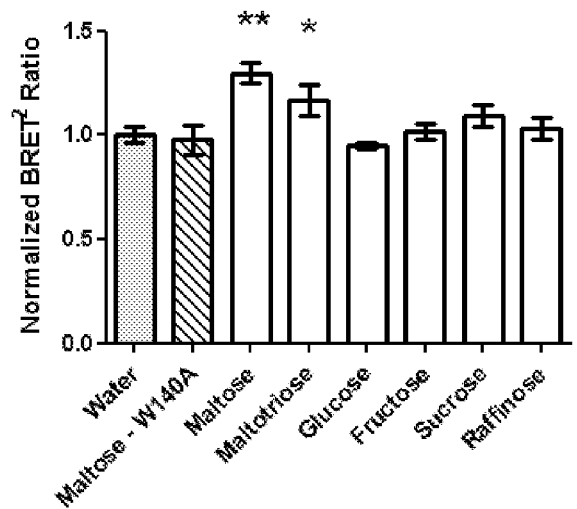

FIG. 28—Effect of 0.1 mM of various sugars on the BRET$^2$ ratio of the GFP$^2$-MBP-RLuc2 sensor. BRET$^2$ ratio (Mean±SD, n=3) was recorded following addition of 16.7 µM coelenterazine 400a to 1 µM GFP$^2$-MBP-RLuc2 or W140A mutant (hatched bar) following incubation with water (grey bar) or 0.1 mM of the stated sugars for 30 minutes at 28° C. BRET$^2$ ratios were normalized by the water response. ** P<0.01 and P *<0.05.

Figure 29:
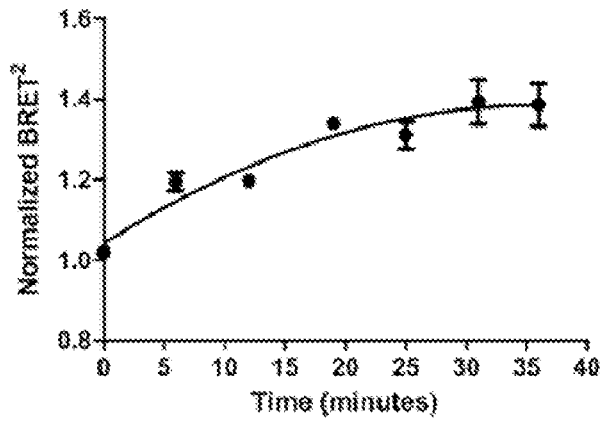

FIG. 29—Response time (minutes, mean±S.D., n=3) of 1 µM GFP$^2$-MBP-RLuc2 to 0.1 mM Maltose upon addition of 16.67 µM coelenterazine 400a. The BRET$^2$ response following incubation with maltose for any time period was normalized by the BRET$^2$ response following incubation with water for the same time period.

Figure 30:
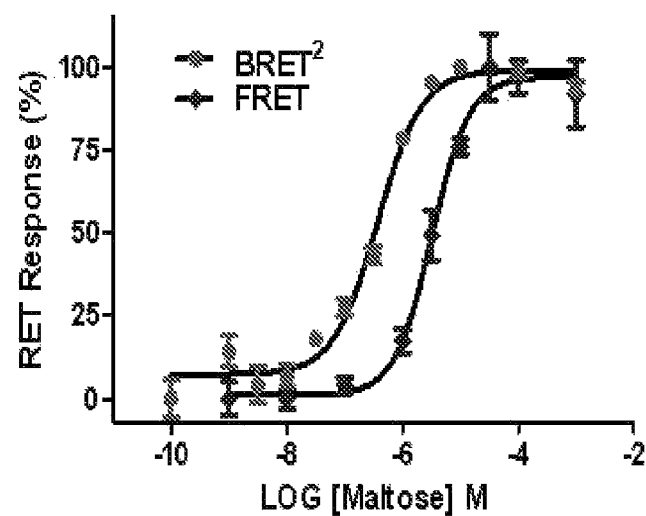
Figure 30:
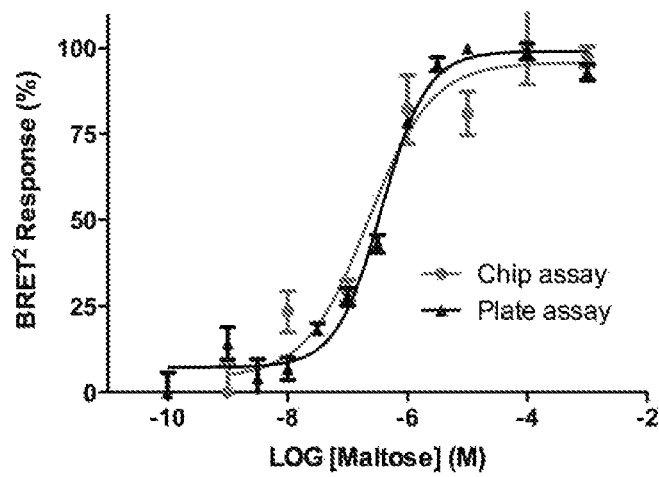

FIG. 30—(A) FRET vs BRET$^2$. Maltose concentration dependence of the BRET$^2$ response (mean±SD, n=11) of 1 µM GFP$^2$-MBP-RLuc2 fusion protein upon addition of 16.67 µM coelenterazine 400a compared to the FRET response (mean±SD, n=3) of FLIPmal-2µ (530/485-nm ratio). The latter dose-response curve was re-plotted from data presented by Fehr et al. (2002). Data was fitted to a log [Agonist] vs response. BRET2 EC50=0.4 µM and FRET EC50=3.2 µM. (B) Comparison of BRET$^2$-based MBP assay for maltose on a microfluidic chip versus using a microplate assay.

Figure 31:
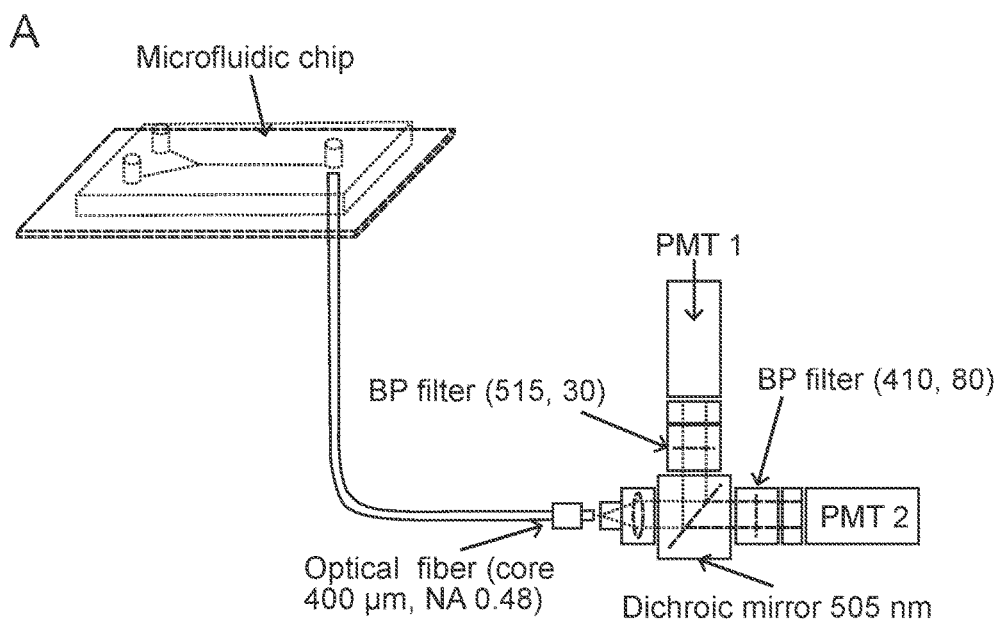
Figure 31:
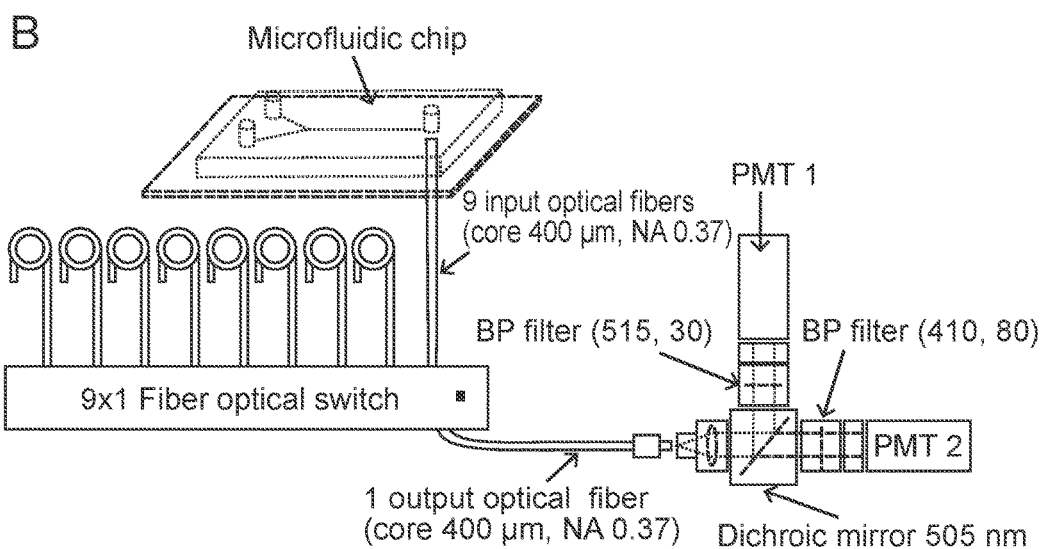

FIG. 31—Experimental setup for collecting data from a microfluidic chip system without (A) and with (B) an in-line optical fibre switch. BP—band pass, PMT—photomultiplier; NA—numerical aperture.

Figure 32:
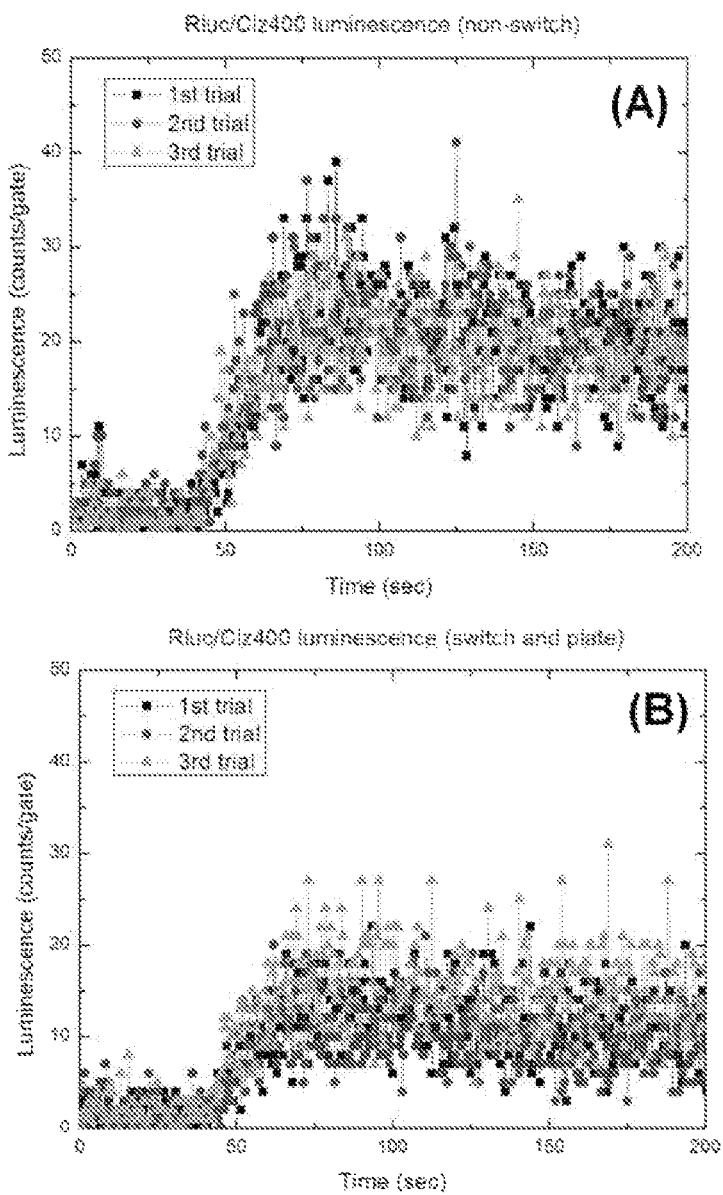

FIG. 32—Real-time Rluc/Clz400a bioluminescent signal collected without (A) and with optical switch (B) for three runs.

Figure 33:
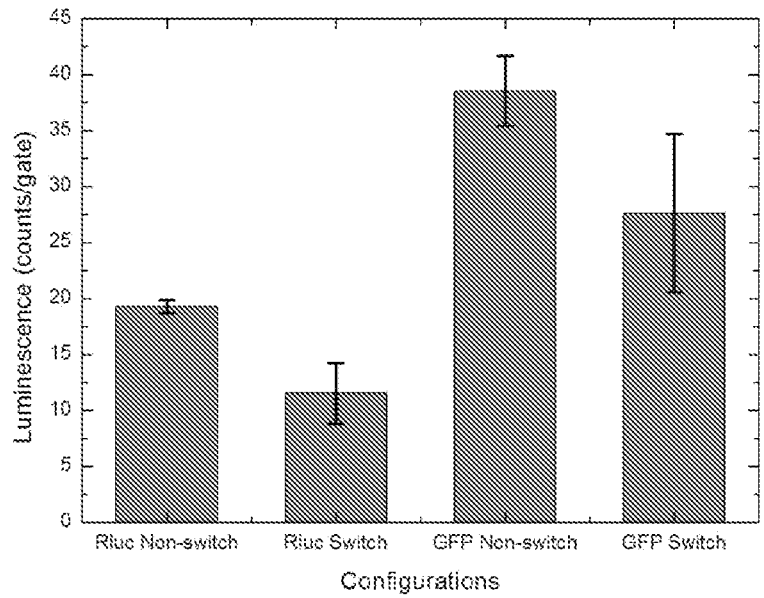

FIG. 33—Mean bioluminescent signal comparison for Rluc/Clz400a and GFP channels without and with optical switch.

Figure 34:
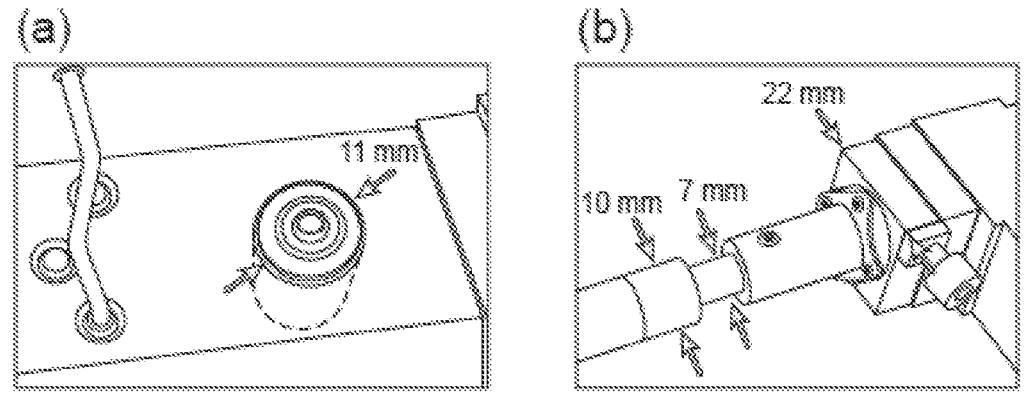

FIG. 34—Example showing arrangement of increased diameter BRET reaction chamber (Ø=4 mm, h=2 mm) coupled through a liquid light guide to the photodetector.

Figure 35:
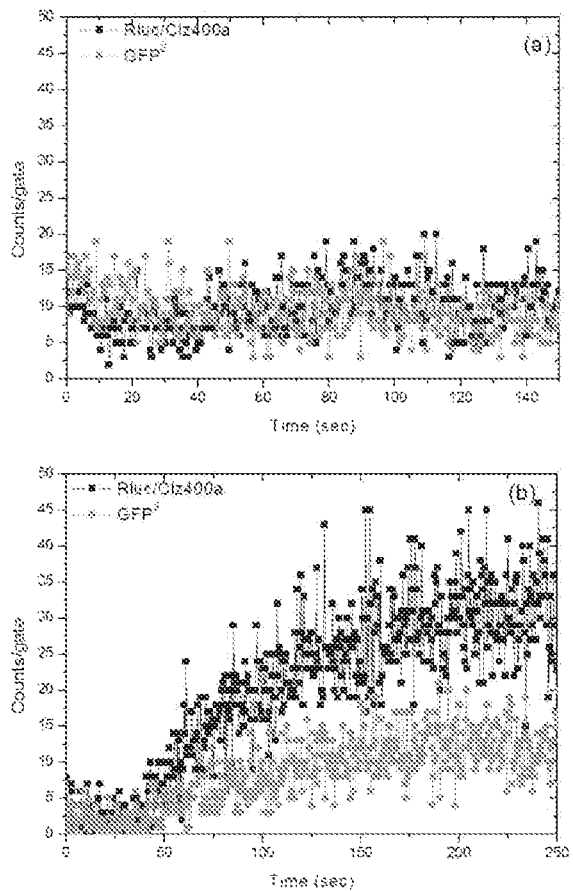

FIG. 35—Comparison of performance of narrow vs wide bore BRET detection chamber/optical system. In both cases BRET emissions are measured from a 1/100 dilution of an OGOR2 sensor flowing through the microfluidic channel. (a) narrow bore system (chamber size Ø=2 mm, h=2 mm; fiber core diameter=1 mm, NA=0.48). (b) wide bore system (chamber size Ø=4 mm, h=2 mm, light guide core diameter=5 mm, NA=0.59).

Figure 36:
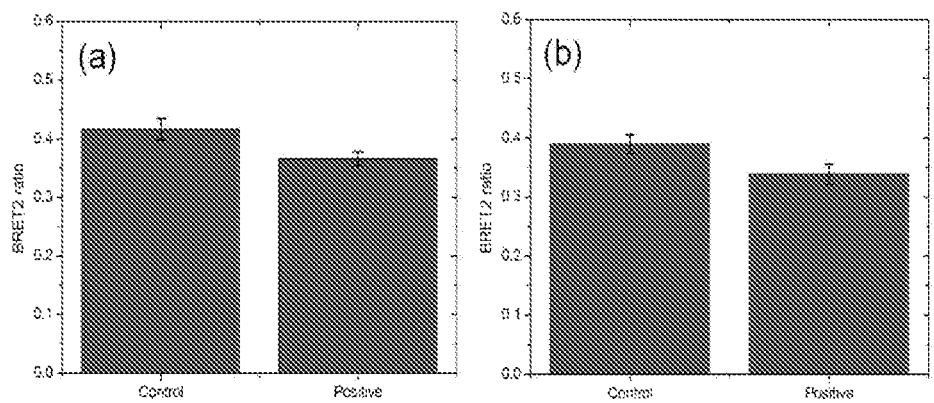

FIG. 36—Demonstration of detection of 1 µM diacetyl using highly diluted OGOR2 sensors, using a more efficient light capture system based on a wider diameter BRET reaction chamber (4 mm) and a wide bore liquid light guide. (a) 100 times sensor dilution. Diacetyl-dependent reduction in BRET$^2$ ratio=13.7% and (b) 50 times sensor dilution, Diacetyl-dependent reduction in BRET$^2$ ratio=14.7%. Error bars represent the standard deviation for 3 experiments (N=3).

Figure 37:
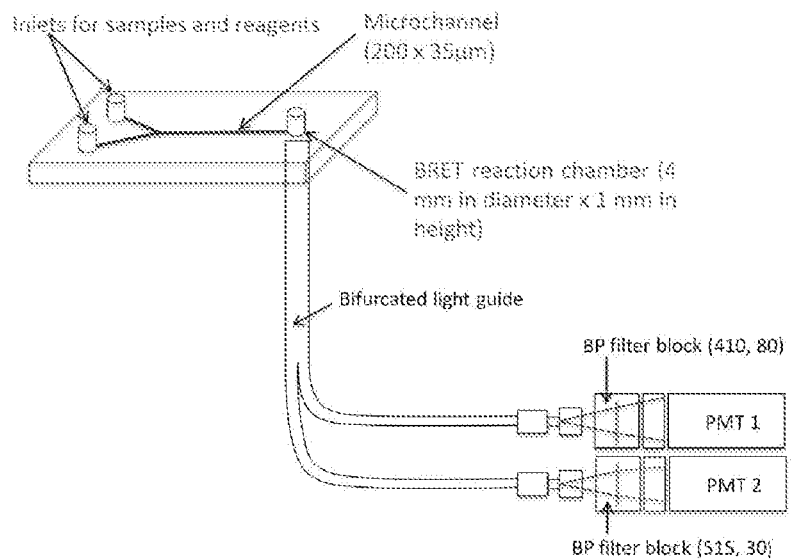

FIG. 37—Example of a single microfluidic channel and BRET light collection system using bifurcated light guide and without dichroic block. Additional sets of bifurcated light guides with filters and pairs of photodetectors can be added to accommodate one or more additional microfluidic channels and/or BRET reaction chambers.

Figure 38:
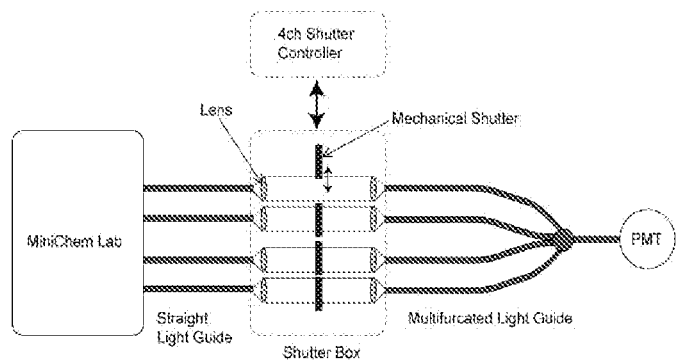
Figure 39:
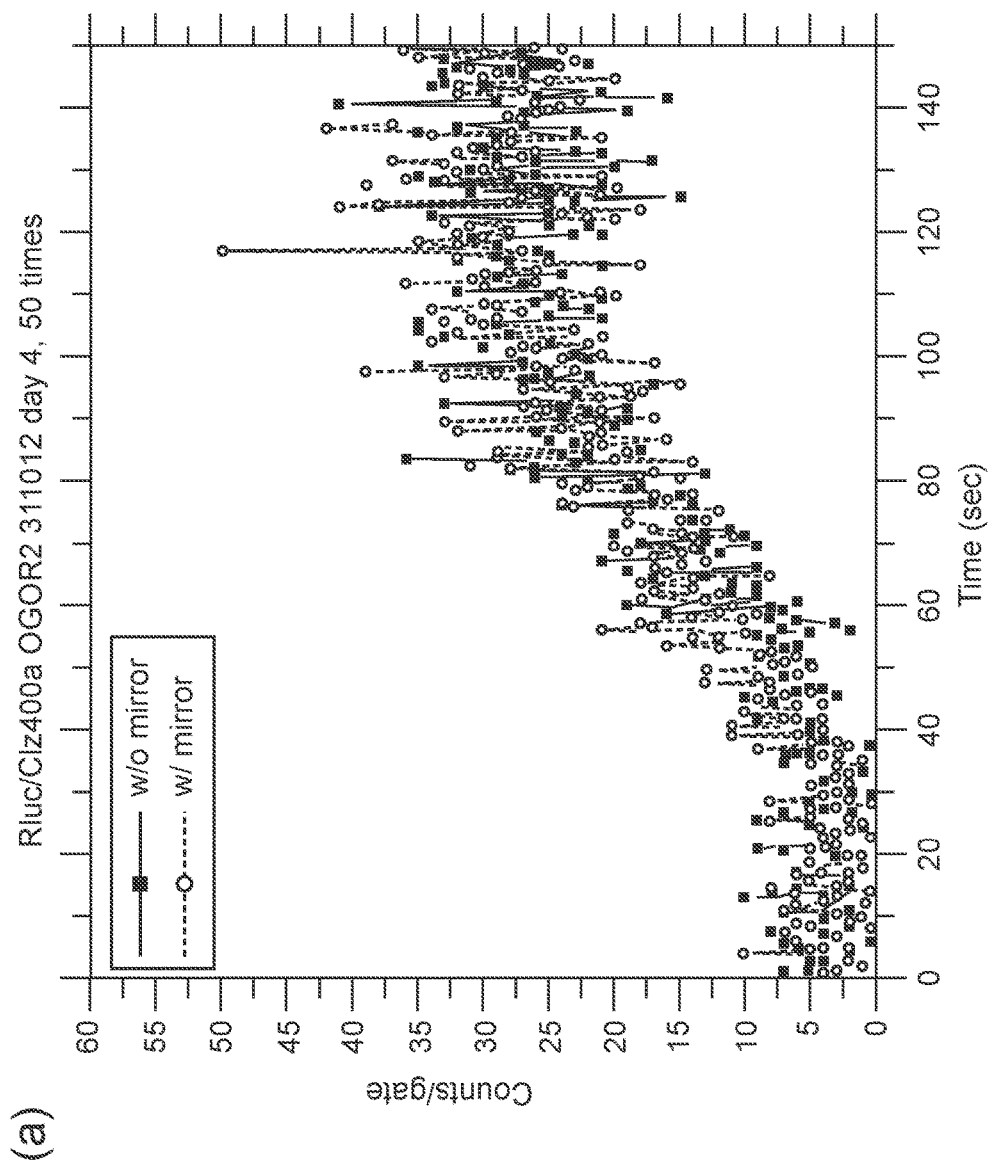
Figure 39:
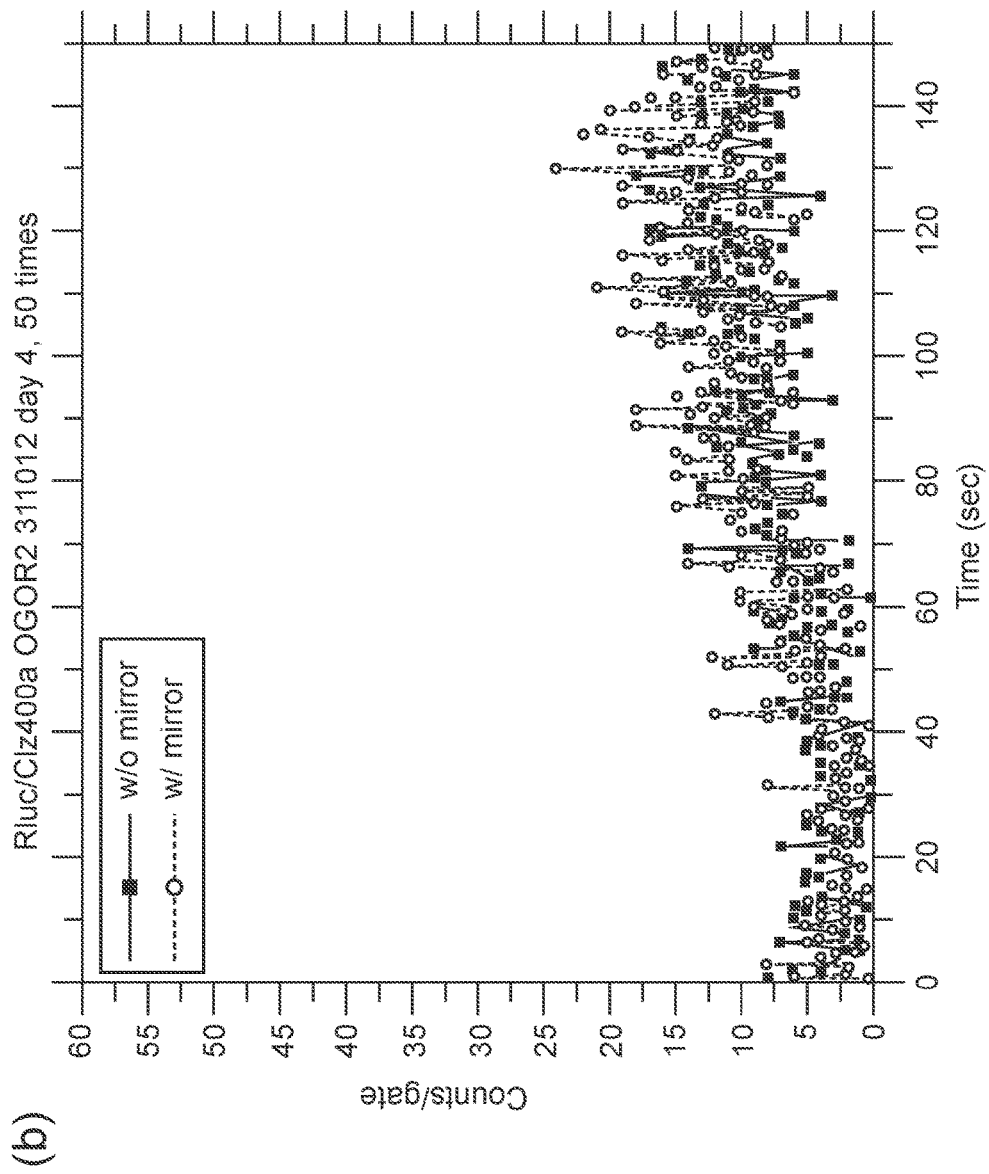
Figure 39:
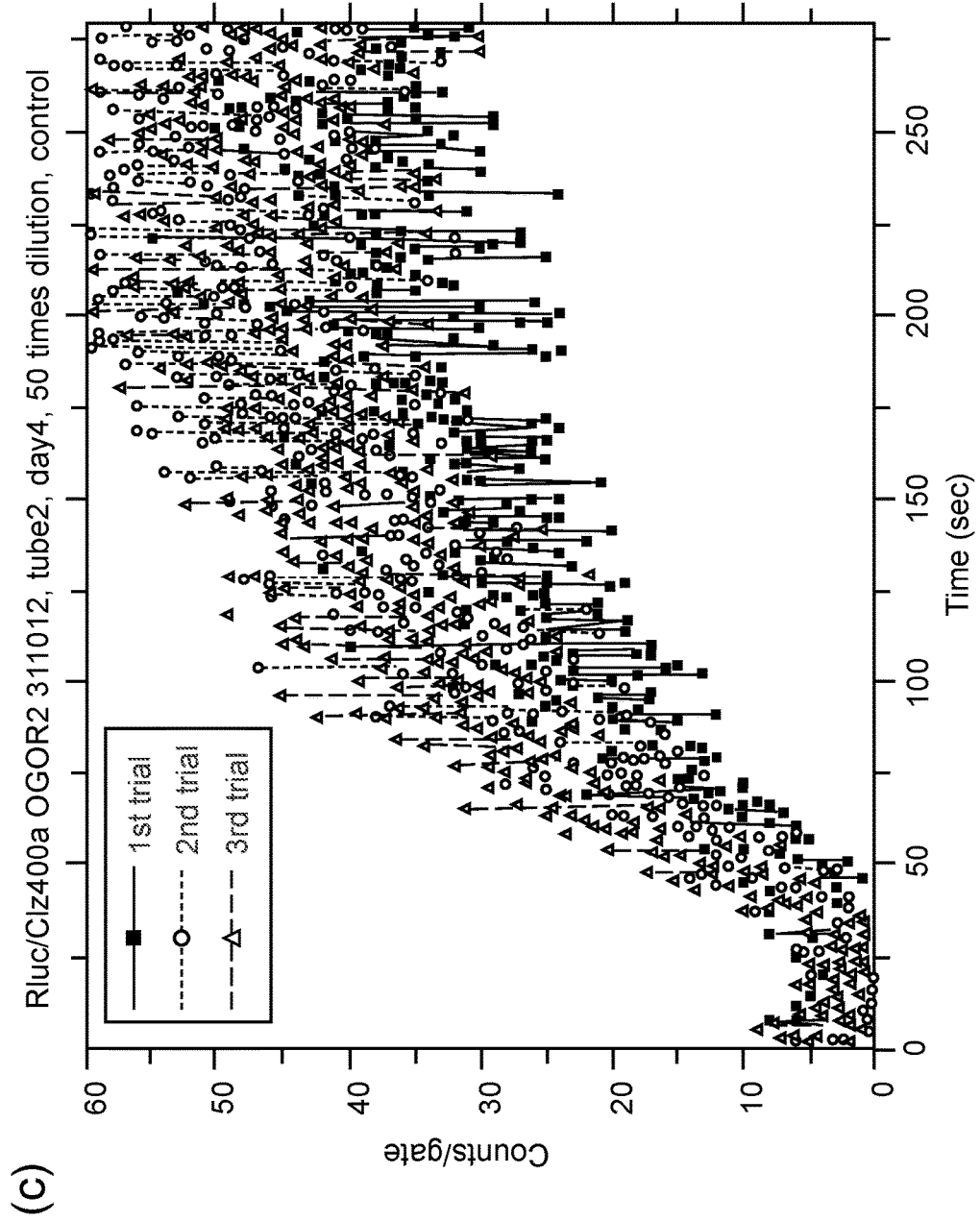
Figure 39:
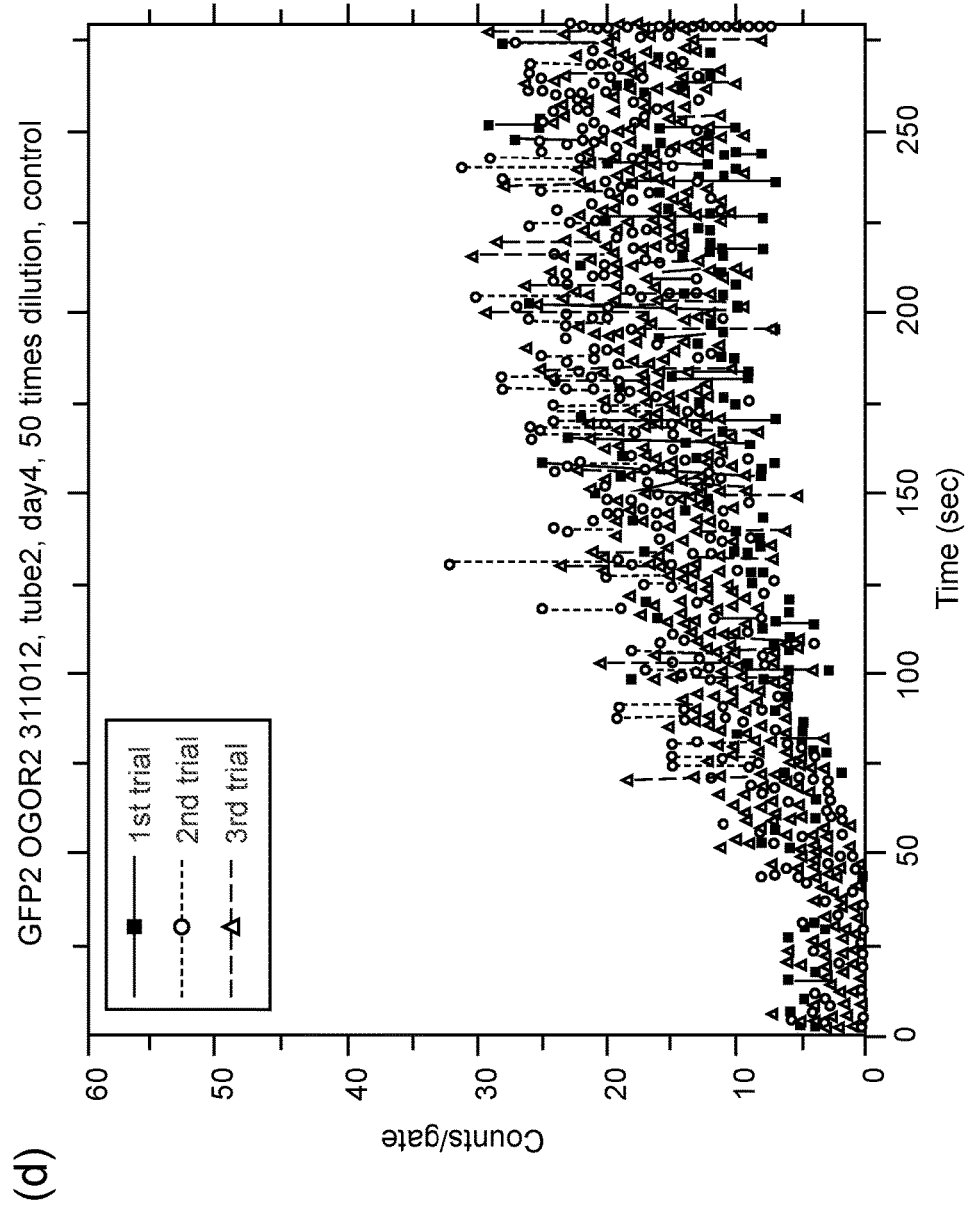

FIG. 38—Optical architecture with a shutter box facilitating multichannel measurements FIG. 39—Comparison of the strength of BRET signals detected with a bifurcated light guide or a dichroic block. a, b: bifurcated light guide, reaction chamber dimensions Ø=4 mm; h=1 mm, with and without reflective lid. c,d: single light guide with dichroic block, reaction chamber dimensions Ø=4 mm; h=2 mm (i.e. double the volume of a, b). All panels show the increase in signal with time, following initiation of flow at t=0. Panels a & c blue channel, panels b & d green channel FIG. 40—Multifurcated light guide arrangement suitable for measuring BRET outputs from a shutterbox.

Figure 40:
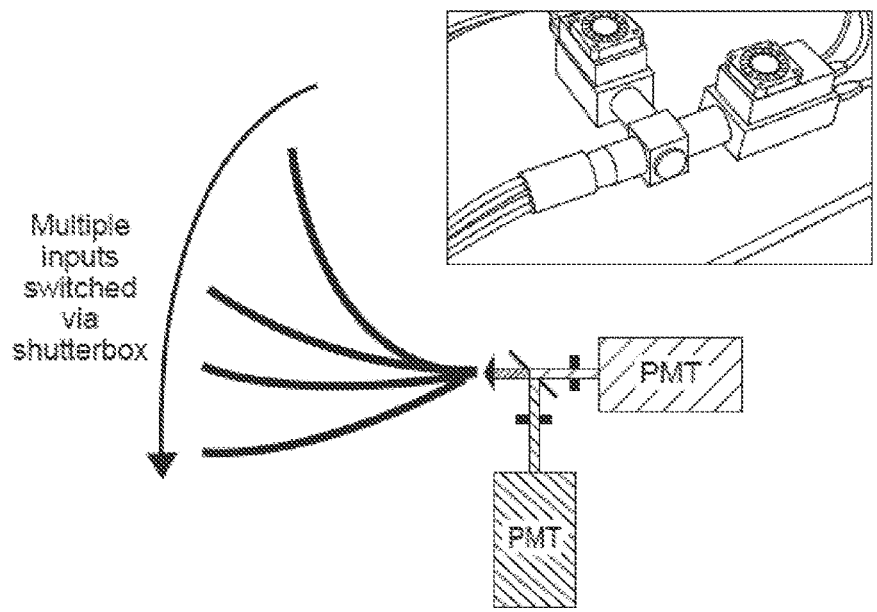
Figure 41:
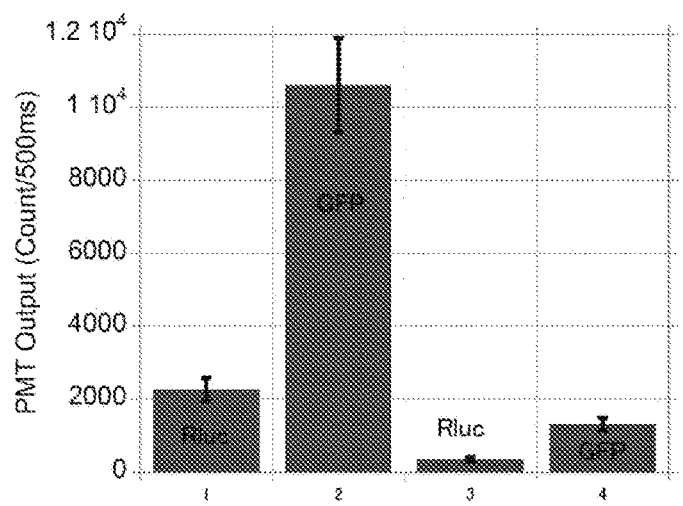

FIG. 41—Comparison of multifurcated light guide converging on a single dichroic block against bifurcated light guides diverging to two separate colour filters. Relative light intensity collected in the blue (RLuc; 1, 3) and green (GFP; 2, 4) channels. 1, 2: Multifurcated light guide with inputs allocated to different microfluidic channels and output directed to a pair of PMTs via an optimised dichroic filter as per FIGS. 38 & 40. 3, 4: Bifurcated light guide with output allocated to different spectral channels, as per FIG. 37.

Figure 42:
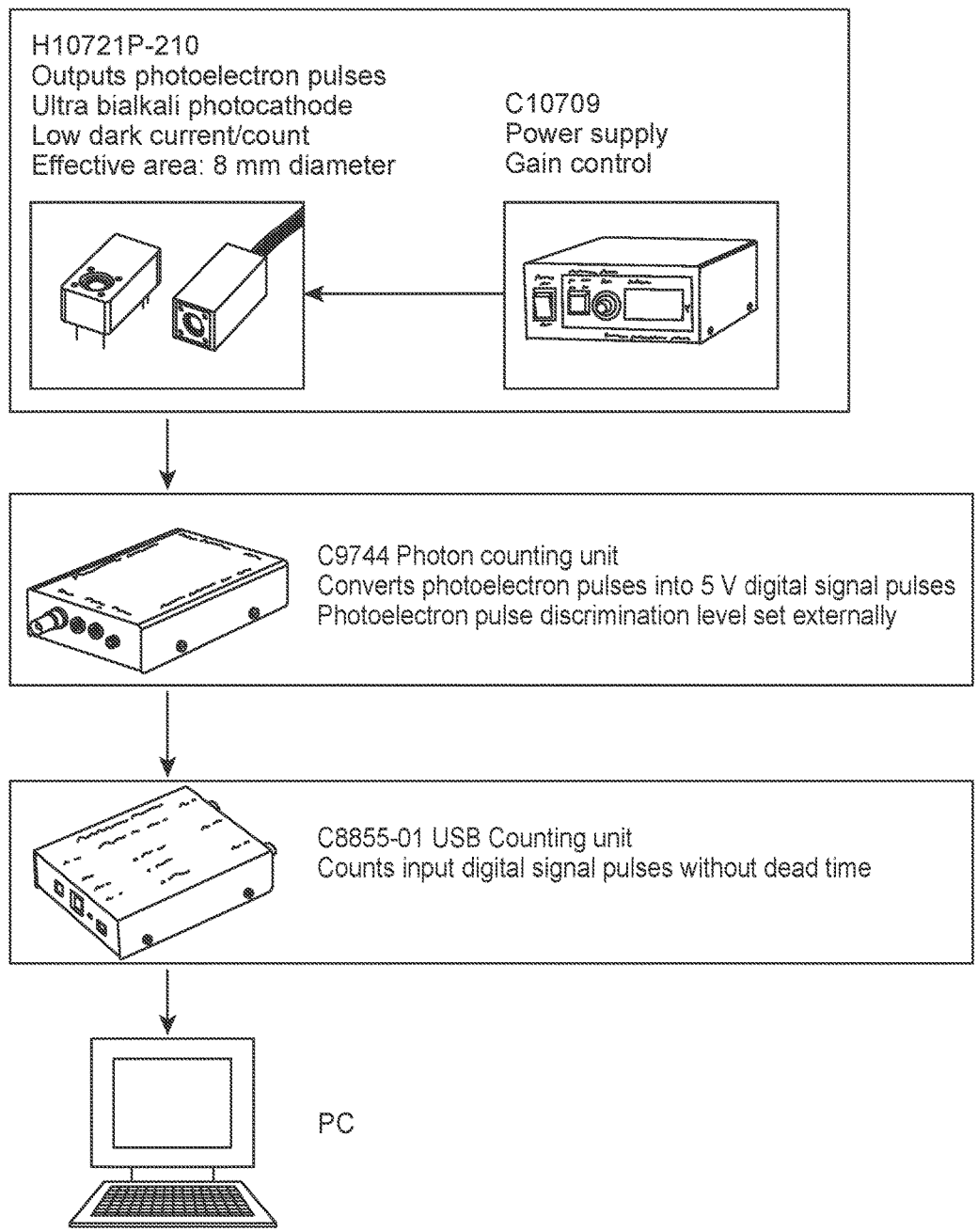

FIG. 42—Example of an ultra low level light photodetector using vacuum photomultiplier technology. Source Hamamatsu FIG. 43—Example of an ultra low light level photodetector implemented using solid state technology. Dimensions in mm. Source: Hamamatsu FIG. 44—Direct visualisation of laminar flow and diffusional mixing in a three-inlet microfluidic device operating at two different flow rates. Two of the three aqueous inputs are colored with blue or red food colouring. The device was operated with a single syringe pump working in withdrawal mode. Direction of flow: right to left.

Figure 45:
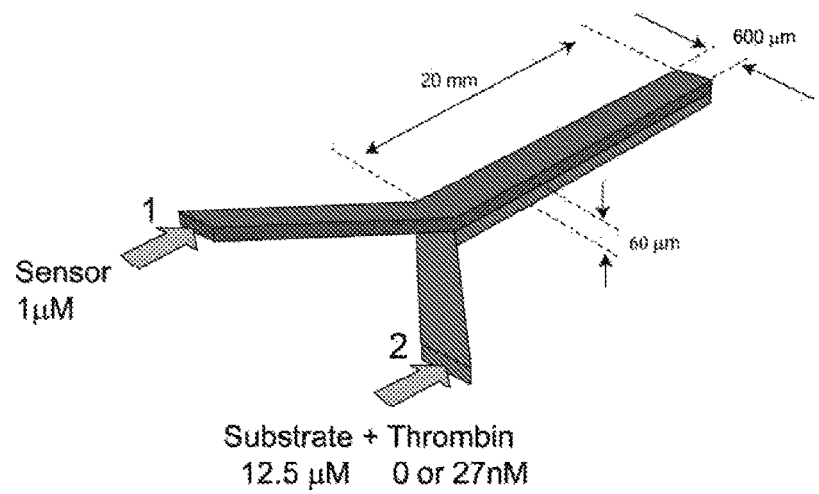

FIG. 45—Passive mixing example design based on vertically stacked streams The width of the channel is starting from 600 μm up to 2 mm, the thickness is 20-60 μm. The length is flexible starting from 20 mm to 100 mm, the angle is 45 degrees (which may be varied over a wide range, from 0° to close to approximately 170° or indeed at an angle to the plane of the microfluidic chip).

Figure 46:
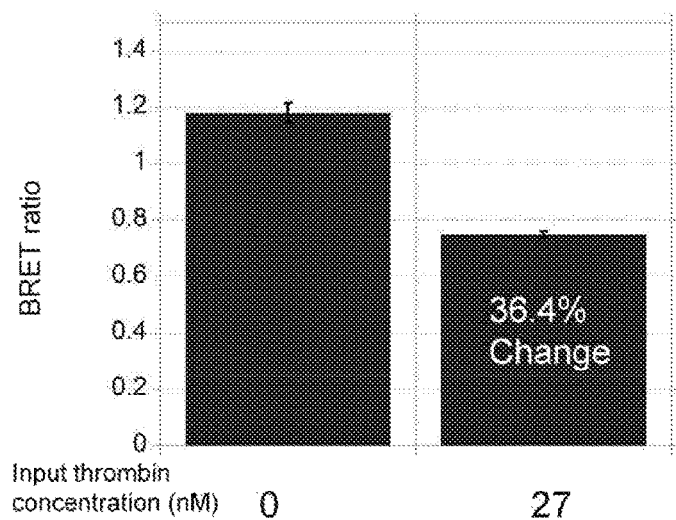

FIG. 46—Comparison of BRET ratio measurements. Error bars reflect the standard deviation (n=3).

Figure 47:
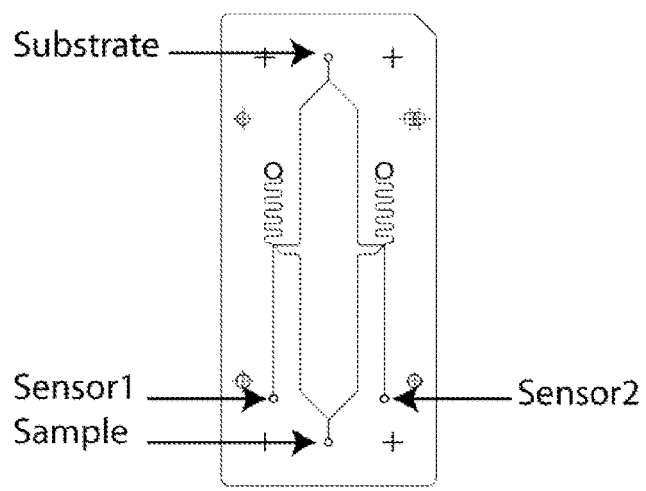

FIG. 47—Microfluidic chip design example for multiplexed detection. The inlet at the top is designated for substrate while the three inlets at the bottom are used for introducing sensor 1, sample and sensor 2.

Figure 48:
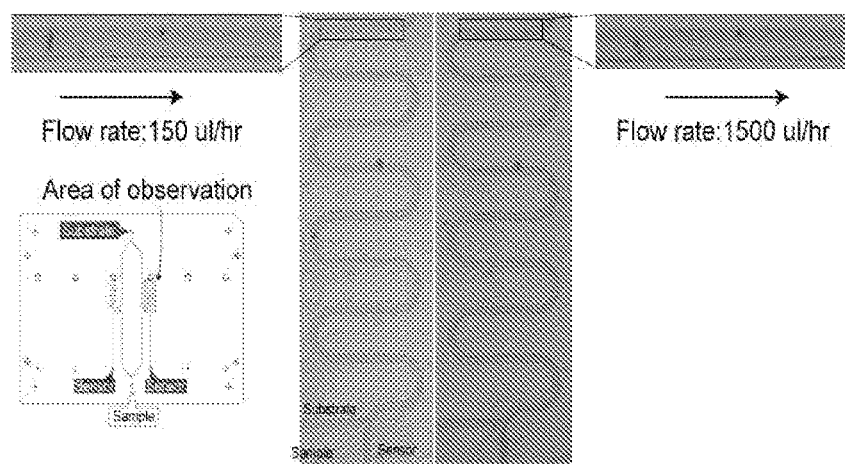

FIG. 48—Microfluidic chip design example for parallel detection. Flow direction is bottom to top. Flow rates were 150 μl/hr and 1500 μl/hr. Red food dye was introduced from the substrate inlet and blue dye was introduced from the sensor inlet. No food coloring was used for the sample inlet.

Figure 49:
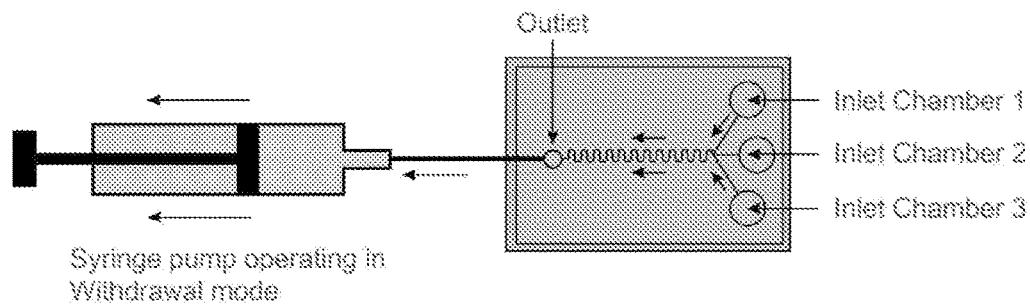

FIG. 49—Three inlet microfluidic device operated by a single suction pump in withdrawal mode. A pump in suction mode creates negative pressure at the device outlet. Sample, sensor and substrate streams are sucked into the common channel (shown as a serpentine arrangement) and are passively mixed. A BRET reaction chamber is situated just before the outlet. The pump used here is a syringe pump, a wide variety of pumping methods could also be used.

Figure 50:
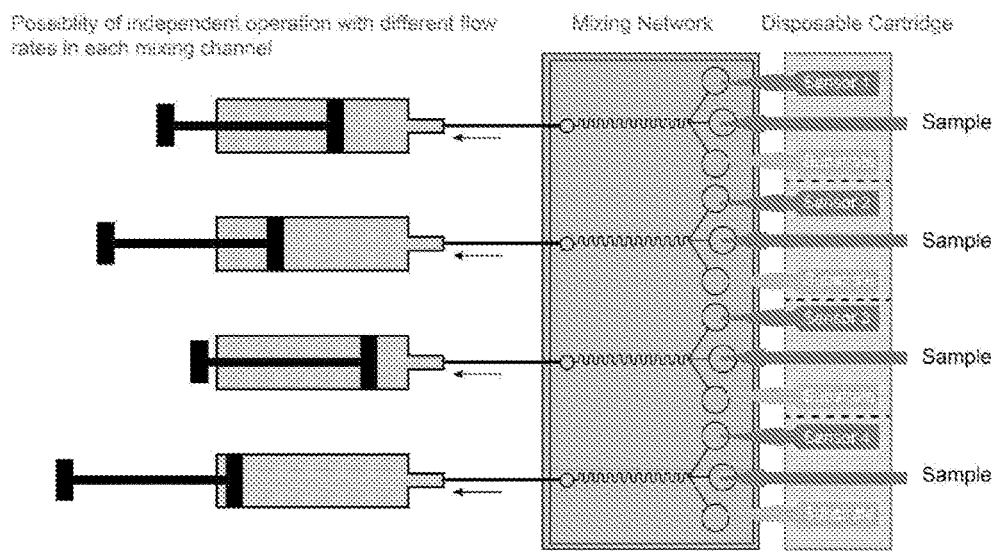

FIG. 50—Architecture for parallel independent operation using syringe pumps working in withdrawal mode. An example in which four sensor channels are operated independently, in parallel, by using four separate syringes. This enables the operation of the sensor channels at different flow rates to meet a range of different requirements.

Figure 51:
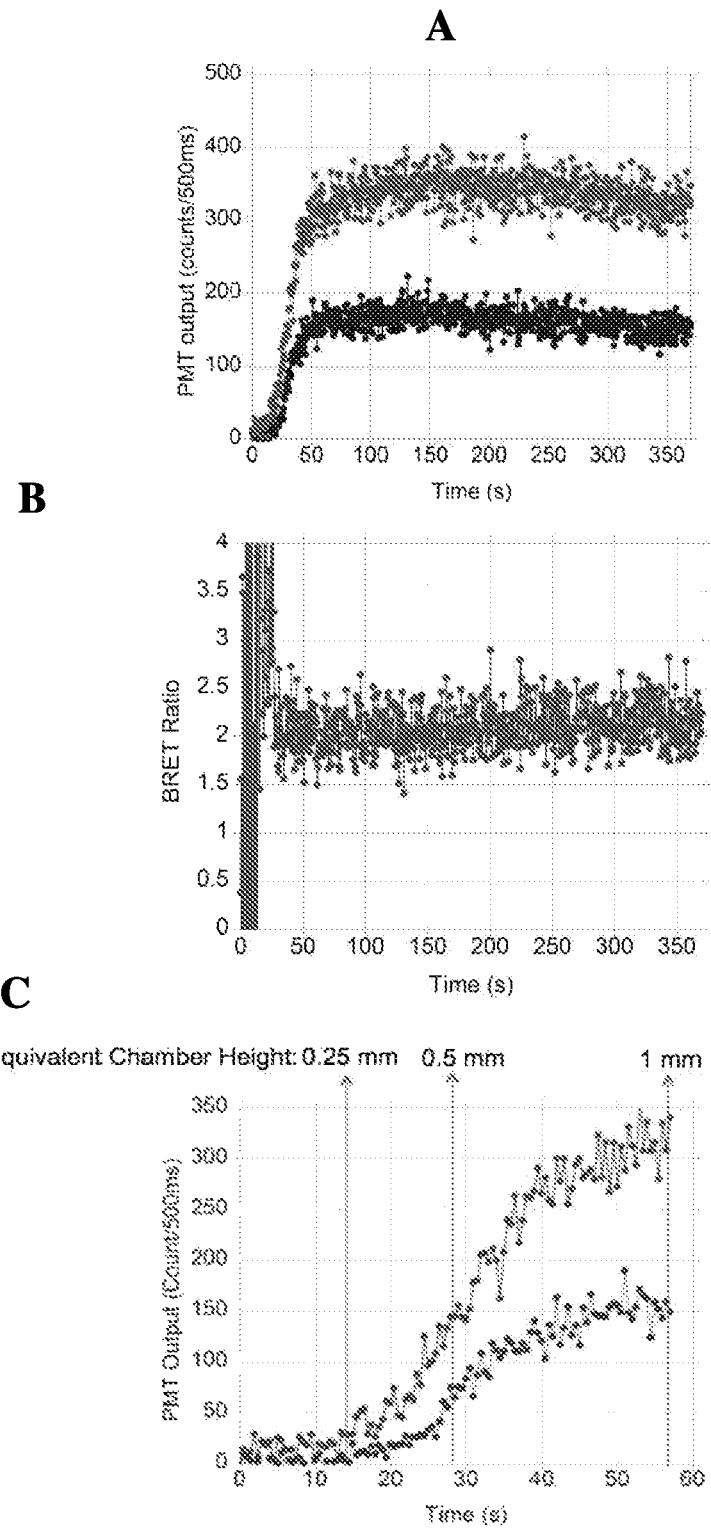

FIG. 51—a. RLuc and GFP signals from on chip thrombin sensor operating in suction mode with multifurcated light guide and optimised dichroic block. Reaction chamber Ø=2 mm, H=1 mm b. BRET$^2$ signal from "a". c. Demonstration of expected signal for chambers of the same diameter and varying heights based on the equivalent residence times.

Figure 52:
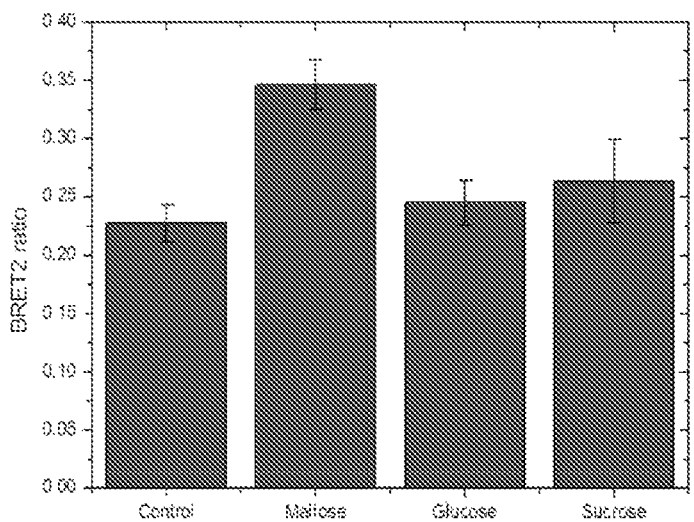

FIG. 52—Specific maltose detection achieved in a microfluidic format. Comparison of the BRET$^2$ responses of a BRET$^2$-MBP sensor to 0.1 mM maltose, glucose and sucrose.

Figure 53:
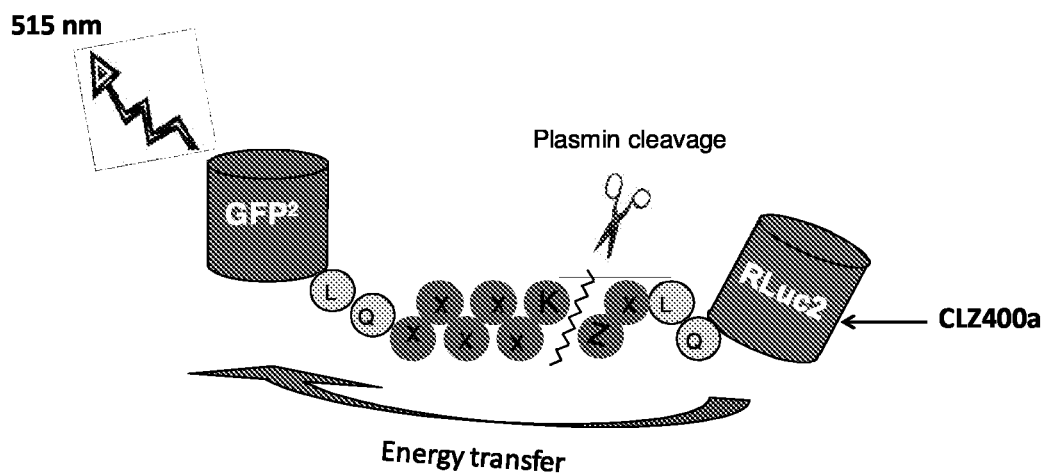

FIG. 53—BRET$^2$ thrombin sensor with GFP$^2$ at the N-terminus and RLuc2 at the C-terminus has been modified to mimic plasmin's κ-casein target sequence: XKZX, where Z=K, Y, V or E.

Figure 54:
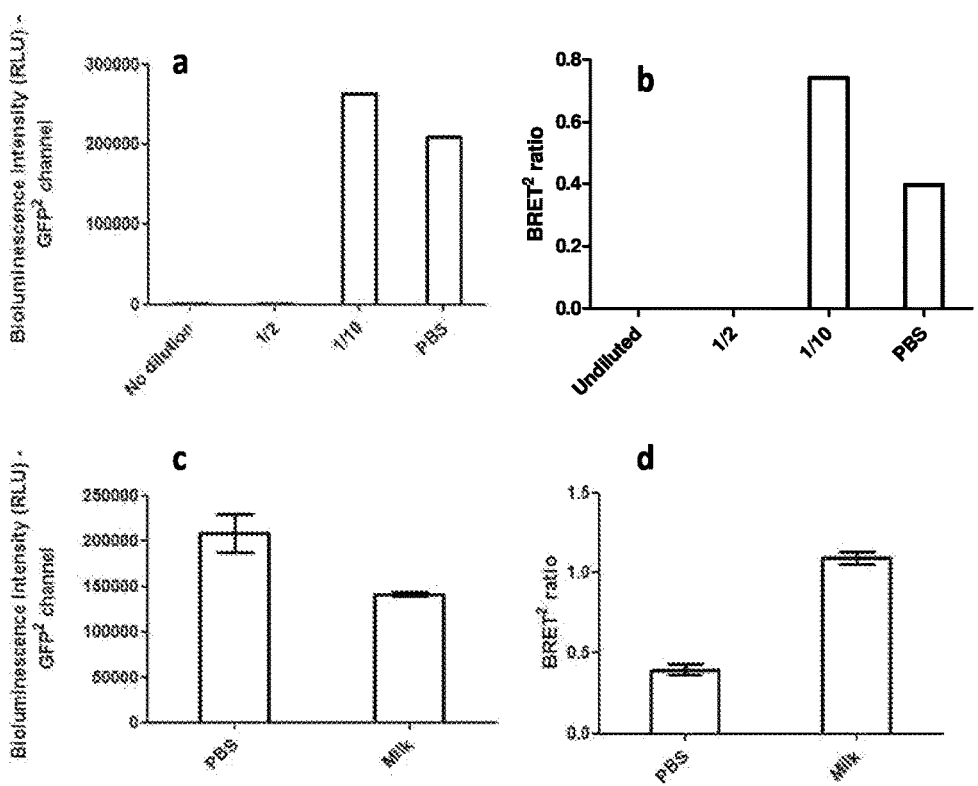
Figure 55:
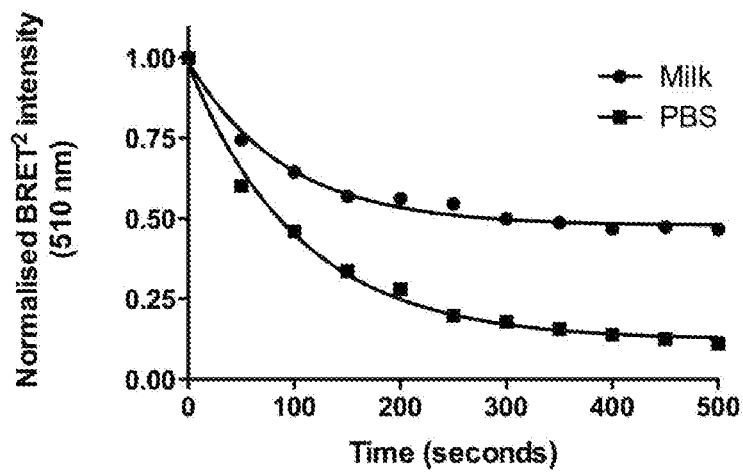
Figure 55:
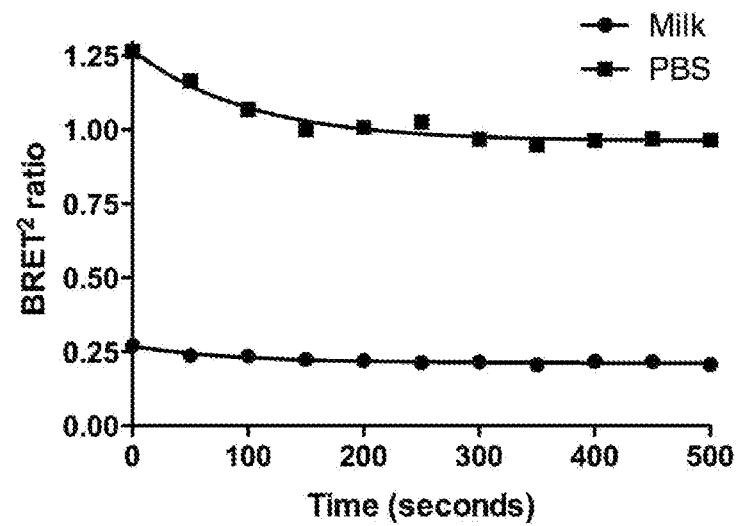

FIG. 54—BRET$^2$ signal intensity and ratio generated in various dilutions of PBS, milk c) and d) or orange juice (a and b) using the GFP$^2$-FL$_1$-RLuc2 sensor in the presence of 5 μM coelenterazine FIG. 55—Time course of a BRET$^2$ signal generated in undiluted whole milk using the GFP$^2$-FL$_1$-RLuc2 sensor in the presence of 5 μM coelenterazine A. a. Intensity. b. BRET$^2$ ratio.

Figure 56:
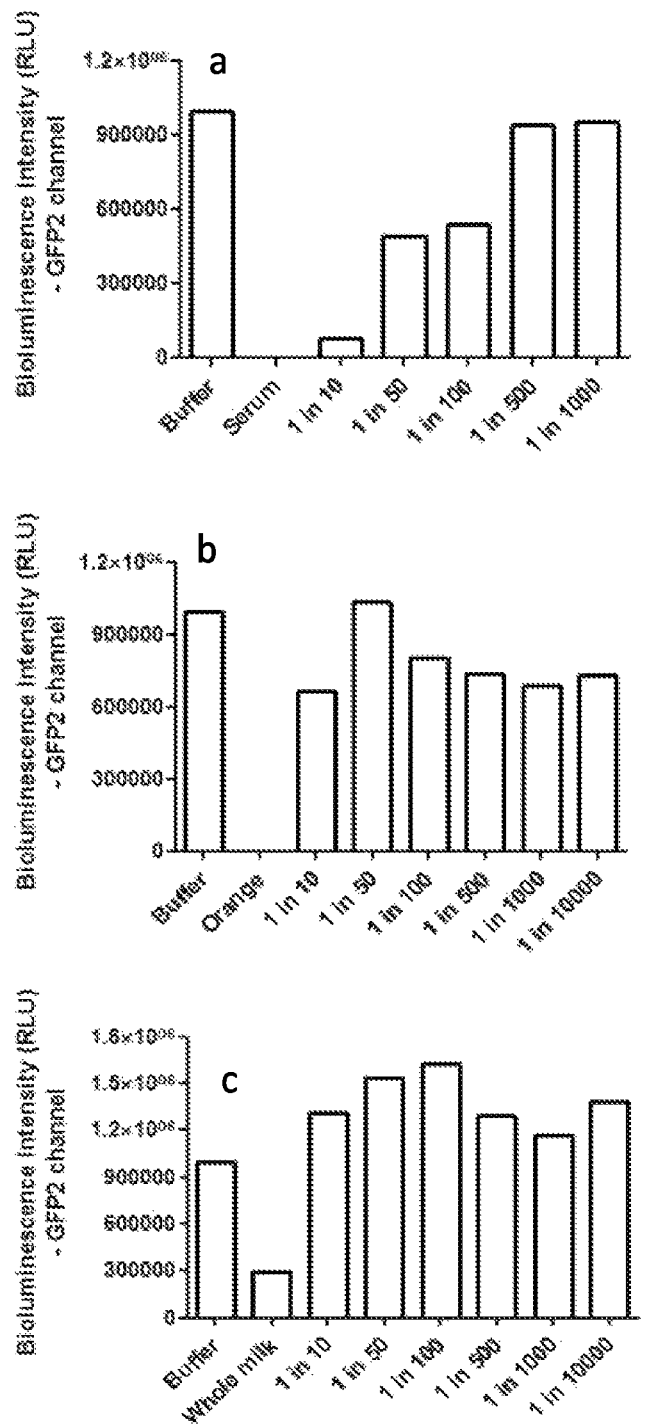

FIG. 56—Bioluminescent intensity (GFP$^2$ channel—515 nm bandpass 30 nm) for GTR2 protein in thrombin cleavage buffer or various dilutions of (a) serum (b) orange or (c) milk.

Figure 57:
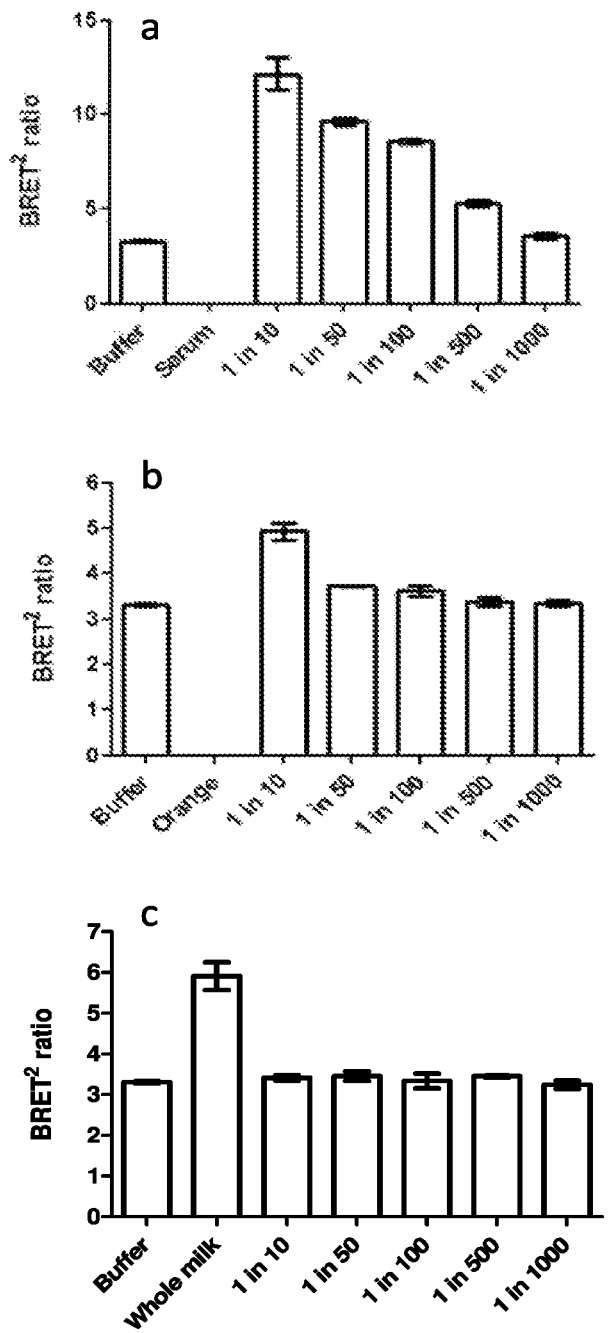

FIG. 57—BRET$^2$ ratio GTR2 protein in thrombin cleavage buffer or various dilutions of (a) serum (b) orange or (c) milk.

Figure 58:
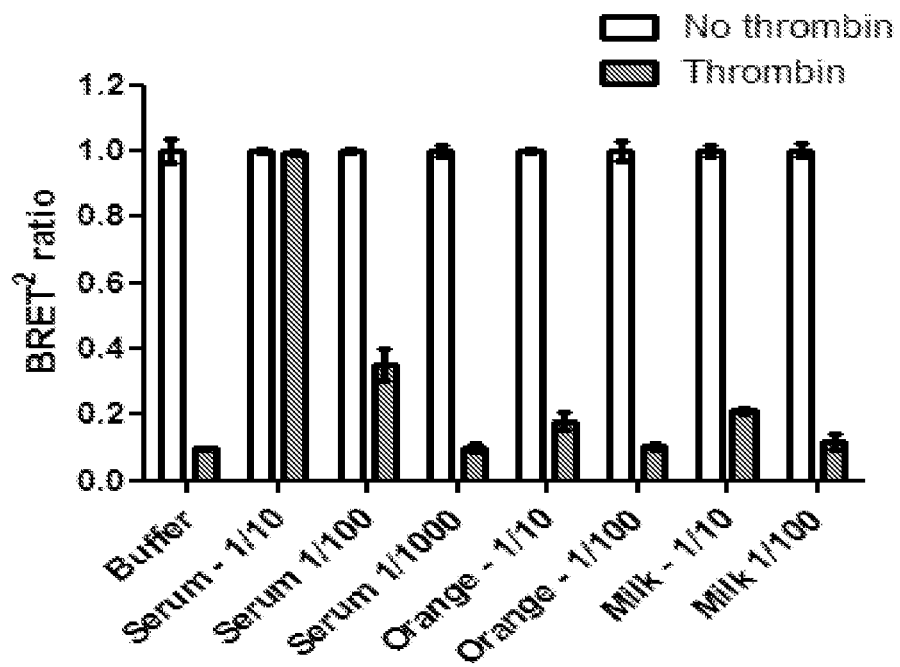

FIG. 58—Detection of thrombin protease activity (2 units) in thrombin cleavage buffer, diluted milk, orange juice or serum using GTR2. Results are presented as normalised BRET$^2$ ratios because the absolute BRET$^2$ ratios vary according to the sample and its dilution. Note that the absence of an effect in the 1/10 dilution of serum is possibly due to the inactivation of added thrombin by residual activated antithrombin III generated by the heparin used in serum preparation.

Figure 59:
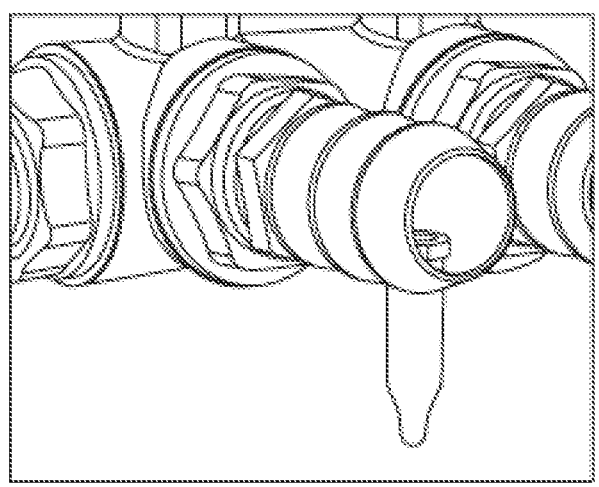

FIG. 59—Specimen holder for gas-liquid partition experiments

Figure 60:
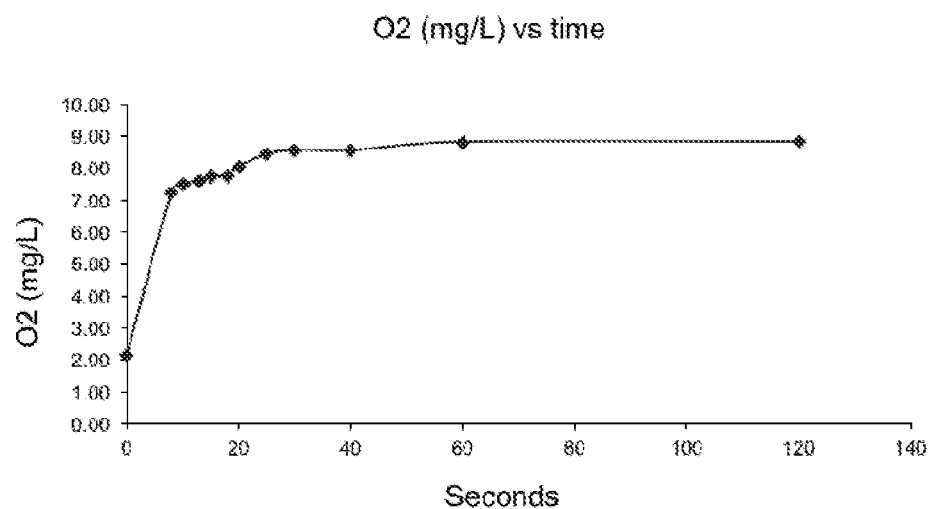

FIG. 60—Timecourse of uptake of oxygen into deoxygenated SASS2400 sample fluid following fan start up at time=0.

Figure 61:
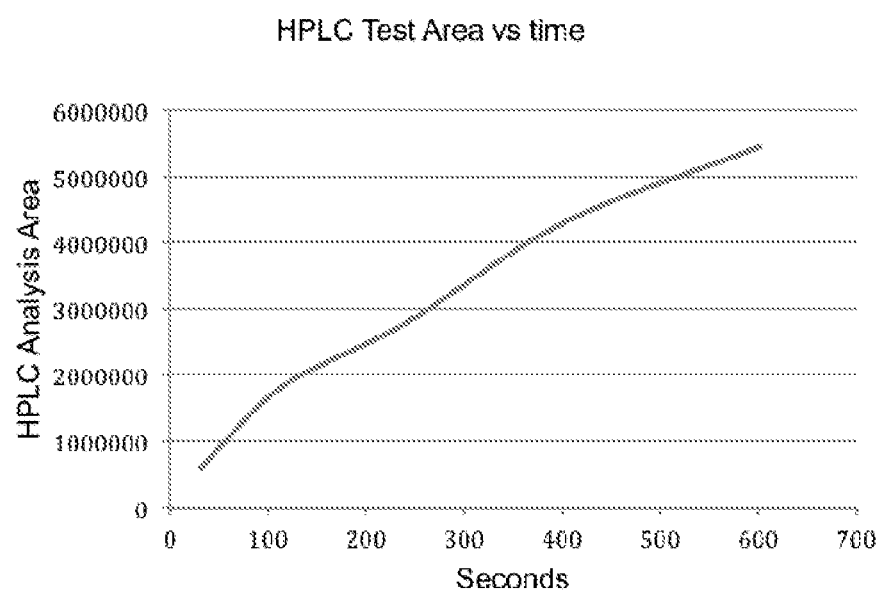

FIG. 61—Timecourse of phenol uptake into SASS2400 sample fluid following fan start up at time=0. Relative phenol concentration indicated using arbitrary units.

Figure 62:
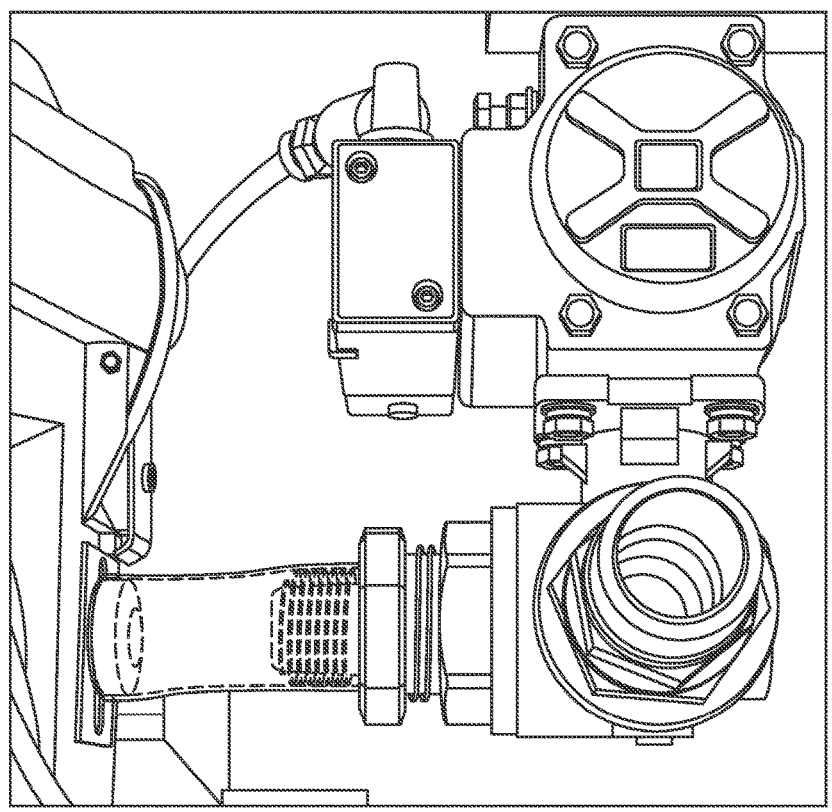

FIG. 62—3-way L port pneumatically operated ball valve. This allows rapid (≤1 s) switching of the volatile headspace into the SASS2400 air inflow during active sampling.

Figure 63:
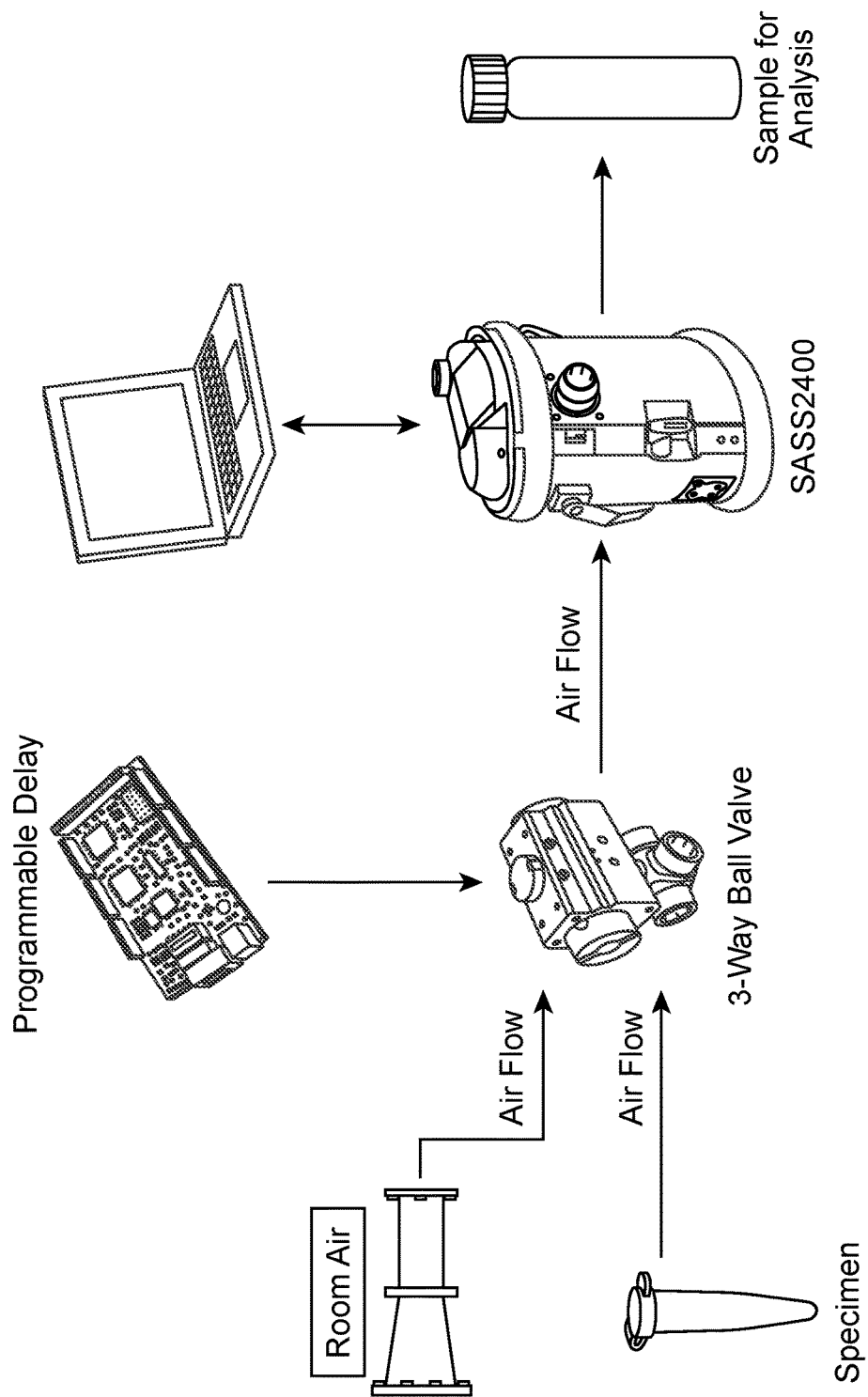
Figure 64:
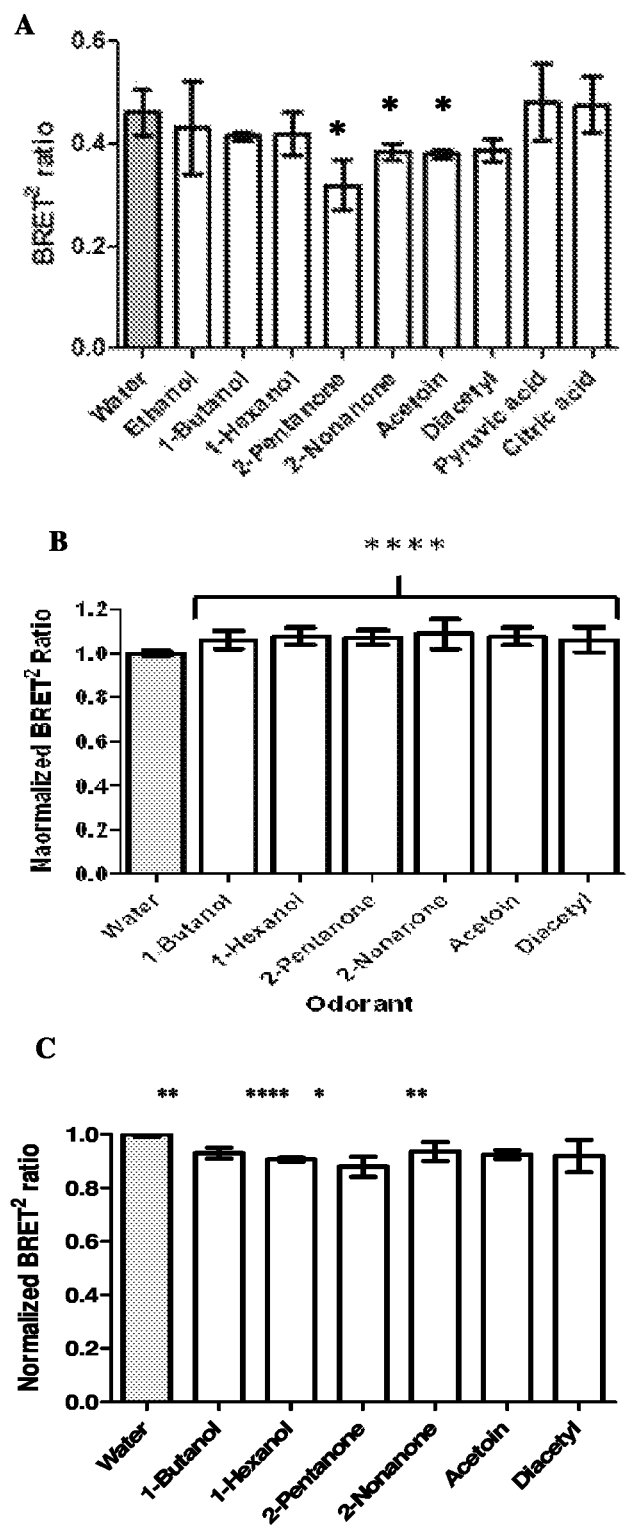

FIG. 63—Schematic showing set up for SASS2400 testing with three way valve for rapid switching of air intake FIG. 64—Selectivity of Str 112 (A), Str114/113 (B) and Str113 (C). BRET2 response of Str112 (mean±SD, n=3), Str114/113 (mean±SD, n=14) and Str113 (mean±SD, n=6) to 1 μM of odorant or water (grey bar). ** P<0.0001,  P<0.001 and * P<0.05.

Figure 65:
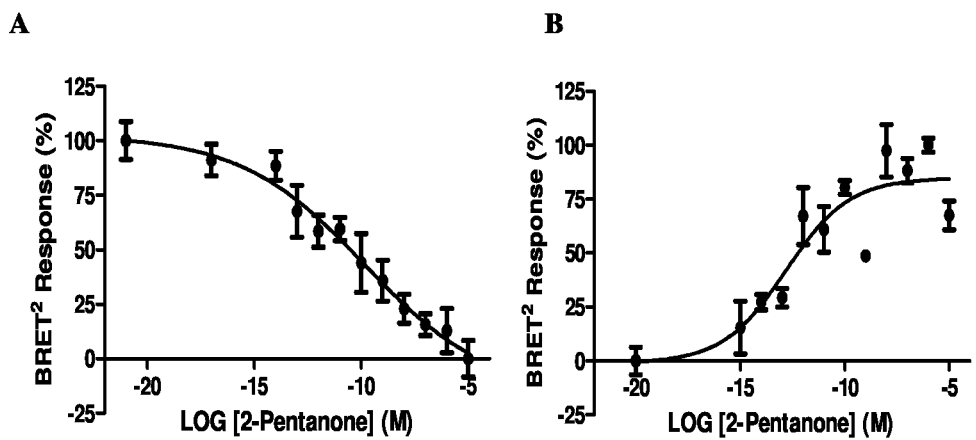

FIG. 65—BRET responses of BRET tagged SGSR-112 (A) and SGSR-114/113 (B) nematode odorant receptors to 2-pentanone.

Figure 66:
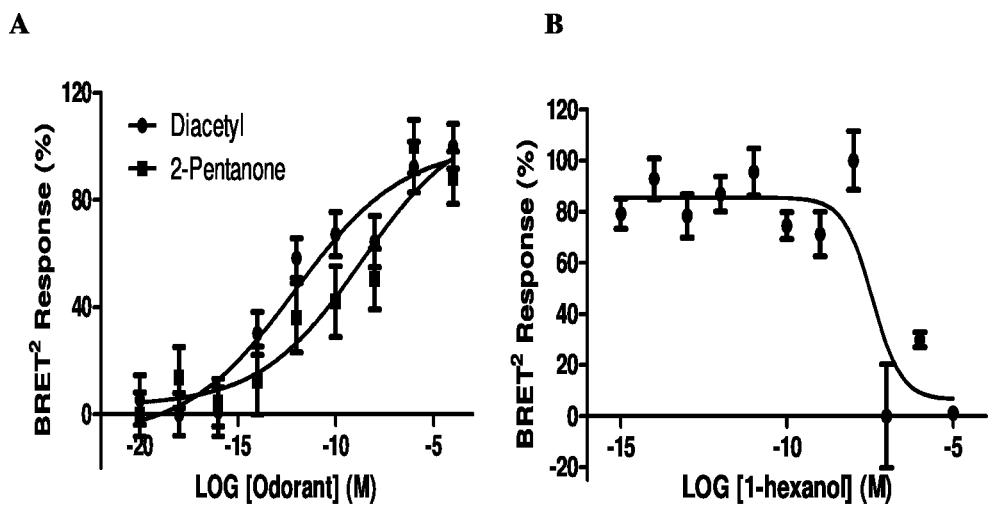

FIG. 66—BRET response of BRET tagged (A) Str114/113 nematode odorant receptor to diacetyl and 2-pentanone and (B) Str-113 nematode odorant receptor to 1-hexanol.

Figure 67:
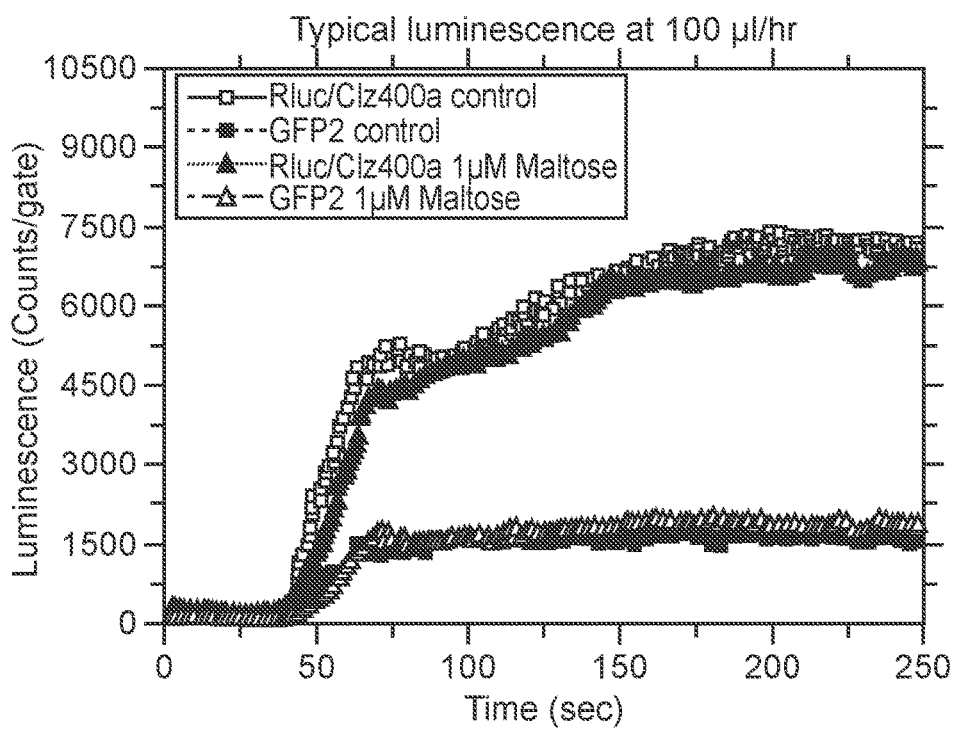
Figure 67:
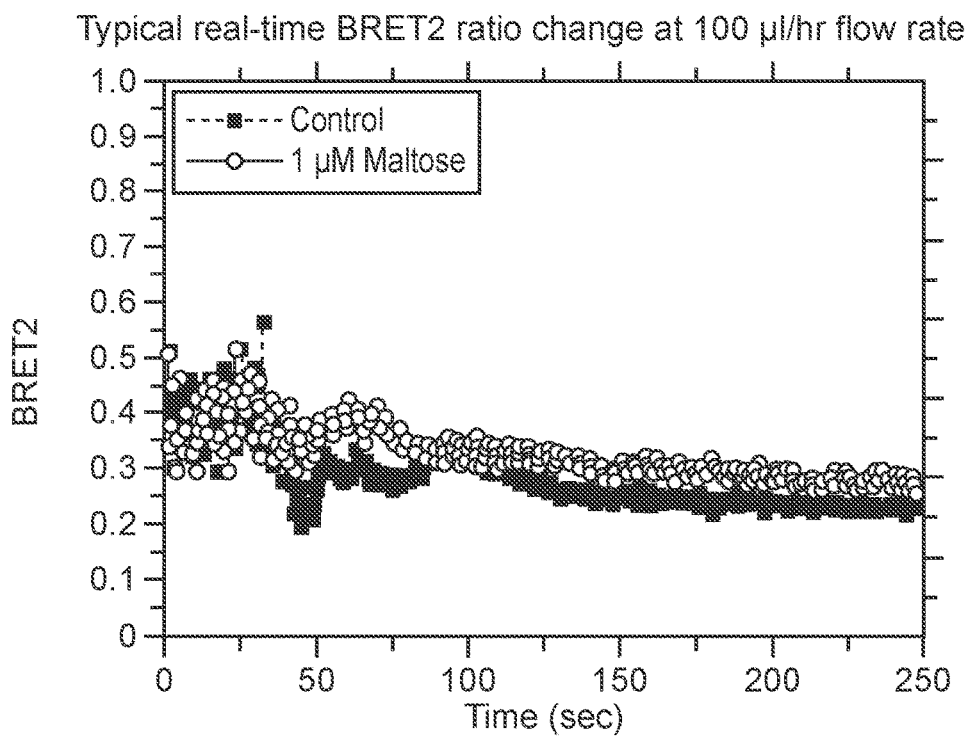
Figure 67:
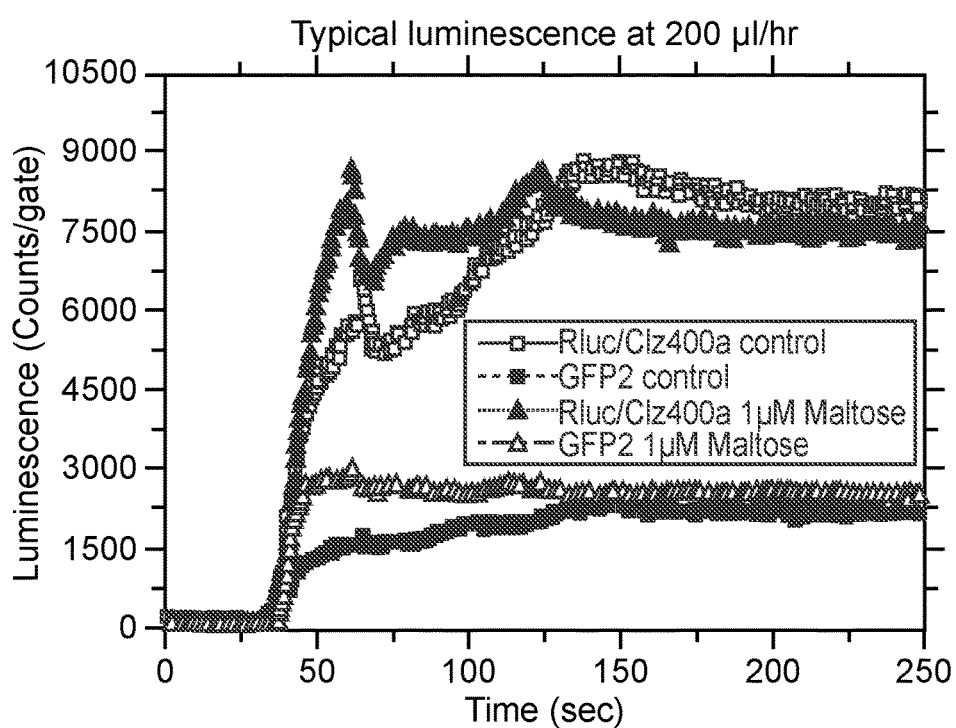
Figure 67:
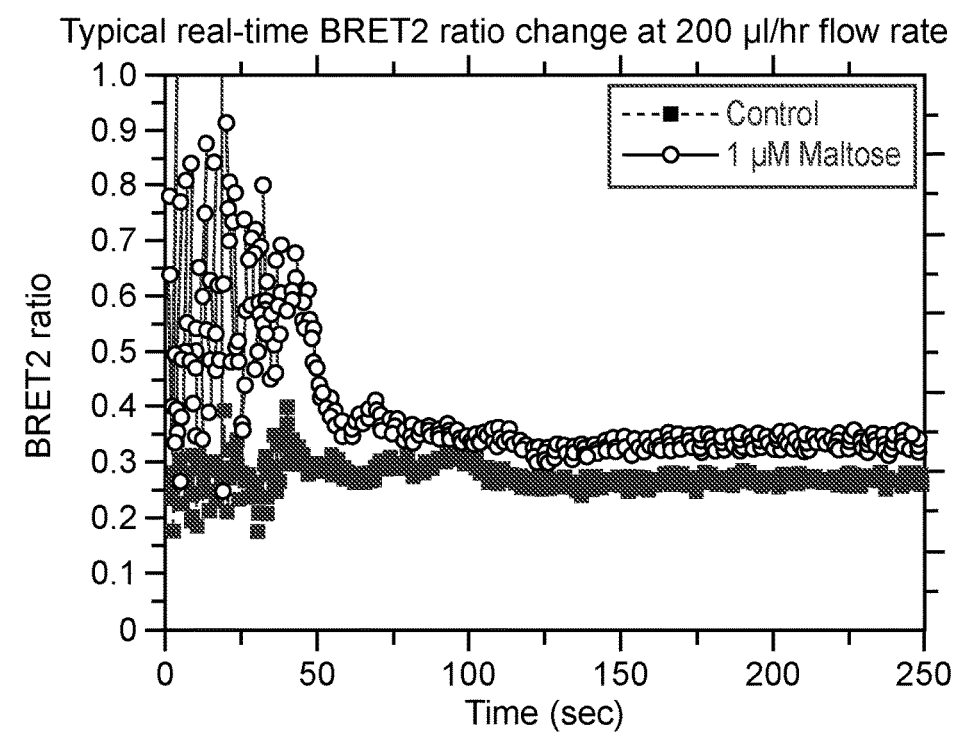
Figure 67:
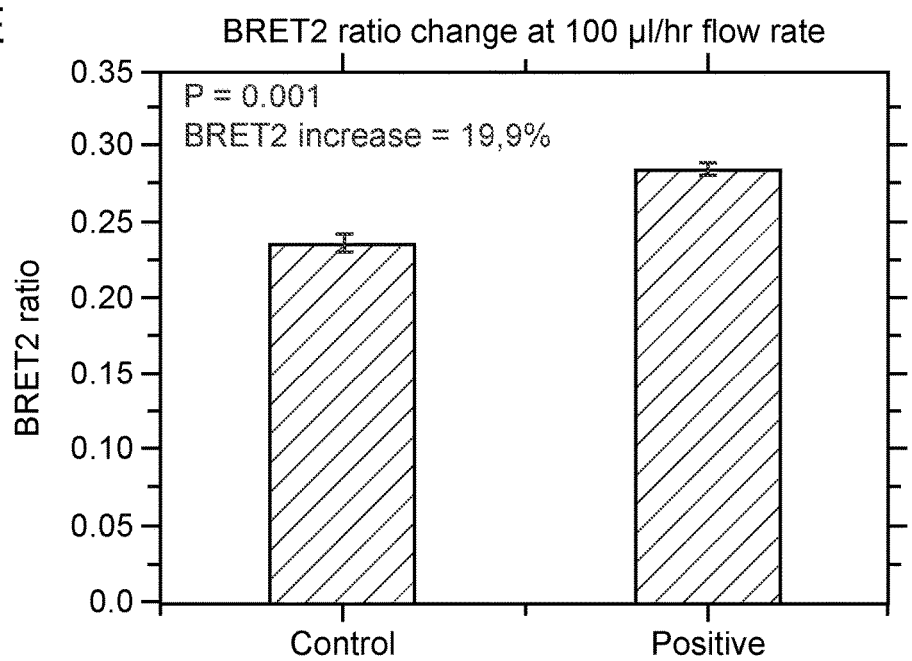
Figure 67:
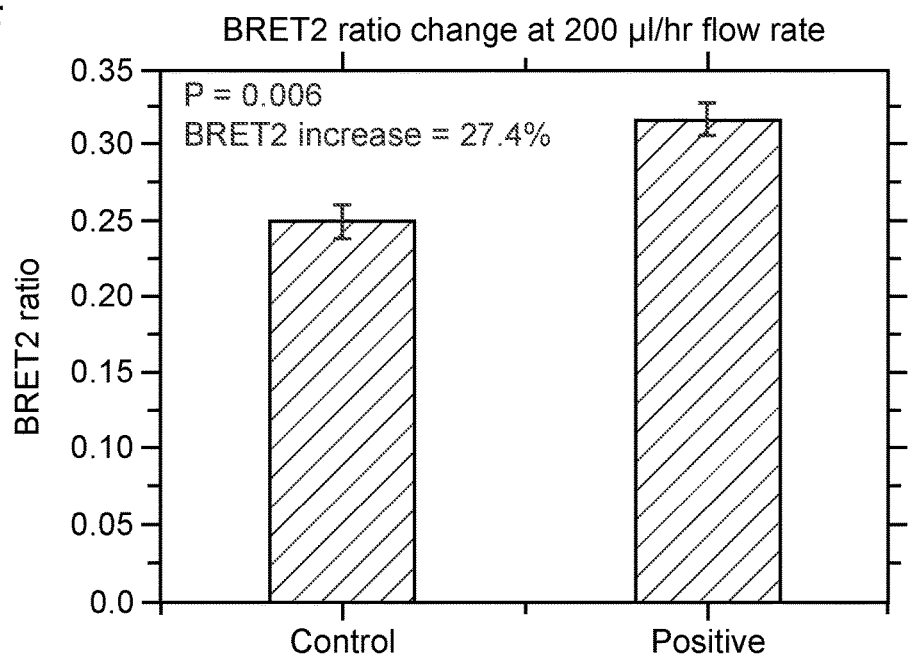

FIG. 67—Real time, continuous, on-chip detection of 1 μM maltose using GMR BRET$^2$-based sensor. A) Channel luminance changing with time at 100 μL/hour input rate B) BRET$^2$ ratio changing with time at 100 μL/hour input. C) Channel luminance changing with time at 200 μL/hour input rate D) BRET$^2$ ratio changing with time at 200 μL/hour input rate. E) Comparison of BRET$^2$ ratio between water control and 1 μM maltose averaged from 200-250 seconds at 100 μL/hour. F) Comparison of BRET$^2$ ratio between water control and 1 μM maltose averaged from 200-250 seconds at 200 μL/hour.

KEY TO SEQUENCE LISTING

SEQ ID NO:1—Nucleotide sequence encoding OGOR2 fusion protein.
SEQ ID NO:2—OGOR2 fusion protein.
SEQ ID NO:3—Nucleotide sequence encoding GFP$^2$-MBP-RLuc2 fusion protein.

SEQ ID NO:4—GFP$^2$-MBP-RLuc2 fusion protein.
SEQ ID NO:5—Nucleotide sequence encoding GFP$^2$-MBP-RLuc2 W140A fusion protein.
SEQ ID NO:6—GFP$^2$-MBP-RLuc2 W140A fusion protein.
SEQ ID NOs:7 to 12—Oligonucleotide primers.
SEQ ID NO:13—GFP$^2$-str-112 SGSR-RLuc fusion protein.
SEQ ID NO:14—GFP$^2$-str-113 SGSR-RLuc fusion protein.
SEQ ID NO:15—GFP$^2$-str-114 SGSR-RLuc fusion protein.
SEQ ID NO:16—GFP$^2$-str-115 SGSR-RLuc fusion protein.
SEQ ID NO:17—GFP$^2$-str-116 SGSR-RLuc fusion protein.
SEQ ID NO:18—GFP$^2$-str-114/113 SGSR-RLuc fusion protein.
SEQ ID NO:19—Nucleotide sequence encoding GFP$^2$-str-112 SGSR-RLuc fusion protein.
SEQ ID NO:20—Nucleotide sequence encoding GFP$^2$-str-113 SGSR-RLuc fusion protein.
SEQ ID NO:21—Nucleotide sequence encoding GFP$^2$-str-114 SGSR-RLuc fusion protein.
SEQ ID NO:22—Nucleotide sequence encoding GFP$^2$-str-115 SGSR-RLuc fusion protein.
SEQ ID NO:23—Nucleotide sequence encoding GFP$^2$-str-116 SGSR-RLuc fusion protein.
SEQ ID NO:24—Nucleotide sequence encoding GFP2-str-114/113 SGSR-RLuc fusion protein.
SEQ ID NO:25—GFP$^2$-OGOR-RLuc2 fusion protein.
SEQ ID NO:26—GFP$^2$-OGOR mutant-RLuc2 fusion protein.
SEQ ID NO:27—GFP$^2$-str-112 SGSR-RLuc2 fusion protein.
SEQ ID NO:28—GFP$^2$-str-113 SGSR-RLuc2 fusion protein.
SEQ ID NO:29—GFP$^2$-str-114 SGSR-RLuc2 fusion protein.
SEQ ID NO:30—GFP$^2$-str-114/113 SGSR-RLuc2 fusion protein.
SEQ ID NO:31—GFP$^2$-str-115 SGSR-RLuc2 fusion protein.
SEQ ID NO:32—GFP$^2$-str-116 SGSR-RLuc2 fusion protein.
SEQ ID NO:33—Nucleotide sequence encoding GFP$^2$-OGOR-RLuc2 fusion protein.
SEQ ID NO:34—Nucleotide sequence encoding GFP$^2$-OGOR mutant-RLuc2 fusion protein.
SEQ ID NO:35—Nucleotide sequence encoding GFP$^2$-str-112 SGSR-RLuc2 fusion protein.
SEQ ID NO:36—Nucleotide sequence encoding GFP$^2$-str-113 SGSR-RLuc2 fusion protein.
SEQ ID NO:37—Nucleotide sequence encoding GFP$^2$-str-114 SGSR-RLuc2 fusion protein.
SEQ ID NO:38—Nucleotide sequence encoding GFP$^2$-str-114/113 SGSR-RLuc2 fusion protein.
SEQ ID NO:39—Nucleotide sequence encoding GFP$^2$-str-115 SGSR-RLuc2 fusion protein.
SEQ ID NO:40—Nucleotide sequence encoding GFP$^2$-str-116 SGSR-RLuc2 fusion protein.
SEQ ID NO:41—*C. elegans* str-112.
SEQ ID NO:42—*C. elegans* str-113.
SEQ ID NO:43—*C. elegans* str-114/113 chimeric protein.
SEQ ID NO:44—Open reading frame encoding *C. elegans* str-112.
SEQ ID NO:45—Open reading frame encoding *C. elegans* str-113.
SEQ ID NO:46—Open reading frame encoding *C. elegans* str-114/113 chimeric protein.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Unless the context suggests otherwise, the mention of a term in singular such as sensor molecule and substrate clearly means the plural as well. For instance, logically many individual sensor molecules will be flowed through the device rather than a single molecule.

As used herein, the term about, unless stated to the contrary, refers to +/−20%, more preferably +/−10%, even more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Detection/Classification/Screening System

The present invention relates to a method of detecting an analyte in a sample, the method comprising
i) flowing through a microfluidic device comprising one or more microchannels,
  a) the sample,
  b) a sensor molecule comprising a domain that binds the analyte, a chemiluminescent donor domain and an acceptor domain, wherein the separation and relative orientation of the chemiluminescent donor domain and the acceptor domain, in the presence and/or the absence of analyte, is within ±50% of the Forster distance,
  c) a substrate of the chemiluminescent donor,
ii) mixing the sensor molecule, sample and substrate in the device, and iii) detecting modification of the substrate by the chemiluminescent donor using an electro-optical sensing device, wherein the spatial location and/or dipole orientation of the chemiluminescent donor domain relative to the acceptor domain is altered when the analyte binds the sensor molecule.

The present invention also relates to a microfluidic system for performing the method of the invention, the system comprising i) at least one reservoir suitable for containing (or comprising) a sensor molecule comprising a domain that binds the analyte, a chemiluminescent donor domain and an acceptor domain, wherein the separation and relative orientation of the chemiluminescent donor domain and the acceptor domain, in the presence and/or the absence of analyte, is within ±50% of the Forster distance, ii) a microfluidic device comprising one or more microchannels, iii) means for mixing the sensor molecule, the sample and a substrate of the chemiluminescent donor domain in the device, iv) a reaction chamber for detecting binding of the analyte to the sensor molecule, and v) an electro-optical sensing device, wherein the spatial location and/or dipole orientation of the chemiluminescent donor domain relative to the acceptor domain is altered when the analyte binds the sensor molecule.

As the skilled person would appreciate, the methods and systems of the invention can be used to detect the presence or absence of an analyte in a sample, and if present may also be used to determine the concentration of the analyte.

The present invention has numerous advantages over the prior art, particularly when compared to methods and systems where the sensor molecule is fixed to the device. First, there is no need to regenerate (re-set) the device. Second, there is less drift in signal in the methods and systems of the invention. Third, costs are reduced because the device can be re-used many more times than when the sensor molecule is fixed. Fourth, the invention avoids the problem of low signal with fixed configurations due to surface area and density of sensor molecule. Fifth, the current technique is a volume-based detection technique, not a surface-based technique such as surface plasmon resonance in which the sensor molecules need to be attached to the surface. The sensor-analyte reaction happens much more rapidly, thereby reducing analysis time even without active control.

Furthermore, BRET has several advantages over fluorescence based technologies because it does not require excitation of the donor with an external light source. BRET does not suffer from autofluorescence, light scattering, photobleaching and/or photoisomerization of the donor moiety or photodamage to cells. The absence of an external light source in BRET assays results in a very low background and consequently increased detection sensitivity. For example, BRET is 50 times more sensitive than FRET for monitoring thrombin-catalysed proteolytic cleavage (Dacres et al., 2009b).

With regard to the use of a method of the invention for classifying a sample, a sensor molecule, more typically a set of sensor molecules, can be used to detect patterns of substances (analytes) that are representative for a specific sub-population. As an example, the method can be used to classify different types, age, quality etc of beer, wine, cheese or other consumables. The method can also be used broadly with samples of foods, beverages, perfumes, fragrances and the like to classify or quantify their organoleptic properties such as sweetness, bitterness, umami character, "heat" for example in relation to capsaicin or hydroxy-α-sanshool, "coolness" for example in relation to menthol and/or any olfactory notes for which suitable sensor molecules can be isolated or engineered. The method can also be used to classify a wide range of other samples based on chemical signatures, for example the health, nutritional or disease status of humans, animals or plants based on samples of headspace, breath, sweat, urine, other biological fluids. Another use of the method is to classify samples based on their toxicity or noxiousness, such as the presence of explosives or explosive-associated components, toxic industrial chemicals, chemical or biological warfare agents or pathogenic microbes. The method can also be used for monitoring of industrial processes including conformity to specifications or the presence, absence of levels of any group or groups of chemicals. The method can also be used to classify environmental samples either in real time or in batch mode, for example to determine air quality, presence or level of unpleasant odours or toxic chemicals or, similarly, the quality of natural or reticulated water systems, sewerage systems or ground water or to classify fluids in contact with soils or rocks.

Classification of samples is usually performed by generating a discriminating function or classifier based on the pattern of electro-optical responses to a training set of samples representing or encompassing all the classes of samples that one wishes to discriminate. This may be achieved routinely using multivariate statistical approaches, such as principal components analysis, linear discriminant analysis, stepwise discrimination analysis and the like. Alternately, a wide variety of machine learning approaches may be used, one example being support vector machines. A similar approach is to use Bayesian networks or train an artificial neural network to make such discriminations among samples of the test set. One viable approach is then to capture a pattern of electro-optical responses from the test or unknown sample(s) process them in real time and compare them with saved patterns, obtained with the training set of samples, assigning them to known classes according to the best matches or assigning them to a novel class or classes if a similar pattern has not previously been observed. For classification methods it is not essential that the actual analyte(s) be known, simply that a sensor molecule (or group of sensor molecules) reproducibly produce a different pattern of signals with different classes of sample, which enables the user to classify the sample(s) being analysed.

With regard to sensitivity, concentrations of analyte as low as micromolar, nanomolar, femtomolar, attomolar or even lower can be detected. In an embodiment, the method of the invention is at least 5 fold, or at least 10 fold, or a 5 fold to 1,000 fold, or 5 fold to 100 fold, or 5 fold to 50 fold, or 5 fold to 20 fold, or and in some circumstances up to 100 to 1,000 fold more sensitive than if the method was performed on a microwell plate with the same concentration of reagents.

The present invention is particularly useful for detecting an analyte in real time. As used herein, the term "real time" means that a certain state is substantially simultaneously displayed in another form (e.g., as an image on a display or a graph with processed data). In such a case, the "real time" lags behind an actual event by the time required for data processing. Such a time lag is included in the scope of "real time" if it is substantially negligible. Such a time lag may be typically within 10 seconds, and preferably within 1 second, without limitation. In a preferred embodiment, the method of the invention is performed within about 1s to about 100 s.

As used herein, the "Förster distance" is the distance between the donor and acceptor at which the energy transfer is (on average) 50% efficient. Förster distance (Ro) is dependent on a number of factors, including the quantum yield of the donor in the absence of acceptor, the refractive index of the solution, the dipole angular orientation of each domain, and the spectral overlap integral of the donor and acceptor.

As used herein, "quantum yield" refers to a measure of final emission of original energy donation.

As used herein, "Stokes shift" is the difference in wavelength between positions of the band maxima of the absorption and emission spectra of the same electronic transition.

In an embodiment, the invention is used to analyse, on the device, an increasing (for example, through synthesis of the anaylyte on the chip) or decreasing (for example, degradation or modification of the anaylyte on the chip) concentration of the analyte. Typically, this will require detecting modification of the substrate at two different points on the device, for instance in a first and second reaction chamber through which the analyte flows. Thus, in an embodiment, the analyte releasing from the sensor molecule results in a change in BRET ratio which is ≥15%, ≥20%, ≥30%, ≥35%, about 15% to about 50%, or about 15% to about 40%, of the maximum observed BRET ratio.

In a further embodiment, the sensor molecule may enter the input microchannel bound to a ligand, and the analyte to be detected (for example catalytic enzyme) cleaves and/or modifies the ligand such that the modified ligand releases from (is no longer bound) to the sensor molecule.

The BRET sensing in the methods and systems of the invention is realized in a microfluidic device. In one configuration, the system comprises several modules which include (1) sample delivery, (2) reagent storage and handling, (3) microfluidic chip and loading system, (4) optionally temperature control, (5) electro-optical system for light collection, (6) electro-optical detection system, (7) data acquisition and processing, and (8) software and embedded control system (FIG. 13).

Sample Delivery

The "sample" can be any substance or composition known or suspected of comprising the analyte to be detected detected or from which it is expected or required that a particular substance, set of substances or composition is absent. Examples of samples include air, liquid, and biological material. The sample may be obtained directly from the environment or source, or may be at least partially purified by a suitable procedure before a method of the invention is performed.

The sample can be in any form that is capable of being flowed through a microfluidic device. Examples include, but are not necessarily limited to, a liquid, gas, emulsion or suspension. In an embodiment, the sample is a liquid, which has been pre-equilibrated with a gas. Examples of suspensions include, but are not necessarily limited to, water-in-oil, oil-in-water and gas in liquid.

In a more specific embodiment, ambient air or other gases from a location of interest or the headspace from any object or sample of interest is brought into close contact with water or an aqueous solution so that rapid mass transfer of analytes may occur from the gas phase to the liquid phase based on the gaseous concentration, solubility and partition coefficients of the analytes and the composition of the liquid phase. Any method that generates a gas-liquid interface with a large area, relative to the volume of the liquid, is potentially suitable. Example methods include wetted wall cyclones, misting or bubbling systems. The SASS2400 wetted wall cyclone is a specific example of a suitable device for accelerating the partition of volatiles from air into an aqueous phase. Preferably, the method allows a large volume of air to come into contact with a smaller volume of liquid, thereby permitting large volumes of the gas phase to be sampled and providing a concentration step. Based on the published specifications of the SASS2400 it is possible to contact 1 volume of water or aqueous solution with 40,000 volumes of gas at standard temperature and pressure per minute. Depending on the dimensions and operational characteristics of equipment used, much lower or higher gas-liquid ratios may be sampled.

In one embodiment, the suspension is, or comprises, a cell-free extract. In an alternate embodiment, the suspension comprises cells.

The sample (and the sensor molecule and substrate) can be flowed through the microfluidic device by any suitable means such as, but are not necessarily limited to, one or more of pumping, vacuum, hydraulics, suction, electrokinesis, chemiosmosis, capillary force, acoustics, electromagnetics, piezoelectrics and so on. Pumping mechanisms can be realised in compact, miniaturised and micron-size pumps for the applications. There may be a pre-conditioning device to filter out debris such as particles, organic droplets and so on from the sample, and/or a condition monitoring device which measures some basic parameters of the samples such as temperature, humidity, flow rate and volume of samples.

Reagent Storage and Handling

A disposable and retractable liquid storage system for multiple reagents (BRET reagent, cleaning DI water, substrate etc.) storage can be used. The device can be pre-loaded in the laboratory and be inserted into the sensing device during operation.

Microfluidic Device and Loading System

Microfluidic devices (also referred to in the art as a chip or "lab-on-a-chip") perform chemical or biochemical reactions or analyses by manipulating fluid reagents in chambers and passages which are generally sized in cross-section from approximately 10 to 50 μm (micrometers) up to approximately 100 to 1000 μm, and which are formed on or in a usually flat substrate having linear dimensions from approximately 1 mm to approximately 20 cm. A microfluidic device may manipulate fluid reactants as they flow through the passages and chambers of the device, either as continuous flows from input reservoirs through the device to outlet ports, or as semi-continuous flows of fluid aliquots substantially filling the passages and chambers of the device during operation. Alternatively, microfluidic devices may manipulate fluid reagents as separate and discrete micro-droplets that are characterized by having lengths that are approximately an order of magnitude or more smaller than the dimensions of the device.

The microfluidic device may maintain connection with all sample and reagent delivery outlet once it is inserted into a chip loading system. This loading system can form part of the temperature control and optical components. Single to multiple reactors can be integrated into a chip (FIG. 14). Three reagent (sample, sensor molecule and substrate) flows can be pumped into the chip and mixed in the mixing region. In an alternate configuration, there are two input microchannels, one for the substrate and the other for a pre-mixture of the sensor molecule and sample. In a further configuration, there are two input microchannels, one for the sensor molecule and the other for a pre-mixture of the substrate and sample.

The mixed reagents will undergo BRET reactions and the products can be continuously pumped through the detection chamber before being collected from the waste outlets (FIG. 15).

As used herein, the term "mixing" or variations thereof mean that the analyte(s), sensor molecule and substrate come into contact through any kind of means whether it be diffusion (for example resulting from linear (laminar) flow) and/or through some sort of active mixing means. Thus, in one embodiment the "means for mixing" can be passive diffusion in a linear (laminar) flow. In this embodiment, although complete mixing is not achieved, the present inventors have found that a sufficient amount of mixing occurs for the methods of the invention to function properly. In an embodiment, the diffusion mixing results in at least 20% of the microchannel comprising the sample, sensor molecule and substrate having a homogeneous mixture of these components.

The angle at least two microchannels converge to form the common microchannel can vary from 0° to close to approximately 170° or indeed at an angle to the plane of the microfluidic chip (device).

As used herein, the term "common microchannel" or variations thereof refers to a microchannel, or section thereof, comprising the sample, sensor molecule and the substrate.

As used herein, the term "input microchannel" or variations thereof refers to the microchannel through which a particular reagent such as the sample, sensor molecule or the substrate, or combination of reagents, enters the microfluidic device.

In at least some embodiments, due to the existence of a laminar flow region, a mixing means is preferably implemented in the mixing region for enhancing the contact of the reactants. The mixing means may include passive mixing (FIG. 8 and FIG. 44) and/or active mixing such as with an acoustic mixer (for example as described in WO 2006/105616). Other mixing techniques can also be implemented for such a purpose such as that described in WO 2003/015923.

As used herein, the term "mixing the sensor molecule, sample and substrate in the device" and variations thereof encompasses mixing the sensor molecule, sample and substrate in a reservoir of the device, mixing the sensor molecule, sample and substrate in tubes which flow into the microchannels of the device, mixing the sensor molecule, sample and substrate in the microchannels of the device or mixing the sensor molecule, sample and substrate in a reaction chamber, or a combination or two or more thereof. In a preferred embodiment, the sensor molecule, sample and substrate are mixed in a microchannel. Preferably, if the sensor molecule and sample are not mixed in the microchannels they are mixed shortly before (for example 10 seconds, more preferably 1 second, or less) before entering the microchannels.

In an embodiment, the mixing step results in the sensor molecule, substrate and analyte forming a mixture which is at least 20%, at least 30%, at least 40%, at least 50%, at least 60%, at least 70%, at least 80%, at least 90%, or at least 95%, homogeneous. As indicated above, active mixing will result in greater levels of homogeneity for any given flow rate and channel architecture, but this is not necessarily required to perform the invention.

The methods of the invention can be used to simultaneously or sequentially detect two or more different analytes using the same microfluidic device, for example using a device as shown in FIGS. 14b and 14c. In an embodiment, different sensor molecules are flowed into the device using different microchannels. For convenience, if the sample to be analysed is the same for each of the analytes there may be a single flow of sample into the device which then branches and joins with other channels comprising different sensor molecules (see FIGS. 14b and 14c). The same applies if the substrate for each of the sensor molecules is the same. The skilled person can readily design a suitable configuration for the microchannels depending on the number of samples to be analysed, the number of sensor molecules required to detect each target analyte, and the number of corresponding substrates required in light of the different sensor molecules being used.

Microfluidic devices can be fabricated from any material that has the necessary characteristics of chemical compatibility and mechanical strength. Examples of such substances include, but are not necessarily limited to, silicon, glass (e.g. fused silica, fused quartz, boro-silicate, or any type of glass with different additives), polydimethylsiloxane, polyimide, polyethylene terephthalate, polymethylmethacrylate, polyurethane, polyvinylchloride, polystyrene polysulfone, polycarbonate, polymethylpentene, polypropylene, a polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly (ethylene glycol), styrene-acrylonitrile resin, poly(trimethylene terephthalate), polyvinyl butyral, polyvinylidenedifluoride, poly(vinyl pyrrolidone), cyclic olefin-copolymer and any combination thereof.

The device (chip) can be constructed using standard techniques in the art such as single and multilayer soft lithography (MSL) techniques and/or sacrificial-layer encapsulation methods (see, e.g., Unger et al. (2000); WO 01/01025). Further methods of fabricating microfluidic devices include micromachining, micromilling, laser-based machining, chemical etching, (deep) reactive ion etching, imprinting techniques. These techniques can be used in conjunction with hot embossing and/or injection moulding techniques for mass production of the microdevices. There is a large body of prior art in fabrication techniques. Some of these are also described in U.S. Pat. Nos. 5,858,195, 5,126,022, 4,891,120, 4,908,112, 5,750,015, 5,580,523, 5,571,410, 5,885,470 and 6,793,753. Freestanding structures can be made to have very thin or very thick walls in relation to the channel width and height. The walls, as well as the top and bottom of a channel can all be of different thickness and can be made of the same material or of different materials or a combination of materials such as a combination of glass, silicon, and a biologically-compatible material such as PDMS. Sealed channels or chambers can be made entirely from biologically-compatible material such as PDMS.

Devices useful for the invention can have one or more channels and/or reaction chambers. For example, the device can comprise 2, 3, 4, 5, 6, 7, 8, 9, 10 or more channels. Furthermore, the device can comprise 1, 2, 3, 4, 5, 6, 7, 8, 9, 10 or more reactions chambers.

The reaction chamber and microchannels can be any suitable shape known in the art such as, but are not limited to, cylindrical, rectangular, semi-spherical or trapezoidal.

In an embodiment, where the device is capable of performing more than one reaction the channel design is such that each component flows through channels with the same length, size and configuration such as the bilaterally symmetrical parallel channel layout provided in FIG. 47.

In another embodiment, the function of the microchannels and the functions of the reaction chamber may be fulfilled by a single combined microfluidic element in which mixing occurs and from which light is collected.

The microfluidic device will typically have one or more reaction chamber volumes of about 1 pl (i.e. picoliter or a trillionth of a liter) to about 200 µl. However, reaction chamber volumes of between about 0.01 nl (i.e. nanoliter or a billionth of a liter) to about 100 nl, or between about 0.01 nl and 10 nl may be advantageous in certain applications. Some embodiments may optimally perform when the volume of each reaction chambers is between about 0.20 nl to about 5 nl. An additional embodiment is where the volume of each reaction chambers is between about 0.25 nl to about 2 nl. In a further embodiment, the reaction chamber(s) have a volume of about 1 µl to about 12 µl. Other possible reaction chamber volumes may be used where appropriate.

In a preferred embodiment, the reaction chamber is wider than it is short. In one example, the reaction chamber has a cross-sectional area of about 1 $mm^2$ to 1 $cm^2$ and a height of no more than about 5 mm.

In some circumstances it may be desirable to use reaction chambers of more than one size and shape. For example, the present inventors have observed that larger reaction chambers generate more light and allow the detection of more weakly emitting sensor molecules, often at the expense of a slower response time (time to peak change in BRET ratio) upon presentation of a sample containing a target analyte and a longer off-time when the analyte is removed. Different channels may therefore be equipped with reaction chambers of different sizes in order to match the sensitivity, precision and time dynamics of particular combinations of sensor molecules and analytes or sets of analytes. It would also be possible, and may in some cases be desirable, to implement more than one reaction chamber per sensor channel. This would allow near simultaneous detection of samples with higher luminance and quantitative precision (large chamber) and higher time resolution (smaller chamber). This could easily be achieved by fitting the large and smaller chambers with their own light path to the detector via an optical switch or equivalent, or fitting each with separate solid state light detectors.

Dimensions of the microchannels can be chosen based on the specific application of the device. Accordingly, width of the microchannel can range from, for example, about 0.1 mm to about 10 mm. In some embodiments, the width of the microchannel is from about 0.5 mm to about 5 mm. In some embodiments, the width of the microchannel is from about 1 mm to about 4 mm. In some embodiments, the width of the microchannel is about 2.5 mm. Depth or height of the microchannel can also be chosen based on the specific application of the device. Accordingly, the depth of the microchannel can range from, for example, about 5 µm to about 2000 µm. In some embodiments, the depth of the microchannel is from about 100 µm to about 1000 µm. In some embodiments, the depth of the microchannel is from about 250 µm to about 750 µm. In some embodiments, the depth of the microchannel is about 560 µm. In another embodiment, each microchannel has a cross-sectional area of about 1 $µm^2$ to about 1 $mm^2$.

As the skilled person will understand, the device will have suitable inlet ports and outlet ports to enable the relevant components to flow through the device.

The skilled artisan is well aware that the flow through a microfluidic device is dependent on various factors including, but not limited to, dimensions of the microchannels, viscosity of the fluid, and the detection and method employed. Accordingly, the sample (sensor molecule and substrate) can flow through the chip microchannel at a rate of about 1 µl/hr to about 10 ml/hr. In some embodiments, the sample (sensor molecule and substrate) can flow through the device microchannel at a rate of about 1 µl/hr to about 100 µl/hr, about 5 µl/hr to about 200 µl/hr, from about 7.5 µl/hr to about 500 µl/hr, or about 10 µl/hr to about 1 ml/hr.

In one embodiment, the device comprises multiple reaction chambers for sensing, for example, different analytes in the same source (sample). Due to the likely need to use different sensor molecules to detect different analytes, in some instances it may be desirable to modify the flow rate in different, preferably parallel, channels. In this regard, each individual flow rate can be set to optimize the sensitivity for each individual sensor molecule.

In one embodiment, in a device comprising multiple reaction chambers the flow rate to and from each reaction chamber is controlled by separate means, for instance a separate suction pump controls the flow rate to and from each reaction chamber. This configuration allows the simultaneous operation of multiple sensor channels independently of each other with potentially different flow rates and consequently different balances between speed and sensitivity.

The surface of the microfluidic channels may be passivated by exposure to a solution of a suitable reagent, such as a 0.1-5% (w/v) aqueous solution of bovine serum albumin, diluted mammalian serum, fish-skin gelatin, fat free milk proteins and/or using a solution of a non-ionic detergent, such as Tween-20 or by using a suspension of yeast microsomes.

After the reagents (sample, sensor molecule, substrate) have passed through the device, the device can be washed by flowing an appropriate fluid, e.g., a washing fluid such as a buffer, through the microchannels. This enables the device to be re-used. According, in some embodiments, the method further comprises the step of flowing a fluid, such as a buffer, through the microdevice after the analyte has been detected. The amount of fluid to be flown through the microdevice can be any amount and can be based on the volume of the chip. In some embodiments, the amount of the washing fluid is from about 0.5× to about 10× total volume of the microchannels in the device. In one embodiment, the amount of the washing fluid is from about 1.5× to about 2.5× total volume of the microchannels in the device.

Temperature Control

If present, this module is used to maintain desired temperatures for reagent storage, 1-8° C., preferably 2-4° C. and BRET reactions, 20-37° C., preferably 25-28° C. The BRET temperature control can be integrated with the loading mechanism and the electro-optical collection device. In particular they are constructed according to a technology that uses local resistive heating or Peltier-device cooling for control functions. For example, a thermally-controlled processor can be maintained at baseline temperature by a temperature-controlled heat sink or a cooling element, such as a Peltier device, with actuators controlled by localized heating above the baseline. Alternatively, cooling may be provided using a miniature heat pump. Localized heating may preferably be provided by low power resistive heaters of less than approximately 1 to 2 W, advantageously controlled by low voltages, for example, less than 50, 25, 15 or 10 V.

Electo-Optical System for Light Collection

The term "signal" as used herein refers to luminescence measured as a change in absorbance. In some embodiments, the signal will be "emitted light", wherein the step of detecting the signal will be the detection of photons of specific wavelengths of light by one or more photodetectors.

Example photodetectors include photomultiplier tubes (PMTs), photodiodes, avalanche photodiodes, silicon or other solid state photomultipliers (http://en.wikipedia.org/wiki/Silicon_photomultiplier) or CCD cameras, which may be cooled. Preferably, the photodetector has a photon detecting efficiency of ≥10%, more preferably ≥30% and most preferably ≥50%. Preferably these efficiencies operate in the blue and green bands of the optical spectrum. The detector further comprises a means of restricting the detected light to specific wavelength(s) or specific ranges of wavelengths. This can be, for example, suitable filters optionally mounted to a filter wheel or a filter slide or a monochromator or a dichroic mirror or a combination of two or more of these devices.

The electro-optical system may mainly consist of optical fibres and an optical switch (FIG. 16). The optical fibre can be replaced by fibre bundles or liquid light guides. The fibres with core diameters from about 10 µm to about 3000 µm can be fixed into the loading system. For fibre bundles or liquid light guides, the core diameter can be in the range from 0.5 mm to 10 mm. The flat ends of the fibres may be located right below the reaction chambers, each fibre collecting light from a particular chamber. Two BRET electro-optical detection elements can be designed which can be integrated with the reaction chamber (see FIG. 17). A spherical microlens might be incorporated into the reaction chamber to help focus BRET light into the core of the optical fiber.

In another embodiment, the optical fibre/liquid light guide system can be replaced by a set of lenses and mirrors so that light from each chamber is relayed to the detectors. The switching for multiple channel system can be realised by a mechanical chopper or other switching mechanisms.

To further increase the BRET signal collected, a flat or aspherical mirror might be placed on top of the reaction chamber (FIG. 17b). In this case, most of the BRET light emitted to the top will be reflected back into the optical fibers. For multi-channel detection, an optical switch can be used to collect lights from all channels. The material for this element can be in glass or polymeric materials, which have excellent optical, chemical properties such as polydimethylsiloxane, cyclic olefin co-polymer (COC) and so on. The BRET reaction chamber will be connected to the microfluidic network designed above for sample delivery and mixing.

Digital Photon Integration

Ultra low level light detection requires a highly sensitive photomultiplier tube (PMT) and digital signal processing unit to eliminate the dark current. FIG. 42 illustrates an example system for use in the invention composed of three units: PMT, Photon counting unit, USB counting unit. H10721P-210 is a current output PMT with ultrabialkali photocathode providing high sensitivity in visible wavelengths. The photosensitive area is round shape with a diameter of 8 mm. When a photon reaches to the ultrabialkali photocathode, photoelectrons are generated. The photoelectrons are accelerated towards a series of cascaded electrode structures at which the number of electrons increased exponentially at each stage. At the final stage the PMT outputs the sum of the generated electrons as a photoelectron pulse or current.

The dark current is defined as the current output appearing from a PMT in the absence of incident light. By identifying and eliminating the so-called the "dark pulses" it is possible to minimize the dark current. In this example, a signal processing unit (C9744 Photon counting unit) is used to eliminate the dark pulses. The unit allows implementation of a user set threshold value such that only the pulses with amplitude higher than the threshold value are sent to output. The remaining pulses are filtered out of the output signal. In this unit, the pulses which pass the discrimination criteria are converted to 5 V digital signal pulses and sent to the output terminal.

C8855-01 is an USB interface counting unit designed to count digital signal pulses without dead time. The signal generated in C9744 Photon counting unit is input to the counting unit and results are sent to a PC with a USB connection.

Optical Detection System

Detection can be achieved using detectors that are incorporated into the device or that are separate from the device but aligned with the region of the device to be detected.

The optical detection system samples the light output from each microfluidic channel, including each BRET reaction chamber. Each microfluidic channel may be equipped with a dedicated photodetector. For example, a fraction of the optical output of a single BRET reaction chamber may be channeled through a blue band-pass filter, while the remainder may be channeled through a green band-pass filter (or other suitable band-pass characteristics depending on the type of BRET in use). Light from these filters may be directed to separate photomultipliers using optical fibres, bundles of optical fibres or liquid light guides. Alternatively, silicon or other highly sensitive solid-state photomultipliers may be placed in close proximity to the band pass filters so as to sample the light emissions directly from each microfluidic channel and BRET reaction chamber. In an other embodiment, an aspherical lens or set of aspherical lenses might be placed at the end of the optical fibre, bundles of optical fibre or liquid light guide to collimate the output beam before entering the PMTs, thus reducing the optical loss due to rays diverging outside the sensitive area of the PMTs. In a preferred embodiment, the bandpass filters are placed on opposite sides of the microfluidic chip and in close contact with it and solid state photomultipliers or other photodectors are placed in close contact with both of the bandpass filters on each of the microfluidic channels. The advantages of providing a dedicated detection system for each microfluidic channel are that it minimises the complexity of the optical system and minimise potential photon losses, including those due to the switching dead time, where each microfluidic channel is optically silent for the majority of the polling cycle.

Alternatively, each microfluidic channel may be polled sequentially by one or more shared photodectors.

In one embodiment, the detection system may consist of an optical or optomechanical switching device, which receives light via an optical fiber or light guide from each of the microfluidic channels and sequentially outputs the optical signal of each of these inputs via a single optical fiber or light guide. The switching time from chamber to chamber could be in the range of nanoseconds to a few seconds (for example 2 or 3), preferably in the range of a 10-500 milliseconds or less. The output of the optical switching device impinges on and a photodetector such as a dichroic mirror to split the light into two wavelength ranges corresponding to the emissions of BRET donor and acceptor, respectively and two photomultiplier tubes for simultaneously detecting the light in each of these wavelength ranges (FIG. 16). Optionally, the dichroic block may be augmented by band pass filters tuned to the BRET donor and acceptor emission spectra.

In an alternative embodiment, a shutter box may be used instead of the optical switch. In such an arrangement, the output of the shutter box may be a many-to-one multifurcated light guide, which constrains the output of all optical channels into a single light guide that directs light to the photodetector. In this arrangement the shutters are operated so that the light from each single microfluidic channel is passed to the photodetector sequentially. The potential advantage of a switching system is that it allows a smaller number of photodetectors to sample the optical output of a larger number of microfluidic channels with cost, weight and power savings.

In another embodiment, the operating characteristics of the paired solid state photodetectors may be chosen so that their peak photon detection efficiencies (PDEs) are selective or semi-selective for the peak emissions of the BRET donor and acceptor. In this case, it is possible to dispense with the spectral filters and dichroic block and rely on the inherent differential spectral sensitivities different types of solid state photodetector to generate a BRET ratio.

Data Acquisition and Processing

The BRET signal of donors and acceptors in terms of counts/gate versus time will be collected by suitable software. A BRET ratio is calculated based on the ratio of light collected from the acceptors channel to the light collected from the donor channel. This BRET ratio should be constant if the ratio of flows of the sensor molecule and substrate remains constant and without the analyte to be detected in the BRET chamber. However, in the presence of the analyte, the BRET ratio will change corresponding to the amount of reagent in the reaction chambers.

Software and Embedded Control System

Preferably, the system comprises a trainable data processing and output software algorithm that can learn and discriminate the response patterns characteristic of different chemical samples. The software will capture salient features of the signal from each microfluidic channel, such as the baseline BRET ratio, the steady state BRET ratio when exposed to a sample and various features of the time course of changes in BRET ratio. These features from each channel will be input into a variety of discriminating algorithms, such as principle components analysis, linear discriminant analysis, stepwise discriminant analysis, machine learning algorithms such as support vector machines, Bayesian network analysis or neural network algorithms and compared with the results of previously learned sample classifications. Tentative sample analysis or classification is provided to the operator, preferably through a GUI and/or acoustical output. Alternatively, the signal strength in each channel may be output visually and/or acoustically so that the operator may match response patterns with those they have previously been trained to recognise.

In one embodiment, GUI software is used for controlling all in-device compositions such as the speed and concentration ratio of the sampling subsystem, the rate of flow of the microfluidic channels, the timing of flushing and purging cycles, pumps, the rate and intensity of any active mixing, the sensitivity and integration time of the photodetector systems, the temperature of the reagent reservoirs and the reaction chamber and all aspects of data acquisition and processing. Optionally many of these functions may be carried out through an embedded microcontroller. Some or all of the functions may be carried out on a laptop or tablet computer or equivalent device.

Chemiluminescence Resonance Energy Transfer

Chemiluminescence is the emission of energy with limited emission of heat (luminescence), as the result of a chemical reaction. The term "chemiluminescence" is used herein to encompass bioluminescence, which relies upon the activity of an enzyme.

As used herein, bioluminescent resonance energy transfer (BRET) is a proximity assay based on the non-radioactive transfer of energy between the bioluminescent protein donor and the acceptor molecule.

As used herein, the term "spatial location" refers to the three dimensional positioning of the donor relative to the acceptor molecule which changes as a result of the analyte binding or releasing from the sensor molecule.

As used herein, the term "dipole orientation" refers to the direction in three-dimensional space of the dipole moment associated either with the donor and/or the acceptor molecule relative their orientation in three-dimensional space. The dipole moment is a consequence of a variation in electrical charge over a molecule.

Using BRET as an example, in an embodiment the energy transfer occurring between the bioluminescent protein and acceptor molecule is presented as calculated ratios from the emissions measured using optical filters (one for the acceptor molecule emission and the other for the bioluminescent protein emission) that select specific wavelengths (see equation 1).

$$Ea/Ed = \text{BRET ratio} \qquad (1)$$

where Ea is defined as the acceptor molecule emission intensity (emission light is selected using a specific filter adapted for the emission of the acceptor) and Ed is defined as the bioluminescent protein emission intensity (emission light is selected using a specific filter adapted for the emission of the bioluminescent protein).

It should be readily appreciated by those skilled in the art that the optical filters may be any type of filter that permits wavelength discrimination suitable for BRET. For example, optical filters used in accordance with the present invention can be interference filters, long pass filters, short pass filters, etc. Intensities (usually in counts per second (CPS) or relative luminescence units (RLU)) of the wavelengths passing through filters can be quantified using either a photo-multiplier tube (PMT), photodiode, including a cascade photodiode, photodiode array or a sensitive camera such as a charge coupled device (CCD) camera. The quantified signals are subsequently used to calculate BRET ratios and represent energy transfer efficiency. The BRET ratio increases with increasing intensity of the acceptor emission.

Generally, a ratio of the acceptor emission intensity over the donor emission intensity is determined (see equation 1), which is a number expressed in arbitrary units that reflects energy transfer efficiency. The ratio increases with an increase of energy transfer efficiency (see Xu et al., 1999).

Energy transfer efficiencies can also be represented using the inverse ratio of donor emission intensity over acceptor emission intensity (see equation 2). In this case, ratios decrease with increasing energy transfer efficiency. Prior to performing this calculation the emission intensities are corrected for the presence of background light and autoluminescence of the substrate. This correction is generally made by subtracting the emission intensity, measured at the appropriate wavelength, from a control sample containing the substrate but no bioluminescent protein, acceptor molecule or polypeptide of the invention.

$$Ed/Ea = \text{BRET ratio} \qquad (2)$$

where Ea and Ed are as defined above.

The light intensity of the bioluminescent protein and acceptor molecule emission can also be quantified using a monochromator-based instrument such as a spectrofluorometer, a charged coupled device (CCD) camera or a diode array detector. Using a spectrofluorometer, the emission scan is performed such that both bioluminescent protein and acceptor molecule emission peaks are detected upon addition of the substrate. The areas under the peaks represent the relative light intensities and are used to calculate the ratios, as outlined above. Any instrument capable of measuring lights for the bioluminescent protein and acceptor molecule from the same sample, can be used to monitor the BRET system of the present invention.

In an alternative embodiment, the acceptor molecule emission alone is suitable for effective detection and/or quantification of BRET. In this case, the energy transfer efficiency is represented using only the acceptor emission intensity. It would be readily apparent to one skilled in the art that in order to measure energy transfer, one can use the acceptor emission intensity without making any ratio calculation. This is due to the fact that ideally the acceptor molecule will emit light only if it absorbs the light transferred from the bioluminescent protein. In this case only one light filter is necessary.

In a related embodiment, the bioluminescent protein emission alone is suitable for effective detection and/or quantification of BRET. In this case, the energy transfer efficiency is calculated using only the bioluminescent protein emission intensity. It would be readily apparent to one skilled in the art that in order to measure energy transfer, one can use the donor emission intensity without making any ratio calculation. This is due to the fact that as the acceptor molecule absorbs the light transferred from the bioluminescent protein there is a corresponding decrease in detectable emission from the bioluminescent protein. In this case only one light filter is necessary.

In an alternative embodiment, the energy transfer efficiency is represented using a ratiometric measurement which only requires one optical filter for the measurement. In this case, light intensity for the donor or the acceptor is determined using the appropriate optical filter and another measurement of the samples is made without the use of any filter (intensity of the open spectrum). In this latter measurement, total light output (for all wavelengths) is quantified. Ratio calculations are then made using either equation 3 or 4. For the equation 3, only the optical filter for the acceptor is required. For the equation 4, only the optical filter for the donor is required.

$$Ea/Eo-Ea=\text{BRET ratio or}=Eo-Ea/Ea \quad (3)$$

$$Eo-Ed/Ed=\text{BRET ratio or}=Ed/Eo-Ed \quad (4)$$

where Ea and Ed are as defined above and Eo is defined as the emission intensity for all wavelengths combined (open spectrum).

It should be readily apparent to one skilled in the art that further equations can be derived from equations 1 through 4. For example, one such derivative involves correcting for background light present at the emission wavelength for bioluminescent protein and/or acceptor molecule.

In performing a BRET assay, light emissions can be determined from each well using the BRETCount. The BRETCount instrument is a modified TopCount, wherein the TopCount is a microtiterplate scintillation and luminescence counter sold by Packard Instrument (Meriden, Conn.). Unlike classical counters which utilise two photomultiplier tubes (PMTs) in coincidence to eliminate background noise, TopCount employs single-PMT technology and time-resolved pulse counting for noise reduction to allow counting in standard opaque microtiter plates. The use of opaque microtiterplates can reduce optical crosstalk to negligible level. TopCount comes in various formats, including 1, 2, 6 and 12 detectors (PMTs), which allow simultaneous reading of 1, 2, 6 or 12 samples, respectively. Beside the BRETCount, other commercially available instruments are capable of performing BRET: the Victor 2 (Wallac, Finland (Perkin Elmer Life Sciences)) and the Fusion (Packard Instrument, Meriden). BRET can be performed using readers that can detect at least the acceptor molecule emission and preferably two wavelengths (for the acceptor molecule and the bioluminescent protein) or more.

Chemiluminescence

Non-enzymatic chemiluminescence is the result of chemical reactions between an organic dye and an oxidizing agent in the presence of a catalyst. Chemiluminescence emission occurs as the energy from the excited states of organic dyes, which are chemically induced, decays to ground state. The duration and the intensity of the chemiluminescence emission are mostly dependent on the extent of the chemical reagents present in the reaction solution.

As used herein, the term "bioluminescent protein" refers to any protein capable of acting on a suitable substrate to generate luminescence.

It is understood in the art that a bioluminescent protein is an enzyme which converts a substrate into an activated product which then releases energy as it relaxes. The activated product (generated by the activity of the bioluminescent protein on the substrate) is the source of the bioluminescent protein-generated luminescence that is transferred to the acceptor molecule.

There are a number of different bioluminescent proteins that can be employed in this invention (see, for example, Table 1). Light-emitting systems have been known and isolated from many luminescent organisms including bacteria, protozoa, coelenterates, molluscs, fish, millipedes, flies, fungi, worms, crustaceans, and beetles, particularly click beetles of genus *Pyrophorus* and the fireflies of the genera *Photinus, Photuris*, and *Luciola*. Additional organisms displaying bioluminescence are listed in WO 00/024878, WO 99/049019 and Viviani (2002).

One very well known example is the class of proteins known as luciferases which catalyze an energy-yielding chemical reaction in which a specific biochemical substance, a luciferin (a naturally occurring fluorophore), is oxidized by an enzyme having a luciferase activity (Hastings, 1996). A great diversity of organisms, both prokaryotic and eukaryotic, including species of bacteria, algae, fungi, insects, fish and other marine forms can emit light energy in this manner and each has specific luciferase activities and luciferins which are chemically distinct from those of other organisms. Luciferin/luciferase systems are very diverse in form, chemistry and function. Bioluminescent proteins with luciferase activity are thus available from a variety of sources or by a variety of means. Examples of bioluminescent proteins with luciferase activity may be found in U.S. Pat. Nos. 5,229,285, 5,219,737, 5,843,746, 5,196,524, and 5,670,356. Two of the most widely used luciferases are: (i) *Renilla* luciferase (from *R. reniformis*), a 35 kDa protein, which uses coelenterazine as a substrate and emits light at 480 nm (Lorenz et al., 1991); and (ii) Firefly luciferase (from *Photinus pyralis*), a 61 kDa protein, which uses luciferin as a substrate and emits light at 560 nm (de Wet et al., 1987).

*Gaussia* luciferase (from *Gaussia princeps*) has been used in biochemical assays (Verhaegen et al., 2002). *Gaussia* luciferase is a 20 kDa protein that oxidises coelenterazine in a rapid reaction resulting in a bright light emission at 470 nm.

Luciferases useful for the present invention have also been characterized from *Anachnocampa* sp (WO 2007/019634). These enzymes are about 59 kDa in size and are ATP-dependent luciferases that catalyze luminescence reactions with emission spectra within the blue portion of the spectrum.

detection chamber volumes and/or faster on-chip flow rates with concomitant improvement in time resolution at any given combination of detection chamber volume and flow rate. Alternatively, it permits more economical use of reagents for any given time resolution.

TABLE 1

Exemplary bioluminescent proteins.

| Species | Name | Organism | MW kDa × $10^{-3}$ | Emission (nm) | Example of Substrate |
|---|---|---|---|---|---|
| Insect | FFluc | *Photinus pyralis* (North American Firefly) | ~61 | 560 | D-(−)-2-(6'-hydroxybenzothiazolyl)-$\Delta^2$-thiazoline-4-carboxylic acid, HBTTCA ($C_{11}H_8N_2O_3S_2$) (luciferin) |
| Insect | FF'luc | *Luciola cruciata* (Japanese Firefly) | | 560-590 (many mutants) | Luciferin |
| Insect | | Phengodid beetles (railroad worms) | | | |
| Insect | | *Arachnocampa* sp. | | | Luciferin |
| Insect | | *Orphelia fultoni* (North American glow worm) | | | |
| Insect | Clluc | *Pyrophorus plagiophthalamus* (click beetle) | | 546, 560, 578 and 593 | Luciferin |
| Jellyfish | Aequorin | *Aequorea* | 44.9 | 460-470 | Coelenterazine |
| Sea pansy | Rluc | *Renilla reniformis* | 36 | 480 | Coelenterazine |
| Sea pansy (modified) | Rluc8 | *Renilla reniformis* (modified) | 36 | 487 (peak) | Coelenterazine/Deep Blue C |
| Sea pansy (modified) | Rluc2 | *Renilla reniformis* (modified M185V/Q235A) | 36 | 480 | Coelenterazine |
| Sea pansy (modified) | RLuc8.6-535 | *Renilla reniformis* (modified) | 36 | 535 | Coelenterazine |
| Sea pansy | Rmluc | *Renilla mullerei* | 36.1 | ~480 | Coelenterazine |
| Sea pansy | | *Renilla kollikeri* | | | |
| Crustacea (shimp) | Vluc | *Vargula hilgendorfii* | ~62 | ~460 | coelenterazine * |
| Crustaeca | | *Cypridina* (sea firefly) | 75 | 460 | coelenterazine ** |
| Dinofagellate (marine alga) | | *Gonyaulax polyedra* | 130 | ~475 | Tetrapyrrole |
| Mollusc | | *Latia* (fresh water limpet) | 170 | 500 | Enol formate, terpene, aldehyde |
| Hydroid | | *Obelia biscuspidata* | ~20 | ~470 | Coelenterazine |
| Shrimp | | *Oplophorus gracilorostris* | 31 | 462 | Coelenterazine |
| Others | Ptluc | *Ptilosarcus* | | ~490 | Coelenterazine |
| | Gluc | *Gaussia* | ~20 | ~475 | Coelenterazine |
| | Plluc | *Pleuromamma* | 22.6 | ~475 | Coelenterazine |

Biologically active variants or fragments of naturally occurring bioluminescent protein can readily be produced by those skilled in the art. Three examples of such variants useful for the invention are Rluc2 (Loening et al., 2006), Rluc8 (Loening et al., 2006) and Rluc8.6-535 (Loening et al., 2007) which are each variants of *Renilla* luciferase. In a further preferred embodiment, the sequence of the BRET chemiluminescent donor is chosen to have greater thermal stability than sensor molecules incorporating native *Renilla* luciferase sensors. RLuc2 or RLuc8 are convenient examples of suitable choices, which consequently exhibit ≥5× or ≥10× higher luminance than sensors incorporating the native *Renilla* luciferase sequence. Such enhanced luminance has significant benefits as it permits the use of lower As used herein, a "biologically active fragment" is a portion of a polypeptide as described herein which maintains a defined activity of the full-length polypeptide. As used herein, a "biologically active variant" is a molecule which differs from a naturally occurring and/or defined molecule by one or more amino acids but maintains a defined activity, such as defined above for biologically active fragments. Biologically active variants are typically least 50%, more preferably at least 80%, more preferably at least 90%, more preferably at least 95%, more preferably at least 97%, and even more preferably at least 99% identical to the naturally occurring and/or defined molecule.

Alternative, non-luciferase, bioluminescent proteins that can be employed in this invention are any enzymes which can act on suitable substrates to generate a luminescent signal. Specific examples of such enzymes are β-galactosidase, lactamase, horseradish peroxidase, alkaline phophatase, β-glucuronidase and β-glucosidase. Synthetic luminescent substrates for these enzymes are well known in the art and are commercially available from companies, such as Tropix Inc. (Bedford, Mass., USA).

An example of a peroxidase useful for the present invention is described by Hushpulian et al. (2007).

In a preferred embodiment, a bioluminescent protein with a small molecular weight is used to prevent an inhibition of the interaction due to steric hindrance. The bioluminescent protein preferably consists of a single polypeptide chain. Also the bioluminescent proteins preferably do not form oligomers or aggregates. The bioluminescent proteins *Renilla* luciferase, *Gaussia* luciferase and Firefly luciferase meet all or most of these criteria.

Substrates

As used herein, the term "substrate" refers to any molecule that can be used in conjunction with a chemiluminescent donor to generate or absorb luminescence. The choice of the substrate can impact on the wavelength and the intensity of the light generated by the chemiluminescent donor.

A widely known substrate is coelenterazine which occurs in cnidarians, copepods, chaetgnaths, ctenophores, decapod shrimps, mysid shrimps, radiolarians and some fish taxa (Greer and Szalay, 2002). For *Renilla* luciferase for example, coelenterazine analogues/derivatives are available that result in light emission between 418 and 512 nm (Inouye et al., 1997). A coelenterazine analogue/derivative (400A, DeepBlueC) has been described emitting light at 400 nm with *Renilla* luciferase (WO 01/46691). Other examples of coelenterazine analogues/derivatives are EnduRen and ViviRen.

As used herein, the term "luciferin" refers to a class of light-emitting biological pigments found in organisms capable of bioluminescence, which are oxidised in the presence of the enzyme luciferase to produce oxyluciferin and energy in the form of light. Luciferin, or 2-(6-hydroxybenzothiazol-2-yl)-2-thiazoline-4-carboxylic acid, was first isolated from the firefly *Photinus pyralis*. Since then, various forms of luciferin have been discovered and studied from various different organisms, mainly from the ocean, for example fish and squid, however, many have been identified in land dwelling organisms, for example, worms, beetles and various other insects (Day et al., 2004; Viviani, 2002).

There are at least five general types of luciferin, which are each chemically different and catalysed by chemically and structurally different luciferases that employ a wide range of different cofactors. First, is firefly luciferin, the substrate of firefly luciferase, which requires ATP for catalysis (EC 1.13.12.7). Second, is bacterial luciferin, also found in some squid and fish, that consists of a long chain aldehyde and a reduced riboflavin phosphate. Bacterial luciferase is FMNH-dependent. Third, is dinoflagellate luciferin, a tetrapyrrolic chlorophyll derivative found in dinoflagellates (marine plankton), the organisms responsible for night-time ocean phosphorescence. Dinoflagellate luciferase catalyses the oxidation of dinoflagellate luciferin and consists of three identical and catalytically active domains. Fourth, is the imidazolopyrazine vargulin, which is found in certain ostracods and deep-sea fish, for example, Porichthys. Last, is coelanterazine (an imidazolpyrazine), the light-emitter of the protein aequorin, found in radiolarians, ctenophores, cnidarians, squid, copepods, chaetognaths, fish and shrimp.

Acceptor Molecules

As used herein, the term "fluorescent acceptor domain" (also referred herein to as "acceptor molecule") refers to any compound which can accept energy emitted as a result of the activity of a chemiluminescent donor, and re-emit it as light energy. There are a number of different acceptor molecules that can be employed in this invention. The acceptor molecules may be a protein or non-proteinaceous. Examples of acceptor molecules that are protein include, but are not limited to, green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, Kaede protein or a Phycobiliprotein, or a biologically active variant or fragment of any one thereof. Examples of acceptor molecules that are not proteins include, but are not limited to, Alexa Fluor dye, Bodipy dye, Cy dye, fluorescein, dansyl, umbelliferone, fluorescent microsphere, luminescent microsphere, fluorescent nanocrystal, Marina Blue, Cascade Blue, Cascade Yellow, Pacific Blue, Oregon Green, Tetramethylrhodamine, Rhodamine, Texas Red, rare earth element chelates, or any combination or derivatives thereof.

One very well known example is the group of fluorophores that includes the green fluorescent protein from the jellyfish *Aequorea victoria* and numerous other variants (GFPs) arising from the application of molecular biology, for example mutagenesis and chimeric protein technologies (Tsien, 1998). GFPs are classified based on the distinctive component of their chromophores, each class having distinct excitation and emission wavelengths: class 1, wild-type mixture of neutral phenol and anionic phenolate: class 2, phenolate anion: class 3, neutral phenol: class 4, phenolate anion with stacked s-electron system: class 5, indole: class 6, imidazole: and class 7, phenyl.

A naturally occurring acceptor molecule which has been mutated (variants) can also be useful for the present invention. One example of an engineered system which is suitable for BRET is a *Renilla* luciferase and enhanced yellow mutant of GFP (EYFP) pairing which do not directly interact to a significant degree with one another alone in the absence of a mediating protein(s) (in this case, the G protein coupled receptor) (Xu et al., 1999).

In another embodiment, the acceptor molecule is a fluorescent nanocrystal. Nanocrystals, or "quantum dots", have several advantages over organic molecules as fluorescent labels, including resistance to photodegradation, improved brightness, non-toxicity, and size dependent, narrow emission spectra that enables the monitoring of several processes simultaneously. Additionally, the absorption spectrum of nanocrystals is continuous above the first peak, enabling all sizes, and hence all colors, to be excited with a single excitation wavelength.

Fluorescent nanocrystals may be attached, or "bioconjugated", to proteins in a variety of ways. For example, the surface cap of a "quantum dot" may be negatively charged with carboxylate groups from either dihydrolipoic acid (DHLA) or an amphiphilic polymer. Proteins can be conjugated to the DHLA-nanocrystals electrostatically, either directly or via a bridge consisting of a positively charged leucine zipper peptide fused to recombinant protein. The latter binds to a primary antibody with specificity for the intended target. Alternatively, antibodies, streptavidin, or other proteins are coupled covalently to the polyacrylate cap of the nanocrystal with conventional carbodiimide chemistry.

There are colloidal methods to produce nanocrystals, including cadmium selenide, cadmium sulfide, indium arsenide, and indium phosphide. These quantum dots can contain as few as 100 to 100,000 atoms within the quantum dot volume, with a diameter of 10 to 50 atoms. Some quantum dots are small regions of one material buried in another with a larger band gap. These can be so-called core-shell structures, for example, with CdSe in the core and ZnS in the shell or from special forms of silica called ormosil. The larger the dot, the redder (lower energy) its fluorescence spectrum. Conversely, smaller dots emit bluer (higher energy) light. The coloration is directly related to the energy levels of the quantum dot. Quantitatively speaking, the bandgap energy that determines the energy (and hence color) of the fluoresced light is inversely proportional to the square of the size of the quantum dot. Larger quantum dots have more energy levels which are more closely spaced. This allows the quantum dot to absorb photons containing less energy, i.e. those closer to the red end of the spectrum.

In an alternate embodiment, the acceptor molecule is a fluorescent microsphere. These are typically made from polymers, and contain fluorescent molecules (for example fluorescein GFP or YFP) incorporated into the polymer matrix, which can be conjugated to a variety of reagents. Fluorescent microspheres may be labelled internally or on the surface. Internal labelling produces very bright and stable particles with typically narrow fluorescent emission spectra. With internal labelling, surface groups remain available for conjugating ligands (for example, proteins) to the surface of the bead. Internally-labelled beads are used extensively in imaging applications, as they display a greater resistance to photobleaching.

Carboxylate-modified fluorescent microspheres are suitable for covalent coupling of proteins using water-soluble carbodiimide reagents such as 1-ethyl-3-(3-dimethylaminopropyl) carbodiimide hydrochloride (EDAC). Sulfate fluorescent microspheres are relatively hydrophobic and will passively and nearly irreversibly adsorb almost any protein. Aldehyde-sulfate fluorescent microspheres are sulfate microspheres that have been modified to add surface aldehyde groups, and react with proteins.

In another embodiment, the acceptor molecule is a luminescent microsphere. These are typically made from polymers, which contain luminescent molecules (for example complexes of europium or platinum) incorporated into the polymer matrix, which can be conjugated to a variety of reagents.

Examples of non-fluorescent acceptor domains useful for the invention include quenchers such as DABCYL [4-((4-(Dimethylamino) phenyl)azo)benzoic acid], DABSYL (Dimethylaminoazosulfonic acid), metal nanoparticles such as gold and silver, lack hole quenchers (BHQ) and QXL quenchers.

Chemiluminescent Donor Domain and Acceptor Domain Pairs

As used herein, the term "the separation and relative orientation of the chemiluminescent donor domain and the acceptor domain, in the presence and/or the absence of analyte, is within ±50% of the Forster distance" refers to the steady state RET measurements which can be carried out within a range of ±50% of $R_0$. This phrase encompasses an efficiency of luminescence energy transfer from the chemiluminescent donor domain to the acceptor domain in the range of 10-90%. Outside of these distance limits it is still possible to estimate distance but the uncertainty is increased.

A criterion which should be considered in determining suitable pairings is the relative emission/fluorescence spectrum of the acceptor molecule compared to that of the donor. The emission spectrum of the donor should overlap with the absorbance spectrum of the acceptor molecule such that the light energy from the donor luminescence emission is at a wavelength that is able to excite the acceptor molecule and thereby promote acceptor molecule fluorescence when the two molecules are in a proper proximity and orientation with respect to one another. For example, it has been demonstrated that an *Renilla* luciferase/EGFP pairing is not as good as an *Renilla* luciferase/EYEF pairing based on observable emission spectral peaks (Xu, 1999; Wang, et al. (1997) in Bioluminescence and Chemiluminescence: Molecular Reporting with Photons, eds. Hastings et al. (Wiley, New York), pp. 419-422). To study potential pairing, protein fusions (for example) are prepared containing the selected bioluminescent protein and acceptor molecule and are tested, in the presence of an appropriate substrate.

It should also be confirmed that the donor and acceptor molecule do not spuriously associate with each other. This can be accomplished by, for example, separate co-expression of a bioluminescent protein and acceptor molecule in the same cells and then monitoring the luminescence spectrum in order to determine if BRET occurs. This may be achieved, for example, using the method of Xu et al. (1999). The selected bioluminescent protein and acceptor molecule form a suitable BRET pair if little or no BRET is observed.

The donor emission can be manipulated by modifications to the substrate. In the case of luciferases the substrate is coelenterazine. The rationale behind altering the donor emission is to improve the resolution between donor emission and acceptor emissions. The original BRET system uses the *Renilla* luciferase as donor, EYFP (or Topaz) as the acceptor and coelenterazine h derivative as the substrate. These components when combined in a BRET assay, generate light in the 475-480 nm range for the bioluminescent protein and the 525-530 nm range for the acceptor molecule, giving a spectral resolution of 45-55 nm.

Unfortunately, *Renilla* luciferase generates a broad emission peak overlapping substantially the GFP emission, which in turn contributes to decrease the signal to noise of the system. One BRET system of the present invention, using coel400a as the *Renilla* luciferase substrate, provides broad spectral resolution between donor and acceptor emission wavelengths (–105 nm). *Renilla* luciferase with coel400a generates light between 390-400 nm and a GFP was prepared which absorbs light in this range and re-emits light at 505-508 nm. Because of this increase in spectral resolution between *Renilla* luciferase and GFP emissions, this BRET system provides an excellent biological tool to monitor small changes in conformation of a polypeptide of the invention. This is a significant improvement over the system described previously using the coelenterazine h derivative and EYFP, which has a wavelength difference between donor and acceptor of approximately 51 nm.

Various coelenterazine derivatives are known in the art, including coel400a, that generate light at various wavelengths (distinct from that generated by the wild type coelenterazine) as a result of *Renilla* luciferase activity. A worker skilled in the art would appreciate that because the light emission peak of the donor has changed, it is necessary to select an acceptor molecule which will absorb light at this wavelength and thereby permit efficient energy transfer. This can be done, for example by altering a GFP class 4 such that it becomes a class 3 or 1 GFP. Spectral overlapping between light emission of the donor and the light absorption peak of the acceptor is one condition among others for an efficient energy transfer. Class 3 and 1 GFPs are known to absorb light at 400 nm and re-emit between 505-511 nm. This results in a wavelength difference between donor and acceptor emissions of approximately 111 nm.

Examples of further bioluminescent protein and acceptor molecule pairs are provided in Table 2.

Sensor Molecule

As used herein, the term "sensor molecule" refers to any molecule, complex of two or more covalently or non-covalently associated molecules, or two or more molecules which can be at least at some stage closely associated to enable RET between the donor and acceptor. Furthermore, if present, the two or more separate molecules which form the domain can be associated via an intermediate molecule. In one example, the sensor molecule can be a protein complex, where each subunit of the complex is non-covalently associated and the acceptor and domain may be on the same or different subunits of the protein complex. In another example, the sensor molecule is two separate nucleic acid strands, one labelled with the acceptor and the other labelled with the donor, such that hybridization to a target (analyte) results in the donor and acceptor being sufficiently close to result in RET. In this example, it can be considered that the sensor molecule is formed when it binds the analyte.

TABLE 2

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| Rluc2 Rluc8 | Native coelenterazine | 470 nm | Venus | 515/528 nm |
| Rluc2 Rluc8 | Native coelenterazine | 470 nm | mOrange | 548/562 nm |
| Rluc2 Rluc8 | Native Coelenterazine | 470 nm | EYFP/Topaz | 514/527 nm |
| Rluc2 Rluc8 | Native Coelenterazine | 470 nm | mCitrine | 516/529 nm |
| Rluc Rluc2 Rluc8 | Native Coelenterazine | 470 nm | YPet | 517/530 nm |
| Rluc2 Rluc8 | Native Coelenterazine | 470 nm | Fluorescein | 495/519 nm |
| Rluc2 Rluc8 | Native Coelenterazine | 470 nm | Acridine yellow | 470/550 nm |
| Rluc2 Rluc8 | Native Coelenterazine | 470 nm | Nile red | 485/525 nm |
| Rluc2 Rluc8 | Native Coelenterazine | 470 nm | R-Phycoerythrin | 480/578 |
| Rluc2 Rluc8 | Native Coelenterazine | 470 nm | Red 613 | 480/613 |
| Rluc2 Rluc8 | Native Coelenterazine | 470 nm | TruRed | 490/695 |
| RLuc8.6-5.35 | Native Coelenterazine | 535 nm | mOrange | 548/562 nm |
| Rluc2 Rluc8 | Coelenterazine h | 470 nm | Venus | 515/528 nm |
| Rluc2 Rluc8 | Coelenterazine h | 470 nm | mOrange | 548/528 nm |
| Rluc2 Rluc8 | Coelenterazine h | 470 nm | EYFP/Topaz | 514/527 nm |
| Rluc2 Rluc8 | Coelenterazine h | 470 nm | mCitrine | 516/529 nm |
| Rluc2 Rluc8 | Native Coelenterazine | 470 nm | YPet | 517/530 nm |
| Rluc Rluc2 Rluc8 | Coelenterazine h | 470 nm | Fluorescein | 490/525 nm |
| Rluc Rluc2 Rluc8 | Coelenterazine h | 470 nm | Acridine yellow | 470/550 nm |
| Rluc Rluc2 Rluc8 | Coelenterazine h | 470 nm | Nile red | 485/525 nm |
| Rluc Rluc2 Rluc8 | Coelenterazine h | 470 nm | R-Phycoerythrin | 480/578 |
| Rluc Rluc2 Rluc8 | Coelenterazine h | 470 nm | Red 613 | 480/613 |
| Rluc Rluc2 Rluc8 | Coelenterazine h | 470 nm | TruRed | 490/695 |
| RLuc8.6-5.35 | Coelenterazine h | 535 nm | mOrange | 548/562 nm |

TABLE 2-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| Rluc Rluc2 Rluc8 | Coelenterazine 400a | 400 nm | GFP2 | 396/508 nm |
| Rluc Rluc2 Rluc8 | Coelenterazine 400a | 400 nm | GFP10 | 400/510 nm |
| Rluc Rluc2 Rluc8 | Coelenterazine 400a | 400 nm | Wild type GFP | 396 (475)/508 nm |
| Rluc Rluc2 Rluc8 | Coelenterazine 400a | 400 nm | TagBFP | 402/457 nm |
| Rluc Rluc2 Rluc8 | Coelenterazine 400a | 400 nm | Cerulean/mCFP | 433/475 nm |
| Rluc Rluc2 Rluc8 | Coelenterazine 400a | 400 nm | ECFP/CyPet | 434/477 nm |
| Rluc Rluc2 Rluc8 | Coelenterazine 400a | 400 nm | Y66W | 436/485 nm |
| Rluc Rluc2 Rluc8 | Coelenterazine 400a | 400 nm | dKeima-Red | 440/616 nm |
| Rluc Rluc2 Rluc8 | Coelenterazine 400a | 400 nm | mKeima-Red | 440/620 nm |
| Rluc Rluc2 Rluc8 | Coelenterazine 400a | 400 nm | Quin-2 | 365/490 nm |
| Rluc Rluc2 Rluc8 | Coelenterazine 400a | 400 nm | Pacific blue | 403/551 nm |
| Rluc Rluc2 Rluc8 | Coelenterazine 400 | 400 nm | Dansychloride | 380/475 nm |
| Firefly luciferase | Luciferin | 560 nm | Cyanine Cy3 | 575/605 nm |
| Firefly luciferase | Luciferin | 560 nm | Texas red | 590/615 |
| Firefly luciferase | Luciferin | 560 nm | TurboRed | 553/574 nm |
| Firefly luciferase | Luciferin | 560 nm | tdTomato | 554/581 nm |
| Firefly luciferase | Luciferin | 560 nm | TagRFP | 555/584 nm |
| Firefly luciferase | Luciferin | 560 nm | DsRed | 557/592 nm |
| Firefly luciferase | Luciferin | 560 nm | mRFP1 | 584/607 nm |
| Firefly luciferase | Luciferin | 560 nm | mCherry | 587/610 nm |

The domain which binds the analyte (or candidate compound) any be any molecule as long as it can be appropriately associated with the donor and acceptor.

In an embodiment, the domain that binds the analyte is a protein or a nucleic acid. In a preferred embodiment, the domain is a protein. In an embodiment, the protein is a naturally occurring protein which binds one or more analytes (ligand), or a variant of the protein which retains analyte (ligand) binding activity. Examples include, but are not necessarily limited to, a receptor, odorant binding protein, pheromone-binding protein, enzyme (for example a protease, an oxidase, a phytase, a chitinase, an invertase, a lipase, a cellulase, a xylenase, a kinase, a phosphatase, an elongase, a transferase, a desaturase), ligand carrier or bacterial periplasmic binding protein. In an embodiment, the receptor is a G protein coupled receptor such as an odorant receptor or a taste receptor (for example a sweet, bitter or umami taste receptor, such as those described in Doty, 2012). In a further embodiment, the odorant receptor or taste receptor is from a nematode or vertebrate or is a mutant thereof.

In one embodiment, the sensor molecule is provided as a cell-free composition. As used herein, the term "cell free composition" refers to an isolated composition which contains few, if any, intact cells and which comprises the sensor molecule. Examples of cell free compositions include cell (such as yeast cell) extracts and compositions containing an isolated and/or recombinant sensor molecules (such as proteins). Methods for preparing cell-free compositions from cells are well-known in the art and are described in WO 2010/085844. In certain embodiments, the sensor molecule is embedded in a lipid bilayer such as of a liposome preparation, in cell or cell-free extract.

G Protein Coupled Receptors

As used herein, unless specified otherwise, the term "G protein coupled receptor" refers to a seven transmembrane receptor which signals through G proteins. The receptor may be a single subunit, or two or more receptor subunits. When two or more receptor subunits are present they may be the same, different, or a combination thereof (for example, two of one subunit and a single of another subunit). Furthermore, unless specified or implied otherwise the terms "G protein coupled receptor" and "subunit of a G protein coupled receptor", or variations thereof, are used interchangeably.

As used herein, the term "odorant receptor", "olfactory receptor", "OR" or variations thereof refers to a polypeptide which, when present in a cell of an organism, is involved in chemosensory perception. In an embodiment, the cell is a neuron. Furthermore, the term "odorant receptor" or "olfactory receptor" refers to a polypeptide which binds an odorant ligand, or forms part of a protein complex that binds to an odorant ligand, resulting in a physiologic response.

As used herein, the term "forms part of" refers to the bioluminescent protein or acceptor molecule being located within the specified region of the G protein coupled receptor, or subunit thereof. This term also includes the possibility that the bioluminescent protein and/or acceptor molecule is attached to or binds the G protein coupled receptor but does not form a continuous chain of amino acids. In one embodiment, the bioluminescent protein or acceptor molecule completely replaces the specified region of the G protein coupled receptor. In another embodiment, some, but not all, of the specified region of the G protein coupled receptor is replaced. In yet another embodiment, none of the specified region of the G protein coupled receptor is replaced. As the skilled addressee will appreciate, the bioluminescent protein or acceptor molecule will not be inserted such that it makes the G protein coupled receptor portion of a polypeptide incapable of binding the analyte to result in a spatial change to the location and/or dipole orientation of the bioluminescent protein relative to the acceptor molecule.

G protein-coupled receptors (GPCRs) are also known as seven transmembrane receptors, 7TM receptors, serpentine receptors, heptahelical receptors, and G protein linked receptors (GPLR). GPCRs are a large protein family of transmembrane receptors that sense molecules outside the cell and activate inside signal transduction pathways and, ultimately, cellular responses. The ligands that bind and activate these receptors include light-sensitive compounds, odors, pheromones, hormones, and neurotransmitters, and vary in size from small molecules to peptides to large proteins. GPCRs are involved in many diseases, but are also the target of around half of all modern medicinal drugs. GPCRs can be grouped into at least 5 classes based on sequence homology and functional similarity:

Class A rhodopsin-like,
Class B secretin-like,
Class C metabotropic/pheromone,
Class D fungal pheromone, and
Class E cAMP receptors.

Class A Rhodopsin like receptors include: Amine receptors: Acetylcholine, Alpha Adrenoceptors, Beta Adrenoceptors, Dopamine, Histamine, Serotonin, Octopamine, and Trace amine; Peptide receptors: Angiotensin, Bombesin, Bradykinin, C5a anaphylatoxin, Finet-leu-phe, APJ like, Interleukin-8, Chemokine receptors (C-C Chemokine, C-X-C Chemokine, BONZO receptors (CXC6R), C-X3-C Chemokine, and XC Chemokine), CCK receptors, Endothelin receptors, Melanocortin receptors, Neuropeptide Y receptors, Neurotensin receptors, Opioid receptors, Somatostatin receptors, Tachykinin receptors, (Substance P (NK1), Substance K (NK2), Neuromedin K (NK3), Tachykinin like 1, and Tachykinin like 2), Vasopressin-like receptors (Vasopres sin, Oxytocin, and Conopressin), Galanin like receptors (Galanin, Allatostatin, and GPCR 54), Proteinase-activated like receptors (e.g., Thrombin), Orexin & neuropeptide FF, Urotensin II receptors, Adrenomedullin (G10D) receptors, GPR37/endothelin B-like receptors, Chemokine receptor-like receptors, and Neuromedin U receptors; Hormone protein receptors: Follicle stimulating hormone, Lutropin-choriogonadotropic hormone, Thyrotropin, and Gonadotropin; (Rhod)opsin receptors; Olfactory receptors; Prostanoid receptors: Prostaglandin, Prostacyclin, and Thromboxane; Nucleotide-like receptors: Adenosine and Purinoceptors; Cannabis receptors; Platelet activating factor receptors; Gonadotropin-releasing hormone receptors; Thyrotropin-releasing hormone & Secretagogue receptors: Thyrotropin-releasing hormone, Growth hormone secretagogue, and Growth hormone secretagogue like; Melatonin receptors; Viral receptors; Lysosphingolipid & LPA (EDG) receptors; Leukotriene B4 receptor: Leukotriene B4 receptor BLT1 and Leukotriene B4 receptor BLT2; and Class A Orphan/other receptors: Platelet ADP & KI01 receptors, SREB, Mas proto-oncogene, RDC1, ORPH, LGR like (hormone receptors), GPR, GPR45 like, Cysteinyl leukotriene, Mas-related receptors (MRGs), and GP40 like receptors.

Class B (the secretin-receptor family) of the GPCRs includes receptors for polypeptide hormones (Calcitonin, Corticotropin releasing factor, Gastric inhibitory peptide, Glucagon, Glucagon-like peptide-1,-2, Growth hormone-releasing hormone, Parathyroid hormone, PACAP, Secretin, Vasoactive intestinal polypeptide, Diuretic hormone, EMR1, Latrophilin), molecules thought to mediate intercellular interactions at the plasma membrane (Brain-specific angiogenesis inhibitor (BAI)) and a group of *Drosophila* proteins (Methuselah-like proteins) that regulate stress responses and longevity.

Class C Metabotropic glutamate/pheromone receptors include Metabotropic glutamate, Metabotropic glutamate group I, Metabotropic glutamate group II, Metabotropic glutamate group III, Metabotropic glutamate other, Extracellular calcium-sensing, Putative pheromone Receptors, GABA-B, GABA-B subtype 1, GABA-B subtype 2, and Orphan GPRC5 receptors.

Sensor molecules useful for the invention may comprise G protein coupled receptors which, when expressed in a cell the N-terminus of the receptor is outside the cell and the C-terminus is inside the cell. The person skilled in the art is aware of suitable techniques for detecting the orientation of a transmembrane protein. Such techniques comprise but are not limited to crystallography, NMR-studies, modeling studies as well as microscopy techniques, like immunolabeling combined with detergent permeabilisation controls for light or electron microscopy preparation, fragment complementation tagging of two polypeptides and the like.

In a preferred embodiment, the G protein coupled receptor is a Class A GPCR. In a further preferred embodiment, the class A (rhodopsin-like) GPCR is an odorant receptor, dopamine receptor, muscarinic receptor or an adrenergic receptor, more preferably an odorant receptor. The odorant receptor can be from any source as long as when expressed in a cell the N-terminus of the receptor is outside the cell and the C-terminus is inside the cell. Examples include, but are not limited to, a chordate receptor, a nematode receptor, or a biologically active variant or fragment of any one thereof. Examples of chordate receptors include, but are not limited to mammalian receptors, avian receptors and fish receptors.

In a preferred embodiment, the odorant receptor is a nematode receptor or biologically active variant or fragment thereof. In an embodiment, the nematode receptor is a *Caenorhabditis elegans* receptor, or biologically active variant or fragment thereof. Examples of odorant receptors that can be used to produce polypeptides of the invention and/or used in the methods of the invention are described in Buck and Axel (1991), Robertson (1998 and 2001), Aloni et al, (2006), Feldmesser (2006), Olender et. al. (2004a and b), Glusman et al, (2000a, 2000b and 2001), Fuchs et al. (2001), Pilpel and Lancet (1999), Sharon et at (1998), Zozulya et al. (2001), Niimura and Nei (2003), Lander et al, (2001), Zhang and Firestein (2002), Young et al. (2002), and Fredriksson and Schioth (2005). Furthermore, a comprehensive list of odorant receptors are available from the SenseLab website (http://senselab.med.yale.edu).

In other embodiments, the GPCR is a Class B or Class C receptor, with Class C being more preferred of these two embodiments.

In a particularly preferred embodiment, the G protein coupled receptor comprises seven transmembrane domains.

The bioluminescent protein can form part of the first, third, fifth non-transmembrane loops (domains) or the C-terminus of the G protein coupled receptor (or polypeptide of the invention). The acceptor molecule also can form part of the first, third, fifth non-transmembrane loops (domains) or the C-terminus of the G protein coupled receptor (or polypeptide of the invention). Each of these regions is intracellular when the G protein coupled receptor is expressed and present in a cell.

The acceptor molecule cannot be in the same region as the bioluminescent protein when part of the same molecule (namely, the same single polypeptide chain), however, the acceptor molecule can be in the equivalent region as the bioluminescent protein when the G protein coupled receptor is present as a dimer or higher multimer. For example, the bioluminescent protein can form part of the C-terminus of one subunit of the receptor, and the acceptor molecule can form part of the C-terminus of another subunit of the receptor. In this example, the subunit to which the label is associated can be the same or different, for instance the two subunits can be identical apart from one labelled with the bioluminescent protein and the other labelled with the acceptor molecule.

In one embodiment, the bioluminescent protein forms part of the third non-transmembrane loop of the GPCR subunit, and the acceptor molecule forms part of the fifth non-transmembrane loop. In an alternate embodiment, the acceptor molecule forms part of the third non-transmembrane loop of the GPCR subunit, and the bioluminescent protein forms part of the fifth non-transmembrane loop.

In another embodiment, the bioluminescent protein forms part of the first non-transmembrane loop of the GPCR subunit, and the acceptor molecule forms part of the third non-transmembrane loop. In another embodiment, the acceptor molecule forms part of the first non-transmembrane loop of the GPCR subunit, and the bioluminescent protein forms part of the third non-transmembrane loop.

In a preferred embodiment, the bioluminescent protein forms part of the fifth non-transmembrane loop of the GPCR subunit, and the acceptor molecule forms part of the C-terminus. In an alternate embodiment, the acceptor molecule forms part of the fifth non-transmembrane loop of the GPCR subunit, and the bioluminescent protein forms part of the C-terminus.

In another embodiment, the G protein coupled receptor comprises at least two subunits, where the bioluminescent protein forms part of the third non-transmembrane loop of a first subunit, and the acceptor molecule forms part of the fifth non-transmembrane loop of a second subunit. In an alternate embodiment, the acceptor molecule forms part of the third non-transmembrane loop of a first subunit, and the bioluminescent protein forms part of the fifth non-transmembrane loop of a second subunit.

In another embodiment, the G protein coupled receptor comprises at least two subunits, where the bioluminescent protein forms part of the first non-transmembrane loop of a first subunit, and the acceptor molecule forms part of the third non-transmembrane loop of a second subunit. In another embodiment, the acceptor molecule forms part of the first non-transmembrane loop of a first subunit, and the bioluminescent protein forms part of the third non-transmembrane loop of a second subunit.

In another embodiment, the G protein coupled receptor comprises at least two subunits, where the bioluminescent protein forms part of the fifth non-transmembrane loop of a first subunit, and the acceptor molecule forms part of the C-terminus of a second subunit. In an alternate embodiment, the acceptor molecule forms part of the fifth non-transmembrane loop of a first subunit, and the bioluminescent protein forms part of the C-terminus of a second subunit.

In another embodiment, the G protein coupled receptor comprises at least two subunits and the donor and acceptor molecule are in the same site of the first and second subunits respectively.

In an embodiment, the bioluminescent protein or acceptor molecule is located after the second amino acid of the fifth transmembrane domain and before the second amino acid before the beginning of sixth transmembrane domain. In another embodiment, the bioluminescent protein or acceptor molecule is located after about amino acid 8 after the fifth transmembrane domain or after about amino acid 22 after the fifth transmembrane domain. In a further embodiment, the bioluminescent protein or acceptor molecule is inserted about 10 or 12 amino acids before the sixth transmembrane domain. Most preferably, the bioluminescent protein or acceptor molecule is located in the middle of the third non-transmembrane loop (domain)

With regard to the C-terminus, it is preferred that about 5 to 25 amino acids of the natural C-terminus remain at the end of seventh transmembrane domain. Preferably, the bioluminescent protein or acceptor molecule is inserted after about the 16 or 20 amino acids after the seventh transmembrane.

Turning to the location of the bioluminescent protein or acceptor molecule in the first non-transmembrane loop (domain), it is preferred that said label is inserted about two amino acids after the end of first transmembrane domain and about two amino acids before the beginning of the second transmembrane domain. Most preferably, the bioluminescent protein or acceptor molecule is located in the middle of the first non-transmembrane loop (domain).

In a further embodiment, the bioluminescent protein can form part of the N-terminus, second, fourth, or sixth non-transmembrane loops (domains) of the G protein coupled receptor (or polypeptide of the invention). The acceptor molecule also can form part of the N-terminus, second, fourth, or sixth non-transmembrane loops (domains) of the G protein coupled receptor (or polypeptide of the invention), however, it cannot be in the same region as the bioluminescent protein when part of the same molecule. Each of these regions is extracellular when the G protein coupled receptor is expressed and present in a cell.

The GPCR may be a non-naturally occurring chimera of two or more different GPCRs. In particular, this enables a transduction cassette to be produced where portions of one receptor are always present in the chimera into which other portions of a wide variety of GPCRs are inserted depending on the compound to be detected.

In one embodiment, the subunit comprises the N-terminus and at least a majority of the first transmembrane domain of a first G protein coupled receptor subunit, at least a majority of the first non-transmembrane loop through to at least a majority of the fifth transmembrane domain of a second G protein coupled receptor subunit, and at least a majority of the fifth non-transmembrane loop through to the C-terminal end of the first G protein coupled receptor subunit.

In another embodiment, the subunit comprises the N-terminus through to at least a majority of the fifth transmembrane domain of a first G protein coupled receptor subunit, and at least a majority of the fifth non-transmembrane loop through to the C-terminal end of a second G protein coupled receptor subunit.

As used herein, the term "at least a majority" of a specified portion (domain) of a G protein coupled receptor, refers to at least 51%, more preferably at least 75% and even more preferably at least 90% of the specified region.

The skilled person can readily determine the N-terminal end, transmembrane domains, non-transmembrane loops (domains) and C-terminus of a G protein coupled. For example, a variety of bioinformatics approaches may be used to determine the location and topology of transmembrane domains in a protein, based on its amino acid sequence and similarity with known transmembrane domain of G protein coupled receptors. Alignments and amino acid sequence comparisons are routinely performed in the art, for example, by using the BLAST program or the CLUSTAL W program, Based on alignments with known transmembrane domain-containing proteins, it is possible for one skilled in the art to predict the location of transmembrane domains. Furthermore, the 3 dimensional structures of some membrane-spanning proteins are known, for example, the seven transmembrane G-protein coupled rhodopsin photoreceptor structure has been solved by x-ray crystallography. Based on analyses and comparisons with such 3D structures, it may be possible to predict the location and topology of transmembrane domains in other membrane proteins. There are also many programs available for predicting the location and topology of transmembrane domains in proteins. For example, one may use one or a combination of the TMpred (Hofmann and Stoffel, 1993), which predicts membrane spanning proteins segments; TopPred (von Heijne et al., 1992) which predicts the topology of membrane proteins; PREDATOR (Frishman and Argos, 1997), which predicts secondary structure from single and multiple sequences; TMAP (Persson and Argos, 1994), which predicts transmembrane regions of proteins from multiply aligned sequences; and ALOM2 (Klien et al., 1984), which predicts transmembrane regions from single sequences.

In accordance with standard nomenclature, the numbering of the transmembrane domains and non-transmembrane loops (domains) is relative to the N-terminus of the polypeptide.

Variants of *C. elegans* str-112 (SEQ ID NO:41) and/or str-113 (SEQ ID NO:42) which bind 2-pentanone include, but are not limited to, molecules which are at least 90% identical to str-112 (SEQ ID NO:41) and/or str-113 (SEQ ID NO:42), biologically active fragments which are at least 90% identical to str-112 (SEQ ID NO:41) and/or str-113 (SEQ ID NO:42), and fusion proteins thereof such as str-114/113 (SEQ ID NO:43). As the skilled person would appreciate, when determining the % identity, sections of the proteins comprising labels, such as the acceptor and donor in SEQ ID NOs 13, 14, 18, 27, 28 and 30, are preferably ignored.

Nucleic Acids

In one embodiment, the domain (or molecule of interest) is a nucleic acid. As the skilled addressee would be aware, there are many detection systems which rely on nucleic acid binding which would be adapted for use in the methods of the invention.

Molecular beacons (MBs) have been extensively researched in the construction of probes useful for detecting specific nucleic acids in homogenous solutions. MBs consist of a single stranded nucleic acid sequence that possesses a stem and loop structure and is labelled with BRET components at the 5' and 3' ends. The close proximity of the 5' and 3' ends cause energy transfer to occur. The target DNA sequence hybridises with the probe nucleic acid sequence forcing the BRET components to move apart and causing the BRET ratio to decrease. Although a combination of fluorophore-acceptor pairs have been investigated the method is flawed by requiring an excitation source which could cause autofluorescence of the nucleic acids. Replacing the fluorophore with a bioluminescent protein overcomes this problem.

In another example, an acceptor and donor can be conjugated to two different antisense oligonucleotides, each complementary to different portions of the same target nucleic acid sequence. The different portions of the target sequences are located in closely within the target nucleic acid sequence. BRET components are brought into close proximity upon hybridisation to the target nucleic acid resulting in an increase in the BRET ratio.

In a further example, in the absence of target nucleic acid, acceptor and donor labelled complementary oligonucleotide probes hybridise causing energy transfer. In the presence of target nucleic acid, the target and donor labelled compete to hybridise with the acceptor protein thus lowering the BRET ratio. The decrease in BRET ratio can be correlated with the amount of total nucleic acid present in the sample.

Uses

The present invention can be used to detect the presence or absence or concentration of a wide variety of analytes including small volatile and non-volatile organic molecules, macromolecules, and biological particles and cells. The invention is compatible with almost any biological recognition element that can be functionally coupled to a chemiluminescence transduction system, including G-protein coupled and other receptors, binding proteins, enzymes, peptides and nucleic acid molecules. Examples of uses of microfluidic methods and systems of the invention are described in Li and Lin (2009), Mark et al. (2010), Theberge et al. (2010), Mohammed and Desmulliez (2011), Esch et al. (2011), Yeo et al. (2011), Noh et al. (2011) and Godin et al. (2008).

In a particularly preferred embodiment, the analyte is an odorant. Typically, the odorant will be a volatile organic or inorganic compound or inorganic gas that may be detected by chemosensory odorant receptors of at least one organism. These may include amine- and/or sulphydrl-containing compounds, carboxylic acids, alcohols, aldehydes, alkanes, alkenes, aromatic compounds, esters, terpenes or terpene-derivatives, ethers, $CO_2$ etc. as well as compounds bearing combinations of these features.

Odorants may be indicative of some biological or chemical state of value or of interest to humans. Such indications may include:

The sensory appeal, quality or safety of food and beverages, pharmaceuticals or related materials.

The health, nutritional or exercise status of humans or animals.

The presence or absence of hazardous substances, including pathogens.

The progress or status of industrial processes.

An environmental contamination or state.

The sensory appeal, quality or safety of perfumes, fragrances or other cosmetics.

In a particularly preferred embodiment, the analyte does not bind the donor or acceptor domain.

In another embodiment, the method may be used for screening for a compound which binds the sensor molecule. As the skilled person would appreciate this allows the methods to be use in, for example, drug discovery and/or development. More specifically, the domain to which the analyte binds is a target for potential therapeutics. Thus, in this embodiment it is preferred that the domain bound by the analyte is a clinically important molecule such as, but are not limited to, an adrenergic receptor, a serotinin receptor, a dopamine receptor, metabotropic/glumtamte receptor, a GABA receptor, a vomeronasal receptor, a taste receptor, or a secretin-like receptor.

As another example, a method of the invention could be used to detect spoilage of milk such as ultra-high temperature (UHT) processed milk. In this example, the sensor molecule can be a molecule cleaved by a bacterial protease that causes, at least in part, milk spoilage. For instance, the sensor molecule may comprise a region of a milk protein, such as κ-casein, which is cleaved by the protease(s) labelled with the chemiluminescent donor domain and an acceptor domain.

As the skilled person would be aware, the present invention can also be mutliplexed. In this system, two or more different sensor molecules are provided which bind different compounds. Each different sensor molecule includes a different donor and/or acceptor molecule such that they emit at different wavelengths to enable the detection and quantification of different target compounds.

EXAMPLES

Example 1

Performance of a Hybrid BRET System in a Microfluidic System for Thrombin Cleavage Assay Materials and Methods
BRET System A combination of $BRET^1$ and $BRET^2$ techniques was used and referred to herein as hybrid BRET. Specifically, RLuc with native coelenterazine substrate was used as the bioluminescent donor and $GFP^2$ as the acceptor molecule. The donor and acceptor were linked by a peptide sequence containing the thrombin cleavage site (LQGSLVPR↓GSLQ (RG)) ($GFP^2$-RG-RLuc) and expressed in *E. coli*. Thrombin cleavage of the cleavage site resulted in a change in the hybrid BRET signal. The mechanism of BRET system is shown in FIG. 1A.

Materials $GFP^2$-RG-RLuc biosensor was expressed and purified as reported previously (Dacres et al. 2009a). The purified fusion protein was in thrombin cleavage buffer (10 mM Tris (pH 8.0), 100 mM NaCl, 1 mM EDTA). The final concentration of the native coelenterazine substrate (Biosynth) used for microfluidic based assays was 58.6 μM and 5 μM for plate-reader based assays. 1 unit (U)/μl thrombin protease (Amersham Biosciences) solution was prepared in 1× phosphate buffer saline (PBS).

Microfluidic Chip Fabrication and Experimental Set-Up

Simultaneous dual emission hybrid BRET measurements were carried out both in a microplate using a SpectraMax M2 spectrofluorometer (Molecular Devices) and in the microfluidics apparatus described below. Spectral scans of BRET constructs were recorded using the luminescence scan mode between 400 and 650 nm on addition of 5 μM native coelenterazine substrate to 1 μM of biosensor.

For the microchip BRET measurements, a simple Y-shape microchannel microchip (FIG. 1B), 70 μm wide and 50 μm high was fabricated from polydimethylsiloxane (PDMS) using standard photolithography. The chip design was completed in a commercial drawing package (Adobe Illustrator CS4) and the design pattern was printed on a transparency mask (5,080 dpi, Allardice). Master patterns of the microfluidic devices were fabricated using a laminar dry film resist (Shipley 5038). Multiple layers of resist were laminated at 113° C. onto a substrate of polished stainless steel. The channels were lithographically patterned using a collimated UV source ($\lambda$=350-450 nm) operated at 20 mJ/cm² and a transparency film mask. After exposure, the test pattern was developed in a 20% $Na_2CO_3$ solution.

The pattern in resist was subsequently replicated as a Nickel shim using an initial sputter deposition of 100 nm Ni followed by electroplating to a thickness of 150 μm. Then a 10/1 (w/w) ratio of PDMS and curing agent was poured over the shim, degassed and baked overnight at 75° C. The device was cut and peeled off the shim and then exposed to air plasma for 10 minutes. The PDMS was then immediately sealed with a glass slide; after baking for three hours at 75° C., the PDMS adhered strongly to the surface of the glass and the PDMS glass microchip was ready to use.

A schematic of the set-up for microfluidic measurement is shown in FIG. 1C. A neMESYS high pressure pump system (Cetoni, Germany) was used to pump the fluids from two SGE syringes (Supelco) with 50 μl capacity onto the microchip. The flow rates of both streams were 20 μl/h. The microchip was placed on a microscope (Nikon Eclipse TE2000-U) stage for visualization and measurement. A sapphire laser (488 nm, Coherent) was used to locate the detection spot. Emitted bioluminescence was collected with a 20× objective (Plan Fluor, Nikon). Bandpass filters (Nikon) of 515 nm-555 nm for $GFP^2$ and 430 nm-455 nm for RLuc were used for the two channels. De-magnification lenses (Nikon C-0.45×) were used to focus light emitted from each channel onto the photomultiplier tube (Hamamatsu H7421). Integration time was 200 ms for data acquisition for each channel of light. The measurement position was varied along the main channel starting at the first confluence of the input channels (x=0) to the end of microchip.

Thrombin Assay

Various concentrations of thrombin were added to purified $GFP^2$-RG-RLuc biosensor and incubated at 30° C. for 90 minutes. To measure the extent of thrombin cleavage the sample mixture following incubation and the native CLZ solution were pumped from separate syringes into the two inlet channels and allowed to flow through the main channel. Diffusion between the two streams induced a BRET reaction at the interface. Recombinant hirudin from yeast (Sigma)

was incubated with thrombin at room temperature for ten minutes prior to the protease assay.

Sodium Dodecyl Sulfate Polyacrylamide Gel Electrophoresis (SDS-PAGE)

To confirm complete thrombin cleavage of the GFP$^2$-RG-RLuc biosensor, SDS-PAGE analysis was carried out. Proteins (2.5 µg) were diluted in 1× sample loading buffer (Invitrogen) for SDS-gel electrophoresis in a 12% Bis-Tris gel with MOPS running buffer (NuPAGE, Invitrogen). Bands were stained with Fast Stain™ (Fisher) and then visualised.

Data Analysis

Using the microplate spectrometer, hybrid BRET ratios were calculated as the ratio of bioluminescence emissions measured at 500 nm and 470 nm. Using the microchip system, the hybrid BRET ratio was calculated as ratio of the long wavelength emission (515 nm-555 nm) to the short wavelength emission (430 nm-455 nm) (Pfleger and Eidne, 2006). To allow comparison between the two different detection systems, the Hybrid BRET ratios were normalized by expressing them as a multiple of the BRET ratio without added thrombin, in the same measurement system. All data are reported as means±standard deviation (SD). Two-tailed unpaired t-tests were performed using Graphpad prism (version 5.00 for Windows, Graphpad Software, San Diego, Calif., USA). Statistical significance is defined as p<0.05.

Results

Effect of Thrombin on BRET Spectra and Ratio

The bioluminescent spectrum of the thrombin biosensor before thrombin treatment was bimodal with a peak at 470 nm representing RLuc emission and a second peak at 500 nm representing GFP$^2$ emission (FIG. 2A). This indicates energy transfer from the excited state of native coelenterazine to GFP$^2$. Upon thrombin cleavage the green component of the spectrum was reduced, demonstrating that thrombin cleavage of the thrombin biosensor had reduced the efficiency of energy transfer between donor and acceptor.

SDS-PAGE (FIG. 2B) confirmed that following thrombin treatment, the fusion protein was cleaved into two components with molecular weights of 32.4 KDa and 36.4 KDa (Lane 5, FIG. 2B) corresponding to His-tagged GFP$^2$ and untagged RLuc. Pre-incubation of the BRET biosensor with hirudin inhibited the formation of the two components demonstrating thrombin specificity (Lane 6).

The effect of thrombin on the biosensor cleavage was quantified using the change in BRET$^H$ ratio. Following thrombin cleavage, the BRET$^H$ ratio decreased significantly (P=0.0009), by approximately 32%, from 1.11±0.06 to 0.75±0.04. The hybrid BRET ratio of 0.79±0.05 following thrombin cleavage was not significantly different (P=0.3309) from those obtained by mixing 1 µM each of RLuc and GFP$^2$ (FIG. 3, control). Pre-addition of hirudin prevented the thrombin induced reduction in the BRET$^H$ ratio of 1.08±0.14. This was not significantly different to the ratio measured without thrombin (P=0.7663).

On-Chip BRET Measurement

To optimize the flow conditions for detecting the BRET biosensor, a series of experiments were carried out to image and quantify the BRET luminance at different locations, flow rates and biosensor concentrations (FIG. 5). In the initial stage of contact of the two fluid streams of fusion protein and substrate, the diffusion layer was narrow and only a small volume of the liquid emitted bioluminescence (data not shown). The intensity of the bioluminescence was also low (~457) but significantly higher than the background (~2.3). From x=1 to 5 mm, the bioluminescence intensities remained almost constant but there was a significant increase at x=7 mm. This increase may reflect increased mixing in the region. Regardless of the intensity of the bioluminescence, the BRET$^H$ ratio remained almost constant (~5.2) throughout the entire measurement region. To benchmark the on-chip measurements, the BRET ratios were compared with the microplate data measured using a commercial BRET detection instrument. The relative changes of BRET ratio, i.e. BRET ratio measured with thrombin vs that measured without, are very consistent between microchip and microplate measurements (to within ±4%).

The effect of varying flow rate and biosensor concentration on the BRET$^H$ ratio was also investigated (FIG. 6). The flow rate dependence was measured at two locations, x=0 and 4.9 mm (FIG. 6a). At x=0, the BRET$^H$ ratio was also constant (to within ±1.1%) for the range of flow rates studied, i.e. 20-60 µl/h. At x=4.9 mm, there was a slightly larger variation (to within ±2%) of the BRET ratio due to the change in flow conditions. However, the overall uncertainty between the two measurement locations was within ±5%. FIG. 6b shows hybrid BRET ratio as a function of the biosensor concentration. Even though the uncertainty for low protein concentration was relatively high (e.g. standard deviation=7.7% at 1.49 µM biosensor concentration), the overall variation in mean BRET$^H$ ratios varied less than with biosensor concentration, i.e. a standard deviation of 2.7%. The small variation in the BRET$^H$ ratio under different measurement conditions is an important finding since it means that the completeness of the BRET$^H$ reaction is not crucial for quantification as long as bioluminescence can be measured. Although more complete mixing would be predicted to increase the luminosity of the system our data imply that it would have little effect in BRET$^H$ ratio. This potentially simplifies the design requirements of microfluidic devices for BRET-based detection, at least for the levels of thrombin concentration considered in the study.

Effect of Thrombin Concentration

Using a flow rate of 20 µl/h and biosensor concentration 2.972 µM (FIG. 6) with the measurement fixed at x=2.1 mm (FIG. 5) we compared the microchip and the microplate systems for measuring thrombin using a range of thrombin concentrations (FIG. 7). The BRET$^H$ ratio changed linearly with increasing concentrations of thrombin up to 0.24 nM for microfluidic measurements and 2.7 nM for microplate measurements. At higher concentrations, the change of BRET ratio is much less pronounced due to the saturation of thrombin. In the low thrombin concentration regions, calibrations were linear with R$^2$ values exceeding 0.995. Comparison of the gradients of the calibrations revealed that the microfluidic method is 4.7 times more sensitive to changing thrombin concentrations than the microplate method. The detection limits for thrombin are 27 pM for the microchip-based technique compared to 310 pM using the microplate-based technique. The microchip-based BRET$^H$ system has a detection limit intermediate between the values calculated for the BRET$^2$ and BRET$^1$ microplate-based assays of 15 pM and 53 pM, respectively (Dacres et al. 2009a).

Conclusion

Bioluminescence resonance energy transfer method has been demonstrated for the first time in a flow format using a fluid phase thrombin-sensitive biosensor. The BRET$^H$ technique used is a combination of BRET$^1$ and BRET$^2$ which allows testing of the BRET$^2$ components with measurable luminosity. The BRET reaction and detection were carried out in a Y-shape microchannel network in a microchip. Experiments quantified the effects of measurement location, flow rate and biosensor concentration. These factors affected the bioluminescence intensities in both optical channels but not the BRET$^H$ ratio. The microchip-based technique showed an improved sensitivity for detecting thrombin compared to an equivalent microplate-based technique measured with a commercial instrument. The detection limits for thrombin were 27 pM for the microchip-based technique compared to 310 pM using the microplate-based technique.

Example 2

Performance of BRET$^2$ in a Microfluidic System

In a BRET$^2$ system, *Renilla* luciferase (RLuc) with coelenterazine 400a (CLZ400A) substrate was used as the photon donor and GFP$^2$ was used as the acceptor molecule. As the luminescence of BRET$^2$ is 100-fold smaller than that of the BRET$^{1.5}$, the BRET$^2$ reaction requires efficient mixing at optimal temperature, detection chamber size, flow rates and concentrations to produce highest bioluminescence signal. Thus, this system is used to evaluate different mixing mechanisms (FIG. 8), reaction chamber designs and reaction conditions.

PDMS chips with a Y-shaped microchannel with three mixing elements (FIG. 8), with a rectangular cross section in the microchannels (200 µm in width and 30 µm in height) was used to monitor BRET$^2$ assays. The detection chambers with different diameter and height were located at the end of the microchannels. The emitting bioluminescence was collected by a multimode optical fiber located underneath the detection chamber. The emissions will be split by dichroic block and going through two band pass filters corresponding to emission band of the donor (430 nm-455 nm) and the emission band of the acceptor (515 nm-555 nm) before going into two corresponding photomultiplier tubes (Hamamatsu H7421).

The method involves flowing the protein solution in one the inlet of the Y-shaped channel and flowing coelenterazine 400a substrate in another inlet of the channel.

The method requires efficient mixing of the protein flow and the substrate flow by the passive mixing elements at a suitable flow rate.

The method aims to collect as high bioluminescence signal as possible by varying mixing elements, chamber size, protein and substrate concentration, flow rate, temperature etc. As a result, the optimum microfluidic mixing chip design and reaction conditions will be obtained and be translated into other BRET assays.

In order to enhance the efficiency, a fluidic chip integrated with a large optical detection chamber is used. By locating an optical fibre under the chamber the light emitted from BRET$^2$ reaction is collected and transmitted to the detection sub-system (FIG. 9). This approach ensures minimal losses and therefore high sensitivity and allows simultaneous capture of minute changes in emission levels at two wavelengths.

The inventors tested the detection sensitivity using a sensor protein capable of detecting a model protease (thrombin). The results indicated five fold improvement in BRET$^2$ detection sensitivity in comparison to commercially available microplate readers. In these tests we also confirmed that the detection limit was less than 20 pM.

FIG. 10 shows sample data from the sensitivity tests. Emission counts for GFP and Rluc are indicated with green (top line in the first panel, bottom line in the second panel) and blue lines (bottom line in the first panel, top line in the second panel) respectively. The raw data are shown for the no thrombin blank and the condition with 270 pM thrombin. The ratio between emission levels (BRET$^2$ ratio:GFP/RLuc) indicates an approximately tenfold change in response to digestion of the sensor with 270 pM of thrombin.

FIG. 11 shows the response of the sensor when the thrombin concentration is varied from 0 to 270 pM. The figure also indicates results when the same experiment was repeated with a commercially available instrument. The sensitivity (slope) is five fold higher in the microfluidic system. The calculated limit of detection is less than 20 pM.

The BRET$^2$ ratio was measured with a two-inlet microfluidic device upon mixing sensor protein (1 µM) with a preparation involving thrombin (540 nM) and substrate (12.5 µM). Control experiment was carried out by mixing sensor protein (1 µM) with substrate (12.5 µM). Approximately 75% decrease in BRET$^2$ signal was measured for on-chip reaction at input flow rate of 50 µL/hr (FIG. 12).

Example 3

Performance of a BRET$^2$ Based Odorant Sensor in a Microfluidic System

The BRET$^2$ system is more suitable for measuring ligand-induced molecular re-arrangements in GPCRs compared to FRET (WO 2010/085844) or standard BRET. This is because the 6.8 nm separation of the BRET pair in preferred GPCR constructs (Dacres et al., 2010 and 2011) is well matched to the Förster distance of the BRET$^2$ donor and acceptor combination. However, one tradeoff is the low quantum yield for the RLuc donor when using BRET$^2$ chemistry. This results in fewer photons being available for detection. The use of RLuc2 and 8 mutations has been shown to improve the quantum yield (De et al., 2007) of the BRET$^2$ system whilst only having minimal effects on the Förster distance of the BRET$^2$ system (FIG. 1). The present inventors replaced RLuc with RLuc2 or RLuc8 in a OGOR sensor in an attempt to increase photon yield without detriment to the sensitivity of the odorant assay. FIG. 18 shows the transduction scheme for diacetyl detection using OGOR2 incorporating RLuc2.

Materials and Methods

Construction of BRET$^2$-GPCR Sensors Incorporating Tagged *C. elegans* Odorant Receptors Chimaeric BRET$^2$ tagged odorant receptors have the BRET$^2$ components inserted into the third intracellular loop (IC3) and at the C-terminus of the *C. elegans* odorant receptor with green fluorescent protein, GFP$^2$ at IC3 and *Renilla* luciferase, RLuc at the C-terminus of the protein (OGOR). Using site-directed mutagenesis the RLuc2 mutations were introduced into the pYES-DEST-52 OGOR sequence. Primers 1 and 2 (Table 3) were used to introduce the mutation C124A and primer pair 3 and 4 was used to introduce the M185 V mutation to make the construct named OGOR2 (FIG. 18, SEQ ID NO:1, SEQ ID NO:2).

TABLE 3

Primers for introducing the RLuc2 mutations. C124A and M185V, into the pYES-DEST52-OGOR sequence.

| Primer name | Sequence |
| --- | --- |
| 1 C124A | CACGACTGGGGCGCCGCCCTGGCCTTCCACTAC (SEQ ID NO: 7) |
| 2 C124A Antisense | GTAGTGGAAGGCCAGGGCGGCGCCCCAGTCGTG (SEQ ID NO: 8) |

TABLE 3-continued

Primers for introducing the RLuc2 mutations.
C124A and M185V, into the pYES-DEST52-OGOR
sequence.

| Primer name | Sequence |
|---|---|
| 3 M185V | CTTCTTCGTGGAGACCGTGCTGCCCAGCAAGATC (SEQ ID NO: 9) |
| 4 M185V Antisense | GATCTTGCTGGGCAGCACGGTCTCCACGAAGAAG (SEQ ID NO: 10) |

OGOR2 Sample Preparation

Yeast colonies were inoculated in 10 mL SCMM-U (*S. cerevisiae* minimal media, composition per 200 mL: 1.34 g yeast extract without amino acids and 0.38 g yeast supplementation media without uracil) supplemented with 2% glucose and incubated overnight at 28° C. An aliquot of the overnight culture was used to inoculate SCMM-U supplemented with 2% raffinose and 2% galactose to a final $O.D._{600}$ of 0.4 and incubated for an additional 72 h at 15° C. with shaking at 200 rpm.

Cell cultures were centrifuged at 1500×g for 5 minutes at 4° C. Cells were resuspended in 1 mL of sterile water and centrifuged for 1 minute at 10,000×g. Cells were resuspended in 4 mL phosphate buffer solution (PBS). The cells were lysed by French press (~18000 psi) and cellular debris was removed by centrifugation at 15000×g (4° C.) for 15 minutes. Following this the supernatant fraction was centrifuged at 40,000 rpm (Beckman Coulter L-80 ultra-centrifuge) for 1 hour at 4° C. The supernatant was decanted and the membrane pellet was resuspended in 1 mL of PBS and stored at 4° C. for 48 hrs.

Diacetyl Assay

All ligand solutions were prepared directly in water. The OGOR concentration was normalized using $GFP^2$ intensity at 510 nm Assays were carried out in 96-well plates (Perkin-Elmer) in a total volume of 100 μL in phosphate buffered saline. OGOR was incubated with each ligand for 45 minutes at 28° C. in wells sealed with Topseal-A™ (Packard).

Plate-Reader Measurements

Following the incubation, Coelenterazine 400a substrate (Biosynth) was added to a final concentration of 5 μM. Simultaneous dual emission $BRET^2$ measurements were recorded with a POLARstar OPTIMA microplate reader (BMG LabTech) using the $BRET^2$ emission filter set, comprising an RLuc/Clz400a emission filter (410 nm bandpass 80 nm) and a $GFP^2$ emission filter (515 nm bandpass 30 nm), with gains set set to 3300 and 4095, respectively, for the two channels, with an integration time of 0.5 s.

Endpoint On-Chip Microfluidic Measurements

Endpoint microfluidic assays were carried out on-chip in two inlet microfluidic mixer devices integrated with an optical detection chamber. Coelenterazine 400a substrate (Biosynth) was prepared to a final concentration 12.5 μM and introduced in first inlet. OGOR and OGOR2 membrane pellets were resuspended in 1 mL of PBS, diluted as required and incubated at 28° C. for 45 minutes with diacetyl solution at concentrations ranging from 1 aM-1 μM. The preparation was introduced in the second inlet. On-chip mixing was initiated with an input flow rate of 400 μl/hr for each inlet. $BRET^2$ measurements were recorded using two photomultiplier tubes, one equipped with an RLuc/Clz400a emission filter (410 nm bandpass 80 nm) and the other with $GFP^2$ emission filter (515 nm bandpass 30 nm). The optical output was collected using an optical fiber with 1 mm core diameter aligned with an on-chip optical detection chamber.

Real-Time On-Chip Microfluidic Measurements

On-chip real-time measurements were carried out in a three-inlet microfluidic mixer device integrated with an optical detection chamber. The first inlet was used to introduce Coelenterazine 400a substrate (Biosynth), which was prepared to give a final concentration of 12.5 μM in PBS. The second inlet contained diacetyl (2,3-butanedione) diluted to give a final concentration of 1 fM in PBS, or PBS only as a control. The third inlet was used to introduce sensor protein suspension, which was prepared by resuspending the membrane pellet describe above in 1 mL of PBS and further diluting as required. The on-chip mixing was initiated by using input flow rates ranging from 50-400 μl/hr. $BRET^2$ measurements were recorded using two photomultiplier tubes, one equipped with an RLuc/Clz400a emission filter (410 nm bandpass 80 nm) and the other with $GFP^2$ emission filter (515 nm bandpass 30 nm). The optical output was collected using an optical fiber with 1 mm core diameter aligned with an on-chip optical detection chamber.

Analysis $BRET^2$ signals were calculated as the ratio of emission intensity at 515 nm to that at 410 nm. All data are reported as the mean±standard deviation (SD) or mean±standard error of the mean (SEM) as described in the text. Curves were fitted with log [agonist] vs response curves with variable slopes following normalization of data, using Graphpad Prism version 5.03 for Windows. Two-tailed unpaired t-tests were carried out in Graphpad prism. Statistical significance was defined as p<0.05.

Results

Intensity

Introducing the RLuc2 mutation into OGOR increased the bioluminescence intensity by a factor of approximately ~150 from 1766±125 RLU for OGOR to 272886±26754 RLU for OGOR2 (FIG. 19). This mutant version of OGOR therefore showed potential for facilitating $BRET^2$ detection of odorant binding by OGOR2 on a microfluidic chip. This prediction was confirmed by on chip measurements. The RLuc2 mutation increased the bioluminescence intensity by a factor of approximately ~126 from 6.45±2.9 RLU to 809.74±116RLU (FIG. 20).

Demonstration of Odorant Binding by OGOR2 in a Multi-well Plate

There was a 21.4% decrease in $BRET^2$ signal upon addition of 1 μM diacetyl to membrane preparations containing OGOR2 (FIG. 21) in the wells of a microplate. The diacetyl-induced change in the $BRET^2$ signal is significantly different (P=0.0136) from the control response to water. The percentage change in the signal in response to diacetyl is smaller than seen with the original OGOR sensor (32%) incorporating native RLuc. However, there was less variance in the blank measurements for OGOR2, 1.0±7.0% (n=3) compared with 1.0±13.5% (n=4) for OGOR. Therefore the OGOR2 sensor is potentially capable of detecting lower concentrations of diacetyl than the OGOR sensor because detection limit is calculated as the blank signal ±3× S.D.

The OGOR2 response to diacetyl (FIG. 22) is dose-dependent, with a linear range (spanning six log units, from $10^{-18}$ to $10^{-12}$ M (FIG. 22). The calculated $EC_{50}$ value is 11.4 aM diacetyl. This is two orders of magnitude lower than for the OGOR response in a microwell, suggesting improved sensitivity for diacetyl.

Detection of Diacetyl Binding by OGOR2 Using a Microfluidic Endpoint Assay

Following incubation of 10 fM diacetyl with membrane suspensions containing OGOR2, microfluidic on-chip measurements showed a 36.9% decrease in BRET$^2$ signal (FIG. 23). The decrease in the BRET$^2$ signal was 1.5 fold greater than equivalent measurements made using a plate reader (FIG. 21). This indicates that microfluidic measurements using the OGOR family of biosensors are potentially more sensitive, sensu stricto, than plate reader measurements.

The concentration-dependent response of OGOR2, spans 2 log units from 10-18 to 10-16 M (FIG. 24). The calculated $EC_{50}$ value is approximately ~10 aM diacetyl. This level is in good agreement with plate-reader measurements (FIG. 22).

Real-Time On-Chip Detection of Odorant Binding by OGOR2 with a Microfluidic Device Real-time on-chip measurements showed a 27.4% decrease in the BRET$^2$ ratio following on-chip mixing of 1 fM diacetyl with 290 nM of protein and 12.5 µM substrate at input flow rates of 50, 100, 200 and 300 µl/hr (FIGS. 25 and 26).

Example 4

Performance of a BRET$^2$ Based Periplasmic Binding Protein Sensor in a Microfluidic System Periplasmic binding proteins (PBPs) form a large and diverse family of soluble proteins found in bacteria. PBPs bind a diverse range of chemically disparate species including carbohydrates, amino acids, and neurotransmitters, metals and ions to name a few (Medintz et al., 2006). Although PBPs are unrelated at the primary sequence they all undergo a large ligand-induced conformational rearrangement commonly referred to as the 'venus-fly-trap' mechanism (Sharif et al., 1992 and 1993; Spurlino et al., 1991).

The measured distance between a FRET tagged N and C terminus of MBP of 6.93 nm (Park et al., 2009) is of a similar scale to the measured distance within the GPCR suggesting that BRET may be a better option compared to FRET for measuring distance in this range. Measurement of ligand binding by a PBP on a microfluidic chip could lead to a generic transduction platform with a wide range of applications areas including security, food and drink quality control, environmental and health-care. The inventors chose MBP as the initial test of this concept because it is a well-characterised member of the PBP superfamily and potentially representative of all PBPs. The BRET$^2$ transduction mechanism for maltose binding by periplasmic protein MBP is shown in FIG. 27. This sensor is a proof-of-concept for all PBPs with a similar structure and/or ligand binding mechanism to MBP. It is well known that the affinity of MBP-based biosensors for maltose can be altered by targetted mutations of the MBP domain. A similar approach is applicable to other PBPs.

Materials and Methods
Construction of BRET Proteins

RLuc2 was amplified by polymerase chain reaction (PCR) and cloned into pGEM®-T Easy vector (Promega, Australia). This resulted in a BstBI site being introduced downstream of the amplified gene and a XhoI restriction site directly upstream from the amplified gene. DNA sequencing confirmed the correct amplicon sequence. The amplicon was inserted into the BstBI and XhoI sites of pRSET GFP$^2$-FL1-RLuc (Dacres et al., 2010) replacing RLuc to give pRSET GFP$^2$-FL1-RLuc2.

MBP was amplified and ligated into the pGEM®-T Easy vector. During this process, a BstBI site was inserted upstream of the amplified gene and a PstI site downstream. MBP was restriction cloned into the PstI and BstBI sites of the pRSET GFP$^2$-FL1-RLuc2 replacing the FL1 sequence with MBP to generate pRSET GFP$^2$-MBP-RLuc2.

The W140 mutation was introduced into pRSET GFP$^2$-MBP-RLuc2 using site-directed mutagenesis (Stratagene) using primers C1 (CAGATGTCCGCTTTCGCGTATGC-CGTGCGTAC) (SEQ ID NO:11) and C2 (GTACGCACG-GCATACGCGAAAGCGGACATCTG) (SEQ ID NO:12). Nucleotide and amino acid sequences for BRET$^2$ tagged MBP receptor provided as SEQ ID NOs: 3 to 6).

Expression and Purification of BRET$^2$ Proteins

Proteins were expressed in *E. coli* strain BL21 DE3 (Novagen). An overnight culture was grown from a single colony in LB (10 g tryptone, 5 g yeast extract, 5 g NaCl (pH 7.4)) containing 100 µg/mL ampicillin and 2% glucose at 37° C., 200 rpm. Expression was induced by inoculating 500 mL LB containing 100 µg/mL ampicillin to an $A_{600}$ of 0.1 and incubating at 37° C. (200 rpm) for 3.5 hours followed by overnight incubation at 22° C. (200 rpm). Cells were harvested 24 hr after inoculation.

For protein purification, cells were harvested by centrifugation at 4335×g (4° C.) for 15 minutes and resuspended in equilibration buffer (50 mM sodium phosphate buffer, 300 mM NaCl, pH 7.0). The cells suspension was passed through a homogeniser (Avestin emulsiflex C3 (ATA Scientific, Australia)) at a pressure of ~22000 psi and the soluble protein fractions were isolated by centrifugation at 15000×g (4° C.) for 15 minutes. Proteins were purified using cobalt affinity chromatography according to the supplied instructions (BD Talon (BD Biosciences, Clontech, Australia)). Following elution of the purified protein with 150 mM imidazole, the sample was dialysed against 50 mM Tris (pH 8), 100 mM NaCl, and 1 mM EDTA using a cellulose membrane (12,000 molecular weight cut off (Sigma)). Aliquots of 500 µL protein were snap frozen on dry ice and stored at −80° C. Protein concentrations were determined by absorbance at 280 nm and calculated according to the method of Gill and von Hippel (1989).

Spectral Scans

All spectral scans were recorded with a SpectraMax M2 plate-reading spectrofluorometer (Molecular Devices, Australia). The reactions were carried out in 96-well plates (Perkin-Elmer, Australia). Bioluminescence scans of BRET$^2$ constructs were recorded using the luminescence scan mode scanning between 360 and 650 nm with 20 nm intervals.

End-Point On-Chip Microfluidic Measurements

On-chip measurements were carried out with microfluidic mixers with two inlets, a passive micromixer and an integrated optical detection chamber. BRET$^2$ measurements were recorded by using two photo multiplier tubes one equipped with an RLuc/Clz400a emission filter (410 nm bandpass 80 nm) and the other with a GFP$^2$ emission filter (515 nm bandpass 30 nm). The optical emission was collected by using an optical fiber with 1 mm core diameter aligned with on-chip optical detection chamber through a dichroic mirror.

Real-Time On-Chip Microfluidic Measurements

Real-time on-chip measurements were carried out with microfluidic mixers with three inlets, a passive micromixer and an integrated optical detection chamber. BRET$^2$ measurements were recorded by using two photo multiplier tubes one equipped with an RLuc/Clz400a emission filter (410 nm bandpass 80 nm) and the other with a GFP$^2$ emission filter (515 nm bandpass 30 nm). The optical emission was collected using an optical fiber with 1 mm core diameter aligned with on-chip optical detection chamber through a dichroic mirror.

BRET Protein Assays

1 µM purified protein was used for all the energy transfer assays (final volume of 100 µL). 1 µM purified protein was prepared by diluting the protein in phosphate buffer solution (PBS, 0.058M $Na_2H_2PO_4$, 0.017 $NaH_2PO_4$, 0.068 M NaCl (pH 7.4)). Purified protein was incubated with the sugar dissolved in double deionised water or water for 30 minutes at 28° C. Following incubation 16.67 µM coelenterazine 400a was added and the signal was recorded immediately.

On-Chip BRET Protein Assays

For on-chip assays 1 µM purified protein was incubated with 1 mM maltose solution at 28° C. for 40 minutes. The preparation was then mixed on-chip with 5 µM coelenterazine 400a and the optical signal was recorded from the detection chamber. The control experiments was carried out by incubating protein preparations with water and mixing on the chip under the same conditions. The results were compared to determine the percentage change in $BRET^2$ signal upon addition of maltose and extended to determine the maltose sensitivity.

Real-Time On-Chip BRET Protein Assays

For real-time assays the protein preparation, maltose and the substrate were mixed on the chip simultaneously. 1 µM purified protein was mixed with 1 mM maltose solution and 5 µM coelenterazine 400a substrate solution. The optical signal was recorded from the detection chamber. The on-chip reaction time was controlled by varying the flow rate. The change in the $BRET^2$ signal was measured for different reaction times and results were compared with a control experiment with water.

BRET Ratio Determinations

BRET ratios were calculated as the ratio of maximum acceptor emission intensity to maximum donor emission intensity.

Real-Time On-Chip Detection of Maltose

A y-shaped chip with two input channels and a serpentine common channel of length 18 mm was used. The cross-sectional dimensions of the common channel were 0.2 mm×0.035 mm. The BRET reaction chamber was Ø=4 mm and H=1 mm. There was no mirror on the upper surface of the chamber. Light was captured and transferred to the standard dichroic detector using a bifurcated light guide with input (trunk diameter of 6 mm and NA=0.59). PMT gate time was 500 milliseconds. Two different flow rates were tested: 200 µL per hour and 400 µL in the common channel.

Input A was prepared to contain 1 µM maltose and 31.25 µM Clz400a substrate or in the case of the negative control, 31.25 µM Clz400a substrate only. Input B contained 1 µM GMR sensor. A and B were pumped into separate arms of the Y-shaped microfluidic chip at input flow rates of 100 µL/hour or 200 µL/hour to give common channel flow rates of 200 µL/hour or 400 µL/hour, respectively. Total residence times were estimated at approximately 230 seconds in the first case and 115 seconds in the latter case. $BRET^2$ ratios were determined on the average data collected from 200-250 seconds after flow was commenced.

Data Analysis

All data analysis was carried out using GraphPad Prism (version 5 for Windows, Graphpad Software, San Diego, Calif., USA). All data will be reported as means±standard deviation (SD) unless otherwise stated in the text. Two-tailed unpaired t-tests will be performed using Graphpad prism. Statistical significance is defined as p<0.05.

Results

Maltose Detection by MBP BRET Ratio—Plate Reader Assay

The selectivity of the BRET tagged MBP protein was determined by testing the response to a range of sugars including monosaccharides, disaccharides and trisaccharides (FIG. 28). Only maltose (P=0.001) and maltotriose (P=0.02) produced significant (P<0.05) changes in the BRET signal from the BRET tagged MBP. The BRET biosensor did not respond to glucose, fructose, sucrose or raffinose. Fehr et al. (2002) demonstrated that the FRET biosensor was able to detect maltose and a range of maltose oligosaccharides but did not specifically recognise any pentoses, hexoses, sugar alcohols, disaccharides or trisaccharides that do not contain the α-1,4-glucosidic link. The amplitude of the change in BRET ratio decreased from 29.65% to 17.03% with increasing length of the maltose chain from two units (maltose) to three (maltotriose) (FIG. 28). This is in agreement with reduced closing movement in the presence of larger α 1,4-oligomaltoside chains as demonstrated by electroparamagnetic resonance (EPR) studies (Hall et al., 1997) and FRET measurements (Fehr et al., 2002). Comparison of the relative size of the $BRET^2$ response to that of the FRET response reported in the literature (Fehr et al., 2002) demonstrated that substitution of BRET components for FRET components can increase the dynamic range of the biosensor resulting in signal changes of 29.65±1.11% for BRET compared to ~12% for FRET (Fehr et al., 2002). The inventors expect the signal change for classic $BRET^1$ would be of the same order as that for FRET, based on the similarities in Forster distance.

Introduction of the W140A mutant into $GFP^2$-MBP-RLuc2 abolished the $BRET^2$ response to maltose (FIG. 28). No significant difference (P=0.63) was observed between the $BRET^2$ response to either water or maltose. The W140A mutant has a dissociation constant higher than 100 mM for maltose and was previously used as a control for the FRET tagged MBP when applied to monitoring the uptake of maltose into yeast (Fehr et al., 2002). The lack of response of the W140A mutant to maltose indicates that the effect of maltose on the $BRET^2$ ratio of $GFP^2$-MBP-RLuc2 is not due to a direct interaction between maltose and the BRET components themselves. These results confirm the potential suitability of the $GFP^2$-MBP-RLUC2 (GMR) and similar sensors in a $BRET^2$ based microfluidic chip assay.

Response Time

The $BRET^2$ response increased with increasing incubation time until 30 minutes when the response reached a maximum (FIG. 29). Thirty minutes was used for further assays. In the present microplate assay format it is not possible to record the $BRET^2$ response in real-time but real-time maltose assay could be carried out using a microfluidic chip format.

Sensitivity

The $BRET^2$ tagged MBP biosensor was capable of quantifying different concentrations of maltose spanning three log units ranging from to $1\times10^{-8}$ M to $3.16\times10^{-6}$ M with an $EC_{50}$ of $3.71\times10^{-7}$ M (FIG. 30a). The response of the FRET tagged MBP receptor is linear only over two log units ranging from 0.26-21.12 µM with an $EC_{50}$ of 3.24 µM.

On-Chip Assay Measurements

Sensitivity assays were carried out on a two input microfluidic mixing device (FIG. 8b) with a serpentine common channel of L≈18 mm. The BRET reaction chamber was Ø=4 mm and H=1 mm with no mirror. A bifurcated light guide was used with a 6 mm trunk and NA=0.59.1 µM GMR sensor was incubated with maltose at concentrations ranging from $10^{-9}$ to $10^{-3}$ M for 40 min at 28° C. The incubated sample and 31.25 µM Clz400a substrate were each pumped onto the chip at input flow rates of 400 µl/hr. The trunk end of the light guide was used to collect signal from the BRET reaction chamber. Two branches of the light guide were directed toward to two sets of filter blocks (410/80 for blue, 515/30 for green) in front of two PMTs. The BRET$^2$ signal was measured at each concentration. The experiment was repeated on each of three days, using the same batch of GMR sensor. Nine chips were used, one for each concentration tested, across all three days. The log concentration response curve for on-chip detection was effectively identical to that of the previous plate based measurements as was the $EC_{50}=2.2\times10^{-7}$M (FIG. 30b).

The specificity of the sensor for maltose over the saccharides glucose and sucrose was investigated on chip. The amplitudes of the emissions were high with Rluc/Clz400a signals in the range of 10000 to 25000 counts/gate (500 ms) and GFP2 signal in the range of 2000 to 10000 counts/gate (500 ms). In the absence of analyte, the BRET$^2$ ratio was 0.225. Binding of maltose (FIG. 52) resulted in a large change in BRET$^2$ ratio with a mean BRET$^2$ ratio of 0.35 for 0.1 mM maltose, an increase over the no sugar control of 52%. Reactions with glucose and sucrose resulted in 7 and 15% increases in BRET$^2$ ratio, respectively, confirming that the selectivity of the BRET$^2$-based sensor for maltose is maintained in a microfluidic format.

Real-Time On-Chip Detection of Maltose

As the inventors have previously shown for protease and volatile detection, the invention is capable of mixing sample with sensor and substrate on chip, so that the entire detection reaction can be performed in a continuous flow format on the chip. The inventors demonstrated that this works with three inputs: sample, sensor and the coelenterazine 400A substrate using OGOR2 sensor and diacetyl (FIG. 26) and using two inputs for thrombin (see, for example, FIG. 51). The inventors extended this work to show that the same process works with the BRET-based maltose sensor. In this case, for convenience, the inventors also used a two input microfluidic chip. The coelenterazine substrate and a sample solution containing maltose (or a negative control without maltose) were premixed and pumped into one input and the GMR sensor solution was pumped into the other input.

Signals were detected approximately 40 seconds after initiating flow at both flow rates but stabilised more quickly (60 seconds vs approximately 130 seconds) in the case of the faster flow rate (200 µL per hour inputs) (FIG. 67). Total luminance was strong and easily detected 1000-1500 counts/gate for Rluc/Clz400a and 6000-7000 counts/gate for GFP$^2$ at 100 µl/hr or 2000-3000 counts/gate for Rluc/Clz400a and 7000-9000 counts/gate for GFP$^2$ at 200 µl/hr.

Once stabilised, 1 µM maltose was easily distinguished from control at both flow rates (FIG. 64), with the slower flow rate giving a change in BRET$^2$ ratio of ≈20% and the faster flow rate showing a change of ≈27%.

Example 5

Comparison of Bioluminescent Signal Collection with and without Fiber Optical Switch One of the highly preferred requirements of the instrument for use in the invention is multiplexing, meaning the instrument must be able to detect several analytes nearly at the same time (i.e. with very small time delay between one analyte to the next one). To reduce the cost and space as well as weight of the instrument, optical fiber switch could be used to enable multiplexing. In an embodiment, several input optical fibers will concurrently collect bioluminescent signal from at least six detection chambers. The optical switch will then connect one particular input fiber for a short period of time (few hundred milliseconds) to the single output fiber which connects to the optical blocks for splitting and band-passing the signal into two photomultiplier tubes (PMT). In the same fashion, the switch will turn on the next input fiber. In the current example, the switch takes 50 ms to change between input fibers. Optical switching inevitably introduces optical losses in the collected signal. Thus, this experiment was done to confirm if it is possible to collect signal through the optical switch and calculate the amount of signal loss due to optical switching.

Experimental Setup

The experimental setup is shown in FIG. 31. FIG. 31A shows the set-up without the optical switch. A single fiber was manipulated to align below the optical detection chamber of the microfluidic chip. The fiber is then connected directly the optical blocks. FIG. 31B shows the set-up with the optical switch. A Leoni 1×9 mol fiber optical switch was used. The 9 inputs are terminated by the sub miniature A (SMA) connectors while the single output fiber is terminated by ferrule connector (FC). A stainless plate was machined to contain an array of SMA receptacles allowing connection of optical fibers from the bottom. On the top of the plate sat the microfluidic chip with optical chamber aligned at the tip of the fiber. For this experiment one input fiber was used. The output fiber was then connected to the optical blocks.

Materials and Methods

Endpoint microfluidic assays were carried out on-chip in two inlet microfluidic mixer devices integrated with an optical detection chamber. Coelenterazine 400a substrate (Biosynth) was prepared to a final concentration 12.5 µM TE buffer (10 mM Tris (pH 8.0), 100 mM NaCl, 1 mM EDTA) and introduced in first inlet. GTR membrane protein was diluted in TE buffer (10 mM Tris (pH 8.0), 100 mM NaCl, 1 mM EDTA) at concentration of 1 µM. The prepared GTR solution was introduced in the second inlet. On-chip mixing was initiated with an input flow rate of 400 µl/hr for each inlet. BRET2 measurements were recorded using two photomultiplier tubes, one equipped with an RLuc/Clz400a emission filter (410 nm bandpass 80 nm) and the other with GFP2 emission filter (515 nm bandpass 30 nm). The optical output was collected using one single input fiber for both cases in FIG. 31. The gate time was 500 ms.

Results

FIG. 32 shows the real-time bioluminescent signal in the Rluc/Clz400 channel collected without and with optical switching for three runs. The GFP also shows similar behaviour (data not shown). From these results, it is confirmed that bioluminescent signal has been successful passed through the optical switch. In term of loss, FIG. 33 compares the luminescent signals collected without and with optical switch in both RLuc/Clz400a and GFP channels. The loss due to the optical switch for the RLuc/Clz400a channel was 40% while for the GFP channel it was 28%.

Example 6

Optimisation of Overall System Luminance and Photon Detection Efficiency

One of the important features of the invention is its ability to detect very low levels of analyte in real time with economical use of reagents. One of the keys to achieving this is to generate the maximum number of photons per unit volume of sensor solution. Incorporation of improvements like the RLuc2 mutation assist with this. It is also vital to minimise loss of photons in the optical detection system. High photon detection efficiency permits a desirable combination of response time, reagent economy and signal to noise ratio. Increasing the volume of the BRET reaction chamber and the common channels tends to increase the available light signal, which improves the signal to noise ratio but reduces the time resolution of the system. Increasing the flow rate in the device, other things being equal, improves the time resolution of the device but reduces its reagent economy and the signal to noise ratio. It is also vital to minimise losses in the optical detection system. A number of alternative experimental set ups were developed to improve the photon detection efficiency.

Experimental Set Up

On-chip measurements were carried out with a microfluidic chip similar to that shown in FIG. 31A with two inlets, a passive mixing element and a detection chamber. An aluminium mirror was placed on top of the reaction chamber to enhance the BRET signal. BRET emissions were recorded using two photo multiplier tubes one equipped with an RLuc/Clz400a emission filter (410 nm bandpass 80 nm) and the other with a $GFP^2$ emission filter (515 nm bandpass 30 nm).

A number of variations were compared with the original set up (FIG. 31A). The diameter of the reaction chamber was increased to 4 mm (FIG. 34A) from an original diameter of 2 mm. The height of the reaction chamber was varied between 1 and 2 mm. A single optical fiber of diameter 0.4-1.0 mm (FIG. 31A) was replaced with a liquid light guide or fibre-optic bundle of 5 mm core diameter NA=0.59, feeding into a dichroic block (FIG. 34A), or a bifurcated light guide of trunk core diameter 6 mm branch core diameter of 4 mm (FIG. 37) or a multifurcated light guide of trunk core diameter 8 mm and branch core diameter 4 mm (FIGS. 38 and 40).

Materials and Methods

OGOR2 sensor solution was prepared at day 4 in PBS at high (100 and 50 times) dilution ratios from stock solution. Clz400a was prepared in PBS at 31.25 µM. When diacetyl was included, it was added to the OGOR2 sensor solution at a final concentration of 1 µM. For the control experiment, only DI water was added. The sensor tubes without and with diacetyl were both incubated at 28° C. in 30 min.

Results

Light collection was compared between the original system with fiber diameter 1.0 mm and the modified system using a single 5 mm core liquid light guide (FIG. 35). At a 100 fold dilution of sensor, the original system had high noise levels and neither the RLuc2 nor the $GFP^2$ signals could be discriminated from noise. In contrast, using the liquid light guide, background noise levels were substantially lower and both emission channels could be clearly discriminated from noise by approximately 50 seconds after switching the system on. Maximum signal levels were achieved by approximately 200 seconds after reagent pumping commenced. It should be noted that because the newer configuration has a BRET reaction chamber volume 4 fold greater than the original one, it takes up to 100 seconds longer for the signal to saturate in this condition. Nevertheless, discrimination from baseline can be detected by 50 seconds. Similar results were observed for the 50 times dilution ratio (results not shown). With the improved system, it was possible to detect analyte using OGOR2 at 50× and 100× dilutions (FIG. 36).

If each microfluidic channel has a dedicated photodetector then a scheme such as that shown in (FIG. 37), in which each microfluidic channel is interfaced with a bifurcated light guide that channels light into a pair of photomultipliers or equivalent detectors, is a suitable arrangement. Comparison of this arrangement with a dichroic block shows that it may have better photon detection efficiency and signal to noise characteristics under otherwise comparable conditions (FIG. 39).

If light guides (core diameter ≥1.0 mm) are used instead of optical fibres (core diameter ≤1.0) it is difficult to obtain a suitable optical switch for time domain switching of the optical detection system between different microfluidic channels. In this case, a shutter box may be used. An example of a suitable optical architecture is shown in FIG. 38. Light collected from the multichannel chip is directed to the shutter box and the output is channeled to the optical detector via a multifurcated fiber bundle. The shutters are located in the input side of the multifurcated fiber bundle allowing software selection of the sequence of channels and the duration of monitoring.

A suitable multifurcated light guide arrangement is shown in FIG. 40. Results obtained comparing this arrangement with channel-specific bifurcated light guides (FIG. 37) indicate that the dichroic filter gives an 8× higher signal in the GFP channel and a 6.6× higher signal in the Rluc channel compared with bifurcated light guides (FIG. 41). The $BRET^2$ ratio was 4.67±0.07 with the dichroic filter and 3.85±0.25 for the bifurcated arrangement.

Example 7

Examples of Suitable Valve and Solid State-Based Photodetectors

Figure 43:
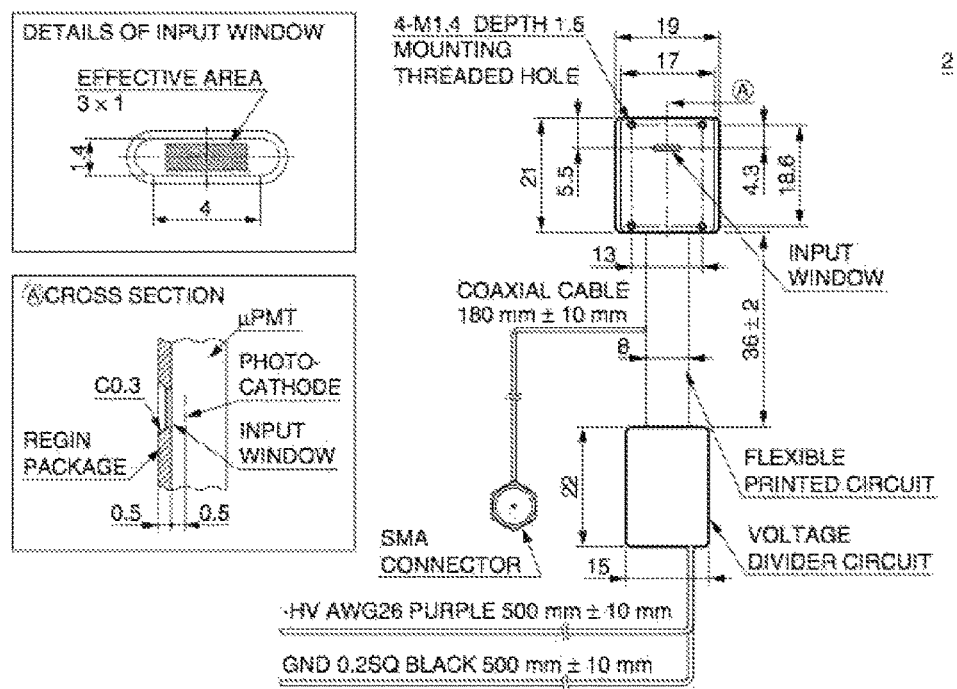

A very wide variety of vacuum based and solid state sensors are commercially available, which can be interfaced with the microfluidic chip in order to measure the light produced by the BRET reaction. FIG. 42 illustrates a high counting efficiency, high gain, low dark-noise assembly using traditional vacuum tubes. FIG. 43 illustrates a high photon detection efficiency, high gain, low dark-noise assembly implemented using solid-state technology. Many variants on these two approaches are available.

Example 8

Figure 44:
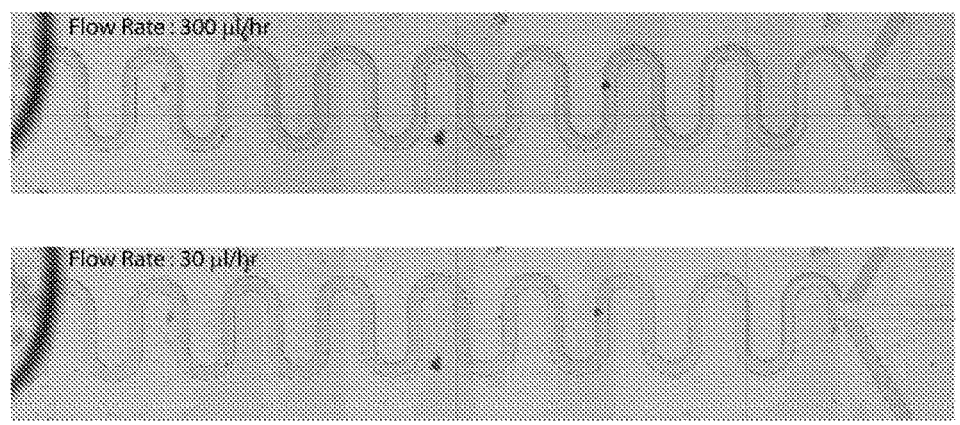

Experimental and Theoretical Optimisation of Diffusional Mixing in the Microfluidic Chip Laminar flow conditions may pertain in a microfluidic chip of typical dimensions used in this invention. In this case mixing occurs principally by diffusion and may require slow flow rates and long residence times to approach completion. Slow flow rates are undesirable because they result in a slower time to first detection of analyte or analytes than would otherwise be the case. This limitation may be overcome by forcing turbulent mixing, using for example more complex microfluidic geometries and/or pulsatile flow and/or micromechanical mixing and/or acoustic and/or electrokinetic means. All of these methods, whilst feasible, potentially involve additional engineering complexity and cost. The inventors therefore investigated simple passive design features that can enhance diffusive mixing in a laminar flow environment Experimental Setup For investigations with dyes, the inventors used a three inlet microfluidic network (FIG. 44). Thrombin detection experiments used a two-inlet microfluidic network, with Y-shaped geometry (FIG. 31a). The BRET reaction chamber (not shown) was either 2 mm or 4 mm in diameter. The dimensions of all microchannels were 200 µm wide by 35 µm deep. In the original (side-by-side) set up, the channels contacted each other along their vertical (35 µm) sides and were fabricated with a serpentine mixing region approximately 28 mm long (FIG. 44). In a modified (pancake stack) set up (FIG. 45), the two input channels were 30 µm deep and 600 µm wide and were stacked on top of each other, in contact via their horizontal (600 µm) sides to form a linear common channel 600 µm wide and 60 µm deep. The length of the common channel was 20 mm.

For dye experiments, solutions of food dyes were drawn from three input microchannels using a single pump in withdrawal mode at flow rates of 30-300 µL per hour. For thrombin sensing experiments we used 12.5 µM coelenterazine A substrate, which was premixed with the test concentration of thrombin and pumped into one arm of the Y-shaped microchannel. 1 µM of a BRET$^2$ based thrombin biosensor, prepared as previously described (Dacres et al., 2009b) was pumped into the other arm of the microchannel. Input channel flow rates were varied from 50-400 µL per hour. The limits of detection were estimated informally as the lowest concentration of thrombin for which the operator could discern a change in the BRET$^2$ ratio at a input reagent flow rate of 50 µL per hour.

Results

As shown in FIG. 44, using a side-by-side configuration, flow is laminar at high flow rates (common channel flow rate=300 µL hour), corresponding to residence times of 2.35 seconds, and there is little or no observable mixing Flow remains laminar at lower flow rates (common channel flow rate=30 µL per hour) corresponding to a residence time of 23.5 seconds, but significant diffusional mixing can be detected over this period.

Calculations of Residence Times i) For withdrawal flow rates of 300 µL per hour and the three input network: Volume of the serpentine region is 0.2 mm×0.035 mm×28 mm=>0.196 µL.
Flow rate in the common channel is 300 µL per hour. 0.196/300=6.53×10$^{-4}$ hours=2.352 seconds.

ii) For input flow rates of 30 µL per hour:
The residence time is 10× longer, i.e. 23.52 seconds.

iii) For the side by side stack:
Volume of the serpentine region is 0.2 mm×0.035 mm×28 mm=>0.196 µL. Flow rate in the common channel is 100 µL per hour.
0.196/100=1.96×10$^{-3}$ hours=7.056 seconds.
Volume of the BRET reaction chamber ($\pi 1^2 \times 1$ mm$^3$)=3.14 µL
Flow rate is 100 µL per hour. 3.14/100=0.0314 per hour=113 seconds
Total residence time is 120 seconds.

iv) For the pancake stack:
Volume of channel is 0.6 mm×0.06×20 mm=>0.72 µL. Flow rate in the channel is 100 µL per hour
0.72/100=7.2×10$^{-3}$ per hour=25.92 seconds
Volume of the BRET reaction chamber ($\pi 2^2 \times 1$ mm$^3$)=12.6 µL
Flow rate is 100 µL per hour. 12.6/100=0.126 per hour=452 seconds.
Total residence time is 478 seconds or 7 minutes 58 seconds.

The thrombin assay is very sensitive to sub-optimal mixing because both the analyte and the sensor are macromolecules with slow diffusion coefficients and also because thrombin ($k_{cat} \approx 85$ s$^{-1}$) has to process a large number of sensors by proteolytic cleavage before a signal can be detected and this takes time.

Using a traditional side-by-side network, with a flow rate of 50 µl per hour in each input arm, the lowest concentration of thrombin observable in real time (120 seconds) was 540 nM. Using a pancake stack network at the same flow rate (478 second residence time) 27 nM thrombin could be detected easily (FIG. 46). Thrombin was detected down to 14 nM, the lowest concentration tested. After adjusting for the fourfold difference in residence times there is at least a tenfold benefit in detecting a lower concentration of thrombin for the pancake stack.

The inventors attribute this improvement to improved diffusional mixing in the pancake stack architecture. They therefore compared the length of microfluidic channels (28 mm in the side-by-side example and 20 mm in the pancake stack example) with the theoretical distance required for complete mixing in these different configurations.

Calculation of distance required for complete diffusional mixing
L: Channel length (mm)
Q: Volumetric flow rate (µl/hr) or (mm$^3$/s)

$Q$=200 µl/hr=200 mm$^3$/hr=0.055 mm$^3$/s

D: Diffusion coefficient (for thrombin) D=4.16 10$^{-5}$ mm$^2$/s
U: average velocity in channel (mm/s)=Q/width×height (channel cross sectional area)
X: Diffusional distance travelled in period t is estimated by X$^2$=t D.

The X value for complete mixing depends on the channel configuration. Assuming a two-input channel architecture, for the side-by-side design, X is half the common channel width and, for the pancake stack design, X is half the channel height.

Residence time for complete mixing=$L/U=X^2/D => QX^2$/width×height×$D$

Therefore:
1. Current (side-by-side) design where:
H (Channel Height)=34 µm=0.034 mm and
W (Channel Width)=200 µm=0.2 mm $L \approx QW^2/4WHD$=0.055 mm$^3$/s×0.04 mm$^2$/4×0.2 mm×0.034 mm×4.16 10$^{-5}$ mm$^2$/s==1944 mm 2. Current (pancake stack) design where:
H (Channel Height)=60 µm=0.060 mm and
W (Channel Width)=600 µm=0.6 mm $L \approx QH^2/4WHD$=0.055 mm$^3$/s×3.6 10-3 mm$^2$/4×0.6 mm×0.06 mm×4.16 10$^{-5}$ mm$^2$/s=33 mm 3. Optimised (pancake stack) design where:
H (Channel Height)=14 µm=14×10$^{-3}$ mm and
W (Channel Width)=1200 µm=1.2 mm $L \approx QH^2/4WHD$=0.055 mm$^3$/s×196 10-6 mm$^2$/4×1.2 mm×14 10$^{-3}$ mm×4.16 10$^{-5}$ mm$^2$/s=3.9 mm Therefore the side-by-side stack provides only 28 mm (i.e. 1.4%) of the 1944 mm required for complete mixing whereas the pancake stack arrangement tested provided 20 (i.e 61%) of the 33 mm required for complete mixing. Calculations demonstrate that with minor additional changes it would be feasible to arrange for diffusive mixing to be complete within 7.7 mm i.e. less than 40% of the length available in the current design.

Example 9

Improvements to Microfluidic Network Designs and Pumping Arrangements

Microfluidic networks where the lengths of multiple reagent input channels connected to a common port vary as, for example in FIG. 14, had poor reliability (results not shown) because of the tendency for the differences in back pressure to prevent flow in longer channels, routing all flow through shorter channels. These designs are also very susceptible to blocking by bubbles, for similar reasons. The inventors therefore tested a number of different design features and pumping arrangements to improve the reliability of the multichannel device.

Experimental Setup for Paired Symmetrical Microfluidic Sensors

In one example (FIG. 47), the inventors designed a network with a bilaterally symmetrical parallel channel layout to obtain two simultaneous reactions using two different sensors. This arrangement can be replicated to obtain any even number of sensor channels.

Results

The inventors demonstrated fluid flow on the chip using food-colouring dye at two flow rates (FIG. 48). Diffusive mixing was largely complete at a flow rate of 150 µl/hr, whereas at 1500 µl/hr the input streams remained largely separate.

Flow was continuous and even along both arms of the network and blockage occurred less frequently than with asymmetric designs. Nevertheless, this design is still susceptible to blockage or uneven flow if a bubble or other obstruction lodges in one of the two parallel arms. The inventors therefore investigated other approaches for driving the sample and reagents through the microfluidic network.

It is desirable that each common channel has its own dedicated pressure source(s) that is/are not shared with any other common channel. This means that, should there be variation in the backpressures in the network for any reason, then flow cannot be diverted to a different common channel. Unfortunately, when operating in positive pressure mode, observation of this principle would mean that each common channel requires three dedicated pumps: one each for the sensor, substrate and sample, resulting in a system with complex and potentially expensive engineering requirements. An elegant and superior alternative is to drive the reagents through individual common channels using a single dedicated pump operating in suction (negative) mode. This only requires a single pump per common channel, as shown in FIG. 49. The quality of laminar flow in a network driven by suction pressure is even and reliable as shown in FIG. 44. In the worst case, blockage or partial obstruction in one common channel or the microfluidic channels leading into it only affects that sensor channel.

An ancillary benefit of providing a dedicated source(s) of pressure for each common microfluidic channel (and therefore for each different sensor) is that it allows the simultaneous operation of multiple sensor channels independently of each other with potentially different flow rates and consequently different balances between speed and sensitivity (FIG. 50). This might for example, allow two or more channels to use the same sensor at different flow rates in order to give a range of different limits of detection and time constants. Another option is to operate several channels with different sensors, at different flow rates optimised for each sensor. An extreme example of this would be to run completely different sensor types such as a GPCR-based volatile sensor and a protease sensor in parallel on the same chip, with the same or different samples, and tailor the flow rates for the very different reaction kinetics of the two reaction classes. It would also be possible to use suction pumping, as described here, to support the use of different types or dilutions of sample or substrate chemistry on the same chip at the same time.

Use of suction mode is fully compatible with the concept of providing reagents in simple disposable cartridges on the inlet side of the network. Changing cartridges would allow simple and rapid switching of applications or targets, using the same basic hardware. An additional advantage is that the need to decontaminate the pumping device, between samples or after analyte detection is minimised in the suction mode.

The inventors performed an additional experiment incorporating the preferred light collection and detection setup from Example 6 together with the preferred suction mode pumping of this Example and a BRET$^2$-based thrombin sensor from Example 2. In this experiment, we used a simple Y-shaped microfluidic network with a serpentine common channel having dimensions of 0.2 mm×0.035 mm×28 mm. The BRET reaction chamber was Ø=2 mm and height 1 mm, giving a volume of 3.14 µL. Light from the reaction chamber was fed into one branch of a four-branch fibreoptic bundle and thence into a 25.4 mm (1 inch) diameter optical block for simultaneous dual wavelength measurement with a dedicated dichroic filter and two PMTs. The chip was primed with buffer and 50 µL input reservoirs were loaded with 50 µL of 1 µM GTR thrombin sensor and 50 µL of 12.5 µM coelenterazine 400a substrate. Flow was started using negative pressure (suction mode) at the outlet with a common channel flow rate of 200 µL/hr=0.055 µL/sec. Under these conditions, the BRET reaction chamber residence time was 57 seconds.

As shown in FIG. 51, after startup was complete, the system generated very strong signals in both optical channels with excellent signal to noise ratios (compare with FIG. 10a). Based on the rate at which signal develops and the BRET reaction chamber residence time, for a chamber with diameter 2 mm, we estimate that a minimum chamber height of 300 µm would still give measurable signals above background (FIG. 51c). At the specified flow rate, this would correspond to a reaction mixture integration time of approximately 20 seconds. A chamber diameter of 4 mm, would potentially allow the chamber height to be reduced to 75 µm, whilst retaining the same signal strength and reaction mixture integration time.

Example 10

Example of Application of the Invention to Beverages and Other Fluids, Including Prophetic Example of Predicting Plasmin Spoilage of UHT Milk Background The invention is readily applicable to any analytes that will dissolve in water or an aqueous solution, including volatile chemicals that will partition into an aqueous solution. Analytes that are already present in an aqueous liquid, including milk, fruit juices, other beverages and bodily fluids including blood serum are especially amenable to detection because there is no need for a preliminary gas-liquid partition prior to analyte measurement.

A simple example of an application in this area includes prediction of spoilage of UHT milk. Proteases from bacteria that have been killed by UHT treatment may cause increased viscosity, gelation, and bitterness in whole and skimmed UHT milk during storage, thereby leading to loss of shelf-life. Specifically, it is proteolysis of casein by plasmin that causes these problems in UHT milk. Commonly used assays for detecting proteases are slow and are insufficiently sensitive to easily detect the very low levels of protease that can result in spoilage of UHT milk after 6-9 months or more of storage at ambient temperature. The invention could measure such very low levels of plasmin in UHT milk with great sensitivity and in real time. It would be applicable to an in-line monitoring in a commercial setting. This will allow estimation of product shelf life and identify any need for additional processing prior to packaging. Based on our previous $BRET^2$ sensors for thrombin and caspase proteases, we would construct a biosensor for detection of plasmin activity in milk, by incorporating the target peptide sequence, preferably Lysine-X (where X=Lysine, Tyrosine, Valine or Glutamic acid), into the linker between BRET donor and acceptor (FIG. 53). This sensor would be incorporated into a version of the invention suitable for on-farm and in-factory use. However, because we did not have such a sensor readily to hand, we used some existing sensors, including one that detects thrombin, to demonstrate the feasibility of using our method to detect proteases in milk or indeed other commercially or medically important fluids such as orange juice and mammalian serum.

Method

In one experiment, we used the $GFP^2$-$FL_1$-RLuc2 construct described by Dacres et al. (2012) diluted 1/125 (i.e. ≈0.5 µM) with 5 µM coelenterazine A in PBS or in various dilutions of full fat "Canberra Milk" brand milk, "Just Juice" reconstituted orange juice and mammalian blood or serum.

In another experiment, the inventors used the GTR $BRET^2$-based thrombin sensor described in Examples 1 and 2 with RLuc replaced by RLuc2 ($GFP^2$-RG-RLuc2 (GTR2)), construct described by Dacres et al. (2012) diluted 1/100 (≈0.5 µM) with 5 µM coelenterazine A in thrombin cleavage buffer or various dilutions of milk, orange juice or serum. Thrombin cleavage of GTR2 in various dilutions of milk, orange juice or serum was assessed by spiking the samples with 2 units of exogenous thrombin to simulate an endogenous protease. Serum was prepared from mammalian heparinized (250 IU/ml) blood samples. To prepare serum blood sample were left undisturbed at room temperature for 30 minutes and then centrifuged at 1,000-2,000×g for 15 minutes. The supernatant is designated serum. The serum samples were maintained at 2-8° C. while handling. All experiments were performed in 100 µL final volume in a microwell plate and $BRET^2$ signals were read in a Polarstar Optima microplate reader (BMG Labtech) as described previously.

Results

Preliminary results, using $GFP^2$-$FL_1$-RLuc2, demonstrated that the $BRET^2$ chemistry functions well in the aqueous environment of whole milk and orange juice, diluted 1/10 with PBS (FIG. 54). FIG. 55 shows the time dependent decay of the $BRET^2$ signal of $GFP^2$-$FL_1$-RLuc2 in whole milk.

Results using GTR2 demonstrate that the $BRET^2$ chemistry also functions in serum when diluted 1/10 in thrombin cleavage buffer (FIGS. 56 and 57). Bioluminescence activity was completely recovered when diluted 1/500 for serum, 1/50 for orange and 1/10 for milk in thrombin assay buffer compared to resuspension in thrombin assay buffer alone (FIG. 56). The $BRET^2$ ratio was higher for all serum dilutions compared to buffer except for 1/1000 dilutions in buffer (FIG. 57a). When resuspended in orange the $BRET^2$ ratio was higher when diluted 1/10 in buffer compared to buffer alone but was a consistent value for all other dilutions (FIG. 57 b). Only GTR2 resuspended in undiluted milk resulted in a $BRET^2$ ratio higher than when resuspended in buffer alone compared to all other milk dilutions (FIG. 57c).

Thrombin activity was detected in 1/10 dilutions of milk and orange juice (FIG. 58). In serum a 1/100 dilution of the serum sample in buffer resulted in thrombin activity. All dilutions resulting in thrombin activity produced significant changes (P<0.0001) in the $BRET^2$ ratio compared to samples without addition of thrombin. Thrombin activity in serum diluted 1/1000, orange diluted 1/100 and milk diluted 1/100 in buffer resulted in $BRET^2$ signal changes not significantly different (P>0.25) from those generated in thrombin cleavage buffer.

Example 11

Demonstration of Gas Liquid Transfer of Volatiles Using a Wetted Wall Cyclone

One of the advantages of the invention is that it can be applied to detection of volatile analytes. However, because the sensors are necessarily dissolved or suspended in aqueous solution, volatile analytes must partition from the gas phase into aqueous solution before they are available to contact the sensors. The inventors set out to demonstrate the feasibility of transferring volatile chemicals from air to liquid in a format compatible with the invention. There are a number of methods that could be used rapidly to equilibrate ambient air or target headspace with an aqueous based sample liquid, including gas in liquid bubbling or misting. However, the inventors selected a wetted-wall cyclone to demonstrate the concept because suitable equipment is available commercially.

Experimental Set Up for Initial Tests

Initial tests were completed using the SASS2400 wetted-wall cyclone (Research International). The internal fan draws air at 40 L/min and equilibrates it with 1 mL water. To compensate for evaporation, the sample level is monitored and replenished from a 1300 mL reservoir of de-ionised water.

The sample chemical was placed in a 1.7-2 mL eppendorf tube. A hole was drilled in an 80 mm section of aluminium tubing to mount the tube in the inlet port of the SASS2400 (similar to FIG. 59). Sampling time for these tests was inclusive of fan start-up and sample liquid filling times.

Method

Two consecutive runs were done for each test, to give a total volume of 2 mL of sample. Tests were done following the time kinetics of re-absorption of oxygen into de-ionised water that had been de-oxygenated by sparging with nitrogen and with acetaldehyde and phenol. Oxygen concentration was measured with an oxygen electrode. Volatile concentrations in the SASS2400 sample fluid were estimated by liquid or gas chromatography, relative to standards.

Results

The wetted wall action of the sampler exposes a large area of the sample fluid to the sampled air flow and was very efficient in re-oxygenating the nitrogen sparged sample (FIG. 60). At the earliest time point that could be measured with this equipment, 80% saturation with oxygen was achieved within about 7 seconds and the process was complete in under 60 seconds.

Phenol was detected in the SASS2400 sample at the earliest time point measured (FIG. 61) and continued to accumulate in an approximately linear fashion with time up to the last sample point at 60 seconds.

Using this protocol, results obtained with acetaldehyde were unreliable with the concentration decreasing with using longer sampling times. The inventors attributed this to the very volatile nature of acetaldehyde and its propensity to degas rapidly from the sample reservoir.

Modified Equipment Setup

In order to improve the time resolution of experiments at early time points, the inventors modified the equipment to allow rapid re-direction of the input airflow after the SASS2400 fan was up to speed and the sample chamber had been filled, which takes up to about 12 seconds, usually about 9 seconds.

The fan in the SASS2400 is designed to draw in air from ambient around the device. Restricting the airflow through narrow or excessive lengths of plumbing could affect the designed airflow of 40 L/min and switching of the air path needs to be fast so the sampling times are consistent (FIG. 63). Solenoid valves or butterfly valves were considered less than ideal because of their effects on air-flow. A 3-way L port pneumatically operated ball valve (BLS3L6B) was chosen to allow rapid switching of air intake from room air to room air plus the volatile specimen (FIG. 60). The valve was connected with 1" BSP fittings for minimal constriction for the air flow and as it is a 3-way valve there was minimal additional plumbing required and the valve could be mounted very close to the SASS2400 air inlet. The valve was driven through a double acting solenoid and a 12 solenoid (ENS1275) connected to a 6 Bar air supply.

A microcontroller circuit controlled the operation of the solenoid valve. The operating time is programmable and was set to 15 seconds. No digital output was available from the SAS2400 to synchronise the microcontroller so it was triggered by a manual push button activated at the start of the SASS2400 test cycle. The response of the 3-way valve was below one second.

All testing was done in a fume hood because of the nature of the volatile samples. Specimens could not simply be placed near the inlet of the 3-way valve as specimen concentration drawn into the SASS2400 may have varied with any air-flow change in the fume hood. A 1¼ inch pvc barb fitting was attached to the specimen inlet side of the solenoid (FIG. 62). A hole to mount a 2 ml safe-lock conical tube was drilled on the lower side of the PVC fitting 20 mm in from the end furthest from the solenoid. The air-flow at this point should be constant at 40 L/s due to the fan in the SASS2400. Specimens to be tested were placed in 1.7-2 ml safe-lock conical tubes with the lids removed. The conical tubes were filled to the upper rim at the start of each test. The constant surface area exposed to the air-flow should ensure a constant rate of evaporation within each test cycle.

Modified Test Procedure

All experiments were conducted in a fume hood. Personal protection equipment including gowns, gloves, shoe covers and a full face mask were used.

After powering up and establishing a computer connection, the SASS2400 was set to run for 20 seconds, drawing only from room air with no sample exposure, to flush the system. The solenoid and valves were not active at this stage. The solenoid and its control circuitry were powered up and several operations of the solenoid valve were run to ensure that air pressure was adequate for quick operation of the valve.

The SASS was programmed for the duration of the test run. This was the desired exposure time for sampling plus an addition fifteen seconds for initial fan start-up during which the 3-way air intake valve was switched away from the specimen.

A clean 8 mL sample bottle was placed in the collection position on the front of the sampler. 0.6 mL of de-ionised water was placed in a new 2 ml sample vial ready to take the sample after the test. Temperature, humidity and atmospheric pressure were recorded.

The lid was removed from a clean 2 mL safe-lock tube. Phenol specimens were placed in the safe lock tube, filling it as close as possible to the rim, before placing the tube in the mounting hole. For liquid specimens the tube was placed in its mount and then filled with specimen. Care was taken to ensure that the liquid was filled to the rim of the specimen tube so that a consistent surface area of the liquid was exposed to the air-flow.

The SASS2400 and the delay trigger for the solenoid were activated simultaneously. After fifteen seconds the specimen was switched into the SASS2400 air intake. At the end of the sampling time, the fan was switched off and the sample was pumped to a 8 ml collection bottle on the front of the SASS2400 for 20 seconds to ensure that all of the sample was transferred to the sample bottle.

At the end of each test cycle the SASS2400 was programmed to run an internal peristaltic pump for 20 seconds to transfer the 1 mL test sample into an 8 ml bottle fitted to the front of the SASS2400. 0.8 mL of the sample was transferred from the collection bottle to the analysis vial and a further 0.6 mL of de-ionised water was used to fill the vial before it was sealed and sent for analysis. Tests were run for acetaldehyde and phenol for sampling times from 5 seconds to 600 seconds and sent for chromatographic analysis.

Results Using New Procedure

Mean phenol concentration was 7.7 µg/mL (i.e=8 ppm w/v) in the SASS2400 sample after only 15 seconds exposure to ≈1 gram sample of phenol with a Ø=6 mm surface area. Phenol is an example of a highly volatile compound with a vapour pressure=$0.474 \times 10^{-4}$ atmospheres at 20° C. Even after only a few seconds exposure, acetaldehyde concentrations in the sample vial were off-scale (i.e. >>mg/L) demonstrating very rapid partition of acetaldehyde into the water. Rapid uptake and equilibration of these volatile organic compounds demonstrate the feasibility of the wetted wall cyclone as a gas-liquid transfer module prior to on-chip microfluidic detection.

Example 12

Additional GPCR Volatile Sensors Developed

The inventors previously described the construction of a BRET$^2$-based diacetyl sensor by inserting RLuc or RLuc2 and GFP$^2$ domains into the sequence of the odr-10 diacetyl receptor from *C. elegans*. This sensor was expressed in *S. cerevisiae* and a crude membrane suspension was prepared and demonstrated to respond with exquisite sensitivity and selectivity for diacetyl in a plate based assay and also in the microfluidic format described in Example 3 above. As noted however, one of the advantages of the current invention is that multiple microfluidic sensor channels can be operated simultaneously in order to detect multiple individual analytes or, with appropriate selection of sensors, to provide a chemical fingerprint of a complex sample. To enable this it is necessary to derive a number of compatible volatile sensors with distinct specificities. The inventors therefore selected five additional putative chemoreceptor cDNAs from C. elegans as starting points for the engineering of novel BRET$^2$-based sensors. The inventors also constructed a chimaera between str-113 and str-114 in order to demonstrate the feasibility of deriving sensors that are synthetic molecular hybrids of naturally occurring receptors, with potentially novel ligand specificity that is not available readily from naturally occurring sequences.

SGSRs are chimaeras of C. elegans str-112, str-113, str-114, str-115, str-116 and str-114/113 with the BRET$^2$ tags GFP$^2$ and RLuc or RLuc2 inserted in the third intracellular loop and at the C-terminus, respectively. The positions of the third intracellular loops of STR proteins were predicted using "TMAP" an algorithm from "The Biology Workbench" (a web-based tool for prediction of transmembrane segments http://seqtool.sdsc.edu). These were named SGSR-112, SGSR-113, SGSR-114/113, SGSR-114, SGSR-115 and SGSR-116.

Method for Design and Construction of BRET$^2$ Tagged C. elegans Str Odorant Receptors Except for SGSR-112, which was commercially synthesised, SGSR expression cassettes were designed and made by introducing multiple restriction sites into the relevant gene-specific PCR primers. PCR products containing those sites were cloned into TOPO PCR vectors (Invitrogen) and then digested with the corresponding restriction enzymes (REs) and ligated into the expression cassettes. Some alterations were made to suit particular genes if they possessed one or more RE sites used by the cassettes.

RE sites for str fragment 1 were NcoI (5') and BspEI (3'), for GFP2 are BspEI and SalI, for str fragment 2 are SalI and KpnI/EcoRI as EcoRI cuts Str116 fragment2, and, for Renilla luciferase, KpnI/EcoRI and NotI.

The SGSR 114/113 chimera was constructed by modifying C. elegans SGSR-113 (by replacing the first fragment of str-113, 113-1 using the restriction sites NcoI and BspEI in the cassette with the corresponding fragment of str-114, str-1,4-1). Str114-1 contains the first 720 str-114 nucleotides of, corresponding to its first 240 amino acids and was amplified by high fidelity PCR using primers incorporating the restriction sites, NcoI at the 5' end and BspEI at the 3' end.

All constructs were confirmed to be error free by restriction digestion and DNA sequencing.

The amino acid sequences of GFP2 Rluc labelled SGSR-112, SGSR-113, SGSR-114, SGSR-115, SGSR-116 and SGSR-114/113 receptors are provided as SEQ ID NOs 13 to 18 respectively, whereas the corresponding open reading frames are provided as SEQ ID NOs 19 to 24 respectively.

Results with Additional Six Sensors

All SGSR yeast membrane preps had strong GFP$^2$ and BRET$^2$ signals after induction by galactose at 15° C. for 72 hours and all of them showed changes in BRET$^2$ ratio when exposed to a medium conditioned with OP50 E. coli bacteria (a food source for C. elegans) compared to LB medium alone. The inventors selected a number of specific volatiles (including 1-hexanol, 1 butanol, butane-2,3-dione, 3-hydroxybutanone, 2-pentanone and 2 noanone) for further testing based on GC-MS analysis of the headspace of OP50 bacteria grown on LB. The volatile ligand, 2-pentanone, tested positive for three of these sensors SGSR-112, SGSR-113 and SGSR-114/113 (FIG. 64). This is the first time that a volatile ligand (or indeed any ligand) has been identified for a BRET-based GPCR sensor, in the absence of prior knowledge of the ligand based on research with the unmodified parental GPCR. It is a demonstration of the utility of the BRET system for de-orphaning receptors generally and C. elegans chemoreceptors in particular.

Concentration-response characteristics (FIG. 65) indicate an $EC_{50}$ likely to be in the picomolar range. Not only does this reduce to practice the process of engineering, de-orphaning and characterising novel volatile sensors, it also demonstrates, at lease in the case of SGSR-112 a viable method for de-orphaning the parental native receptors, the first time this has been achieved for almost 20 years.

The BRET$^2$ tagged SGSR-114/113 and SGSR-113 sensors responded to a range of volatile ligands including alcohols and ketones (FIG. 64). The inventors identified six volatile ligands for SGSR-114/113 and four for SGSR-113. The SGSR-112 response to 2-pentanone was linear over 9 log units from $1 \times 10^{-14}$ M to $1 \times 10^{-5}$ M with an $EC_{50}$ of $1.5 \times 10^{-10}$ M (1.3 ppt) (FIG. 65). This broad concentration-dependency is consistent with the response of the BRET$^2$ tagged ODR-10 which was also linear over 9 log units and also the response of the whole organism.

The inventors quantified the sensitivity of, SGSR-114/113 in vitro, for two of its ligands, 2-pentanone and diacetyl and of SGSR-113 to 1-hexanol (FIG. 66). The BRET$^2$ tagged Str114/113 receptor can detect parts per quadrillion (sub pM) levels of diacetyl and parts per billion levels (nM) levels of 2-pentanone and the Str-113 receptor can detect parts per billion (nM) levels of 1-hexanol. These would be particularly useful semi-broad sensors for use in the invention.

Construction of BRET$^2$ Tagged C. elegans Odorant Receptors with RLuc2

Following de-orphaning of the five additional natural and one chimaeric BRET$^2$ tagged sensors, which was accomplished in a plate based assay, the inventors incorporated the RLuc2 mutations into each of them. This was required because, as described above, the RLuc2 variant has been shown to be much brighter and therefore essential for practical use at a microfluidic scale.

The BRET$^2$ components were inserted into the third intracellular loop (IC3) and at the C-terminus of the C. elegans odorant receptor with green fluorescent protein, GFP$^2$ at $IC_3$ and Renilla luciferase, RLuc at the C-terminus of the protein. Using site-directed mutagenesis the RLuc2 mutations were introduced into the pYES-DEST-52 BRET2 tagged odorant receptor sequence. Primers 1 and 2 (Table 3) were used to introduce the mutation C124A and primer pair 3 and 4 were used to introduce the M185 V mutation. The RLuc2 mutations were introduced into all of the sensors based on OGOR, Str-112, Str-113, Str-114, Str-114/113, Str-115 and Str-116 as well as an additional model receptor called OGOR mutant which contains the original odr-10 mutation (H110Y) identified by Sengupta et al. (1996) that has previously been shown previously to be unresponsive to diacetyl.

The amino acid sequence of GFP2 Rluc2 labelled OGOR, OGOR mutant, SGSR-112, SGSR-113, SGSR-114, SGSR-114/113 SGSR-115 and SGSR-116 and receptors are provided as SEQ ID NOs 25 to 32 respectively, whereas the corresponding open reading frames are provided as SEQ ID NOs 33 to 40 respectively.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/624,899 filed 16 Apr. 2012, and AU 2013204332 filed 12 Apr. 2013, the entire contents of both of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Aloni et al. (2006) Genome Biol. 7:R88.
Buck and Axel Cell (1991) 65: 175-187.
Dacres et al. (2009a) Anal. Biochem. 385:194-202.
Dacres et al. (2009b) Biosensors and Bioelectronics 24:1164-1170.
Dacres et al. (2010) Anal. Chem. 82: 432-435.
Dacres et al. (2011) Biosens. Bioelectron 29: 119-124.
Dacres et al. (2012) Biochem. Biophys. Res. Commun. 425:625-629.
Day et al. (2004) Luminescence 19:8-20.
De et al. (2007) Cancer Res. 67: 7175-7183.
De et al. (2009) FASEB Journal 23:2702-2709.
de Wet et al. (1987) Mol. Cell. Biol. 2987:725-737.
Doty (2012) Gustation. Wiley Interdisciplinary Reviews-Cognitive Science, 3:29-46.
Esch et al. (2011) Annu. Rev. Biomed. Eng. 13:55-72.
Fang et al. (2005) Anal. Chem. 77:6528-6534.
Fehr et al. (2002) PNAS 99: 9846-9851.
Feldmesser et al. (2006) BMC Genomics. 7:121.
Fredriksson and Schioth (2005) Mol. Pharmacol., 67, 14144425.
Frishman and Argos (1997) Proteins 27:329-335.
Fuchs et al. (2001) Human Genetics 108:1-13.
Gill and von Hippel (1989) Anal. Biochem. 182: 319-326.
Glusman et al. (2000a) Mammalian Genome 11: 1016-1023
Glusman et al. (2000b) Genomics 63: 227-245.
Glusman et al. (2001) Genome Res. 11:685-702.
Godin et al. (2008) J. Biophotonics 1:355-376.
Greer and Szalay (2002) Luminescence 17:43-74.
Hall et al. (1997) J. Biol. Chem. 272: 17610-17614.
Hastings (1996) Gene 173:5-11.
Hofmann and Stoffel (1993) Biol. Chem. 374:166.
Holden and Cremer (2005) Annu. Rev. Phys. Chem. 56:369-387.
Hushpulian et al. (2007) Biotransformation 25:2-4.
Inouye et al. (1997) Biochem. J. 233:349-353.
Klein et al. (1984) Biochim Biophys. Acta 787:221-226
Lander et al. (2001) Nature 409:860-921.
Li and Lin (2008) Anal Bioanl. Chem. 555-567.
Loening et al. (2006) Protein Eng. Des. Sel. 19:391-400.
Loening et al. (2007) Nature Methods 4:641-643.
Lorenz et al. (1991) Proc. Natl. Acad. Sci. USA 88:4438-4442.
Mark et al. (2010) Chem. Soc. Rev. 39:1153-1182.
Medintz et al. (2006) Curr. Opin. Biotech. 17: 17-27.
Mohammed and Desmulliez (2011) Lab. Chip. 11:569-595.
Morin and Hastings (1971) J. Cell. Physiol. 77:313-318.
Niimura and Nei (2003) Proc. Natl. Acad. Sci. USA. 100: 12235-12240.
Noh et al. (2011) Top. Curr. Chem. 304:117-52.
Olender et al. (2004a) Genet Mol. Res. 3:545-53.
Olender et al. (2004b) Genomics. 83:361-72.
Park et al. (2009) Biochem. Biophys. Res. Commun 388: 560-564.
Persson and Argos (1994) J. Mol. Biol. 237:182-192.
Pfleger and Eidne (2006) Nature Methods 3:165-174.
Pilpel and Lancet (1999) Protein Science 8: 969-77.
Robertson (1998) Genome Research 8:449-463.
Robertson (2001) Chem Senses 26:151-159.
Sengupta et al. (1996) Cell 84:899-909.
Sharff et al. (1992) Biochemistry 31: 10657-10663.
Sharff et al. (1993) Biochemistry 32: 10553-10559.
Sharon et al. (1998) Ann N Y Acad. Sci. 30; 855:182-93
Spurlino et al. (1991) J. Biol. Chem. 266: 5202-5219.
Theberge et al. (2010) Angew. Chem. Int. Ed 49:5846-5868.
Tsien (1998) Ann. Rev. Biochem. 63:509-544.
Unger et al. (2000) Science 288:113-116.
Verhaegen et al. (2002) Anal. Chem. 74: 4378-4385
Viviani (2002) Cell. Mol. Life. Sci. 59:1833-1850.
von Heijne (1992) J. Mol. Biol. 225:487-494.
Xu et al. (1999) Proc. Natl. Acad. Sci. USA. 96:151-156.
Yeo et al. (2011) Small 1: 12-48.
Young et al. (2002) J. Human Mol. Genet. 11:535-4.
Zhang and Firestein (2002) Nat. Neurosci. 5:81.
Zozulya et al. (2001) Genome Biol. 2:0018.1-0018.12.

The invention claimed is:

1. A method of detecting an analyte in a sample, the method comprising
   i) flowing through a microfluidic device comprising one or more microchannels,
      a) the sample,
      b) a sensor molecule comprising a domain that binds the analyte, a chemiluminescent donor domain and an acceptor domain, wherein the separation and relative orientation of the chemiluminescent donor domain and the acceptor domain, in the presence and/or the absence of analyte, is within ±50% of the Forster distance, and wherein the sensor molecule is not fixed to the device,
      c) a substrate of the chemiluminescent donor,
   ii) mixing the sensor molecule, sample and substrate in the device, and
   iii) detecting modification of the substrate by the chemiluminescent donor using an electro-optical sensing device and calculating as a ratio the energy transfer occurring between the chemiluminescent donor domain and the acceptor domain,
   wherein the spatial location and/or dipole orientation of the chemiluminescent donor domain relative to the acceptor domain is altered when the analyte binds the sensor molecule.

2. The method of claim 1, wherein the method can be used to detect the analyte in real time and/or which is performed within about 1 s to about 100 s.

3. The method of claim 1, wherein the sensor molecule and substrate enter the device through different microchannels.

4. The method of claim 1, wherein one or more or all of the following features apply;
   i) the Forster distance of the chemiluminescent donor domain and the acceptor domain is at least 5.6 nm,
   ii) the analyte binding or releasing from the sensor molecule results in a change in BRET ratio which is ≥15% of the maximum observed BRET ratio, or
   iii) the acceptor domain has a Stokes Shift of between about 50 nm and about 150 nm.

5. The method of claim 1, wherein the quantum yield detected by the electro-optical sensing device is less than about 8%, or less than about 5%, or less than about 2%.

6. The method of claim 1, wherein the sample is a liquid, gas, liquid which has been pre-equilibrated with a gas, emulsion or suspension.

7. The method of claim 1, wherein
   i) the flow rate through the microfluidic device is between about 1 μl/hour to about 1.5 ml/hour, and/or
   ii) flowing through the microfluidic device is continuous flow, batch flow or stop flow.

8. The method of claim 1, wherein step iii) is performed in a reaction chamber with a volume of about 1 pl to about 200 μl.

9. The method of claim 1, wherein the domain that binds the analyte is a protein or a nucleic acid.

10. The method of claim 9, wherein the protein is a receptor, odorant binding protein, pheromone-binding protein, enzyme, ligand carrier, bacterial periplasmic binding protein or a G protein coupled receptor.

11. The method of claim 1, wherein one or more or all of the following features apply;
    i) the chemiluminescent donor domain is a bioluminescent protein,
    ii) the substrate is luciferin, calcium, coelenterazine, or a derivative or analogue of coelenterazine, or,
    ii) the acceptor domain is a fluorescent acceptor domain.

12. The method of claim 1, wherein
    i) the bioluminescent protein is a luciferase or a biologically active variant or fragment, and/or
    ii) the substrate is luciferin, coelenterazine, or a derivative or analogue of coelenterazine, and/or
    iii) the acceptor domain is green fluorescent protein (GFP), Venus, mOrange, or a biologically active variant or fragment of any one thereof.

13. The method of claim 1 which comprises simultaneously or sequentially detecting two or more different analytes using the same microfluidic device.

14. The method of claim 1, wherein the microfluidic device comprises one or more sets of
    a) three input microchannels, one each for the sensor molecule, substrate and sample, or
    b) two input microchannels, one for the substrate and the other for a pre-mixture of the sensor molecule and sample, or
    c) two input microchannels, one for the sensor molecule and the other for a pre-mixture of the substrate and sample.

15. The method of claim 1, wherein one or more or all of the following features apply:
    i) at least one microchannel comprises a reaction chamber which has a different volume to at least one other microchannel;
    ii) at least one microchannel comprises two or more reaction chambers of the same or different volume, or
    iii) the electro-optical sensing device has at least two different wavelength channels.

16. A microfluidic system comprising
    i) at least one reservoir suitable for containing a sensor molecule,
    ii) a sensor molecule comprising a domain that binds the analyte, a chemiluminescent donor domain and an acceptor domain, wherein the separation and relative orientation of the chemiluminescent donor domain and the acceptor domain, in the presence and/or the absence of analyte, is within ±50% of the Forster distance,
    iii) a microfluidic device comprising one or more microchannels, iv) means for mixing the sensor molecule, the sample and a substrate of the chemiluminescent donor domain in the device,
v) a reaction chamber for detecting binding of the analyte to the sensor molecule, and
vi) an electro-optical sensing device,
wherein the spatial location and/or dipole orientation of the chemiluminescent donor domain relative to the acceptor domain is altered when the analyte binds the sensor molecule, and
wherein the sensor molecule is not fixed to the microfluidic device.

17. The system of claim 16
i) which can be used to detect the analyte in real time, and/or
ii) wherein the microfluidic device is designed to enable the detection of two or more analytes.

18. A method of classifying a sample, the method comprising
i) flowing through a microfluidic device comprising one or more microchannels,
 a) the sample,
 b) a sensor molecule comprising a domain that binds one or more analytes, a chemiluminescent donor domain and an acceptor domain, wherein the separation and relative orientation of the chemiluminescent donor domain and the acceptor domain, in the presence and/or the absence of analyte(s), is within ±50% of the Forster distance, and wherein the sensor molecule is not fixed to the device,
 c) a substrate of the chemiluminescent donor,
ii) mixing the sensor molecule, sample and substrate in the device,
iii) detecting modification of the substrate by the chemiluminescent donor using an electro-optical sensing device and calculating as a ratio the energy transfer occurring between the chemiluminescent donor domain and the acceptor domain,
iv) processing at least one signal from the electro-optical sensing device and correlating the pattern of electro-optical responses with one or more pre-determined characteristics of one or more samples of interest, and
v) classifying the sample based on the correlation of the pattern of responses,
wherein the spatial location and/or dipole orientation of the chemiluminescent donor domain relative to the acceptor domain is altered when the one or more analytes binds the sensor molecule.

19. The method of claim 18, wherein one or more of the analytes are unknown.

* * * * *

SEQUENCE LISTING

```
<160> NUMBER OF SEQ ID NOS: 46

<210> SEQ ID NO 1
<211> LENGTH: 2670
<212> TYPE: DNA
<213> ORGANISM: Artificial Sequence
<220> FEATURE:
<223> OTHER INFORMATION: Nucleotide sequence encoding OGOR2 fusion
      protein

<400> SEQUENCE: 1
atgtcgggag aattgtggat tacectagtt gacacagcgg acattgtcgg cgtcaccctc      60
accttctgtg tcaacattgt tcttctcgga cttctgaaaa cacgtggaaa aaacttgggc     120
acttataaat atctcatggc gtttttctca gtattctcga ttttttacgc catcatcgag     180
ttcatattac gacctataat gcatattgag aacaccactt tcttttttgat ctcaaggaaa     240
```

```
agattcaact actccaccaa acttggaaaa atcaactctg cgttttactg tgcttgtttt       300
gccaccagtt ttgttgtctc aggagttcac tttgtttatc gatattttgc aacttgcaaa       360
ccgaatctac ttcgtttgtt caacttgcca actcttctac tttggccact tggttgcagt       420
gtacccgtga caatgtgggc tagtgtctca tattttttgt atccagatac cgagtacacg       480
gaagcggctg tcaccaatgt actaaataac cactataact ggatcaaaaa ggagaatgta       540
tcgtacattg catacgtcta ttaccaatac gaaaacggag taaggcatat ctacctcaaa       600
aacttgcttg gatgctttgt tcattacttt gtcatgtcga tgacgtttgt tgtgatgttc       660
tactgcggat atgccacgtg gaaaactatg aatgaacaca aggatgtatc tgatagaact       720
atggtgagca agggcgagga gctgttcacc ggggtggtgc ccatcctggt cgagctggac       780
ggcgacgtaa acggccacaa gttcagcgtg tccggcgagg gcgagggcga tgccacctac       840
ggcaagctga ccctgaagtt catctgcacc accggcaagc tgcccgtgcc ctggcccacc       900
ctcgtgacca cctgagcta cggcgtgcag tgcttcagcc gctacccga ccacatgaag        960 cagcacgact tcttcaagtc cgccatgccc gaaggctacg tccaggagcg caccatcttc      1020
ttcaaggacg acggcaacta caagacccgc gccgaggtga agttcgaggg cgacaccctg      1080
gtgaaccgca tcgagctgaa gggcatcgac ttcaaggagg acggcaacat cctggggcac      1140
aagctggagt acaactacaa cagccacaac gtctatatca tggccgacaa gcagaagaac      1200
ggcatcaagg tgaacttcaa gatccgccac aacatcgagg acggcagcgt gcagctcgcc      1260
gaccactacc agcagaacac ccccatcggc gacggccccg tgctgctgcc cgacaaccac      1320
tacctgagca cccagtccgc cctgagcaaa gaccccaacg agaagcgcga tcacatggtc      1380
ctgctggagt tcgtgaccgc cgccgggatc actctcggca tggacgagct gtacaagcga      1440
gcgctacaga acaacttttt caaagcttta gttcttcaga cactcatccc aactatcttc      1500
atgtacgccc caactggagt catgttcatc gcaccgtttt ttgacgtgaa tttgaatgca      1560
aacgccaatt tcattgtgtt ttgctcattt ctgtacccgg gactcgatcc actcattctg      1620
attttgatca ttcgtgattt ccgaagaaca atattcaatt tcttgtgtgg aaagaaaaac      1680
agtgttgatg aatcccgctc gacaacaaga gccaatttgt ctcaagttcc gacgatgacc      1740
agcaaggtgt acgaccccga gcagaggaag aggatgatca ccggcccca gtggtgggcc       1800 aggtgcaagc agatgaacgt gctggacagc ttcatcaact actacgacag cgagaagcac      1860
gccgagaacg ccgtgatctt cctgcacggc aacgccgcta gcagctacct gtggaggcac      1920
gtggtgcccc acatcgagcc cgtggccagg tgcatcatcc ccgatctgat cggcatgggc      1980
aagagcggca agagcggcaa cggcagctac aggctgctgg accactacaa gtacctgacc      2040
gcctggttcg agctcctgaa cctgcccaag aagatcatct tcgtgggcca cgactggggc      2100
gccgccctgg ccttccacta cagctacgag caccaggaca agatcaaggc catcgtgcac      2160
gccgagagcg tggtggacgt gatcgagagc tgggacgagt ggccagacat cgaggaggac      2220
atcgccctga tcaagagcga ggagggcgag aagatggtgc tggagaacaa cttcttcgtg      2280
gagaccgtgc tgcccagcaa gatcatgaga aagctggagc ccgaggagtt cgccgcctac      2340
ctggagccct tcaaggagaa gggcgaggtg agaagaccca ccctgagctg gcccagagag      2400 atcccctgg tgaagggcgg caagcccgac gtggtgcaga tcgtgagaaa ctacaacgcc       2460
tacctgagag ccagcgacga cctgcccaag atgttcatcg agagcgaccc cggcttcttc      2520
agcaacgcca tcgtggaggg cgccaagaag ttccccaaca ccgagttcgt gaaggtgaag      2580
ggcctgcact tcagccagga ggacgccccc gacgagatgg gcaagtacat caagagcttc      2640
```
gtggagagag tgctgaagaa cgagcagtaa                                    2670

<210> SEQ ID NO 2
<211> LENGTH: 889
<212> TYPE: PRT
<213> ORGANISM: Artificial Sequence
<220> FEATURE:
<223> OTHER INFORMATION: OGOR2 fusion protein

<400> SEQUENCE: 2

```
Met Ser Gly Glu Leu Trp Ile Thr Leu Val Asp Thr Ala Asp Ile Val
1               5                   10                  15

Gly Val Thr Leu Thr Phe Cys Val Asn Ile Val Leu Leu Gly Leu Leu
            20                  25                  30

Lys Thr Arg Gly Lys Asn Leu Gly Thr Tyr Lys Tyr Leu Met Ala Phe
        35                  40                  45

Phe Ser Val Phe Ser Ile Phe Tyr Ala Ile Ile Glu Phe Ile Leu Arg
    50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val His Phe Val
            100                 105                 110

Tyr Arg Tyr Phe Ala Thr Cys Lys Pro Asn Leu Leu Arg Leu Phe Asn
        115                 120                 125

Leu Pro Thr Leu Leu Leu Trp Pro Leu Gly Cys Ser Val Pro Val Thr
    130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
                165                 170                 175

Lys Glu Asn Val Ser Tyr Ile Ala Tyr Val Tyr Tyr Gln Tyr Glu Asn
            180                 185                 190

Gly Val Arg His Ile Tyr Leu Lys Asn Leu Leu Gly Cys Phe Val His
        195                 200                 205

Tyr Phe Val Met Ser Met Thr Phe Val Val Met Phe Tyr Cys Gly Tyr
    210                 215                 220

Ala Thr Trp Lys Thr Met Asn Glu His Lys Asp Val Ser Asp Arg Thr
225                 230                 235                 240

Met Val Ser Lys Gly Glu Glu Leu Phe Thr Gly Val Val Pro Ile Leu
                245                 250                 255

Val Glu Leu Asp Gly Asp Val Asn Gly His Lys Phe Ser Val Ser Gly
            260                 265                 270

Glu Gly Glu Gly Asp Ala Thr Tyr Gly Lys Leu Thr Leu Lys Phe Ile
        275                 280                 285

Cys Thr Thr Gly Lys Leu Pro Val Pro Trp Pro Thr Leu Val Thr Thr
    290                 295                 300

Leu Ser Tyr Gly Val Gln Cys Phe Ser Arg Tyr Pro Asp His Met Lys
305                 310                 315                 320

Gln His Asp Phe Phe Lys Ser Ala Met Pro Glu Gly Tyr Val Gln Glu
                325                 330                 335

Arg Thr Ile Phe Phe Lys Asp Asp Gly Asn Tyr Lys Thr Arg Ala Glu
            340                 345                 350
```

-continued

```
Val Lys Phe Glu Gly Asp Thr Leu Val Asn Arg Ile Glu Leu Lys Gly
            355                 360                 365

Ile Asp Phe Lys Glu Asp Gly Asn Ile Leu Gly His Lys Leu Glu Tyr
        370                 375                 380

Asn Tyr Asn Ser His Asn Val Tyr Ile Met Ala Asp Lys Gln Lys Asn
385                 390                 395                 400

Gly Ile Lys Val Asn Phe Lys Ile Arg His Asn Ile Glu Asp Gly Ser
                405                 410                 415

Val Gln Leu Ala Asp His Tyr Gln Gln Asn Thr Pro Ile Gly Asp Gly
            420                 425                 430

Pro Val Leu Leu Pro Asp Asn His Tyr Leu Ser Thr Gln Ser Ala Leu
        435                 440                 445

Ser Lys Asp Pro Asn Glu Lys Arg Asp His Met Val Leu Leu Glu Phe
450                 455                 460

Val Thr Ala Ala Gly Ile Thr Leu Gly Met Asp Glu Leu Tyr Lys Arg
465                 470                 475                 480

Ala Leu Gln Lys Gln Leu Phe Lys Ala Leu Val Leu Gln Thr Leu Ile
                485                 490                 495

Pro Thr Ile Phe Met Tyr Ala Pro Thr Gly Val Met Phe Ile Ala Pro
            500                 505                 510

Phe Phe Asp Val Asn Leu Asn Ala Asn Ala Asn Phe Ile Val Phe Cys
        515                 520                 525

Ser Phe Leu Tyr Pro Gly Leu Asp Pro Leu Ile Leu Ile Leu Ile Ile
    530                 535                 540

Arg Asp Phe Arg Arg Thr Ile Phe Asn Phe Leu Cys Gly Lys Lys Asn
545                 550                 555                 560

Ser Val Asp Glu Ser Arg Ser Thr Thr Arg Ala Asn Leu Ser Gln Val
                565                 570                 575

Pro Thr Met Thr Ser Lys Val Tyr Asp Pro Glu Gln Arg Lys Arg Met
            580                 585                 590

Ile Thr Gly Pro Gln Trp Trp Ala Arg Cys Lys Gln Met Asn Val Leu
        595                 600                 605

Asp Ser Phe Ile Asn Tyr Tyr Asp Ser Glu Lys His Ala Glu Asn Ala
610                 615                 620

Val Ile Phe Leu His Gly Asn Ala Ala Ser Ser Tyr Leu Trp Arg His
625                 630                 635                 640

Val Val Pro His Ile Glu Pro Val Ala Arg Cys Ile Ile Pro Asp Leu
                645                 650                 655

Ile Gly Met Gly Lys Ser Gly Lys Ser Gly Asn Gly Ser Tyr Arg Leu
            660                 665                 670

Leu Asp His Tyr Lys Tyr Leu Thr Ala Trp Phe Glu Leu Leu Asn Leu
        675                 680                 685

Pro Lys Lys Ile Ile Phe Val Gly His Asp Trp Gly Ala Ala Leu Ala
    690                 695                 700

Phe His Tyr Ser Tyr Glu His Gln Asp Lys Ile Lys Ala Ile Val His
705                 710                 715                 720

Ala Glu Ser Val Val Asp Val Ile Glu Ser Trp Asp Glu Trp Pro Asp
                725                 730                 735

Ile Glu Glu Asp Ile Ala Leu Ile Lys Ser Glu Gly Glu Lys Met
            740                 745                 750

Val Leu Glu Asn Asn Phe Phe Val Glu Thr Val Leu Pro Ser Lys Ile
        755                 760                 765

Met Arg Lys Leu Glu Pro Glu Glu Phe Ala Ala Tyr Leu Glu Pro Phe
```

```
                  770                   775                   780
Lys Glu Lys Gly Glu Val Arg Arg Pro Thr Leu Ser Trp Pro Arg Glu
785                 790                 795                 800

Ile Pro Leu Val Lys Gly Gly Lys Pro Asp Val Val Gln Ile Val Arg
                805                 810                 815

Asn Tyr Asn Ala Tyr Leu Arg Ala Ser Asp Asp Leu Pro Lys Met Phe
                820                 825                 830

Ile Glu Ser Asp Pro Gly Phe Phe Ser Asn Ala Ile Val Glu Gly Ala
                835                 840                 845

Lys Lys Phe Pro Asn Thr Glu Phe Val Lys Val Lys Gly Leu His Phe
                850                 855                 860

Ser Gln Glu Asp Ala Pro Asp Glu Met Gly Lys Tyr Ile Lys Ser Phe
865                 870                 875                 880

Val Glu Arg Val Leu Lys Asn Glu Gln
                885

<210> SEQ ID NO 3
<211> LENGTH: 2823
<212> TYPE: DNA
<213> ORGANISM: Artificial Sequence
<220> FEATURE:
<223> OTHER INFORMATION: Nucleotide sequence encoding GFP2-MBP-RLuc2
      fusion protein

<400> SEQUENCE: 3
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgagcta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagctg     720
cagggtggta ccggaggcgg catgaaaatc gaagaaggta aactggtaat ctggattaac     780
ggcgataaag ctataacgg tctcgctgaa gtcggtaaga aattcgagaa agataccgga     840
attaaagtca ccgttgagca tccggataaa ctggaagaga aattcccaca ggttgcggca     900
actggcgatg ccctgacat tatcttctgg gcacacgacc gctttggtgg ctacgctcaa     960
tctggcctgt tggctgaaat cacccccgac aaagcgttcc aggacaagct gtatccgttt    1020
acctgggatg ccgtacgtta aacggcaagc tgattgctt acccgatcgc tgttgaagcg    1080
ttatcgctga tttataacaa agatctgctg ccgaacccgc caaaaacctg gaagagatc    1140 ccggcgctgg ataaagaact gaaagcgaaa ggtaagagcg cgctgatgtt caacctgcaa    1200
gaaccgtact tcacctggcc gctgattgct gctgacgggg ttatgcgtt caagtatgaa    1260 aacggcaagt acgacattaa agacgtgggc gtggataacg ctggcgcgaa agcgggtctg    1320
accttcctgg ttgacctgat taaaaacaaa cacatgaatg cagacaccga ttactccatc    1380
```

```
gcagaagctg cctttaataa aggcgaaaca gcgatgacca tcaacggccc gtgggcatgg    1440
tccaacatcg acaccagcaa agtgaattat ggtgtaacgg tactgccgac cttcaagggt    1500
caaccatcca aaccgttcgt tggcgtgctg agcgcaggta ttaacgccgc cagtccgaac    1560
aaagagctgg caaagagtt cctcgaaaac tatctgctga ctgatgaagg tctggaagcg     1620
gttaataaag acaaaccgct gggtgccgta gcgctgaagt cttacgagga gagttggtg     1680 aaagatccgc gtattgccgc cactatggaa aacgcccaga aggtgaaat catgccgaac     1740 atcccgcaga tgtccgcttt ctggtatgcc gtgcgtactg cggtgatcaa cgccgccagc    1800
ggtcgtcaga ctgtcgatga agccctgaaa gacgcgcaga ctgccctgaa agacgcgcag    1860
actggcggcg gtaccggtgg attcgaaatg gcttccaagg tgtacgaccc cgagcaacgc    1920
aaacgcatga tcactgggcc tcagtggtgg gctcgctgca agcaaatgaa cgtgctggac    1980
tccttcatca actactatga ttccgagaag cacgccgaga acgccgtgat ttttctgcat    2040
ggtaacgctg cctccagcta cctgtggagg cacgtcgtgc ctcacatcga gcccgtggct    2100
agatgcatca tccctgatct gatcggaatg ggtaagtccg gcaagagcgg aatggctca    2160 tatcgcctcc tggatcacta caagtacctc accgcttggt tcgagctgct gaaccttcca    2220
aagaaaatca tctttgtggg ccacgactgg ggggctgctc tggcctttca ctactcctac    2280
gagcaccaag acaagatcaa ggccatcgtc catgctgaga gtgtcgtgga cgtgatcgag    2340
tcctgggacg agtggcctga catcgaggag gatatcgccc tgatcaagag cgaagagggc    2400
gagaaaatgg tgcttgagaa taacttcttc gtcgagaccg tgctcccaag caagatcatg    2460
cggaaactgg agcctgagga gttcgctgcc tacctggagc cattcaagga aagggcgag    2520 gttagacggc ctaccctctc ctggcctcgc gagatccctc tcgttaaggg aggcaagccc    2580
gacgtcgtcc agattgtccg caactacaac gcctaccttc gggccagcga cgatctgcct    2640
aagatgttca tcgagtccga ccctgggttc ttttccaacg ctattgtcga gggagctaag    2700
aagttcccta acaccgagtt cgtgaaggtg aagggcctcc acttcagcca ggaggacgct    2760
ccagatgaaa tgggtaagta catcaagagc ttcgtggagc gcgtgctgaa gaacgagcag    2820
taa                                                                  2823
```

<210> SEQ ID NO 4
<211> LENGTH: 940
<212> TYPE: PRT
<213> ORGANISM: Artificial Sequence
<220> FEATURE:
<223> OTHER INFORMATION: GFP2-MBP-RLuc2 fusion protein

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

-continued

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Leu
225                 230                 235                 240

Gln Gly Gly Thr Gly Gly Met Lys Ile Glu Glu Gly Lys Leu Val
                245                 250                 255

Ile Trp Ile Asn Gly Asp Lys Gly Tyr Asn Gly Leu Ala Glu Val Gly
            260                 265                 270

Lys Lys Phe Glu Lys Asp Thr Gly Ile Lys Val Thr Val Glu His Pro
        275                 280                 285

Asp Lys Leu Glu Glu Lys Phe Pro Gln Val Ala Ala Thr Gly Asp Gly
290                 295                 300

Pro Asp Ile Ile Phe Trp Ala His Asp Arg Phe Gly Gly Tyr Ala Gln
305                 310                 315                 320

Ser Gly Leu Leu Ala Glu Ile Thr Pro Asp Lys Ala Phe Gln Asp Lys
                325                 330                 335

Leu Tyr Pro Phe Thr Trp Asp Ala Val Arg Tyr Asn Gly Lys Leu Ile
            340                 345                 350

Ala Tyr Pro Ile Ala Val Glu Ala Leu Ser Leu Ile Tyr Asn Lys Asp
        355                 360                 365

Leu Leu Pro Asn Pro Pro Lys Thr Trp Glu Glu Ile Pro Ala Leu Asp
370                 375                 380

Lys Glu Leu Lys Ala Lys Gly Lys Ser Ala Leu Met Phe Asn Leu Gln
385                 390                 395                 400

Glu Pro Tyr Phe Thr Trp Pro Leu Ile Ala Ala Asp Gly Gly Tyr Ala
                405                 410                 415

Phe Lys Tyr Glu Asn Gly Lys Tyr Asp Ile Lys Asp Val Gly Val Asp
            420                 425                 430

Asn Ala Gly Ala Lys Ala Gly Leu Thr Phe Leu Val Asp Leu Ile Lys
        435                 440                 445

Asn Lys His Met Asn Ala Asp Thr Asp Tyr Ser Ile Ala Glu Ala Ala
450                 455                 460

Phe Asn Lys Gly Glu Thr Ala Met Thr Ile Asn Gly Pro Trp Ala Trp
465                 470                 475                 480

Ser Asn Ile Asp Thr Ser Lys Val Asn Tyr Gly Val Thr Val Leu Pro
                485                 490                 495

Thr Phe Lys Gly Gln Pro Ser Lys Pro Phe Val Gly Val Leu Ser Ala
            500                 505                 510

Gly Ile Asn Ala Ala Ser Pro Asn Lys Glu Leu Ala Lys Glu Phe Leu

```
            515                 520                 525
Glu Asn Tyr Leu Leu Thr Asp Glu Gly Leu Glu Ala Val Asn Lys Asp
            530                 535                 540
Lys Pro Leu Gly Ala Val Ala Leu Lys Ser Tyr Glu Glu Glu Leu Val
545                 550                 555                 560
Lys Asp Pro Arg Ile Ala Ala Thr Met Glu Asn Ala Gln Lys Gly Glu
                565                 570                 575
Ile Met Pro Asn Ile Pro Gln Met Ser Ala Phe Trp Tyr Ala Val Arg
            580                 585                 590
Thr Ala Val Ile Asn Ala Ala Ser Gly Arg Gln Thr Val Asp Glu Ala
                595                 600                 605
Leu Lys Asp Ala Gln Thr Ala Leu Lys Asp Ala Gln Thr Gly Gly Gly
            610                 615                 620
Thr Gly Gly Phe Glu Met Ala Ser Lys Val Tyr Asp Pro Glu Gln Arg
625                 630                 635                 640
Lys Arg Met Ile Thr Gly Pro Gln Trp Trp Ala Arg Cys Lys Gln Met
                645                 650                 655
Asn Val Leu Asp Ser Phe Ile Asn Tyr Tyr Asp Ser Glu Lys His Ala
            660                 665                 670
Glu Asn Ala Val Ile Phe Leu His Gly Asn Ala Ala Ser Ser Tyr Leu
                675                 680                 685
Trp Arg His Val Val Pro His Ile Glu Pro Val Ala Arg Cys Ile Ile
            690                 695                 700
Pro Asp Leu Ile Gly Met Gly Lys Ser Gly Lys Ser Gly Asn Gly Ser
705                 710                 715                 720
Tyr Arg Leu Leu Asp His Tyr Lys Tyr Leu Thr Ala Trp Phe Glu Leu
                725                 730                 735
Leu Asn Leu Pro Lys Lys Ile Ile Phe Val Gly His Asp Trp Gly Ala
                740                 745                 750
Ala Leu Ala Phe His Tyr Ser Tyr Glu His Gln Asp Lys Ile Lys Ala
                755                 760                 765
Ile Val His Ala Glu Ser Val Val Asp Val Ile Glu Ser Trp Asp Glu
            770                 775                 780
Trp Pro Asp Ile Glu Glu Asp Ile Ala Leu Ile Lys Ser Glu Glu Gly
785                 790                 795                 800
Glu Lys Met Val Leu Glu Asn Asn Phe Phe Val Glu Thr Val Leu Pro
                805                 810                 815
Ser Lys Ile Met Arg Lys Leu Glu Pro Glu Glu Phe Ala Ala Tyr Leu
                820                 825                 830
Glu Pro Phe Lys Glu Lys Gly Glu Val Arg Arg Pro Thr Leu Ser Trp
            835                 840                 845
Pro Arg Glu Ile Pro Leu Val Lys Gly Gly Lys Pro Asp Val Val Gln
            850                 855                 860
Ile Val Arg Asn Tyr Asn Ala Tyr Leu Arg Ala Ser Asp Asp Leu Pro
865                 870                 875                 880
Lys Met Phe Ile Glu Ser Asp Pro Gly Phe Phe Ser Asn Ala Ile Val
                885                 890                 895
Glu Gly Ala Lys Lys Phe Pro Asn Thr Glu Phe Val Lys Val Lys Gly
                900                 905                 910
Leu His Phe Ser Gln Glu Asp Ala Pro Asp Glu Met Gly Lys Tyr Ile
            915                 920                 925
Lys Ser Phe Val Glu Arg Val Leu Lys Asn Glu Gln
            930                 935                 940
```

<210> SEQ ID NO 5
<211> LENGTH: 2823
<212> TYPE: DNA
<213> ORGANISM: Artificial Sequence
<220> FEATURE:
<223> OTHER INFORMATION: Nucleotide sequence encoding GFP2-MBP-RLuc2 W140A fusion protein

<400> SEQUENCE: 5

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgagcta cggcgtgcag tgcttcagcc gctacccgga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagctg     720
cagggtggta ccgaggcgg catgaaaatc gaagaaggta aactggtaat ctggattaac     780
ggcgataaag gctataacgg tctcgctgaa gtcggtaaga aattcgagaa agataccgga     840
attaaagtca ccgttgagca tccggataaa ctggaagaga attcccaca ggttgcggca     900
actggcgatg ccctgacat tatcttctgg gcacacgacc gctttggtgg ctacgctcaa     960
tctggcctgt tggctgaaat caccccggac aaagcgttcc aggacaagct gtatccgttt    1020
acctgggatg ccgtacgtta caacggcaag ctgattgctt acccgatcgc tgttgaagcg    1080
ttatcgctga tttataacaa agatctgctg ccgaacccgc caaaaacctg gaagagatc     1140
ccggcgctgg ataaagaact gaaagcgaaa ggtaagagcg cgctgatgtt caacctgcaa    1200
gaaccgtact tcacctggcc gctgattgct gctgacgggg ttatgcgtt caagtatgaa     1260
aacggcaagt acgacattaa agacgtgggc gtggataacg ctggcgcgaa agcgggtctg    1320
accttcctgg ttgacctgat taaaaacaaa cacatgaatg cagacaccga ttactccatc    1380
gcagaagctg cctttaataa aggcgaaaca gcgatgacca tcaacggccc gtgggcatgg    1440
tccaacatcg acaccagcaa agtgaattat ggtgtaacgg tactgccgac cttcaagggt    1500
caaccatcca aaccgttcgt tggcgtgctg agcgcaggta ttaacgccgc cagtccgaac    1560
aaagagctgg caaagagtt cctcgaaaac tatctgctga ctgatgaagg tctggaagcg    1620
gttaataaag acaaaccgct gggtgccgta gcgctgaagt cttacgagga agagttggtg    1680
aaagatccgc gtattgccgc cactatggaa aacgcccaga aggtgaaat catgccgaac    1740
atcccgcaga tgtccgcttt cgcgtatgcc gtgcgtactg cggtgatcaa cgccgccagc    1800
ggtcgtcaga ctgtcgatga agccctgaaa gacgcgcaga ctgccctgaa agacgcgcag    1860
actggcggcg gtaccggtgg attcgaaatg gcttccaagg tgtacgaccc cgagcaacgc    1920
aaacgcatga tcactgggcc tcagtggtgg ggctcgctgca gcaaatgaa cgtgctggac    1980
tccttcatca actactatga ttccgagaag cacgccgaga acgccgtgat ttttctgcat    2040
```

-continued

```
ggtaacgctg cctccagcta cctgtggagg cacgtcgtgc ctcacatcga gcccgtggct    2100
agatgcatca tccctgatct gatcggaatg ggtaagtccg gcaagagcgg gaatggctca    2160
tatcgcctcc tggatcacta caagtacctc accgcttggt tcgagctgct gaaccttcca    2220
aagaaaatca tctttgtggg ccacgactgg ggggctgctc tggcctttca ctactcctac    2280
gagcaccaag acaagatcaa ggccatcgtc catgctgaga gtgtcgtgga cgtgatcgag    2340
tcctgggacg agtggcctga catcgaggag gatatcgccc tgatcaagag cgaagagggc    2400
gagaaaatgg tgcttgagaa taacttcttc gtcgagaccg tgctcccaag caagatcatg    2460
cggaaactgg agcctgagga gttcgctgcc tacctggagc cattcaagga agggcgag    2520
gttagacggc ctaccctctc ctggcctcgc gagatccctc tcgttaaggg aggcaagccc    2580
gacgtcgtcc agattgtccg caactacaac gcctaccttc gggccagcga cgatctgcct    2640
aagatgttca tcgagtccga ccctgggttc ttttccaacg ctattgtcga gggagctaag    2700
aagttcccta acaccgagtt cgtgaaggtg aagggcctcc acttcagcca ggaggacgct    2760
ccagatgaaa tgggtaagta catcaagagc ttcgtggagc gcgtgctgaa gaacgagcag    2820
taa                                                                  2823
```

<210> SEQ ID NO 6
<211> LENGTH: 940
<212> TYPE: PRT
<213> ORGANISM: Artificial Sequence
<220> FEATURE:
<223> OTHER INFORMATION: GFP2-MBP-RLuc2 W140A fusion protein

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
```

```
                210                 215                 220
Val Thr Ala Ala Gly Ile Thr Leu Gly Met Asp Glu Leu Tyr Lys Leu
225                 230                 235                 240

Gln Gly Gly Thr Gly Gly Met Lys Ile Glu Glu Gly Lys Leu Val
                245                 250                 255

Ile Trp Ile Asn Gly Asp Lys Gly Tyr Asn Gly Leu Ala Glu Val Gly
                260                 265                 270

Lys Lys Phe Glu Lys Asp Thr Gly Ile Lys Val Thr Val Glu His Pro
            275                 280                 285

Asp Lys Leu Glu Glu Lys Phe Pro Gln Val Ala Ala Thr Gly Asp Gly
            290                 295                 300

Pro Asp Ile Ile Phe Trp Ala His Asp Arg Phe Gly Gly Tyr Ala Gln
305                 310                 315                 320

Ser Gly Leu Leu Ala Glu Ile Thr Pro Asp Lys Ala Phe Gln Asp Lys
                325                 330                 335

Leu Tyr Pro Phe Thr Trp Asp Ala Val Arg Tyr Asn Gly Lys Leu Ile
                340                 345                 350

Ala Tyr Pro Ile Ala Val Glu Ala Leu Ser Leu Ile Tyr Asn Lys Asp
                355                 360                 365

Leu Leu Pro Asn Pro Lys Thr Trp Glu Glu Ile Pro Ala Leu Asp
            370                 375                 380

Lys Glu Leu Lys Ala Lys Gly Lys Ser Ala Leu Met Phe Asn Leu Gln
385                 390                 395                 400

Glu Pro Tyr Phe Thr Trp Pro Leu Ile Ala Ala Asp Gly Gly Tyr Ala
                405                 410                 415

Phe Lys Tyr Glu Asn Gly Lys Tyr Asp Ile Lys Asp Val Gly Val Asp
                420                 425                 430

Asn Ala Gly Ala Lys Ala Gly Leu Thr Phe Leu Val Asp Leu Ile Lys
                435                 440                 445

Asn Lys His Met Asn Ala Asp Thr Asp Tyr Ser Ile Ala Glu Ala Ala
            450                 455                 460

Phe Asn Lys Gly Glu Thr Ala Met Thr Ile Asn Gly Pro Trp Ala Trp
465                 470                 475                 480

Ser Asn Ile Asp Thr Ser Lys Val Asn Tyr Gly Val Thr Val Leu Pro
                485                 490                 495

Thr Phe Lys Gly Gln Pro Ser Lys Pro Phe Val Gly Val Leu Ser Ala
                500                 505                 510

Gly Ile Asn Ala Ala Ser Pro Asn Lys Glu Leu Ala Lys Glu Phe Leu
                515                 520                 525

Glu Asn Tyr Leu Leu Thr Asp Glu Gly Leu Glu Ala Val Asn Lys Asp
            530                 535                 540

Lys Pro Leu Gly Ala Val Ala Leu Lys Ser Tyr Glu Glu Glu Leu Val
545                 550                 555                 560

Lys Asp Pro Arg Ile Ala Ala Thr Met Glu Asn Ala Gln Lys Gly Glu
                565                 570                 575

Ile Met Pro Asn Ile Pro Gln Met Ser Ala Phe Ala Tyr Ala Val Arg
                580                 585                 590

Thr Ala Val Ile Asn Ala Ser Gly Arg Gln Thr Val Asp Glu Ala
                595                 600                 605

Leu Lys Asp Ala Gln Thr Ala Leu Lys Asp Ala Gln Thr Gly Gly Gly
            610                 615                 620

Thr Gly Gly Phe Glu Met Ala Ser Lys Val Tyr Asp Pro Glu Gln Arg
625                 630                 635                 640
```

Lys Arg Met Ile Thr Gly Pro Gln Trp Trp Ala Arg Cys Lys Gln Met
                645                 650                 655

Asn Val Leu Asp Ser Phe Ile Asn Tyr Tyr Asp Ser Glu Lys His Ala
                660                 665                 670

Glu Asn Ala Val Ile Phe Leu His Gly Asn Ala Ala Ser Ser Tyr Leu
                675                 680                 685

Trp Arg His Val Val Pro His Ile Glu Pro Val Ala Arg Cys Ile Ile
            690                 695                 700

Pro Asp Leu Ile Gly Met Gly Lys Ser Gly Lys Ser Gly Asn Gly Ser
705                 710                 715                 720

Tyr Arg Leu Leu Asp His Tyr Lys Tyr Leu Thr Ala Trp Phe Glu Leu
                725                 730                 735

Leu Asn Leu Pro Lys Lys Ile Ile Phe Val Gly His Asp Trp Gly Ala
                740                 745                 750

Ala Leu Ala Phe His Tyr Ser Tyr Glu His Gln Asp Lys Ile Lys Ala
            755                 760                 765

Ile Val His Ala Glu Ser Val Val Asp Val Ile Glu Ser Trp Asp Glu
            770                 775                 780

Trp Pro Asp Ile Glu Glu Asp Ile Ala Leu Ile Lys Ser Glu Glu Gly
785                 790                 795                 800

Glu Lys Met Val Leu Glu Asn Asn Phe Phe Val Glu Thr Val Leu Pro
                805                 810                 815

Ser Lys Ile Met Arg Lys Leu Glu Pro Glu Glu Phe Ala Ala Tyr Leu
                820                 825                 830

Glu Pro Phe Lys Glu Lys Gly Glu Val Arg Arg Pro Thr Leu Ser Trp
            835                 840                 845

Pro Arg Glu Ile Pro Leu Val Lys Gly Gly Lys Pro Asp Val Val Gln
850                 855                 860

Ile Val Arg Asn Tyr Asn Ala Tyr Leu Arg Ala Ser Asp Asp Leu Pro
865                 870                 875                 880

Lys Met Phe Ile Glu Ser Asp Pro Gly Phe Phe Ser Asn Ala Ile Val
                885                 890                 895

Glu Gly Ala Lys Lys Phe Pro Asn Thr Glu Phe Val Lys Val Lys Gly
                900                 905                 910

Leu His Phe Ser Gln Glu Asp Ala Pro Asp Glu Met Gly Lys Tyr Ile
            915                 920                 925

Lys Ser Phe Val Glu Arg Val Leu Lys Asn Glu Gln
930                 935                 940

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
cacgactggg gcgccgccct ggccttccac tac                           33

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8

```
gtagtggaag gccagggcgg cgccccagtc gtg                                    33

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
cttcttcgtg gagaccgtgc tgcccagcaa gatc                                   34

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
gatcttgctg ggcagcacgg tctccacgaa gaag                                   34

<210> SEQ ID NO 11
<211> LENGTH: 32
<212> TYPE: DNA
<213> ORGANISM: Artificial Sequence
<220> FEATURE:
<223> OTHER INFORMATION: Primer

<400> SEQUENCE: 11
cagatgtccg ctttcgcgta tgccgtgcgt ac                                     32

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
gtacgcacgg catacgcgaa agcggacatc tg                                     32

<210> SEQ ID NO 13
<211> LENGTH: 896
<212> TYPE: PRT
<213> ORGANISM: Artificial Sequence
<220> FEATURE:
<223> OTHER INFORMATION: GFP2-str-112 SGSR-RLuc fusion protein

<400> SEQUENCE: 13

Met Ser Gly Gln Leu Trp Leu Ala Leu Val Asp Ala Ala Asp Met Val
1               5                   10                  15

Gly Phe Thr Leu Thr Ile Ser Ile Asn Ile Ile Leu Gly Leu Ile
            20                  25                  30

Arg Thr Arg Gly Lys Thr Leu Gly Thr Tyr Lys Tyr Leu Met Ser Phe
        35                  40                  45

Phe Ser Phe Phe Ser Ile Phe Tyr Ala Ile Val Glu Ser Ile Leu Arg
    50                  55                  60

Pro Ile Met His Ile Glu Asn Thr Thr Phe Phe Leu Ile Ser Arg Lys
65                  70                  75                  80

Arg Phe Asp Tyr Ser Thr Arg Leu Gly Lys Ile Asn Ser Ala Phe Tyr
                85                  90                  95
```

```
Cys Ala Cys Phe Ala Thr Ser Phe Val Leu Ser Ala Val His Phe Val
            100                 105                 110
Tyr Arg Tyr Phe Ala Ala Cys Lys Pro Asn Leu Leu Arg Leu Phe Asn
            115                 120                 125
Leu Pro His Leu Leu Leu Trp Pro Leu Met Cys Ser Ile Pro Val Thr
            130                 135                 140
Ala Trp Ala Ser Val Ser Tyr Phe Leu Tyr Pro Asp Thr Glu Tyr Thr
145                 150                 155                 160
Glu Ala Ala Val Thr Tyr Val Leu Lys Thr His Tyr Glu Val Ile Lys
                165                 170                 175
Lys Glu Asn Val Ser Tyr Ile Ala Tyr Val Tyr Gln Tyr Glu Asn
            180                 185                 190
Gly Glu Arg His Ile Tyr Ile Lys Asn Leu Leu Gly Cys Phe Val His
            195                 200                 205
Tyr Phe Val Met Ser Met Thr Phe Val Val Phe Tyr Cys Gly Phe
            210                 215                 220
Ser Thr Trp Trp Thr Ile Arg Glu His Arg Gly Ala Ser Asp Arg Thr
225                 230                 235                 240
Met Val Ser Lys Gly Glu Glu Leu Phe Thr Gly Val Val Pro Ile Leu
                245                 250                 255
Val Glu Leu Asp Gly Asp Val Asn Gly His Lys Phe Ser Val Ser Gly
            260                 265                 270
Glu Gly Glu Gly Asp Ala Thr Tyr Gly Lys Leu Thr Leu Lys Phe Ile
            275                 280                 285
Cys Thr Thr Gly Lys Leu Pro Val Pro Trp Pro Thr Leu Val Thr Thr
            290                 295                 300
Leu Thr Tyr Gly Val Gln Cys Phe Ser Arg Tyr Pro Asp His Met Lys
305                 310                 315                 320
Gln His Asp Phe Phe Lys Ser Ala Met Pro Glu Gly Tyr Val Gln Glu
                325                 330                 335
Arg Thr Ile Phe Phe Lys Asp Asp Gly Asn Tyr Lys Thr Arg Ala Glu
            340                 345                 350
Val Lys Phe Glu Gly Asp Thr Leu Val Asn Arg Ile Glu Leu Lys Gly
            355                 360                 365
Ile Asp Phe Lys Glu Asp Gly Asn Ile Leu Gly His Lys Leu Glu Tyr
            370                 375                 380
Asn Tyr Asn Ser His Asn Val Tyr Ile Met Ala Asp Lys Gln Lys Asn
385                 390                 395                 400
Gly Ile Lys Val Asn Phe Lys Ile Arg His Asn Ile Glu Asp Gly Ser
            405                 410                 415
Val Gln Leu Ala Asp His Tyr Gln Gln Asn Thr Pro Ile Gly Asp Gly
            420                 425                 430
Pro Val Leu Leu Pro Asp Asn His Tyr Leu Ser Thr Gln Ser Ala Leu
            435                 440                 445
Ser Lys Asp Pro Asn Glu Lys Arg Asp His Met Val Leu Leu Glu Phe
450                 455                 460
Val Thr Ala Ala Gly Ile Thr Leu Gly Met Asp Glu Leu Tyr Lys Arg
465                 470                 475                 480
His Leu His Arg Gln Leu Phe Lys Ala Leu Val Phe Gln Thr Leu Val
                485                 490                 495
Pro Ser Ile Phe Met Tyr Ile Pro Thr Gly Val Met Phe Ile Ala Pro
            500                 505                 510
Phe Phe Asp Ile Asn Leu Asn Ala Asn Ala Asn Phe Ile Val Phe Cys
```

```
            515                 520                 525
Ser Phe Leu Tyr Pro Gly Leu Asp Pro Leu Ile Leu Ile Phe Ile Ile
530                 535                 540

Arg Glu Phe Arg Val Thr Ile Leu Asn Ile Ile Arg Gly Asn Glu Arg
545                 550                 555                 560

Gly Asn Ala Val Gly Glu Ala Tyr Ser Thr Ser Arg Ile Lys Ser Ser
                565                 570                 575

Gln Pro Ala Ala Val Asn Leu Ser Gly Met Thr Ser Lys Val Tyr Asp
                580                 585                 590

Pro Glu Gln Arg Lys Arg Met Ile Thr Gly Pro Gln Trp Trp Ala Arg
                595                 600                 605

Cys Lys Gln Met Asn Val Leu Asp Ser Phe Ile Asn Tyr Tyr Asp Ser
610                 615                 620

Glu Lys His Ala Glu Asn Ala Val Ile Phe Leu His Gly Asn Ala Ala
625                 630                 635                 640

Ser Ser Tyr Leu Trp Arg His Val Val Pro His Ile Glu Pro Val Ala
                645                 650                 655

Arg Cys Ile Ile Pro Asp Leu Ile Gly Met Gly Lys Ser Gly Lys Ser
                660                 665                 670

Gly Asn Gly Ser Tyr Arg Leu Leu Asp His Tyr Lys Tyr Leu Thr Ala
                675                 680                 685

Trp Phe Glu Leu Leu Asn Leu Pro Lys Lys Ile Ile Phe Val Gly His
690                 695                 700

Asp Trp Gly Ala Cys Leu Ala Phe His Tyr Ser Tyr Glu His Gln Asp
705                 710                 715                 720

Lys Ile Lys Ala Ile Val His Ala Glu Ser Val Val Asp Val Ile Glu
                725                 730                 735

Ser Trp Asp Glu Trp Pro Asp Ile Glu Asp Ile Ala Leu Ile Lys
                740                 745                 750

Ser Glu Glu Gly Glu Lys Met Val Leu Glu Asn Asn Phe Phe Val Glu
                755                 760                 765

Thr Met Leu Pro Ser Lys Ile Met Arg Lys Leu Glu Pro Glu Glu Phe
770                 775                 780

Ala Ala Tyr Leu Glu Pro Phe Lys Glu Lys Gly Glu Val Arg Arg Pro
785                 790                 795                 800

Thr Leu Ser Trp Pro Arg Glu Ile Pro Leu Val Lys Gly Gly Lys Pro
                805                 810                 815

Asp Val Val Gln Ile Val Arg Asn Tyr Asn Ala Tyr Leu Arg Ala Ser
                820                 825                 830

Asp Asp Leu Pro Lys Met Phe Ile Glu Ser Asp Pro Gly Phe Phe Ser
                835                 840                 845

Asn Ala Ile Val Glu Gly Ala Lys Lys Phe Pro Asn Thr Glu Phe Val
850                 855                 860

Lys Val Lys Gly Leu His Phe Ser Gln Glu Asp Ala Pro Asp Glu Met
865                 870                 875                 880

Gly Lys Tyr Ile Lys Ser Phe Val Glu Arg Val Leu Lys Asn Glu Gln
                885                 890                 895
```

<210> SEQ ID NO 14
<211> LENGTH: 897
<212> TYPE: PRT
<213> ORGANISM: Artificial Sequence
<220> FEATURE:
<223> OTHER INFORMATION: GFP2-str-113 SGSR-RLuc fusion protein

<400> SEQUENCE: 14

```
Met Ser Asp Arg His Trp Leu Asp Ile Thr Thr Tyr Ser Asp His Ile
1               5                   10                  15

Gly Phe Thr Ile Ser Thr Ile Ala Asn Phe Val Leu Ile Leu Leu Leu
            20                  25                  30

Val Phe Arg Pro Thr Lys Ser Tyr Gly Ser Tyr Lys Tyr Leu Met Ile
        35                  40                  45

Thr Phe Cys Val Phe Ser Leu Phe Tyr Thr Ser Ile Glu Thr Phe Leu
    50                  55                  60

Arg Pro Leu Ile His Ile Tyr Asp Asn Thr Ile Phe Val Ile Gln Arg
65                  70                  75                  80

Lys Arg Phe Gln Tyr Ser Glu Gly Thr Ala Arg Ala Ile Ser Ser Thr
                85                  90                  95

Tyr Cys Gly Cys Tyr Ala Met Ser Phe Thr Leu Phe Ala Val His Phe
            100                 105                 110

Val Tyr Arg Tyr Tyr Ala Ala Cys Lys Pro Asp Asn Leu Arg Tyr Phe
        115                 120                 125

Gln Gly Cys Tyr Phe Val Ala Trp Val Phe Gly Ala Met Ala Val Ala
    130                 135                 140

Ala Ser Trp Gly Phe Ala Ala Phe Ile Leu Tyr Pro Glu Thr Glu Arg
145                 150                 155                 160

Thr Arg Thr Ala Leu Ile His Val Ile Gln Thr Ser Tyr Glu Leu Asp
                165                 170                 175

Pro Glu Trp Val Gly Asn Val Pro Tyr Ser Tyr Trp Arg Thr Glu Asn
            180                 185                 190

Gly Val Glu Tyr Leu Asn Pro Arg Asn Val Ile Gly Ile Phe Gln His
        195                 200                 205

Gly Val Ile Met Ile Leu Ser Phe Gly Thr Val Phe Tyr Cys Gly Phe
    210                 215                 220

Asn Thr Tyr Lys Thr Leu Asn Gly Ser Leu Gly Val Ser Glu Lys Thr
225                 230                 235                 240

Ser Gly Met Val Ser Lys Gly Glu Glu Leu Phe Thr Gly Val Val Pro
                245                 250                 255

Ile Leu Val Glu Leu Asp Gly Asp Val Asn Gly His Lys Phe Ser Val
            260                 265                 270

Ser Gly Glu Gly Glu Gly Asp Ala Thr Tyr Gly Lys Leu Thr Leu Lys
        275                 280                 285

Phe Ile Cys Thr Thr Gly Lys Leu Pro Val Pro Trp Pro Thr Leu Val
    290                 295                 300

Thr Thr Leu Ser Tyr Gly Val Gln Cys Phe Ser Arg Tyr Pro Asp His
305                 310                 315                 320

Met Lys Gln His Asp Phe Phe Lys Ser Ala Met Pro Glu Gly Tyr Val
                325                 330                 335

Gln Glu Arg Thr Ile Phe Phe Lys Asp Asp Gly Asn Tyr Lys Thr Arg
            340                 345                 350

Ala Glu Val Lys Phe Glu Gly Asp Thr Leu Val Asn Arg Ile Glu Leu
        355                 360                 365

Lys Gly Ile Asp Phe Lys Glu Asp Gly Asn Ile Leu Gly His Lys Leu
    370                 375                 380

Glu Tyr Asn Tyr Asn Ser His Asn Val Tyr Ile Met Ala Asp Lys Gln
385                 390                 395                 400

Lys Asn Gly Ile Lys Val Asn Phe Lys Ile Arg His Asn Ile Glu Asp
                405                 410                 415
```

```
Gly Ser Val Gln Leu Ala Asp His Tyr Gln Gln Asn Thr Pro Ile Gly
            420                 425                 430

Asp Gly Pro Val Leu Leu Pro Asp Asn His Tyr Leu Ser Thr Gln Ser
            435                 440                 445

Ala Leu Ser Lys Asp Pro Asn Glu Lys Arg Asp His Met Val Leu Leu
    450                 455                 460

Glu Phe Val Thr Ala Ala Gly Ile Thr Leu Gly Met Asp Glu Leu Tyr
465                 470                 475                 480

Lys Val Asp Lys Glu Met His Thr Gln Leu Phe Lys Ala Leu Val Leu
                485                 490                 495

Gln Thr Ile Ile Pro Thr Thr Leu Met Tyr Ile Pro Thr Thr Met Leu
            500                 505                 510

Phe Val Thr Pro Phe Val Gly Leu Asn Ile Gly Cys Tyr Gly Asn Ile
            515                 520                 525

Thr Thr Ala Thr Val His Leu Tyr Pro Gly Ile Asp Pro Val Val Leu
    530                 535                 540

Ile Phe Ile Ile Arg Asp Phe Arg Gln Thr Ile Leu Arg Pro Phe Arg
545                 550                 555                 560

Cys Phe Tyr Arg Ser Asn Ser Val Glu Asn Thr Ala Thr Ile Arg Gln
                565                 570                 575

Tyr Gln Gln Ser Ser Ser Lys Gly Ser Arg Met Thr Ser Lys Val Tyr
            580                 585                 590

Asp Pro Glu Gln Arg Lys Arg Met Ile Thr Gly Pro Gln Trp Trp Ala
            595                 600                 605

Arg Cys Lys Gln Met Asn Val Leu Asp Ser Phe Ile Asn Tyr Tyr Asp
    610                 615                 620

Ser Glu Lys His Ala Glu Asn Ala Val Ile Phe Leu His Gly Asn Ala
625                 630                 635                 640

Ala Ser Ser Tyr Leu Trp Arg His Val Pro His Ile Glu Pro Val
                645                 650                 655

Ala Arg Cys Ile Ile Pro Asp Leu Ile Gly Met Gly Lys Ser Gly Lys
            660                 665                 670

Ser Gly Asn Gly Ser Tyr Arg Leu Leu Asp His Tyr Lys Tyr Leu Thr
            675                 680                 685

Ala Trp Phe Glu Leu Leu Asn Leu Pro Lys Lys Ile Ile Phe Val Gly
    690                 695                 700

His Asp Trp Gly Ala Cys Leu Ala Phe His Tyr Ser Tyr Glu His Gln
705                 710                 715                 720

Asp Lys Ile Lys Ala Ile Val His Ala Glu Ser Val Val Asp Val Ile
                725                 730                 735

Glu Ser Trp Asp Glu Trp Pro Asp Ile Glu Glu Asp Ile Ala Leu Ile
            740                 745                 750

Lys Ser Glu Glu Gly Glu Lys Met Val Leu Glu Asn Asn Phe Phe Val
    755                 760                 765

Glu Thr Met Leu Pro Ser Lys Ile Met Arg Lys Leu Glu Pro Glu Glu
            770                 775                 780

Phe Ala Ala Tyr Leu Glu Pro Phe Lys Glu Lys Gly Glu Val Arg Arg
785                 790                 795                 800

Pro Thr Leu Ser Trp Pro Arg Glu Ile Pro Leu Val Lys Gly Gly Lys
                805                 810                 815

Pro Asp Val Val Gln Ile Val Arg Asn Tyr Asn Ala Tyr Leu Arg Ala
            820                 825                 830
```

Ser Asp Asp Leu Pro Lys Met Phe Ile Glu Ser Asp Pro Gly Phe Phe
         835                 840                 845

Ser Asn Ala Ile Val Glu Gly Ala Lys Lys Phe Pro Asn Thr Glu Phe
        850                 855                 860

Val Lys Val Lys Gly Leu His Phe Ser Gln Glu Asp Ala Pro Asp Glu
865                 870                 875                 880

Met Gly Lys Tyr Ile Lys Ser Phe Val Glu Arg Val Leu Lys Asn Glu
                885                 890                 895

Gln

<210> SEQ ID NO 15
<211> LENGTH: 904
<212> TYPE: PRT
<213> ORGANISM: Artificial Sequence
<220> FEATURE:
<223> OTHER INFORMATION: GFP2-str-114 SGSR-RLuc fusion protein

<400> SEQUENCE: 15

Met Ser Asp Ile Tyr Trp Ile Gln Ile Thr Glu Val Cys Ser Phe Val
1               5                   10                  15

Gly Phe Met Leu Ser Val Leu Gly Asn Ser Thr Leu Val Leu Leu
            20                  25                  30

Ser Gly Lys Ser Ile Asp Gly Ile Gly Thr Tyr Arg Tyr Leu Met Ile
        35                  40                  45

Thr Phe Cys Val Phe Ser Leu Leu Phe Thr Ile Leu Glu Asp Phe Ile
    50                  55                  60

Arg Pro Leu Met His His Tyr Asn Asn Thr Ile Val Leu Gln Arg
65                  70                  75                  80

Lys Arg Phe Gln Phe Ser Asp Ser Thr Ala Arg Ile Leu Thr Val Ser
                85                  90                  95

Tyr Cys Gly Cys Phe Ala Met Cys Phe Val Met Phe Ala Val His Phe
            100                 105                 110

Ile Tyr Arg Tyr Leu Val Ala Cys His Pro Thr Lys Leu His Tyr Phe
        115                 120                 125

Arg Pro Lys Asn Phe Ile Phe Trp Leu Ser Gly Met Leu Phe Ile Ala
    130                 135                 140

Gly Ser Trp Val Ala Ile Ala Tyr Val Phe Phe Gln Glu Asp Leu Glu
145                 150                 155                 160

Thr Arg Thr Asp Leu Val Phe Ile Leu Ser Thr Cys Tyr Asn Leu Thr
                165                 170                 175

Pro Asp Asp Val Gly His Val Pro Tyr Ala Phe Tyr Lys Thr Gln Gly
            180                 185                 190

Asn Thr Arg Val Ile Arg Trp Asp Asn Met Ile Gly Val Ile His His
        195                 200                 205

Met Ile Val Met Thr Ile Ser Ile Ser Ala Val Phe Tyr Phe Gly Ile
    210                 215                 220

Lys Thr Tyr Thr Arg Ile Met Ser Phe Lys Gly Lys Ser Gln Lys Thr
225                 230                 235                 240

Ser Gly Met Val Ser Lys Gly Glu Glu Leu Phe Thr Gly Val Val Pro
                245                 250                 255

Ile Leu Val Glu Leu Asp Gly Asp Val Asn Gly His Lys Phe Ser Val
            260                 265                 270

Ser Gly Glu Gly Glu Gly Asp Ala Thr Tyr Gly Lys Leu Thr Leu Lys
        275                 280                 285

Phe Ile Cys Thr Thr Gly Lys Leu Pro Val Pro Trp Pro Thr Leu Val

-continued

```
            290                 295                 300
Thr Thr Leu Ser Tyr Gly Val Gln Cys Phe Ser Arg Tyr Pro Asp His
305                 310                 315                 320

Met Lys Gln His Asp Phe Phe Lys Ser Ala Met Pro Glu Gly Tyr Val
                    325                 330                 335

Gln Glu Arg Thr Ile Phe Phe Lys Asp Asp Gly Asn Tyr Lys Thr Arg
                340                 345                 350

Ala Glu Val Lys Phe Glu Gly Asp Thr Leu Val Asn Arg Ile Glu Leu
            355                 360                 365

Lys Gly Ile Asp Phe Lys Glu Asp Gly Asn Ile Leu Gly His Lys Leu
        370                 375                 380

Glu Tyr Asn Tyr Asn Ser His Asn Val Tyr Ile Met Ala Asp Lys Gln
385                 390                 395                 400

Lys Asn Gly Ile Lys Val Asn Phe Lys Ile Arg His Asn Ile Glu Asp
                    405                 410                 415

Gly Ser Val Gln Leu Ala Asp His Tyr Gln Gln Asn Thr Pro Ile Gly
                420                 425                 430

Asp Gly Pro Val Leu Leu Pro Asp Asn His Tyr Leu Ser Thr Gln Ser
            435                 440                 445

Ala Leu Ser Lys Asp Pro Asn Glu Lys Arg Asp His Met Val Leu Leu
        450                 455                 460

Glu Phe Val Thr Ala Ala Gly Ile Thr Leu Gly Met Asp Glu Leu Tyr
465                 470                 475                 480

Lys Val Asp Lys Asp Leu Gln Asn Gln Phe Phe Thr Ala Leu Val Ala
                    485                 490                 495

Gln Thr Val Val Pro Leu Ile Phe Met Phe Ile Pro Asn Met Val Leu
                500                 505                 510

Thr Thr Ala Ala Leu Ile Asp Gly Thr Phe Gly Ser Trp Ala Asn Ile
            515                 520                 525

Thr Val Val Met Asn His Leu Tyr Pro Ala Ala Asp Pro Phe Val Ile
        530                 535                 540

Leu Phe Ile Ile Lys Gly Phe Arg Asn Ser Ile Arg Asn Val Ile Tyr
545                 550                 555                 560

Arg Cys Thr Lys Thr Lys Lys Ala Ser Val Ser Ser Val Val Arg Gly
                    565                 570                 575

Ile Glu Ala Gln Ser Lys Lys Gln Ser Phe Ser Arg Val Asp Ile Ser
                580                 585                 590

Arg Met Thr Ser Lys Val Tyr Asp Pro Glu Gln Arg Lys Arg Met Ile
            595                 600                 605

Thr Gly Pro Gln Trp Trp Ala Arg Cys Lys Gln Met Asn Val Leu Asp
        610                 615                 620

Ser Phe Ile Asn Tyr Tyr Asp Ser Glu Lys His Ala Glu Asn Ala Val
625                 630                 635                 640

Ile Phe Leu His Gly Asn Ala Ala Ser Ser Tyr Leu Trp Arg His Val
                    645                 650                 655

Val Pro His Ile Glu Pro Val Ala Arg Cys Ile Ile Pro Asp Leu Ile
                660                 665                 670

Gly Met Gly Lys Ser Gly Lys Ser Gly Asn Gly Ser Tyr Arg Leu Leu
            675                 680                 685

Asp His Tyr Lys Tyr Leu Thr Ala Trp Phe Glu Leu Leu Asn Leu Pro
        690                 695                 700

Lys Lys Ile Ile Phe Val Gly His Asp Trp Gly Ala Cys Leu Ala Phe
705                 710                 715                 720
```

```
His Tyr Ser Tyr Glu His Gln Asp Lys Ile Lys Ala Ile Val His Ala
            725                 730                 735

Glu Ser Val Val Asp Val Ile Glu Ser Trp Asp Glu Trp Pro Asp Ile
        740                 745                 750

Glu Glu Asp Ile Ala Leu Ile Lys Ser Glu Gly Leu Lys Met Val
    755                 760                 765

Leu Glu Asn Asn Phe Phe Val Glu Thr Met Leu Pro Ser Lys Ile Met
770                 775                 780

Arg Lys Leu Glu Pro Glu Glu Phe Ala Ala Tyr Leu Glu Pro Phe Lys
785                 790                 795                 800

Glu Lys Gly Glu Val Arg Arg Pro Thr Leu Ser Trp Pro Arg Glu Ile
                805                 810                 815

Pro Leu Val Lys Gly Gly Lys Pro Asp Val Val Gln Ile Val Arg Asn
                820                 825                 830

Tyr Asn Ala Tyr Leu Arg Ala Ser Asp Asp Leu Pro Lys Met Phe Ile
                835                 840                 845

Glu Ser Asp Pro Gly Phe Phe Ser Asn Ala Ile Val Glu Gly Ala Lys
            850                 855                 860

Lys Phe Pro Asn Thr Glu Phe Val Lys Val Lys Gly Leu His Phe Ser
865                 870                 875                 880

Gln Glu Asp Ala Pro Asp Glu Met Gly Lys Tyr Ile Lys Ser Phe Val
                885                 890                 895

Glu Arg Val Leu Lys Asn Glu Gln
            900

<210> SEQ ID NO 16
<211> LENGTH: 890
<212> TYPE: PRT
<213> ORGANISM: Artificial Sequence
<220> FEATURE:
<223> OTHER INFORMATION: GFP2-str-115 SGSR-RLuc fusion protein

<400> SEQUENCE: 16

Met Thr Asp Gln His Trp Val Ile Ile Thr Asp Ile Ala Gly Pro Ile
1               5                   10                  15

Gly Phe Ser Met Ser Ile Phe Ser Asn Ser Ile Leu Leu Phe Leu Ile
                20                  25                  30

Phe Ser His Ser Ser Pro Ile Lys Gly Pro Tyr Lys Arg Met Leu Ile
            35                  40                  45

Val Phe Cys Ile Phe Thr Val Phe Tyr Ser Phe Val Glu Val Met Leu
        50                  55                  60

Gln Pro Leu Ile His Ile Tyr Asp Asp Thr Leu Phe Leu Ile His Arg
65                  70                  75                  80

Lys Arg Ile Asp Leu Pro Lys Trp Leu Thr Arg Leu Val Pro Thr Thr
                85                  90                  95

Tyr Cys Trp Cys Tyr Ala Met Ser Phe Ser Leu Phe Ala Leu Gln Phe
            100                 105                 110

Leu Tyr Arg Tyr Val Ala Val Cys Lys Pro Gln Tyr Val Asp Leu Phe
        115                 120                 125

Val Gly Cys His Phe Tyr Ala Trp Val Val Leu Ile Leu Ser Leu Ala
    130                 135                 140

Thr Ser Trp Gly Leu Thr Ala Ala Phe Met Phe Pro Gln Thr Asp Arg
145                 150                 155                 160

Thr Thr Glu Ile Phe Leu His Ile Ile Tyr Ser Ser Tyr Asp Leu Glu
                165                 170                 175
```

```
Pro Tyr Trp Thr Asp Tyr Val Ala Tyr Lys Tyr Phe Asp Thr Asp Glu
            180                 185                 190

Asn Asn Val Arg Trp Val Asn Val Leu Ser Phe Phe Gly Val Leu Gln
            195                 200             205

His Gly Ile Val Ile Thr Leu Ser Phe Gly Thr Leu Tyr Tyr Cys Gly
            210                 215                 220

Ile Asn Thr Tyr Leu Lys Ile Lys Lys His Thr Gly Thr Ser Asn Arg
225                 230                 235                 240

Thr Ser Gly Met Val Ser Lys Gly Glu Glu Leu Phe Thr Gly Val Val
                245                 250                 255

Pro Ile Leu Val Glu Leu Asp Gly Asp Val Asn Gly His Lys Phe Ser
                260                 265                 270

Val Ser Gly Glu Gly Glu Gly Asp Ala Thr Tyr Gly Lys Leu Thr Leu
                275                 280                 285

Lys Phe Ile Cys Thr Thr Gly Lys Leu Pro Val Pro Trp Pro Thr Leu
                290                 295                 300

Val Thr Thr Leu Ser Tyr Gly Val Gln Cys Phe Ser Arg Tyr Pro Asp
305                 310                 315                 320

His Met Lys Gln His Asp Phe Phe Lys Ser Ala Met Pro Glu Gly Tyr
                325                 330                 335

Val Gln Glu Arg Thr Ile Phe Phe Lys Asp Asp Gly Asn Tyr Lys Thr
                340                 345                 350

Arg Ala Glu Val Lys Phe Glu Gly Asp Thr Leu Val Asn Arg Ile Glu
                355                 360                 365

Leu Lys Gly Ile Asp Phe Lys Glu Asp Gly Asn Ile Leu Gly His Lys
                370                 375                 380

Leu Glu Tyr Asn Tyr Asn Ser His Asn Val Tyr Ile Met Ala Asp Lys
385                 390                 395                 400

Gln Lys Asn Gly Ile Lys Val Asn Phe Lys Ile Arg His Asn Ile Glu
                405                 410                 415

Asp Gly Ser Val Gln Leu Ala Asp His Tyr Gln Gln Asn Thr Pro Ile
                420                 425                 430

Gly Asp Gly Pro Val Leu Leu Pro Asp Asn His Tyr Leu Ser Thr Gln
                435                 440                 445

Ser Ala Leu Ser Lys Asp Pro Asn Glu Lys Arg Asp His Met Val Leu
                450                 455                 460

Leu Glu Phe Val Thr Ala Ala Gly Ile Thr Leu Gly Met Asp Glu Leu
465                 470                 475                 480

Tyr Lys Val Asp Arg Cys Ile Gln Leu Gln Leu Phe Arg Ala Leu Val
                485                 490                 495

Ala Gln Thr Ile Leu Pro Met Phe Met Met Tyr Ile Pro Val Gly Phe
                500                 505                 510

Met Phe Ala Cys Pro Tyr Phe Asp Leu Gln Leu Gly Ala Tyr Thr Asn
                515                 520                 525

Tyr Gln Thr Val Met Ala Gln Leu Tyr Pro Gly Ile Asp Pro Phe Val
                530                 535                 540

Met Leu Phe Leu Ile Asp Ser Tyr Arg Ile Thr Ile Phe Gly Trp Leu
545                 550                 555                 560

Cys Pro Arg Phe Val Tyr Val Lys Pro Met His Ser Tyr Thr Leu
                565                 570                 575

Thr Ser Arg Met Thr Ser Lys Val Tyr Asp Pro Glu Gln Arg Lys Arg
                580                 585                 590
```

-continued

```
Met Ile Thr Gly Pro Gln Trp Trp Ala Arg Cys Lys Gln Met Asn Val
            595                 600                 605

Leu Asp Ser Phe Ile Asn Tyr Tyr Asp Ser Glu Lys His Ala Glu Asn
610                 615                 620

Ala Val Ile Phe Leu His Gly Asn Ala Ala Ser Ser Tyr Leu Trp Arg
625                 630                 635                 640

His Val Val Pro His Ile Glu Pro Val Ala Arg Cys Ile Ile Pro Asp
                645                 650                 655

Leu Ile Gly Met Gly Lys Ser Gly Lys Ser Gly Asn Gly Ser Tyr Arg
            660                 665                 670

Leu Leu Asp His Tyr Lys Tyr Leu Thr Ala Trp Phe Glu Leu Leu Asn
        675                 680                 685

Leu Pro Lys Lys Ile Ile Phe Val Gly His Asp Trp Gly Ala Cys Leu
    690                 695                 700

Ala Phe His Tyr Ser Tyr Glu His Gln Asp Lys Ile Lys Ala Ile Val
705                 710                 715                 720

His Ala Glu Ser Val Val Asp Val Ile Glu Ser Trp Asp Glu Trp Pro
                725                 730                 735

Asp Ile Glu Glu Asp Ile Ala Leu Ile Lys Ser Glu Glu Gly Glu Lys
            740                 745                 750

Met Val Leu Glu Asn Asn Phe Phe Val Glu Thr Met Leu Pro Ser Lys
        755                 760                 765

Ile Met Arg Lys Leu Glu Pro Glu Glu Phe Ala Ala Tyr Leu Glu Pro
    770                 775                 780

Phe Lys Glu Lys Gly Glu Val Arg Arg Pro Thr Leu Ser Trp Pro Arg
785                 790                 795                 800

Glu Ile Pro Leu Val Lys Gly Gly Lys Pro Asp Val Val Gln Ile Val
                805                 810                 815

Arg Asn Tyr Asn Ala Tyr Leu Arg Ala Ser Asp Asp Leu Pro Lys Met
            820                 825                 830

Phe Ile Glu Ser Asp Pro Gly Phe Phe Ser Asn Ala Ile Val Glu Gly
        835                 840                 845

Ala Lys Lys Phe Pro Asn Thr Glu Phe Val Lys Val Lys Gly Leu His
850                 855                 860

Phe Ser Gln Glu Asp Ala Pro Asp Glu Met Gly Lys Tyr Ile Lys Ser
865                 870                 875                 880

Phe Val Glu Arg Val Leu Lys Asn Glu Gln
            885                 890

<210> SEQ ID NO 17
<211> LENGTH: 906
<212> TYPE: PRT
<213> ORGANISM: Artificial Sequence
<220> FEATURE:
<223> OTHER INFORMATION: GFP2-str-116 SGSR-RLuc fusion protein

<400> SEQUENCE: 17

Met Thr Asp Arg Arg Trp Val Ala Ile Thr Asp Ile Ala Gly Pro Ile
1               5                   10                  15

Gly Phe Thr Met Ser Ile Phe Ser Asn Ser Val Leu Leu Ser Leu Ile
            20                  25                  30

Phe Ser Ser Ser Ser Pro Ile Lys Gly Ala Tyr Lys Asn Met Leu Ile
        35                  40                  45

Val Leu Cys Ile Phe Thr Met Phe Tyr Ser Phe Val Glu Ile Met Leu
    50                  55                  60
```

Gln Pro Leu Ile His Ile Tyr Asp Asp Thr Leu Phe Leu Ile His Arg
65                  70                  75                  80

Lys Arg Phe Asp Leu Ser Lys Gly Ile Thr Arg Leu Ile Pro Thr Thr
                85                  90                  95

Tyr Cys Trp Cys Tyr Ala Met Ser Phe Ser Leu Phe Ala Leu Gln Phe
            100                 105                 110

Leu Tyr Arg Tyr Val Ala Val Cys Lys Pro His Leu Val Val Phe Phe
        115                 120                 125

Thr Gly Cys Tyr Phe Tyr Tyr Trp Leu Ala Leu Ile Leu Ser Leu Ala
    130                 135                 140

Thr Ser Trp Gly Leu Thr Ala Ala Phe Met Phe Pro Gln Thr Asn Arg
145                 150                 155                 160

Thr Thr Glu Ser Phe Asn Tyr Val Ile Lys Thr Ser Tyr Asp Leu Asp
                165                 170                 175

Pro Tyr Trp Thr Asp Tyr Val Ala Tyr Lys Tyr Phe Asp Thr Asp Glu
            180                 185                 190

Asn His Val Arg Trp Val Asn Val Leu Ser Leu Phe Gly Val Leu Gln
        195                 200                 205

His Gly Leu Val Ile Thr Leu Ser Phe Gly Thr Leu Phe Tyr Cys Gly
    210                 215                 220

Ile Lys Thr Tyr Leu Ser Ile Thr Glu His Val Gly Met Ser Ser Lys
225                 230                 235                 240

Thr Ser Gly Met Val Ser Lys Gly Glu Glu Leu Phe Thr Gly Val Val
                245                 250                 255

Pro Ile Leu Val Glu Leu Asp Gly Asp Val Asn Gly His Lys Phe Ser
            260                 265                 270

Val Ser Gly Glu Gly Glu Gly Asp Ala Thr Tyr Gly Lys Leu Thr Leu
        275                 280                 285

Lys Phe Ile Cys Thr Thr Gly Lys Leu Pro Val Pro Trp Pro Thr Leu
    290                 295                 300

Val Thr Thr Leu Ser Tyr Gly Val Gln Cys Phe Ser Arg Tyr Pro Asp
305                 310                 315                 320

His Met Lys Gln His Asp Phe Phe Lys Ser Ala Met Pro Glu Gly Tyr
                325                 330                 335

Val Gln Glu Arg Thr Ile Phe Phe Lys Asp Asp Gly Asn Tyr Lys Thr
            340                 345                 350

Arg Ala Glu Val Lys Phe Glu Gly Asp Thr Leu Val Asn Arg Ile Glu
        355                 360                 365

Leu Lys Gly Ile Asp Phe Lys Glu Asp Gly Asn Ile Leu Gly His Lys
    370                 375                 380

Leu Glu Tyr Asn Tyr Asn Ser His Asn Val Tyr Ile Met Ala Asp Lys
385                 390                 395                 400

Gln Lys Asn Gly Ile Lys Val Asn Phe Lys Ile Arg His Asn Ile Glu
                405                 410                 415

Asp Gly Ser Val Gln Leu Ala Asp His Tyr Gln Gln Asn Thr Pro Ile
            420                 425                 430

Gly Asp Gly Pro Val Leu Leu Pro Asp Asn His Tyr Leu Ser Thr Gln
        435                 440                 445

Ser Ala Leu Ser Lys Asp Pro Asn Glu Lys Arg Asp His Met Val Leu
    450                 455                 460

Leu Glu Phe Val Thr Ala Ala Gly Ile Thr Leu Gly Met Asp Glu Leu
465                 470                 475                 480

Tyr Lys Val Asp Arg Ser Leu Gln Leu Gln Leu Phe Arg Ala Leu Val

```
            485             490             495
Ala Gln Thr Cys Leu Pro Met Leu Met Tyr Met Pro Ile Gly Phe
            500             505             510

Met Phe Ser Cys Pro Tyr Phe Asp Leu Gln Leu Gly Ala Val Thr Asn
            515             520             525

Tyr Gln Thr Val Met Ala Gln Leu Tyr Pro Gly Ile Asp Pro Phe Met
        530             535             540

Leu Leu Phe Leu Ile Asn Ala Tyr Arg Lys Thr Val Leu Ser Leu Ile
545             550             555             560

Cys Pro Asn Phe Ile Gln Lys Lys Tyr Val Gln Thr Ala Thr Thr Arg
                565             570             575

Asp Gly Thr Asp Ala Ser Ala Thr Met Asn Ser Val Lys Ser Thr Gln
            580             585             590

Leu Ser Arg Met Thr Ser Lys Val Tyr Asp Pro Glu Gln Arg Lys Arg
        595             600             605

Met Ile Thr Gly Pro Gln Trp Trp Ala Arg Cys Lys Gln Met Asn Val
610             615             620

Leu Asp Ser Phe Ile Asn Tyr Tyr Asp Ser Glu Lys His Ala Glu Asn
625             630             635             640

Ala Val Ile Phe Leu His Gly Asn Ala Ala Ser Ser Tyr Leu Trp Arg
                645             650             655

His Val Val Pro His Ile Glu Pro Val Ala Arg Cys Ile Ile Pro Asp
            660             665             670

Leu Ile Gly Met Gly Lys Ser Gly Lys Ser Gly Asn Gly Ser Tyr Arg
        675             680             685

Leu Leu Asp His Tyr Lys Tyr Leu Thr Ala Trp Phe Glu Leu Leu Asn
690             695             700

Leu Pro Lys Lys Ile Ile Phe Val Gly His Asp Trp Gly Ala Cys Leu
705             710             715             720

Ala Phe His Tyr Ser Tyr Glu His Gln Asp Lys Ile Lys Ala Ile Val
                725             730             735

His Ala Glu Ser Val Val Asp Val Ile Glu Ser Trp Asp Glu Trp Pro
            740             745             750

Asp Ile Glu Glu Asp Ile Ala Leu Ile Lys Ser Glu Glu Gly Glu Lys
        755             760             765

Met Val Leu Glu Asn Asn Phe Phe Val Glu Thr Met Leu Pro Ser Lys
770             775             780

Ile Met Arg Lys Leu Glu Pro Glu Glu Phe Ala Ala Tyr Leu Glu Pro
785             790             795             800

Phe Lys Glu Lys Gly Glu Val Arg Arg Pro Thr Leu Ser Trp Pro Arg
                805             810             815

Glu Ile Pro Leu Val Lys Gly Gly Lys Pro Asp Val Val Gln Ile Val
            820             825             830

Arg Asn Tyr Asn Ala Tyr Leu Arg Ala Ser Asp Asp Leu Pro Lys Met
        835             840             845

Phe Ile Glu Ser Asp Pro Gly Phe Phe Ser Asn Ala Ile Val Glu Gly
850             855             860

Ala Lys Lys Phe Pro Asn Thr Glu Phe Val Lys Val Lys Gly Leu His
865             870             875             880

Phe Ser Gln Glu Asp Ala Pro Asp Glu Met Gly Lys Tyr Ile Lys Ser
                885             890             895

Phe Val Glu Arg Val Leu Lys Asn Glu Gln
            900             905
```

```
<210> SEQ ID NO 18
<211> LENGTH: 901
<212> TYPE: PRT
<213> ORGANISM: Artificial Sequence
<220> FEATURE:
<223> OTHER INFORMATION: GFP2-str-113/114 SGSR-RLuc fusion protein

<400> SEQUENCE: 18

Met Ser Asp Ile Tyr Trp Ile Gln Ile Thr Glu Val Cys Ser Phe Val
1               5                   10                  15

Gly Phe Met Leu Ser Val Leu Gly Asn Ser Thr Leu Leu Val Leu Leu
            20                  25                  30

Ser Gly Lys Ser Ile Asp Gly Ile Gly Thr Tyr Arg Tyr Leu Met Ile
        35                  40                  45

Thr Phe Cys Val Phe Ser Leu Leu Phe Thr Ile Leu Glu Asp Phe Ile
    50                  55                  60

Arg Pro Leu Met His His Tyr Asn Asn Thr Ile Ile Val Leu Gln Arg
65                  70                  75                  80

Lys Arg Phe Gln Phe Ser Asp Ser Thr Ala Arg Ile Leu Thr Val Ser
                85                  90                  95

Tyr Cys Gly Cys Phe Ala Met Cys Phe Val Met Phe Ala Val His Phe
            100                 105                 110

Ile Tyr Arg Tyr Leu Val Ala Cys His Pro Thr Lys Leu His Tyr Phe
        115                 120                 125

Arg Pro Lys Asn Phe Ile Phe Trp Leu Ser Gly Met Leu Phe Ile Ala
    130                 135                 140

Gly Ser Trp Val Ala Ile Ala Tyr Val Phe Phe Gln Glu Asp Leu Glu
145                 150                 155                 160

Thr Arg Thr Asp Leu Val Phe Ile Leu Ser Thr Cys Tyr Asn Leu Thr
                165                 170                 175

Pro Asp Asp Val Gly His Val Pro Tyr Ala Phe Tyr Lys Thr Gln Gly
            180                 185                 190

Asn Thr Arg Val Ile Arg Trp Asp Asn Met Ile Gly Val Ile His His
        195                 200                 205

Met Ile Val Met Thr Ile Ser Ile Ser Ala Val Phe Tyr Phe Gly Ile
    210                 215                 220

Lys Thr Tyr Thr Arg Ile Met Ser Phe Lys Gly Lys Ser Gln Lys Thr
225                 230                 235                 240

Ser Gly Met Val Ser Lys Gly Glu Glu Leu Phe Thr Gly Val Val Pro
                245                 250                 255

Ile Leu Val Glu Leu Asp Gly Asp Val Asn Gly His Lys Phe Ser Val
            260                 265                 270

Ser Gly Glu Gly Glu Gly Asp Ala Thr Tyr Gly Lys Leu Thr Leu Lys
        275                 280                 285

Phe Ile Cys Thr Thr Gly Lys Leu Pro Val Pro Trp Pro Thr Leu Val
    290                 295                 300

Thr Thr Leu Ser Tyr Gly Val Gln Cys Phe Ser Arg Tyr Pro Asp His
305                 310                 315                 320

Met Lys Gln His Asp Phe Phe Lys Ser Ala Met Pro Glu Gly Tyr Val
                325                 330                 335

Gln Glu Arg Thr Ile Phe Phe Lys Asp Asp Gly Asn Tyr Lys Thr Arg
            340                 345                 350

Ala Glu Val Lys Phe Glu Gly Asp Thr Leu Val Asn Arg Ile Glu Leu
        355                 360                 365
```

```
Lys Gly Ile Asp Phe Lys Glu Asp Gly Asn Ile Leu Gly His Lys Leu
        370                 375                 380

Glu Tyr Asn Tyr Asn Ser His Asn Val Tyr Ile Met Ala Asp Lys Gln
385                 390                 395                 400

Lys Asn Gly Ile Lys Val Asn Phe Lys Ile Arg His Asn Ile Glu Asp
                405                 410                 415

Gly Ser Val Gln Leu Ala Asp His Tyr Gln Gln Asn Thr Pro Ile Gly
                420                 425                 430

Asp Gly Pro Val Leu Leu Pro Asp Asn His Tyr Leu Ser Thr Gln Ser
            435                 440                 445

Ala Leu Ser Lys Asp Pro Asn Glu Lys Arg Asp His Met Val Leu Leu
450                 455                 460

Glu Phe Val Thr Ala Ala Gly Ile Thr Leu Gly Met Asp Glu Leu Tyr
465                 470                 475                 480

Lys Val Asp Lys Glu Met His Thr Gln Leu Phe Lys Ala Leu Val Leu
                485                 490                 495

Gln Thr Ile Ile Pro Thr Thr Leu Met Tyr Ile Pro Thr Thr Met Leu
                500                 505                 510

Phe Val Thr Pro Phe Val Gly Leu Asn Ile Gly Cys Tyr Gly Asn Ile
            515                 520                 525

Thr Thr Ala Thr Val His Leu Tyr Pro Gly Ile Asp Pro Val Val Leu
            530                 535                 540

Ile Phe Ile Ile Arg Asp Phe Arg Gln Thr Ile Leu Arg Pro Phe Arg
545                 550                 555                 560

Cys Phe Tyr Arg Ser Asn Ser Val Glu Asn Thr Ala Thr Ile Arg Gln
                565                 570                 575

Tyr Gln Gln Ser Ser Ser Lys Gly Ser Arg Glu Phe Gly Thr Met Ala
            580                 585                 590

Ser Lys Val Tyr Asp Pro Glu Gln Arg Lys Arg Met Ile Thr Gly Pro
            595                 600                 605

Gln Trp Trp Ala Arg Cys Lys Gln Met Asn Val Leu Asp Ser Phe Ile
            610                 615                 620

Asn Tyr Tyr Asp Ser Glu Lys His Ala Glu Asn Ala Val Ile Phe Leu
625                 630                 635                 640

His Gly Asn Ala Ala Ser Ser Tyr Leu Trp Arg His Val Val Pro His
                645                 650                 655

Ile Glu Pro Val Ala Arg Cys Ile Ile Pro Asp Leu Ile Gly Met Gly
                660                 665                 670

Lys Ser Gly Lys Ser Gly Asn Gly Ser Tyr Arg Leu Leu Asp His Tyr
            675                 680                 685

Lys Tyr Leu Thr Ala Trp Phe Glu Leu Leu Asn Leu Pro Lys Lys Ile
            690                 695                 700

Ile Phe Val Gly His Asp Trp Gly Ala Ala Leu Ala Phe His Tyr Ser
705                 710                 715                 720

Tyr Glu His Gln Asp Lys Ile Lys Ala Ile Val His Ala Glu Ser Val
                725                 730                 735

Val Asp Val Ile Glu Ser Trp Asp Glu Trp Pro Asp Ile Glu Glu Asp
                740                 745                 750

Ile Ala Leu Ile Lys Ser Glu Glu Gly Glu Lys Met Val Leu Glu Asn
            755                 760                 765

Asn Phe Phe Val Glu Thr Val Leu Pro Ser Lys Ile Met Arg Lys Leu
            770                 775                 780
```

```
Glu Pro Glu Glu Phe Ala Ala Tyr Leu Glu Pro Phe Lys Glu Lys Gly
785                 790                 795                 800

Glu Val Arg Arg Pro Thr Leu Ser Trp Pro Arg Glu Ile Pro Leu Val
            805                 810                 815

Lys Gly Gly Lys Pro Asp Val Val Gln Ile Val Arg Asn Tyr Asn Ala
                820                 825                 830

Tyr Leu Arg Ala Ser Asp Asp Leu Pro Lys Met Phe Ile Glu Ser Asp
            835                 840                 845

Pro Gly Phe Phe Ser Asn Ala Ile Val Glu Gly Ala Lys Lys Phe Pro
    850                 855                 860

Asn Thr Glu Phe Val Lys Val Lys Gly Leu His Phe Ser Gln Glu Asp
865                 870                 875                 880

Ala Pro Asp Glu Met Gly Lys Tyr Ile Lys Ser Phe Val Glu Arg Val
                885                 890                 895

Leu Lys Asn Glu Gln
            900

<210> SEQ ID NO 19
<211> LENGTH: 2694
<212> TYPE: DNA
<213> ORGANISM: Artificial Sequence
<220> FEATURE:
<223> OTHER INFORMATION: Nucleotide sequence encoding GFP2-str-112
      SGSR-RLuc fusion protein

<400> SEQUENCE: 19
atgggttctg gtcaattatg gttggcttta gttgatgctg cagatatggt tggttttact      60
ttgacaatct caattaatat cattttgtta ggtttgatta gaactagagg taaaaccttg     120
ggtacttaca gtacttgat gtctttcttt tctttctttt ctattttcta tgcaatcgtt      180
gaatctatct tgagaccaat catgcatatc gaaaacacta cattttttctt aatctccaga    240 aagagattcg attacagtac tagattgggt aaaattaatt cagctttcta ctgtgcttgt    300
ttcgcaacat ccttcgtttt gagtgcagtt catttcgttt acagatactt cgctgcttgt    360
aagcctaatt tgttgagatt gtttaactta cctcatttgt tatttgtggcc attgatgtgt   420 tcaattcctg ttactgcttg ggcatctgtt tcatactttt tgtacccaga tacagaatat    480
accgaagctg cagttaccta tgttttgaag actcattacg aagttattaa aaaggaaaac    540
gtttcttaca ttgcttacgt ttactaccaa tacgaaaacg tgaaagaca tatctatatt     600 aaaaacttat tggggttgttt cgttcattac ttcgttatgt ctatgacatt cgttgttgtt   660
ttctattgtg gtttctcaac ttggtggaca attagagaac atagaggtgc ttccgataga    720
acaatggtta gtaagggtga agaattattc accggtgttg ttccaatttt ggttgaatta    780
gatggtgacg ttaatggtca taaatttttcc gttagtggtg aaggtgaagg tgacgcaaca    840
tacggtaaat tgaccttgaa gtttatttgt accactggta aattgccagt ccttggcca    900 accttggtta caaccttaac ttatggtgtt caatgttttt ccagatacccc tgatcatatg    960 aagcaacatg atttctttaa gagtgctatg ccagaaggtt acgttcaaga agaacaatt   1020 ttctttaagg atgatggtaa ctacaagact agagcagagg ttaagttcga aggtgacaca   1080
ttggttaaca gaatcgaatt gaagggtatc gatttcaagg aagatggtaa catcttgggt   1140
cataagttgg aatacaatta caactcccat aacgtttaca tcatggctga taagcaaaag   1200
aatggtatta agttaacttt caagatcaga cataacatcg aagatggttc agttcaattg   1260
gcagatcatt accaacaaaa cacccctatt ggtgacggtc ctgttttgtt gccagataac   1320
```

```
cattacttat caactcaatc cgctttgagt aaggatccaa acgaaaagag agatcatatg    1380
gttttgttgg aattcgttac tgctgcaggt atcacattgg gtatggatga attgtacaag    1440
agacatttgc atagacaatt gtttaaagct ttggttttcc aaaccttggt tccatcaatt    1500
tttatgtaca tccctactgg tgttatgttc atcgcaccat ttttcgatat caatttgaac    1560
gctaacgcaa acttcatcgt tttctgttca tttttgtatc ctggtttgga tccattgatc    1620
ttgattttca ttatcagaga attcagagtt acaattttaa acattattcg tggtaatgaa    1680
cgtggtaacg ctgttggtga agcatactct acctcaagaa ttaaatcttc acaaccagct    1740
gcagttaatt tgtctggtat gacatcaaag gtttacgatc ctgaacaaag aaaaagaatg    1800
attaccggtc cacaatggtg ggctcgttgt aagcaaatga cgttttgga ttctttcatt    1860 aactactacg attcagaaaa gcatgctgaa acgctgtta ttttcttgca tggtaacgct    1920
gcatccagtt atttgtggag acatgttgtt cctcatattg aaccagttgc tagatgtatc    1980
atccctgatt tgatcggtat gggtaaatct ggtaaatctg gtaacggttc ttacagattg    2040
ttggatcatt acaagtactt aactgcatgg ttcgaattgt tgaatttgcc aaagaaaatt    2100
atcttcgttg gtcatgattg gggtgcttgt ttggcatttc attactctta cgaacatcaa    2160
gataaaatta aggctatcgt tcatgcagaa tccgttgttg atgttattga agttgggat    2220 gaatggccag atatcgaaga agatatcgct ttaattaagt ccgaagaagg tgaaaagatg    2280
gttttggaaa acaacttttt cgttgaaact atgttgccta gtaagatcat gagaaagttg    2340
gaacctgaag aatttgctgc atatttggaa ccattcaaag aaagggtga agttagaaga    2400 cctacattat cttggcctag agaaattcca ttggttaaag tggtaaacc agatgttgtt    2460 caaatcgtta gaaactacaa cgcttactta agagcatctg atgatttgcc aaagatgttc    2520
atcgaatctg atcctggttt cttttctaat gctattgttg aaggtgctaa gaaattccct    2580
aacacagaat tcgttaaggt taagggtttg catttctctc aagaagatgc tccagatgaa    2640
atgggtaaat acatcaagtc atttgttgaa agagttttga aaaatgaaca ataa          2694
```

<210> SEQ ID NO 20
<211> LENGTH: 2694
<212> TYPE: DNA
<213> ORGANISM: Artificial Sequence
<220> FEATURE:
<223> OTHER INFORMATION: Nucleotide sequence encoding GFP2-str-113
      SGSR-RLuc fusion protein

<400> SEQUENCE: 20

```
atgtctgacc gtcattggct cgacatcacc acctactcag accacattgg gtttacgatt      60
tccaccatcg ccaatttcgt tctgatcctt ctgctagtct tccgaccgac caaatcatac     120
ggttcataca agtacctgat gatcacattc tgcgtgttca gcctctttta cacctccatt     180
gaaacttttt tgagacctct catccatatc tacgacaata cgatcttcgt gattcagcgc     240
aagagattcc agtactccga gggtaccgct agagccattt catcgaccta ctgcggctgc     300
tacgccatga gcttcaccct gttcgccgtc cactttgtct accgttacta tgcggcttgc     360
aaacccgaca acctccgtta cttccaagga tgctactttg tcgcatgggt attcggagca     420
atggcggtgg cggcgagctg ggggttcgca gcgtttattc tgtacccgga gaccgagagg     480
accaggacgg cgttgataca cgtcatacaa acatcctatg agctggatcc cgagtgggtg     540
ggaaatgttc catatagcta ttggcgcaca gaaaacggag tggaatacct gaatcctcgc     600
aacgtcatcg ggatctttca acacggcgtc atcatgatcc tctccttcgg aacagtcttc     660
```

```
tactgcggat tcaacactta taagactttg aacggaagtc tgggggtgtc tgaaaaaaca    720
tccggaatgg tgagcaaggg cgaggagctg ttcaccgggg tggtgcccat cctggtcgag    780
ctggacggcg acgtaaacgg ccacaagttc agcgtgtccg gcgagggcga gggcgatgcc    840
acctacggca agctgaccct gaagttcatc tgcaccaccg gcaagctgcc cgtgccctgg    900
cccaccctcg tgaccaccct gagctacggc gtgcagtgct tcagccgcta ccccgaccac    960
atgaagcagc acgacttctt caagtccgcc atgcccgaag ctacgtcca ggagcgcacc    1020 atcttcttca aggacgacgg caactacaag acccgcgccg aggtgaagtt cgagggcgac    1080
accctggtga accgcatcga gctgaagggc atcgacttca aggaggacgg caacatcctg    1140
gggcacaagc tggagtacaa ctacaacagc cacaacgtct atatcatggc cgacaagcag    1200
aagaacggca tcaaggtgaa cttcaagatc cgccacaaca tcgaggacgg cagcgtgcag    1260
ctcgccgacc actaccagca gaacaccccc atcggcgacg gccccgtgct gctgcccgac    1320
aaccactacc tgagcaccca gtccgccctg agcaaagacc caacgagaa gcgcgatcac    1380 atggtcctgc tggagttcgt gaccgccgcc gggatcactc tcggcatgga cgagctgtac    1440
aaggtcgaca agaaaatgca cacccaattg ttcaaggcct tggttctaca gactatcatc    1500
cctactacac taatgtacat cccgacaacc atgctctttg tcaccccatt cgttggactc    1560
aacatcggct gttacggcaa catcactact gccaccgtcc atttgtatcc tggaattgac    1620
ccagtcgttt tgatctttat aatccgagac ttccggcaaa cgatttaag accattcaga    1680 tgcttctacc gttcaaatag tgtcgaaaac actgccacca taaggcaata ccagcagagc    1740
agctccaaag gatctagaat gaccagcaag gtgtacgacc ccgagcagag gaagaggatg    1800
atcaccggcc cccagtggtg ggccaggtgc aagcagatga acgtgctgga cagcttcatc    1860
aactactacg acagcgagaa gcacgccgag aacgccgtga tcttcctgca cggcaacgcc    1920
gctagcagct acctgtggag gcacgtggtg ccccacatcg agcccgtggc caggtgcatc    1980
atccccgatc tgatcggcat gggcaagagc ggcaagagcg gcaacggcag ctacaggctg    2040
ctggaccact acaagtacct gaccgcctgg ttcgagctcc tgaacctgcc caagaagatc    2100
atcttcgtgg gccacgactg gggcgcctgc ctggccttcc actacagcta cgagcaccag    2160
gacaagatca aggccatcgt gcacgccgag agcgtggtgg acgtgatcga gagctgggac    2220
gagtggccag acatcgagga ggacatcgcc ctgatcaaga gcgaggaggg cgagaagatg    2280
gtgctggaga caacttcttt cgtggagacc atgctgccca gcaagatcat gagaaagctg    2340
gagcccgagg agttcgccgc ctacctggag ccccttcaagg agaagggcga ggtgagaaga    2400 cccacccctga gctggcccag agatcccc ctggtgaagg gcggcaagcc cgacgtggtg    2460
cagatcgtga gaaactacaa cgcctacctg agaccagcg acgacctgcc caagatgttc    2520
atcgagagcg accccggctt cttcagcaac gccatcgtgg agggcgccaa gaagttcccc    2580
aacaccgagt tcgtgaaggt gaagggcctg cacttcagcc aggaggacgc ccccgacgag    2640
atgggcaagt acatcaagag cttcgtggag agagtgctga agaacgagca gtaa           2694
```

<210> SEQ ID NO 21
<211> LENGTH: 2715
<212> TYPE: DNA
<213> ORGANISM: Artificial Sequence
<220> FEATURE:
<223> OTHER INFORMATION: Nucleotide sequence encoding GFP2-str-114
      SGSR-RLuc fusion protein

<400> SEQUENCE: 21

```
atgtccgata tatactggat acaaattact gaagtttgct ccttcgtcgg atttatgctc      60
tcagttctag ggaacagtac acttttagta ctgctcagtg gaaaatccat agatggaatt    120
ggcacctatc ggtacttgat gatcactttc tgcgttttca gtttattatt tacgatatta    180
gaggatttta tcagaccgct gatgcatcac tataacaata ccataattgt tttacaacgc    240
aagcggtttc agttttctga ttcaacggct agaatcttga cagtctctta ctgcggctgt    300
ttcgcgatgt gcttcgtgat gttcgccgtt catttcatct atcgatatct agttgcttgt    360
cacccgacaa aattgcacta ttttcgaccc aaaaatttca ttttctggct gtccggcatg    420
ttattcatag caggaagctg ggttgcaatt gcatatgtct tttttcaaga agacctagaa    480
accaggacgg atttggtatt tattttgtca acttgttata atttaacgcc agatgatgtc    540
ggacatgtac cgtatgcttt ttacaaaact caaggaaata cacgagtaat tcgatgggat    600
aacatgattg gagtaattca tcatatgata gttatgacaa tctctataag tgccgttttc    660
tactttggca ttaaaaccta cactcgaata atgagtttca agggaaaatc ccagaaaacc    720
tccggaatgg tgagcaaggg cgaggagctg ttcaccgggg tggtgcccat cctggtcgag    780
ctggacggcg acgtaaacgg ccacaagttc agcgtgtccg gcgagggcga gggcgatgcc    840
acctacggca agctgaccct gaagttcatc tgcaccaccg gcaagctgcc cgtgccctgg    900
cccaccctcg tgaccaccct gagctacggc gtgcagtgct tcagccgcta ccccgaccac    960
atgaagcagc acgacttctt caagtccgcc atgcccgaag ctacgtcca ggagcgcacc    1020
atcttcttca aggacgacgg caactacaag acccgcgccg aggtgaagtt cgagggcgac    1080
accctggtga accgcatcga gctgaagggc atcgacttca aggaggacgg caacatcctg    1140
gggcacaagc tggagtacaa ctacaacagc cacaacgtct atatcatggc cgacaagcag    1200
aagaacggca tcaaggtgaa cttcaagatc cgccacaaca tcgaggacgg cagcgtgcag    1260
ctcgccgacc actaccagca gaacaccccc atcggcgacg gccccgtgct gctgcccgac    1320
aaccactacc tgagcaccca gtccgccctg agcaaagacc ccaacgagaa gcgcgatcac    1380
atggtcctgc tggagttcgt gaccgccgcc gggatcactc tcggcatgga cgagctgtac    1440
aaggtcgaca aggatctcca gaatcaatt ttcactgctc tagttgctca aaccgtagtc    1500
cctctgattt tcatgtttat cccaaatatg gtgctcacta cggcagccct tatagatggc    1560
acatttggct catgggccaa tattactgta gttatgaatc atttgtatcc ggctgccgat    1620
ccattcgtta tactgttcat tattaagggg ttccggaata gtattagaaa tgttatatat    1680
cgctgcacaa aaacgaaaaa agcatcggtt agctcagtgg tccgtggtat tgaggctcaa    1740
agcaagaaac aatctttttc tcgagttgat atttctagaa tgaccagcaa ggtgtacgac    1800
cccgagcaga ggaagaggat gatcaccggc ccccagtggt gggccaggtg caagcagatg    1860
aacgtgctgg acagcttcat caactactac gacagcgaga agcacgccga aacgccgtg     1920
atcttcctgc acggcaacgc cgctagcagc tacctgtgga ggcacgtggt gccccacatc    1980
gagcccgtgg ccaggtgcat catccccgat ctgatcggca tgggcaagag cggcaagagc    2040
ggcaacggca gctacaggct gctggaccac tacaagtacc tgaccgcctg gttcgagctc    2100
ctgaacctgc caagaagat catcttcgtg ggccacgact ggggcgcctg cctggccttc    2160
cactacagct acgagcacca ggacaagatc aaggccatcg tgcacgccga gagcgtggtg    2220
gacgtgatcg agagctggga cgagtggcca gacatcgagg aggacatcgc cctgatcaag    2280
agcgaggagg cgcgagaagat ggtgctggag aacaacttct tcgtggagac catgctgccc    2340
agcaagatca tgagaaagct ggagcccgag gagttcgccg cctacctgga gcccttcaag    2400
```

```
gagaagggcg aggtgagaag acccaccctg agctggccca gagagatccc cctggtgaag    2460
ggcggcaagc ccgacgtggt gcagatcgtg agaaactaca acgcctacct gagagccagc    2520
gacgacctgc ccaagatgtt catcgagagc gaccccggct tcttcagcaa cgccatcgtg    2580
gagggcgcca agaagttccc caacaccgag ttcgtgaagg tgaagggcct gcacttcagc    2640
caggaggacg cccccgacga gatgggcaag tacatcaaga gcttcgtgga gagagtgctg    2700
aagaacgagc agtaa                                                     2715
```

<210> SEQ ID NO 22
<211> LENGTH: 2673
<212> TYPE: DNA
<213> ORGANISM: Artificial Sequence
<220> FEATURE:
<223> OTHER INFORMATION: Nucleotide sequence encoding GFP2-str-115
      SGSR-RLuc fusion protein

<400> SEQUENCE: 22

```
atgactgatc aacactgggt tattatcaca gatattgctg gtccaatcgg attttcaatg      60 tccattttt caaactctat tctttttgttt ttgatatttt cacattcatc tccaataaaa     120
ggtccataca aacgaatgct catagtattt tgcatattta ccgtattcta ctcatttgtc     180
gaagtcatgc ttcagccact aatccatatt tacgacgaca ctttattttt gattcatcga     240
aagagaatag acttgccaaa atggttaaca cgtttggttc ctactaccta ttgttggtgt     300
tacgcaatga gtttttcctt gtttgcatta caatttttat atagatatgt ggcagtatgc     360
aaaccgcaat atgttgatct ttttgtcgga tgtcactttt atgcttgggt agttttgatc     420
ttatcactag ccacgagctg ggactcact gcagctttca tgttcccaca aaccgaccga     480
acaactgaaa tttttttgca cataatttat agttcatatg acttggagcc ttattggaca     540
gattatgttg cttataaata ctttgatact gatgagaata atgtgagatg ggtcaatgtt     600
cttagttttt tcggtgtcct tcagcacggg attgtaatta ctctaagttt tggcacccct     660
tattattgtg gcatcaacac gtatctcaaa ataaaaaaac acactggaac atcaaacaga     720
acttccggaa tggtgagcaa gggcgaggag ctgttcaccg gggtggtgcc catcctggtc     780
gagctggacg gcgacgtaaa cggccacaag ttcagcgtgt ccggcgaggg cgagggcgat     840
gccacctacg gcaagctgac cctgaagttc atctgcacca ccggcaagct gcccgtgccc     900
tggcccaccc tcgtgaccac cctgagctac ggcgtgcagt gcttcagccg ctaccccgac     960
cacatgaagc agcacgactt cttcaagtcc gccatgcccg aaggctacgt ccaggagcgc    1020
accatcttct tcaaggacga cggcaactac aagacccgcg ccgaggtgaa gttcgagggc    1080
gacaccctgg tgaaccgcat cgagctgaag ggcatcgact tcaaggagga cggcaacatc    1140
ctggggcaca agctggagta caactacaac agccacaacg tctatatcat ggccgacaag    1200
cagaagaacg gcatcaaggt gaacttcaag atccgccaca acatcgagga cggcagcgtg    1260
cagctcgccg accactacca gcagaacacc cccatcggcg acggccccgt gctgctgccc    1320
gacaaccact acctgagcac ccagtccgcc ctgagcaaag accccaacga gaagcgcgat    1380
cacatggtcc tgctggagtt cgtgaccgcc gccgggatca ctctcggcat ggacgagctg    1440
tacaaggtcg accgatgtat tcaactacaa cttttcagag ctctggttgc acagacaatt    1500
ttaccaatgt tcatgatgta tattcccgtt ggtttcatgt ttgcatgtcc atattttgac    1560
ttgcaattag gtgcatacac caattatcaa acagtcatgg cacaacttta tccgggaatc    1620
gacccatttg tgatgctgtt tttgatagat tcttatagaa taacaatatt tggatggtta    1680
```

```
tgtccaagat tgtttatgt aaagccgatg cattccacat acaccctaac ttctagaatg    1740
accagcaagg tgtacgaccc cgagcagagg aagaggatga tcaccggccc ccagtggtgg    1800
gccaggtgca agcagatgaa cgtgctggac agcttcatca actactacga cagcgagaag    1860
cacgccgaga acgccgtgat cttcctgcac ggcaacgccg ctagcagcta cctgtgggag    1920
cacgtggtgc cccacatcga gcccgtggcc aggtgcatca tccccgatct gatcggcatg    1980
ggcaagagcg gcaagagcgg caacggcagc tacaggctgc tggaccacta caagtacctg    2040
accgcctggt cgagctcct gaacctgccc aagaagatca tcttcgtggg ccacgactgg    2100
ggcgcctgcc tggccttcca ctacagctac gagcaccagg acaagatcaa ggccatcgtg    2160
cacgccgaga gcgtggtgga cgtgatcgag agctgggacg agtggccaga catcgaggag    2220
gacatcgccc tgatcaagag cgaggagggc gagaagatgt gctggagaa caacttcttc    2280 gtggagacca tgctgcccag caagatcatg agaaagctgg agcccgagga gttcgccgcc    2340
tacctggagc ccttcaagga aagggcgag gtgagaagac ccaccctgag ctggcccaga    2400
gagatccccc tggtgaaggg cggcaagccc gacgtggtgc agatcgtgag aaactacaac    2460
gcctacctga gagccagcga cgacctgccc aagatgttca tcgagagcga ccccggcttc    2520
ttcagcaacg ccatcgtgga gggcgccaag aagttcccca cccgagtt cgtgaaggtg    2580 aagggcctgc acttcagcca ggaggacgcc cccgacgaga tgggcaagta catcaagagc    2640
ttcgtggaga gagtgctgaa gaacgagcag taa                                 2673

<210> SEQ ID NO 23
<211> LENGTH: 2721
<212> TYPE: DNA
<213> ORGANISM: Artificial Sequence
<220> FEATURE:
<223> OTHER INFORMATION: Nucleotide sequence encoding GFP2-str-116
      SGSR-RLuc fusion protein

<400> SEQUENCE: 23
atgaccgatc gtcgctgggt cgctattacg acattgccg gaccgattgg gttcacaatg     60 tcaattttt cgaactcggt gctgttatcg ttgatattct caagcagctc tccaattaaa    120
ggagcttaca aaatatgtt gatagtgttg tgtatattca ctatgttcta ctcttttgtt    180
gaaataatgc ttcaaccgtt gattcatatt tatgatgaca cgctgttctt gatccaccgg    240
aaaagatttg acctgtctaa aggaattaca cgtttgatac ctacaacata ttgttggtgt    300
tatgcaatga gttctctcatt attcgccctc cagttttgt acagatatgt ggcagtttgc    360
aaacctcact tagttgttt ttttactgga tgctatttct attattggtt ggcactcatc    420
ttatcacttg ctacaagttg ggggcttact gcagctttta tgttcccgca accaatcga    480 acaactgaaa gcttcaacta cgtaataaaa acttcttatg acttagatcc ttattggacg    540
gattatgttg cctataaata ttttgacacc gatgagaatc atgtgagatg ggtgaatgtt    600
cttagtttat ttggagtctt gcagcacgga ttagtaatta cgttgagttt tggaaccttta    660 ttctactgtg gaattaaaac ttatctcagc attactgaac atgttggaat gtccagcaag    720
acctccggaa tggtgagcaa gggcgaggag ctgttcaccg ggtggtgcc catcctggtc    780 gagctggacg gcgacgtaaa cggccacaag ttcagcgtgt ccggcgaggg cgagggcgat    840
gccacctacg gcaagctgac cctgaagttc atctgcacca ccggcaagct gcccgtgccc    900
tggcccaccc tcgtgaccac cctgagctac ggcgtgcagt gcttcagccg ctaccccgac    960
cacatgaagc agcacgactt cttcaagtcc gccatgcccg aaggctacgt ccaggagcgc   1020
```

```
accatcttct tcaaggacga cggcaactac aagacccgcg ccgaggtgaa gttcgagggc    1080
gacaccctgg tgaaccgcat cgagctgaag ggcatcgact tcaaggagga cggcaacatc    1140
ctggggcaca agctggagta caactacaac agccacaacg tctatatcat ggccgacaag    1200
cagaagaacg gcatcaaggt gaacttcaag atccgccaca acatcgagga cggcagcgtg    1260
cagctcgccg accactacca gcagaacacc cccatcggcg acggccccgt gctgctgccc    1320
gacaaccact acctgagcac ccagtccgcc ctgagcaaag accccaacga gaagcgcgat    1380
cacatggtcc tgctggagtt cgtgaccgcc gccgggatca ctctcggcat ggacgagctg    1440
tacaaggtcg accgaagtct tcaacttcaa ctattccgtg ctttagttgc tcagacatgt    1500
cttccaatgc tcatgatgta catgccaata ggattcatgt tttcttgccc ttactttgat    1560
ttgcaacttg gagcagtcac aaactatcaa accgtcatgg cacagttata cccaggaatc    1620
gacccattta tgttgctatt tcttattaac gcctacagaa agacagtgtt aagcttgatc    1680
tgtcctaatt ttatccagaa aaaatatgtt caaacggcaa ctactcgtga tggcacagat    1740
gcctcggcaa caatgaattc tgttaaatct acacagttat ctagaatgac cagcaaggtg    1800
tacgaccccg agcagaggaa gaggatgatc accggccccc agtggtgggc caggtgcaag    1860
cagatgaacg tgctggacag cttcatcaac tactacgaca gcgagaagca cgccgagaac    1920
gccgtgatct tcctgcacgg caacgccgct agcagctacc tgtggaggca cgtggtgccc    1980
cacatcgagc ccgtggccag gtgcatcatc cccgatctga tcggcatggg caagagcggc    2040
aagagcggca acggcagcta caggctgctg gaccactaca gtacctgacc gcctggttc    2100 gagctcctga acctgcccaa gaagatcatc ttcgtgggcc acgactgggg cgcctgcctg    2160
gccttccact acagctacga gcaccaggac aagatcaagg ccatcgtgca cgccgagagc    2220
gtggtggacg tgatcgagag ctgggacgag tggccagaca tcgaggagga catcgccctg    2280
atcaagagcg aggagggcga gaagatggtg ctggagaaca acttcttcgt ggagaccatg    2340
ctgcccagca agatcatgag aaagctggag cccgaggagt tcgccgccta cctggagccc    2400
ttcaaggaga agggcgaggt gagaagaccc accctgagct ggccagaga atcccctg    2460 gtgaagggcg gcaagcccga cgtggtgcag atcgtgagaa actacaacgc ctacctgaga    2520
gccagcgacg acctgcccaa gatgttcatc gagagcgacc ccggcttctt cagcaacgcc    2580
atcgtggagg gcgccaagaa gttccccaac accgagttcg tgaaggtgaa gggcctgcac    2640
ttcagccagg aggacgcccc cgacgagatg ggcaagtaca tcaagagctt cgtggagaga    2700
gtgctgaaga acgagcagta a                                              2721
```

<210> SEQ ID NO 24
<211> LENGTH: 2706
<212> TYPE: DNA
<213> ORGANISM: Artificial Sequence
<220> FEATURE:
<223> OTHER INFORMATION: Nucleotide sequence encoding GFP2-str-113/114 SGSr-RLuc fusion protein

<400> SEQUENCE: 24

```
atgtccgata tactggat acaaattact gaagtttgct ccttcgtcgg atttatgctc     60
tcagttctag ggaacagtac acttttagta ctgctcagtg gaaaatccat agatggaatt    120
ggcacctatc ggtacttgat gatcactttc tgcgttttca gtttattatt tacgatatta    180
gaggatttta tcagaccgct gatgcatcac tataacaata ccataattgt tttcaacgc     240 aagcggtttc agtttttctga ttcaacggct agaatcttga cagtctctta ctgcggctgt    300
```

-continued

| | |
|---|---|
| ttcgcgatgt gcttcgtgat gttcgccgtt catttcatct atcgatatct agttgcttgt | 360 |
| cacccgacaa aattgcacta ttttcgaccc aaaaatttca ttttctggct gtccggcatg | 420 |
| ttattcatag caggaagctg ggttgcaatt gcatatgtct tttttcaaga agacctagaa | 480 |
| accaggacgg atttggtatt tattttgtca acttgttata atttaacgcc agatgatgtc | 540 |
| ggacatgtac cgtatgcttt ttacaaaact caaggaaata cacgagtaat tcgatgggat | 600 |
| aacatgattg gagtaattca tcatatgata gttatgacaa tctctataag tgccgttttc | 660 |
| tactttggca ttaaaaccta cactcgaata atgagtttca agggaaaatc ccagaaaacc | 720 |
| tccggaatgt gagcaaggg cgaggagctg ttcaccgggg tggtgcccat cctggtcgag | 780 |
| ctggacggcg acgtaaacgg ccacaagttc agcgtgtccg gcgagggcga gggcgatgcc | 840 |
| acctacggca agctgaccct gaagttcatc tgcaccaccg gcaagctgcc cgtgccctgg | 900 |
| cccacccctcg tgaccaccct gagctacggc gtgcagtgct tcagccgcta ccccgaccac | 960 |
| atgaagcagc acgacttctt caagtccgcc atgcccgaag gctacgtcca ggagcgcacc | 1020 |
| atcttcttca aggacgacgg caactacaag acccgcgccg aggtgaagtt cgagggcgac | 1080 |
| accctggtga accgcatcga gctgaagggc atcgacttca aggaggacgg caacatcctg | 1140 |
| gggcacaagc tggagtacaa ctacaacagc cacaacgtct atatcatggc cgacaagcag | 1200 |
| aagaacggca tcaaggtgaa cttcaagatc cgccacaaca tcgaggacgg cagcgtgcag | 1260 |
| ctcgccgacc actaccagca gaacacccc atcggcgacg gccccgtgct gctgcccgac | 1320 |
| aaccactacc tgagcaccca gtccgccctg agcaaagacc ccaacgagaa gcgcgatcac | 1380 |
| atggtcctgc tggagttcgt gaccgccgcc gggatcactc tcggcatgga cgagctgtac | 1440 |
| aaggtcgaca agaaatgca cacccaattg ttcaaggcct tggttctaca gactatcatc | 1500 |
| cctactacac taatgtacat cccgacaacc atgctctttg tcaccccatt cgttggactc | 1560 |
| aacatcggct gttacggcaa catcactact gccaccgtcc atttgtatcc tggaattgac | 1620 |
| ccagtcgttt tgatctttat aatccgagac ttccggcaaa cgattttaag accattcaga | 1680 |
| tgcttctacc gttcaaatag tgtcgaaaac actgccacca taaggcaata ccagcagagc | 1740 |
| agctccaaag gatctagaga attcggtacc atggcttcca aggtgtacga ccccgagcaa | 1800 |
| cgcaaacgca tgatcactgg gcctcagtgg tgggctcgct gcaagcaaat gaacgtgctg | 1860 |
| gactccttca tcaactacta tgattccgag aagcacgccg agaacgccgt gatttttctg | 1920 |
| catggtaacg ctgcctccag ctacctgtgg aggcacgtcg tgcctcacat cgagcccgtg | 1980 |
| gctagatgca tcatccctga tctgatcgga atgggtaagt ccggcaagag cgggaatggc | 2040 |
| tcatatcgcc tcctggatca ctacaagtac ctcaccgctt ggttcgagct gctgaacctt | 2100 |
| ccaaagaaaa tcatctttgt gggccacgac tgggggctg ctctggcctt tcactactcc | 2160 |
| tacgagcacc aagacaagat caaggccatc gtccatgctg agagtgtcgt ggacgtgatc | 2220 |
| gagtcctggg acgagtggcc tgacatcgag gaggatatcg ccctgatcaa gagcgaagag | 2280 |
| ggcgagaaaa tggtgcttga gaataacttc ttcgtcgaga ccgtgctccc aagcaagatc | 2340 |
| atgcggaaac tggagcctga ggagttcgct gcctacctgg agccattcaa ggagaagggc | 2400 |
| gaggttagac ggcctaccct ctcctggcct cgcgagatcc ctctcgttaa gggaggcaag | 2460 |
| cccgacgtcg tccagattgt ccgcaactac aacgcctacc ttcgggccag cgacgatctg | 2520 |
| cctaagatgt tcatcgagtc cgaccctggg ttcttttcca acgctattgt cgagggagct | 2580 |
| aagaagttcc ctaacaccga gttcgtgaag gtgaaggggc tccacttcag ccaggaggac | 2640 |

```
gctccagatg aaatgggtaa gtacatcaag agcttcgtgg agcgcgtgct gaagaacgag    2700
cagtaa                                                              2706
```

<210> SEQ ID NO 25
<211> LENGTH: 889
<212> TYPE: PRT
<213> ORGANISM: Artificial Sequence
<220> FEATURE:
<223> OTHER INFORMATION: GFP2-OGOR-RLuc2 protein

<400> SEQUENCE: 25

```
Met Ser Gly Glu Leu Trp Ile Thr Leu Val Asp Thr Ala Asp Ile Val
1               5                   10                  15

Gly Val Thr Leu Thr Phe Cys Val Asn Ile Val Leu Gly Leu Leu
                20                  25                  30

Lys Thr Arg Gly Lys Asn Leu Gly Thr Tyr Lys Tyr Leu Met Ala Phe
            35                  40                  45

Phe Ser Val Phe Ser Ile Phe Tyr Ala Ile Ile Glu Phe Ile Leu Arg
        50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val His Phe Val
            100                 105                 110

Tyr Arg Tyr Phe Ala Thr Cys Lys Pro Asn Leu Leu Arg Leu Phe Asn
        115                 120                 125

Leu Pro Thr Leu Leu Leu Trp Pro Leu Gly Cys Ser Val Pro Val Thr
    130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
                165                 170                 175

Lys Glu Asn Val Ser Tyr Ile Ala Tyr Val Tyr Tyr Gln Tyr Glu Asn
            180                 185                 190

Gly Val Arg His Ile Tyr Leu Lys Asn Leu Leu Gly Cys Phe Val His
        195                 200                 205

Tyr Phe Val Met Ser Met Thr Phe Val Val Met Phe Tyr Cys Gly Tyr
    210                 215                 220

Ala Thr Trp Lys Thr Met Asn Glu His Lys Asp Val Ser Asp Arg Thr
225                 230                 235                 240

Met Val Ser Lys Gly Glu Glu Leu Phe Thr Gly Val Val Pro Ile Leu
                245                 250                 255

Val Glu Leu Asp Gly Asp Val Asn Gly His Lys Phe Ser Val Ser Gly
            260                 265                 270

Glu Gly Glu Gly Asp Ala Thr Tyr Gly Lys Leu Thr Leu Lys Phe Ile
        275                 280                 285

Cys Thr Thr Gly Lys Leu Pro Val Pro Trp Pro Thr Leu Val Thr Thr
    290                 295                 300

Leu Ser Tyr Gly Val Gln Cys Phe Ser Arg Tyr Pro Asp His Met Lys
305                 310                 315                 320

Gln His Asp Phe Phe Lys Ser Ala Met Pro Glu Gly Tyr Val Gln Glu
                325                 330                 335

Arg Thr Ile Phe Phe Lys Asp Asp Gly Asn Tyr Lys Thr Arg Ala Glu
            340                 345                 350
```

```
Val Lys Phe Glu Gly Asp Thr Leu Val Asn Arg Ile Glu Leu Lys Gly
        355                 360                 365

Ile Asp Phe Lys Glu Asp Gly Asn Ile Leu Gly His Lys Leu Glu Tyr
370                 375                 380

Asn Tyr Asn Ser His Asn Val Tyr Ile Met Ala Asp Lys Gln Lys Asn
385                 390                 395                 400

Gly Ile Lys Val Asn Phe Lys Ile Arg His Asn Ile Glu Asp Gly Ser
                405                 410                 415

Val Gln Leu Ala Asp His Tyr Gln Gln Asn Thr Pro Ile Gly Asp Gly
                420                 425                 430

Pro Val Leu Leu Pro Asp Asn His Tyr Leu Ser Thr Gln Ser Ala Leu
                435                 440                 445

Ser Lys Asp Pro Asn Glu Lys Arg Asp His Met Val Leu Leu Glu Phe
        450                 455                 460

Val Thr Ala Ala Gly Ile Thr Leu Gly Met Asp Glu Leu Tyr Lys Arg
465                 470                 475                 480

Ala Leu Gln Lys Gln Leu Phe Lys Ala Leu Val Leu Gln Thr Leu Ile
                485                 490                 495

Pro Thr Ile Phe Met Tyr Ala Pro Thr Gly Val Met Phe Ile Ala Pro
                500                 505                 510

Phe Phe Asp Val Asn Leu Asn Ala Asn Ala Asn Phe Ile Val Phe Cys
        515                 520                 525

Ser Phe Leu Tyr Pro Gly Leu Asp Pro Leu Ile Leu Ile Leu Ile Ile
        530                 535                 540

Arg Asp Phe Arg Arg Thr Ile Phe Asn Phe Leu Cys Gly Lys Lys Asn
545                 550                 555                 560

Ser Val Asp Glu Ser Arg Ser Thr Thr Arg Ala Asn Leu Ser Gln Val
                565                 570                 575

Pro Thr Met Thr Ser Lys Val Tyr Asp Pro Glu Gln Arg Lys Arg Met
                580                 585                 590

Ile Thr Gly Pro Gln Trp Trp Ala Arg Cys Lys Gln Met Asn Val Leu
                595                 600                 605

Asp Ser Phe Ile Asn Tyr Tyr Asp Ser Glu Lys His Ala Glu Asn Ala
        610                 615                 620

Val Ile Phe Leu His Gly Asn Ala Ala Ser Ser Tyr Leu Trp Arg His
625                 630                 635                 640

Val Val Pro His Ile Glu Pro Val Ala Arg Cys Ile Ile Pro Asp Leu
                645                 650                 655

Ile Gly Met Gly Lys Ser Gly Lys Ser Gly Asn Gly Ser Tyr Arg Leu
                660                 665                 670

Leu Asp His Tyr Lys Tyr Leu Thr Ala Trp Phe Glu Leu Leu Asn Leu
        675                 680                 685

Pro Lys Lys Ile Ile Phe Val Gly His Asp Trp Gly Ala Ala Leu Ala
        690                 695                 700

Phe His Tyr Ser Tyr Glu His Gln Asp Lys Ile Lys Ala Ile Val His
705                 710                 715                 720

Ala Glu Ser Val Val Asp Val Ile Glu Ser Trp Asp Glu Trp Pro Asp
                725                 730                 735

Ile Glu Glu Asp Ile Ala Leu Ile Lys Ser Glu Glu Gly Glu Lys Met
                740                 745                 750

Val Leu Glu Asn Asn Phe Phe Val Glu Thr Val Leu Pro Ser Lys Ile
        755                 760                 765
```

```
Met Arg Lys Leu Glu Pro Glu Phe Ala Ala Tyr Leu Glu Pro Phe
770                 775                 780

Lys Glu Lys Gly Glu Val Arg Arg Pro Thr Leu Ser Trp Pro Arg Glu
785                 790                 795                 800

Ile Pro Leu Val Lys Gly Gly Lys Pro Asp Val Val Gln Ile Val Arg
                805                 810                 815

Asn Tyr Asn Ala Tyr Leu Arg Ala Ser Asp Asp Leu Pro Lys Met Phe
                820                 825                 830

Ile Glu Ser Asp Pro Gly Phe Phe Ser Asn Ala Ile Val Glu Gly Ala
                835                 840                 845

Lys Lys Phe Pro Asn Thr Glu Phe Val Lys Val Lys Gly Leu His Phe
850                 855                 860

Ser Gln Glu Asp Ala Pro Asp Glu Met Gly Lys Tyr Ile Lys Ser Phe
865                 870                 875                 880

Val Glu Arg Val Leu Lys Asn Glu Gln
                885

<210> SEQ ID NO 26
<211> LENGTH: 889
<212> TYPE: PRT
<213> ORGANISM: Artificial Sequence
<220> FEATURE:
<223> OTHER INFORMATION: GFP2-OGOR-RLuc2 mutant protein

<400> SEQUENCE: 26

Met Ser Gly Glu Leu Trp Ile Thr Leu Val Asp Thr Ala Asp Ile Val
1               5                   10                  15

Gly Val Thr Leu Thr Phe Cys Val Asn Ile Val Leu Leu Gly Leu Leu
                20                  25                  30

Lys Thr Arg Gly Lys Asn Leu Gly Thr Tyr Lys Tyr Leu Met Ala Phe
                35                  40                  45

Phe Ser Val Phe Ser Ile Phe Tyr Ala Ile Ile Glu Phe Ile Leu Arg
50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val Tyr Phe Val
                100                 105                 110

Tyr Arg Tyr Phe Ala Thr Cys Lys Pro Asn Leu Leu Arg Leu Phe Asn
                115                 120                 125

Leu Pro Thr Leu Leu Leu Trp Pro Leu Gly Cys Ser Val Pro Val Thr
130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
                165                 170                 175

Lys Glu Asn Val Ser Tyr Ile Ala Tyr Val Tyr Gln Tyr Glu Asn
                180                 185                 190

Gly Val Arg His Ile Tyr Leu Lys Asn Leu Leu Gly Cys Phe Val His
                195                 200                 205

Tyr Phe Val Met Ser Met Thr Phe Val Val Met Phe Tyr Cys Gly Tyr
                210                 215                 220

Ala Thr Trp Lys Thr Met Asn Glu His Lys Asp Val Ser Asp Arg Thr
225                 230                 235                 240
```

```
Met Val Ser Lys Gly Glu Glu Leu Phe Thr Gly Val Pro Ile Leu
                245                 250                 255

Val Glu Leu Asp Gly Asp Val Asn Gly His Lys Phe Ser Val Ser Gly
260                 265                 270

Glu Gly Glu Gly Asp Ala Thr Tyr Gly Lys Leu Thr Leu Lys Phe Ile
            275                 280                 285

Cys Thr Thr Gly Lys Leu Pro Val Pro Trp Pro Thr Leu Val Thr Thr
290                 295                 300

Leu Ser Tyr Gly Val Gln Cys Phe Ser Arg Tyr Pro Asp His Met Lys
305                 310                 315                 320

Gln His Asp Phe Phe Lys Ser Ala Met Pro Glu Gly Tyr Val Gln Glu
                325                 330                 335

Arg Thr Ile Phe Phe Lys Asp Asp Gly Asn Tyr Lys Thr Arg Ala Glu
                340                 345                 350

Val Lys Phe Glu Gly Asp Thr Leu Val Asn Arg Ile Glu Leu Lys Gly
            355                 360                 365

Ile Asp Phe Lys Glu Asp Gly Asn Ile Leu Gly His Lys Leu Glu Tyr
370                 375                 380

Asn Tyr Asn Ser His Asn Val Tyr Ile Met Ala Asp Lys Gln Lys Asn
385                 390                 395                 400

Gly Ile Lys Val Asn Phe Lys Ile Arg His Asn Ile Glu Asp Gly Ser
                405                 410                 415

Val Gln Leu Ala Asp His Tyr Gln Gln Asn Thr Pro Ile Gly Asp Gly
            420                 425                 430

Pro Val Leu Leu Pro Asp Asn His Tyr Leu Ser Thr Gln Ser Ala Leu
            435                 440                 445

Ser Lys Asp Pro Asn Glu Lys Arg Asp His Met Val Leu Leu Glu Phe
450                 455                 460

Val Thr Ala Ala Gly Ile Thr Leu Gly Met Asp Glu Leu Tyr Lys Arg
465                 470                 475                 480

Ala Leu Gln Lys Gln Leu Phe Lys Ala Leu Val Leu Gln Thr Leu Ile
                485                 490                 495

Pro Thr Ile Phe Met Tyr Ala Pro Thr Gly Val Met Phe Ile Ala Pro
            500                 505                 510

Phe Phe Asp Val Asn Leu Asn Ala Asn Ala Asn Phe Ile Val Phe Cys
            515                 520                 525

Ser Phe Leu Tyr Pro Gly Leu Asp Pro Leu Ile Leu Ile Leu Ile Ile
530                 535                 540

Arg Asp Phe Arg Arg Thr Ile Phe Asn Phe Leu Cys Gly Lys Lys Asn
545                 550                 555                 560

Ser Val Asp Glu Ser Arg Ser Thr Thr Arg Ala Asn Leu Ser Gln Val
                565                 570                 575

Pro Thr Met Thr Ser Lys Val Tyr Asp Pro Glu Gln Arg Lys Arg Met
            580                 585                 590

Ile Thr Gly Pro Gln Trp Trp Ala Arg Cys Lys Gln Met Asn Val Leu
            595                 600                 605

Asp Ser Phe Ile Asn Tyr Tyr Asp Ser Glu Lys His Ala Glu Asn Ala
610                 615                 620

Val Ile Phe Leu His Gly Asn Ala Ala Ser Ser Tyr Leu Trp Arg His
625                 630                 635                 640

Val Val Pro His Ile Glu Pro Val Ala Arg Cys Ile Ile Pro Asp Leu
                645                 650                 655

Ile Gly Met Gly Lys Ser Gly Lys Ser Gly Asn Gly Ser Tyr Arg Leu
```

```
                    660                 665                 670
Leu Asp His Tyr Lys Tyr Leu Thr Ala Trp Phe Glu Leu Leu Asn Leu
            675                 680                 685

Pro Lys Lys Ile Ile Phe Val Gly His Asp Trp Gly Ala Ala Leu Ala
            690                 695                 700

Phe His Tyr Ser Tyr Glu His Gln Asp Lys Ile Lys Ala Ile Val His
705                 710                 715                 720

Ala Glu Ser Val Val Asp Val Ile Glu Ser Trp Asp Glu Trp Pro Asp
                725                 730                 735

Ile Glu Glu Asp Ile Ala Leu Ile Lys Ser Glu Glu Gly Glu Lys Met
                740                 745                 750

Val Leu Glu Asn Asn Phe Phe Val Glu Thr Val Leu Pro Ser Lys Ile
                755                 760                 765

Met Arg Lys Leu Glu Pro Glu Glu Phe Ala Ala Tyr Leu Glu Pro Phe
            770                 775                 780

Lys Glu Lys Gly Glu Val Arg Arg Pro Thr Leu Ser Trp Pro Arg Glu
785                 790                 795                 800

Ile Pro Leu Val Lys Gly Gly Lys Pro Asp Val Val Gln Ile Val Arg
                805                 810                 815

Asn Tyr Asn Ala Tyr Leu Arg Ala Ser Asp Asp Leu Pro Lys Met Phe
                820                 825                 830

Ile Glu Ser Asp Pro Gly Phe Phe Ser Asn Ala Ile Val Glu Gly Ala
            835                 840                 845

Lys Lys Phe Pro Asn Thr Glu Phe Val Lys Val Lys Gly Leu His Phe
            850                 855                 860

Ser Gln Glu Asp Ala Pro Asp Glu Met Gly Lys Tyr Ile Lys Ser Phe
865                 870                 875                 880

Val Glu Arg Val Leu Lys Asn Glu Gln
                885

<210> SEQ ID NO 27
<211> LENGTH: 897
<212> TYPE: PRT
<213> ORGANISM: Artificial Sequence
<220> FEATURE:
<223> OTHER INFORMATION: GFP2-str-112 SGSR-RLuc2 mutant protein

<400> SEQUENCE: 27

Met Gly Ser Gly Gln Leu Trp Leu Ala Leu Val Asp Ala Ala Asp Met
1               5                   10                  15

Val Gly Phe Thr Leu Thr Ile Ser Ile Asn Ile Leu Leu Gly Leu
                20                  25                  30

Ile Arg Thr Arg Gly Lys Thr Leu Gly Thr Tyr Lys Tyr Leu Met Ser
            35                  40                  45

Phe Phe Ser Phe Phe Ser Ile Phe Tyr Ala Ile Val Glu Ser Ile Leu
    50                  55                  60

Arg Pro Ile Met His Ile Glu Asn Thr Thr Phe Phe Leu Ile Ser Arg
65                  70                  75                  80

Lys Arg Phe Asp Tyr Ser Thr Arg Leu Gly Lys Ile Asn Ser Ala Phe
                85                  90                  95

Tyr Cys Ala Cys Phe Ala Thr Ser Phe Val Leu Ser Ala Val His Phe
            100                 105                 110

Val Tyr Arg Tyr Phe Ala Ala Cys Lys Pro Asn Leu Leu Arg Leu Phe
            115                 120                 125

Asn Leu Pro His Leu Leu Leu Trp Pro Leu Met Cys Ser Ile Pro Val
```

```
            130                 135                 140
Thr Ala Trp Ala Ser Val Ser Tyr Phe Leu Tyr Pro Asp Thr Glu Tyr
145                 150                 155                 160

Thr Glu Ala Ala Val Thr Tyr Val Leu Lys Thr His Tyr Glu Val Ile
                165                 170                 175

Lys Lys Glu Asn Val Ser Tyr Ile Ala Tyr Val Tyr Gln Tyr Glu
                180                 185                 190

Asn Gly Glu Arg His Ile Tyr Ile Lys Asn Leu Leu Gly Cys Phe Val
                195                 200                 205

His Tyr Phe Val Met Ser Met Thr Phe Val Val Phe Tyr Cys Gly
        210                 215                 220

Phe Ser Thr Trp Trp Thr Ile Arg Glu His Arg Gly Ala Ser Asp Arg
225                 230                 235                 240

Thr Met Val Ser Lys Gly Glu Leu Phe Thr Gly Val Pro Ile
                245                 250                 255

Leu Val Glu Leu Asp Gly Asp Val Asn Gly His Lys Phe Ser Val Ser
                260                 265                 270

Gly Glu Gly Glu Gly Asp Ala Thr Tyr Gly Lys Leu Thr Leu Lys Phe
                275                 280                 285

Ile Cys Thr Thr Gly Lys Leu Pro Val Pro Trp Pro Thr Leu Val Thr
                290                 295                 300

Thr Leu Thr Tyr Gly Val Gln Cys Phe Ser Arg Tyr Pro Asp His Met
305                 310                 315                 320

Lys Gln His Asp Phe Phe Lys Ser Ala Met Pro Glu Gly Tyr Val Gln
                325                 330                 335

Glu Arg Thr Ile Phe Phe Lys Asp Asp Gly Asn Tyr Lys Thr Arg Ala
                340                 345                 350

Glu Val Lys Phe Glu Gly Asp Thr Leu Val Asn Arg Ile Glu Leu Lys
                355                 360                 365

Gly Ile Asp Phe Lys Glu Asp Gly Asn Ile Leu Gly His Lys Leu Glu
                370                 375                 380

Tyr Asn Tyr Asn Ser His Asn Val Tyr Ile Met Ala Asp Lys Gln Lys
385                 390                 395                 400

Asn Gly Ile Lys Val Asn Phe Lys Ile Arg His Asn Ile Glu Asp Gly
                405                 410                 415

Ser Val Gln Leu Ala Asp His Tyr Gln Gln Asn Thr Pro Ile Gly Asp
                420                 425                 430

Gly Pro Val Leu Leu Pro Asp Asn His Tyr Leu Ser Thr Gln Ser Ala
                435                 440                 445

Leu Ser Lys Asp Pro Asn Glu Lys Arg Asp His Met Val Leu Leu Glu
450                 455                 460

Phe Val Thr Ala Ala Gly Ile Thr Leu Gly Met Asp Glu Leu Tyr Lys
465                 470                 475                 480

Arg His Leu His Arg Gln Leu Phe Lys Ala Leu Val Phe Gln Thr Leu
                485                 490                 495

Val Pro Ser Ile Phe Met Tyr Ile Pro Thr Gly Val Met Phe Ile Ala
                500                 505                 510

Pro Phe Phe Asp Ile Asn Leu Asn Ala Asn Ala Asn Phe Ile Val Phe
                515                 520                 525

Cys Ser Phe Leu Tyr Pro Gly Leu Asp Pro Leu Ile Leu Ile Phe Ile
                530                 535                 540

Ile Arg Glu Phe Arg Val Thr Ile Leu Asn Ile Ile Arg Gly Asn Glu
545                 550                 555                 560
```

```
Arg Gly Asn Ala Val Gly Glu Ala Tyr Ser Thr Ser Arg Ile Lys Ser
            565                 570                 575

Ser Gln Pro Ala Ala Val Asn Leu Ser Gly Met Thr Ser Lys Val Tyr
            580                 585                 590

Asp Pro Glu Gln Arg Lys Arg Met Ile Thr Gly Pro Gln Trp Trp Ala
            595                 600                 605

Arg Cys Lys Gln Met Asn Val Leu Asp Ser Phe Ile Asn Tyr Tyr Asp
            610                 615                 620

Ser Glu Lys His Ala Glu Asn Ala Val Ile Phe Leu His Gly Asn Ala
625                 630                 635                 640

Ala Ser Ser Tyr Leu Trp Arg His Val Val Pro His Ile Glu Pro Val
            645                 650                 655

Ala Arg Cys Ile Ile Pro Asp Leu Ile Gly Met Gly Lys Ser Gly Lys
            660                 665                 670

Ser Gly Asn Gly Ser Tyr Arg Leu Leu Asp His Tyr Lys Tyr Leu Thr
            675                 680                 685

Ala Trp Phe Glu Leu Leu Asn Leu Pro Lys Lys Ile Ile Phe Val Gly
            690                 695                 700

His Asp Trp Gly Ala Ala Leu Ala Phe His Tyr Ser Tyr Glu His Gln
705                 710                 715                 720

Asp Lys Ile Lys Ala Ile Val His Ala Glu Ser Val Val Asp Val Ile
            725                 730                 735

Glu Ser Trp Asp Glu Trp Pro Asp Ile Glu Glu Asp Ile Ala Leu Ile
            740                 745                 750

Lys Ser Glu Glu Gly Glu Lys Met Val Leu Glu Asn Asn Phe Phe Val
            755                 760                 765

Glu Thr Val Leu Pro Ser Lys Ile Met Arg Lys Leu Glu Pro Glu Glu
            770                 775                 780

Phe Ala Ala Tyr Leu Glu Pro Phe Lys Glu Lys Gly Glu Val Arg Arg
785                 790                 795                 800

Pro Thr Leu Ser Trp Pro Arg Glu Ile Pro Leu Val Lys Gly Gly Lys
            805                 810                 815

Pro Asp Val Val Gln Ile Val Arg Asn Tyr Asn Ala Tyr Leu Arg Ala
            820                 825                 830

Ser Asp Asp Leu Pro Lys Met Phe Ile Glu Ser Asp Pro Gly Phe Phe
            835                 840                 845

Ser Asn Ala Ile Val Glu Gly Ala Lys Lys Phe Pro Asn Thr Glu Phe
850                 855                 860

Val Lys Val Lys Gly Leu His Phe Ser Gln Glu Asp Ala Pro Asp Glu
865                 870                 875                 880

Met Gly Lys Tyr Ile Lys Ser Phe Val Glu Arg Val Leu Lys Asn Glu
            885                 890                 895

Gln

<210> SEQ ID NO 28
<211> LENGTH: 901
<212> TYPE: PRT
<213> ORGANISM: Artificial Sequence
<220> FEATURE:
<223> OTHER INFORMATION: SFP2-str-113 SGSR-RLuc2 mutant protein

<400> SEQUENCE: 28

Met Ser Asp Arg His Trp Leu Asp Ile Thr Thr Tyr Ser Asp His Ile
1               5                   10                  15
```

```
Gly Phe Thr Ile Ser Thr Ile Ala Asn Phe Val Leu Ile Leu Leu
             20                  25                  30

Val Phe Arg Pro Thr Lys Ser Tyr Gly Ser Tyr Lys Tyr Leu Met Ile
         35                  40                  45

Thr Phe Cys Val Phe Ser Leu Phe Tyr Thr Ser Ile Glu Thr Phe Leu
     50                  55                  60

Arg Pro Leu Ile His Ile Tyr Asp Asn Thr Ile Phe Val Ile Gln Arg
 65              70                  75                  80

Lys Arg Phe Gln Tyr Ser Glu Gly Thr Ala Arg Ala Ile Ser Ser Thr
                 85                  90                  95

Tyr Cys Gly Cys Tyr Ala Met Ser Phe Thr Leu Phe Ala Val His Phe
             100                 105                 110

Val Tyr Arg Tyr Tyr Ala Ala Cys Lys Pro Asp Asn Leu Arg Tyr Phe
         115                 120                 125

Gln Gly Cys Tyr Phe Val Ala Trp Val Phe Gly Ala Met Ala Val Ala
     130                 135                 140

Ala Ser Trp Gly Phe Ala Ala Phe Ile Leu Tyr Pro Glu Thr Glu Arg
145                 150                 155                 160

Thr Arg Thr Ala Leu Ile His Val Ile Gln Thr Ser Tyr Glu Leu Asp
             165                 170                 175

Pro Glu Trp Val Gly Asn Val Pro Tyr Ser Tyr Trp Arg Thr Glu Asn
         180                 185                 190

Gly Val Glu Tyr Leu Asn Pro Arg Asn Val Ile Gly Ile Phe Gln His
     195                 200                 205

Gly Val Ile Met Ile Leu Ser Phe Gly Thr Val Phe Tyr Cys Gly Phe
     210                 215                 220

Asn Thr Tyr Lys Thr Leu Asn Gly Ser Leu Gly Val Ser Glu Lys Thr
225                 230                 235                 240

Ser Gly Met Val Ser Lys Gly Glu Glu Leu Phe Thr Gly Val Val Pro
             245                 250                 255

Ile Leu Val Glu Leu Asp Gly Asp Val Asn Gly His Lys Phe Ser Val
         260                 265                 270

Ser Gly Glu Gly Glu Gly Asp Ala Thr Tyr Gly Lys Leu Thr Leu Lys
     275                 280                 285

Phe Ile Cys Thr Thr Gly Lys Leu Pro Val Pro Trp Pro Thr Leu Val
     290                 295                 300

Thr Thr Leu Ser Tyr Gly Val Gln Cys Phe Ser Arg Tyr Pro Asp His
305                 310                 315                 320

Met Lys Gln His Asp Phe Phe Lys Ser Ala Met Pro Glu Gly Tyr Val
             325                 330                 335

Gln Glu Arg Thr Ile Phe Phe Lys Asp Asp Gly Asn Tyr Lys Thr Arg
         340                 345                 350

Ala Glu Val Lys Phe Glu Gly Asp Thr Leu Val Asn Arg Ile Glu Leu
     355                 360                 365

Lys Gly Ile Asp Phe Lys Glu Asp Gly Asn Ile Leu Gly His Lys Leu
     370                 375                 380

Glu Tyr Asn Tyr Asn Ser His Asn Val Tyr Ile Met Ala Asp Lys Gln
385                 390                 395                 400

Lys Asn Gly Ile Lys Val Asn Phe Lys Ile Arg His Asn Ile Glu Asp
             405                 410                 415

Gly Ser Val Gln Leu Ala Asp His Tyr Gln Gln Asn Thr Pro Ile Gly
         420                 425                 430

Asp Gly Pro Val Leu Leu Pro Asp Asn His Tyr Leu Ser Thr Gln Ser
```

```
                435                 440                 445
Ala Leu Ser Lys Asp Pro Asn Glu Lys Arg Asp His Met Val Leu Leu
450                 455                 460
Glu Phe Val Thr Ala Ala Gly Ile Thr Leu Gly Met Asp Glu Leu Tyr
465                 470                 475                 480
Lys Val Asp Lys Glu Met His Thr Gln Leu Phe Lys Ala Leu Val Leu
                485                 490                 495
Gln Thr Ile Ile Pro Thr Thr Leu Met Tyr Ile Pro Thr Thr Met Leu
                500                 505                 510
Phe Val Thr Pro Phe Val Gly Leu Asn Ile Gly Cys Tyr Gly Asn Ile
                515                 520                 525
Thr Thr Ala Thr Val His Leu Tyr Pro Gly Ile Asp Pro Val Val Leu
                530                 535                 540
Ile Phe Ile Ile Arg Asp Phe Arg Gln Thr Ile Leu Arg Pro Phe Arg
545                 550                 555                 560
Cys Phe Tyr Arg Ser Asn Ser Val Glu Asn Thr Ala Thr Ile Arg Gln
                565                 570                 575
Tyr Gln Gln Ser Ser Ser Lys Gly Ser Arg Glu Phe Gly Thr Met Thr
                580                 585                 590
Ser Lys Val Tyr Asp Pro Glu Gln Arg Lys Arg Met Ile Thr Gly Pro
                595                 600                 605
Gln Trp Trp Ala Arg Cys Lys Gln Met Asn Val Leu Asp Ser Phe Ile
610                 615                 620
Asn Tyr Tyr Asp Ser Glu Lys His Ala Glu Asn Ala Val Ile Phe Leu
625                 630                 635                 640
His Gly Asn Ala Ala Ser Ser Tyr Leu Trp Arg His Val Val Pro His
                645                 650                 655
Ile Glu Pro Val Ala Arg Cys Ile Ile Pro Asp Leu Ile Gly Met Gly
                660                 665                 670
Lys Ser Gly Lys Ser Gly Asn Gly Ser Tyr Arg Leu Leu Asp His Tyr
                675                 680                 685
Lys Tyr Leu Thr Ala Trp Phe Glu Leu Leu Asn Leu Pro Lys Lys Ile
                690                 695                 700
Ile Phe Val Gly His Asp Trp Gly Ala Ala Leu Ala Phe His Tyr Ser
705                 710                 715                 720
Tyr Glu His Gln Asp Lys Ile Lys Ala Ile Val His Ala Glu Ser Val
                725                 730                 735
Val Asp Val Ile Glu Ser Trp Asp Glu Trp Pro Asp Ile Glu Glu Asp
                740                 745                 750
Ile Ala Leu Ile Lys Ser Glu Glu Gly Glu Lys Met Val Leu Glu Asn
                755                 760                 765
Asn Phe Phe Val Glu Thr Val Leu Pro Ser Lys Ile Met Arg Lys Leu
                770                 775                 780
Glu Pro Glu Glu Phe Ala Ala Tyr Leu Glu Pro Phe Lys Glu Lys Gly
785                 790                 795                 800
Glu Val Arg Arg Pro Thr Leu Ser Trp Pro Arg Glu Ile Pro Leu Val
                805                 810                 815
Lys Gly Gly Lys Pro Asp Val Val Gln Ile Val Arg Asn Tyr Asn Ala
                820                 825                 830
Tyr Leu Arg Ala Ser Asp Asp Leu Pro Lys Met Phe Ile Glu Ser Asp
                835                 840                 845
Pro Gly Phe Phe Ser Asn Ala Ile Val Glu Gly Ala Lys Lys Phe Pro
850                 855                 860
```

Asn Thr Glu Phe Val Lys Val Lys Gly Leu His Phe Ser Gln Glu Asp
865                 870                 875                 880

Ala Pro Asp Glu Met Gly Lys Tyr Ile Lys Ser Phe Val Glu Arg Val
                885                 890                 895

Leu Lys Asn Glu Gln
            900

<210> SEQ ID NO 29
<211> LENGTH: 908
<212> TYPE: PRT
<213> ORGANISM: Artificial Sequence
<220> FEATURE:
<223> OTHER INFORMATION: GFP2-str-114 SGSR-RLuc2 mutant protein

<400> SEQUENCE: 29

Met Ser Asp Ile Tyr Trp Ile Gln Ile Thr Glu Val Cys Ser Phe Val
1               5                   10                  15

Gly Phe Met Leu Ser Val Leu Gly Asn Ser Thr Leu Leu Val Leu Leu
                20                  25                  30

Ser Gly Lys Ser Ile Asp Gly Ile Gly Thr Tyr Arg Tyr Leu Met Ile
            35                  40                  45

Thr Phe Cys Val Phe Ser Leu Leu Phe Thr Ile Leu Glu Asp Phe Ile
        50                  55                  60

Arg Pro Leu Met His His Tyr Asn Asn Thr Ile Val Leu Gln Arg
65                  70                  75                  80

Lys Arg Phe Gln Phe Ser Asp Ser Thr Ala Arg Ile Leu Thr Val Ser
                85                  90                  95

Tyr Cys Gly Cys Phe Ala Met Cys Phe Val Met Phe Ala Val His Phe
            100                 105                 110

Ile Tyr Arg Tyr Leu Val Ala Cys His Pro Thr Lys Leu His Tyr Phe
        115                 120                 125

Arg Pro Lys Asn Phe Ile Phe Trp Leu Ser Gly Met Leu Phe Ile Ala
    130                 135                 140

Gly Ser Trp Val Ala Ile Ala Tyr Val Phe Phe Gln Glu Asp Leu Glu
145                 150                 155                 160

Thr Arg Thr Asp Leu Val Phe Ile Leu Ser Thr Cys Tyr Asn Leu Thr
                165                 170                 175

Pro Asp Asp Val Gly His Val Pro Tyr Ala Phe Tyr Lys Thr Gln Gly
            180                 185                 190

Asn Thr Arg Val Ile Arg Trp Asp Asn Met Ile Gly Val Ile His His
        195                 200                 205

Met Ile Val Met Thr Ile Ser Ile Ser Ala Val Phe Tyr Phe Gly Ile
    210                 215                 220

Lys Thr Tyr Thr Arg Ile Met Ser Phe Lys Gly Lys Ser Gln Lys Thr
225                 230                 235                 240

Ser Gly Met Val Ser Lys Gly Glu Glu Leu Phe Thr Gly Val Val Pro
                245                 250                 255

Ile Leu Val Glu Leu Asp Gly Asp Val Asn Gly His Lys Phe Ser Val
            260                 265                 270

Ser Gly Glu Gly Glu Gly Asp Ala Thr Tyr Gly Lys Leu Thr Leu Lys
        275                 280                 285

Phe Ile Cys Thr Thr Gly Lys Leu Pro Val Pro Trp Pro Thr Leu Val
    290                 295                 300

Thr Thr Leu Ser Tyr Gly Val Gln Cys Phe Ser Arg Tyr Pro Asp His
305                 310                 315                 320

```
Met Lys Gln His Asp Phe Phe Lys Ser Ala Met Pro Glu Gly Tyr Val
                325                 330                 335

Gln Glu Arg Thr Ile Phe Phe Lys Asp Asp Gly Asn Tyr Lys Thr Arg
                340                 345                 350

Ala Glu Val Lys Phe Glu Gly Asp Thr Leu Val Asn Arg Ile Glu Leu
                355                 360                 365

Lys Gly Ile Asp Phe Lys Glu Asp Gly Asn Ile Leu Gly His Lys Leu
                370                 375                 380

Glu Tyr Asn Tyr Asn Ser His Asn Val Tyr Ile Met Ala Asp Lys Gln
385                 390                 395                 400

Lys Asn Gly Ile Lys Val Asn Phe Lys Ile Arg His Asn Ile Glu Asp
                405                 410                 415

Gly Ser Val Gln Leu Ala Asp His Tyr Gln Gln Asn Thr Pro Ile Gly
                420                 425                 430

Asp Gly Pro Val Leu Leu Pro Asp Asn His Tyr Leu Ser Thr Gln Ser
                435                 440                 445

Ala Leu Ser Lys Asp Pro Asn Glu Lys Arg Asp His Met Val Leu Leu
                450                 455                 460

Glu Phe Val Thr Ala Ala Gly Ile Thr Leu Gly Met Asp Glu Leu Tyr
465                 470                 475                 480

Lys Val Asp Lys Asp Leu Gln Asn Gln Phe Phe Thr Ala Leu Val Ala
                485                 490                 495

Gln Thr Val Val Pro Leu Ile Phe Met Phe Ile Pro Asn Met Val Leu
                500                 505                 510

Thr Thr Ala Ala Leu Ile Asp Gly Thr Phe Gly Ser Trp Ala Asn Ile
                515                 520                 525

Thr Val Val Met Asn His Leu Tyr Pro Ala Ala Asp Pro Phe Val Ile
                530                 535                 540

Leu Phe Ile Ile Lys Gly Phe Arg Asn Ser Ile Arg Asn Val Ile Tyr
545                 550                 555                 560

Arg Cys Thr Lys Thr Lys Lys Ala Ser Val Ser Ser Val Val Arg Gly
                565                 570                 575

Ile Glu Ala Gln Ser Lys Lys Gln Ser Phe Ser Arg Val Asp Ile Ser
                580                 585                 590

Arg Glu Phe Gly Thr Met Thr Ser Lys Val Tyr Asp Pro Glu Gln Arg
                595                 600                 605

Lys Arg Met Ile Thr Gly Pro Gln Trp Trp Ala Arg Cys Lys Gln Met
                610                 615                 620

Asn Val Leu Asp Ser Phe Ile Asn Tyr Tyr Asp Ser Glu Lys His Ala
625                 630                 635                 640

Glu Asn Ala Val Ile Phe Leu His Gly Asn Ala Ala Ser Ser Tyr Leu
                645                 650                 655

Trp Arg His Val Val Pro His Ile Glu Pro Val Ala Arg Cys Ile Ile
                660                 665                 670

Pro Asp Leu Ile Gly Met Gly Lys Ser Gly Lys Ser Gly Asn Gly Ser
                675                 680                 685

Tyr Arg Leu Leu Asp His Tyr Lys Tyr Leu Thr Ala Trp Phe Glu Leu
                690                 695                 700

Leu Asn Leu Pro Lys Lys Ile Ile Phe Val Gly His Asp Trp Gly Ala
705                 710                 715                 720

Ala Leu Ala Phe His Tyr Ser Tyr Glu His Gln Asp Lys Ile Lys Ala
                725                 730                 735
```

```
Ile Val His Ala Glu Ser Val Val Asp Val Ile Glu Ser Trp Asp Glu
            740                 745                 750

Trp Pro Asp Ile Glu Glu Asp Ile Ala Leu Ile Lys Ser Glu Glu Gly
            755                 760                 765

Glu Lys Met Val Leu Glu Asn Asn Phe Phe Val Glu Thr Val Leu Pro
        770                 775                 780

Ser Lys Ile Met Arg Lys Leu Glu Pro Glu Glu Phe Ala Ala Tyr Leu
785                 790                 795                 800

Glu Pro Phe Lys Lys Gly Glu Val Arg Arg Pro Thr Leu Ser Trp
            805                 810                 815

Pro Arg Glu Ile Pro Leu Val Lys Gly Gly Lys Pro Asp Val Val Gln
            820                 825                 830

Ile Val Arg Asn Tyr Asn Ala Tyr Leu Arg Ala Ser Asp Asp Leu Pro
            835                 840                 845

Lys Met Phe Ile Glu Ser Asp Pro Gly Phe Phe Ser Asn Ala Ile Val
        850                 855                 860

Glu Gly Ala Lys Lys Phe Pro Asn Thr Glu Phe Val Lys Val Lys Gly
865                 870                 875                 880

Leu His Phe Ser Gln Glu Asp Ala Pro Asp Glu Met Gly Lys Tyr Ile
            885                 890                 895

Lys Ser Phe Val Glu Arg Val Leu Lys Asn Glu Gln
            900                 905

<210> SEQ ID NO 30
<211> LENGTH: 901
<212> TYPE: PRT
<213> ORGANISM: Artificial Sequence
<220> FEATURE:
<223> OTHER INFORMATION: GFP2-str-113/114 SGSR-RLuc2 mutant protein

<400> SEQUENCE: 30

Met Ser Asp Ile Tyr Trp Ile Gln Ile Thr Glu Val Cys Ser Phe Val
1               5                   10                  15

Gly Phe Met Leu Ser Val Leu Gly Asn Ser Thr Leu Leu Val Leu Leu
            20                  25                  30

Ser Gly Lys Ser Ile Asp Gly Ile Gly Thr Tyr Arg Tyr Leu Met Ile
            35                  40                  45

Thr Phe Cys Val Phe Ser Leu Leu Phe Thr Ile Leu Glu Asp Phe Ile
        50                  55                  60

Arg Pro Leu Met His His Tyr Asn Asn Thr Ile Ile Val Leu Gln Arg
65                  70                  75                  80

Lys Arg Phe Gln Phe Ser Asp Ser Thr Ala Arg Ile Leu Thr Val Ser
            85                  90                  95

Tyr Cys Gly Cys Phe Ala Met Cys Phe Val Met Phe Ala Val His Phe
            100                 105                 110

Ile Tyr Arg Tyr Leu Val Ala Cys His Pro Thr Lys Leu His Tyr Phe
            115                 120                 125

Arg Pro Lys Asn Phe Ile Phe Trp Leu Ser Gly Met Leu Phe Ile Ala
        130                 135                 140

Gly Ser Trp Val Ala Ile Ala Tyr Val Phe Phe Gln Glu Asp Leu Glu
145                 150                 155                 160

Thr Arg Thr Asp Leu Val Phe Ile Leu Ser Thr Cys Tyr Asn Leu Thr
            165                 170                 175

Pro Asp Asp Val Gly His Val Pro Tyr Ala Phe Tyr Lys Thr Gln Gly
            180                 185                 190
```

```
Asn Thr Arg Val Ile Arg Trp Asp Asn Met Ile Gly Val Ile His His
            195                 200                 205

Met Ile Val Met Thr Ile Ser Ile Ser Ala Val Phe Tyr Phe Gly Ile
    210                 215                 220

Lys Thr Tyr Thr Arg Ile Met Ser Phe Lys Gly Lys Ser Gln Lys Thr
225                 230                 235                 240

Ser Gly Met Val Ser Lys Gly Glu Glu Leu Phe Thr Gly Val Val Pro
                245                 250                 255

Ile Leu Val Glu Leu Asp Gly Asp Val Asn Gly His Lys Phe Ser Val
            260                 265                 270

Ser Gly Glu Gly Glu Gly Asp Ala Thr Tyr Gly Lys Leu Thr Leu Lys
        275                 280                 285

Phe Ile Cys Thr Thr Gly Lys Leu Pro Val Pro Trp Pro Thr Leu Val
    290                 295                 300

Thr Thr Leu Ser Tyr Gly Val Gln Cys Phe Ser Arg Tyr Pro Asp His
305                 310                 315                 320

Met Lys Gln His Asp Phe Phe Lys Ser Ala Met Pro Glu Gly Tyr Val
                325                 330                 335

Gln Glu Arg Thr Ile Phe Phe Lys Asp Asp Gly Asn Tyr Lys Thr Arg
            340                 345                 350

Ala Glu Val Lys Phe Glu Gly Asp Thr Leu Val Asn Arg Ile Glu Leu
        355                 360                 365

Lys Gly Ile Asp Phe Lys Glu Asp Gly Asn Ile Leu Gly His Lys Leu
    370                 375                 380

Glu Tyr Asn Tyr Asn Ser His Asn Val Tyr Ile Met Ala Asp Lys Gln
385                 390                 395                 400

Lys Asn Gly Ile Lys Val Asn Phe Lys Ile Arg His Asn Ile Glu Asp
                405                 410                 415

Gly Ser Val Gln Leu Ala Asp His Tyr Gln Gln Asn Thr Pro Ile Gly
            420                 425                 430

Asp Gly Pro Val Leu Leu Pro Asp Asn His Tyr Leu Ser Thr Gln Ser
        435                 440                 445

Ala Leu Ser Lys Asp Pro Asn Glu Lys Arg Asp His Met Val Leu Leu
    450                 455                 460

Glu Phe Val Thr Ala Ala Gly Ile Thr Leu Gly Met Asp Glu Leu Tyr
465                 470                 475                 480

Lys Val Asp Lys Glu Met His Thr Gln Leu Phe Lys Ala Leu Val Leu
                485                 490                 495

Gln Thr Ile Ile Pro Thr Thr Leu Met Tyr Ile Pro Thr Thr Met Leu
            500                 505                 510

Phe Val Thr Pro Phe Val Gly Leu Asn Ile Gly Cys Tyr Gly Asn Ile
        515                 520                 525

Thr Thr Ala Thr Val His Leu Tyr Pro Gly Ile Asp Pro Val Val Leu
    530                 535                 540

Ile Phe Ile Ile Arg Asp Phe Arg Gln Thr Ile Leu Arg Pro Phe Arg
545                 550                 555                 560

Cys Phe Tyr Arg Ser Asn Ser Val Glu Asn Thr Ala Thr Ile Arg Gln
                565                 570                 575

Tyr Gln Gln Ser Ser Lys Gly Ser Arg Glu Phe Gly Thr Met Thr
            580                 585                 590

Ser Lys Val Tyr Asp Pro Glu Gln Arg Lys Arg Met Ile Thr Gly Pro
        595                 600                 605

Gln Trp Trp Ala Arg Cys Lys Gln Met Asn Val Leu Asp Ser Phe Ile
```

```
              610                 615                 620
Asn Tyr Tyr Asp Ser Glu Lys His Ala Glu Asn Ala Val Ile Phe Leu
625                 630                 635                 640

His Gly Asn Ala Ala Ser Ser Tyr Leu Trp Arg His Val Val Pro His
                645                 650                 655

Ile Glu Pro Val Ala Arg Cys Ile Ile Pro Asp Leu Ile Gly Met Gly
                660                 665                 670

Lys Ser Gly Lys Ser Gly Asn Gly Ser Tyr Arg Leu Leu Asp His Tyr
                675                 680                 685

Lys Tyr Leu Thr Ala Trp Phe Glu Leu Leu Asn Leu Pro Lys Lys Ile
690                 695                 700

Ile Phe Val Gly His Asp Trp Gly Ala Ala Leu Ala Phe His Tyr Ser
705                 710                 715                 720

Tyr Glu His Gln Asp Lys Ile Lys Ala Ile Val His Ala Glu Ser Val
                725                 730                 735

Val Asp Val Ile Glu Ser Trp Asp Glu Trp Pro Asp Ile Glu Glu Asp
                740                 745                 750

Ile Ala Leu Ile Lys Ser Glu Glu Gly Glu Lys Met Val Leu Glu Asn
                755                 760                 765

Asn Phe Phe Val Glu Thr Val Leu Pro Ser Lys Ile Met Arg Lys Leu
770                 775                 780

Glu Pro Glu Glu Phe Ala Ala Tyr Leu Glu Pro Phe Lys Glu Lys Gly
785                 790                 795                 800

Glu Val Arg Arg Pro Thr Leu Ser Trp Pro Arg Glu Ile Pro Leu Val
                805                 810                 815

Lys Gly Gly Lys Pro Asp Val Val Gln Ile Val Arg Asn Tyr Asn Ala
                820                 825                 830

Tyr Leu Arg Ala Ser Asp Asp Leu Pro Lys Met Phe Ile Glu Ser Asp
                835                 840                 845

Pro Gly Phe Phe Ser Asn Ala Ile Val Glu Gly Ala Lys Lys Phe Pro
                850                 855                 860

Asn Thr Glu Phe Val Lys Val Lys Gly Leu His Phe Ser Gln Glu Asp
865                 870                 875                 880

Ala Pro Asp Glu Met Gly Lys Tyr Ile Lys Ser Phe Val Glu Arg Val
                885                 890                 895

Leu Lys Asn Glu Gln
                900

<210> SEQ ID NO 31
<211> LENGTH: 890
<212> TYPE: PRT
<213> ORGANISM: Artificial Sequence
<220> FEATURE:
<223> OTHER INFORMATION: GFP2-str-115 SGSR-RLuc2 mutant protein

<400> SEQUENCE: 31

Met Thr Asp Gln His Trp Val Ile Ile Thr Asp Ile Ala Gly Pro Ile
1               5                   10                  15

Gly Phe Ser Met Ser Ile Phe Ser Asn Ser Ile Leu Leu Phe Leu Ile
                20                  25                  30

Phe Ser His Ser Ser Pro Ile Lys Gly Pro Tyr Lys Arg Met Leu Ile
                35                  40                  45

Val Phe Cys Ile Phe Thr Val Phe Tyr Ser Phe Val Glu Val Met Leu
50                  55                  60

Gln Pro Leu Ile His Ile Tyr Asp Asp Thr Leu Phe Leu Ile His Arg
```

```
                65                  70                  75                  80
Lys Arg Ile Asp Leu Pro Lys Trp Leu Thr Arg Leu Val Pro Thr Thr
                        85                  90                  95

Tyr Cys Trp Cys Tyr Ala Met Ser Phe Ser Leu Phe Ala Leu Gln Phe
                        100                 105                 110

Leu Tyr Arg Tyr Val Ala Val Cys Lys Pro Gln Tyr Val Asp Leu Phe
                        115                 120                 125

Val Gly Cys His Phe Tyr Ala Trp Val Val Leu Ile Leu Ser Leu Ala
            130                 135                 140

Thr Ser Trp Gly Leu Thr Ala Ala Phe Met Phe Pro Gln Thr Asp Arg
145                 150                 155                 160

Thr Thr Glu Ile Phe Leu His Ile Ile Tyr Ser Ser Tyr Asp Leu Glu
                        165                 170                 175

Pro Tyr Trp Thr Asp Tyr Val Ala Tyr Lys Tyr Phe Asp Thr Asp Glu
                        180                 185                 190

Asn Asn Val Arg Trp Val Asn Val Leu Ser Phe Phe Gly Val Leu Gln
                        195                 200                 205

His Gly Ile Val Ile Thr Leu Ser Phe Gly Thr Leu Tyr Tyr Cys Gly
            210                 215                 220

Ile Asn Thr Tyr Leu Lys Ile Lys Lys His Thr Gly Thr Ser Asn Arg
225                 230                 235                 240

Thr Ser Gly Met Val Ser Lys Gly Glu Glu Leu Phe Thr Gly Val Val
                        245                 250                 255

Pro Ile Leu Val Glu Leu Asp Gly Asp Val Asn Gly His Lys Phe Ser
                        260                 265                 270

Val Ser Gly Glu Gly Glu Gly Asp Ala Thr Tyr Gly Lys Leu Thr Leu
            275                 280                 285

Lys Phe Ile Cys Thr Thr Gly Lys Leu Pro Val Pro Trp Pro Thr Leu
            290                 295                 300

Val Thr Thr Leu Ser Tyr Gly Val Gln Cys Phe Ser Arg Tyr Pro Asp
305                 310                 315                 320

His Met Lys Gln His Asp Phe Phe Lys Ser Ala Met Pro Glu Gly Tyr
                        325                 330                 335

Val Gln Glu Arg Thr Ile Phe Phe Lys Asp Asp Gly Asn Tyr Lys Thr
                        340                 345                 350

Arg Ala Glu Val Lys Phe Glu Gly Asp Thr Leu Val Asn Arg Ile Glu
                        355                 360                 365

Leu Lys Gly Ile Asp Phe Lys Glu Asp Gly Asn Ile Leu Gly His Lys
            370                 375                 380

Leu Glu Tyr Asn Tyr Asn Ser His Asn Val Tyr Ile Met Ala Asp Lys
385                 390                 395                 400

Gln Lys Asn Gly Ile Lys Val Asn Phe Lys Ile Arg His Asn Ile Glu
                        405                 410                 415

Asp Gly Ser Val Gln Leu Ala Asp His Tyr Gln Gln Asn Thr Pro Ile
                        420                 425                 430

Gly Asp Gly Pro Val Leu Leu Pro Asp Asn His Tyr Leu Ser Thr Gln
            435                 440                 445

Ser Ala Leu Ser Lys Asp Pro Asn Glu Lys Arg Asp His Met Val Leu
            450                 455                 460

Leu Glu Phe Val Thr Ala Ala Gly Ile Thr Leu Gly Met Asp Glu Leu
465                 470                 475                 480

Tyr Lys Val Asp Arg Cys Ile Gln Leu Gln Leu Phe Arg Ala Leu Val
                        485                 490                 495
```

Ala Gln Thr Ile Leu Pro Met Phe Met Met Tyr Ile Pro Val Gly Phe
            500                 505                 510

Met Phe Ala Cys Pro Tyr Phe Asp Leu Gln Leu Gly Ala Tyr Thr Asn
            515                 520                 525

Tyr Gln Thr Val Met Ala Gln Leu Tyr Pro Gly Ile Asp Pro Phe Val
    530                 535                 540

Met Leu Phe Leu Ile Asp Ser Tyr Arg Ile Thr Ile Phe Gly Trp Leu
545                 550                 555                 560

Cys Pro Arg Phe Val Tyr Val Lys Pro Met His Ser Thr Tyr Thr Leu
                565                 570                 575

Thr Ser Arg Met Thr Ser Lys Val Tyr Asp Pro Glu Gln Arg Lys Arg
            580                 585                 590

Met Ile Thr Gly Pro Gln Trp Trp Ala Arg Cys Lys Gln Met Asn Val
            595                 600                 605

Leu Asp Ser Phe Ile Asn Tyr Tyr Asp Ser Glu Lys His Ala Glu Asn
            610                 615                 620

Ala Val Ile Phe Leu His Gly Asn Ala Ala Ser Ser Tyr Leu Trp Arg
625                 630                 635                 640

His Val Val Pro His Ile Glu Pro Val Ala Arg Cys Ile Ile Pro Asp
                645                 650                 655

Leu Ile Gly Met Gly Lys Ser Gly Lys Ser Gly Asn Gly Ser Tyr Arg
            660                 665                 670

Leu Leu Asp His Tyr Lys Tyr Leu Thr Ala Trp Phe Glu Leu Leu Asn
            675                 680                 685

Leu Pro Lys Lys Ile Ile Phe Val Gly His Asp Trp Gly Ala Ala Leu
            690                 695                 700

Ala Phe His Tyr Ser Tyr Glu His Gln Asp Lys Ile Lys Ala Ile Val
705                 710                 715                 720

His Ala Glu Ser Val Val Asp Val Ile Glu Ser Trp Asp Glu Trp Pro
                725                 730                 735

Asp Ile Glu Glu Asp Ile Ala Leu Ile Lys Ser Glu Gly Glu Glu Lys
            740                 745                 750

Met Val Leu Glu Asn Asn Phe Phe Val Glu Thr Val Leu Pro Ser Lys
            755                 760                 765

Ile Met Arg Lys Leu Glu Pro Glu Glu Phe Ala Ala Tyr Leu Glu Pro
            770                 775                 780

Phe Lys Glu Lys Gly Glu Val Arg Arg Pro Thr Leu Ser Trp Pro Arg
785                 790                 795                 800

Glu Ile Pro Leu Val Lys Gly Gly Lys Pro Asp Val Val Gln Ile Val
                805                 810                 815

Arg Asn Tyr Asn Ala Tyr Leu Arg Ala Ser Asp Asp Leu Pro Lys Met
            820                 825                 830

Phe Ile Glu Ser Asp Pro Gly Phe Phe Ser Asn Ala Ile Val Glu Gly
            835                 840                 845

Ala Lys Lys Phe Pro Asn Thr Glu Phe Val Lys Val Lys Gly Leu His
            850                 855                 860

Phe Ser Gln Glu Asp Ala Pro Asp Glu Met Gly Lys Tyr Ile Lys Ser
865                 870                 875                 880

Phe Val Glu Arg Val Leu Lys Asn Glu Gln
                885                 890

<210> SEQ ID NO 32
<211> LENGTH: 906

<212> TYPE: PRT
<213> ORGANISM: Artificial Sequence
<220> FEATURE:
<223> OTHER INFORMATION: GFP2-str-116 SGSR-RLuc2 mutant protein

<400> SEQUENCE: 32

```
Met Thr Asp Arg Arg Trp Val Ala Ile Thr Asp Ile Ala Gly Pro Ile
1               5                   10                  15

Gly Phe Thr Met Ser Ile Phe Ser Asn Ser Val Leu Leu Ser Leu Ile
            20                  25                  30

Phe Ser Ser Ser Pro Ile Lys Gly Ala Tyr Lys Asn Met Leu Ile
        35                  40                  45

Val Leu Cys Ile Phe Thr Met Phe Tyr Ser Phe Val Glu Ile Met Leu
50                  55                  60

Gln Pro Leu Ile His Ile Tyr Asp Asp Thr Leu Phe Leu Ile His Arg
65                  70                  75                  80

Lys Arg Phe Asp Leu Ser Lys Gly Ile Thr Arg Leu Ile Pro Thr Thr
                85                  90                  95

Tyr Cys Trp Cys Tyr Ala Met Ser Phe Ser Leu Phe Ala Leu Gln Phe
            100                 105                 110

Leu Tyr Arg Tyr Val Ala Val Cys Lys Pro His Leu Val Val Phe Phe
            115                 120                 125

Thr Gly Cys Tyr Phe Tyr Tyr Trp Leu Ala Leu Ile Leu Ser Leu Ala
130                 135                 140

Thr Ser Trp Gly Leu Thr Ala Ala Phe Met Phe Pro Gln Thr Asn Arg
145                 150                 155                 160

Thr Thr Glu Ser Phe Asn Tyr Val Ile Lys Thr Ser Tyr Asp Leu Asp
                165                 170                 175

Pro Tyr Trp Thr Asp Tyr Val Ala Tyr Lys Tyr Phe Asp Thr Asp Glu
            180                 185                 190

Asn His Val Arg Trp Val Asn Val Leu Ser Leu Phe Gly Val Leu Gln
            195                 200                 205

His Gly Leu Val Ile Thr Leu Ser Phe Gly Thr Leu Phe Tyr Cys Gly
210                 215                 220

Ile Lys Thr Tyr Leu Ser Ile Thr Glu His Val Gly Met Ser Ser Lys
225                 230                 235                 240

Thr Ser Gly Met Val Ser Lys Gly Glu Glu Leu Phe Thr Gly Val Val
                245                 250                 255

Pro Ile Leu Val Glu Leu Asp Gly Asp Val Asn Gly His Lys Phe Ser
            260                 265                 270

Val Ser Gly Glu Gly Glu Gly Asp Ala Thr Tyr Gly Lys Leu Thr Leu
            275                 280                 285

Lys Phe Ile Cys Thr Thr Gly Lys Leu Pro Val Pro Trp Pro Thr Leu
290                 295                 300

Val Thr Thr Leu Ser Tyr Gly Val Gln Cys Phe Ser Arg Tyr Pro Asp
305                 310                 315                 320

His Met Lys Gln His Asp Phe Phe Lys Ser Ala Met Pro Glu Gly Tyr
                325                 330                 335

Val Gln Glu Arg Thr Ile Phe Phe Lys Asp Asp Gly Asn Tyr Lys Thr
            340                 345                 350

Arg Ala Glu Val Lys Phe Glu Gly Asp Thr Leu Val Asn Arg Ile Glu
            355                 360                 365

Leu Lys Gly Ile Asp Phe Lys Glu Asp Gly Asn Ile Leu Gly His Lys
370                 375                 380
```

```
Leu Glu Tyr Asn Tyr Asn Ser His Asn Val Tyr Ile Met Ala Asp Lys
385                 390                 395                 400
Gln Lys Asn Gly Ile Lys Val Asn Phe Lys Ile Arg His Asn Ile Glu
                405                 410                 415
Asp Gly Ser Val Gln Leu Ala Asp His Tyr Gln Gln Asn Thr Pro Ile
            420                 425                 430
Gly Asp Gly Pro Val Leu Leu Pro Asp Asn His Tyr Leu Ser Thr Gln
        435                 440                 445
Ser Ala Leu Ser Lys Asp Pro Asn Glu Lys Arg Asp His Met Val Leu
    450                 455                 460
Leu Glu Phe Val Thr Ala Ala Gly Ile Thr Leu Gly Met Asp Glu Leu
465                 470                 475                 480
Tyr Lys Val Asp Arg Ser Leu Gln Leu Gln Leu Phe Arg Ala Leu Val
                485                 490                 495
Ala Gln Thr Cys Leu Pro Met Leu Met Met Tyr Met Pro Ile Gly Phe
            500                 505                 510
Met Phe Ser Cys Pro Tyr Phe Asp Leu Gln Leu Gly Ala Val Thr Asn
        515                 520                 525
Tyr Gln Thr Val Met Ala Gln Leu Tyr Pro Gly Ile Asp Pro Phe Met
    530                 535                 540
Leu Leu Phe Leu Ile Asn Ala Tyr Arg Lys Thr Val Leu Ser Leu Ile
545                 550                 555                 560
Cys Pro Asn Phe Ile Gln Lys Lys Tyr Val Gln Thr Ala Thr Thr Arg
                565                 570                 575
Asp Gly Thr Asp Ala Ser Ala Thr Met Asn Ser Val Lys Ser Thr Gln
            580                 585                 590
Leu Gly Thr Met Thr Ser Lys Val Tyr Asp Pro Glu Gln Arg Lys Arg
        595                 600                 605
Met Ile Thr Gly Pro Gln Trp Trp Ala Arg Cys Lys Gln Met Asn Val
    610                 615                 620
Leu Asp Ser Phe Ile Asn Tyr Tyr Asp Ser Glu Lys His Ala Glu Asn
625                 630                 635                 640
Ala Val Ile Phe Leu His Gly Asn Ala Ala Ser Ser Tyr Leu Trp Arg
                645                 650                 655
His Val Val Pro His Ile Glu Pro Val Ala Arg Cys Ile Ile Pro Asp
            660                 665                 670
Leu Ile Gly Met Gly Lys Ser Gly Lys Ser Gly Asn Gly Ser Tyr Arg
        675                 680                 685
Leu Leu Asp His Tyr Lys Tyr Leu Thr Ala Trp Phe Glu Leu Leu Asn
    690                 695                 700
Leu Pro Lys Lys Ile Ile Phe Val Gly His Asp Trp Gly Ala Ala Leu
705                 710                 715                 720
Ala Phe His Tyr Ser Tyr Glu His Gln Asp Lys Ile Lys Ala Ile Val
                725                 730                 735
His Ala Glu Ser Val Val Asp Val Ile Glu Ser Trp Asp Glu Trp Pro
            740                 745                 750
Asp Ile Glu Glu Asp Ile Ala Leu Ile Lys Ser Glu Glu Gly Glu Lys
        755                 760                 765
Met Val Leu Glu Asn Asn Phe Phe Val Glu Thr Val Leu Pro Ser Lys
    770                 775                 780
Ile Met Arg Lys Leu Glu Pro Glu Glu Phe Ala Ala Tyr Leu Glu Pro
785                 790                 795                 800
Phe Lys Glu Lys Gly Glu Val Arg Arg Pro Thr Leu Ser Trp Pro Arg
```

```
                    805                 810                 815
Glu Ile Pro Leu Val Lys Gly Gly Lys Pro Asp Val Gln Ile Val
            820                 825                 830

Arg Asn Tyr Asn Ala Tyr Leu Arg Ala Ser Asp Asp Leu Pro Lys Met
            835                 840                 845

Phe Ile Glu Ser Asp Pro Gly Phe Phe Ser Asn Ala Ile Val Glu Gly
        850                 855                 860

Ala Lys Lys Phe Pro Asn Thr Glu Phe Val Lys Val Lys Gly Leu His
865                 870                 875                 880

Phe Ser Gln Glu Asp Ala Pro Asp Glu Met Gly Lys Tyr Ile Lys Ser
                885                 890                 895

Phe Val Glu Arg Val Leu Lys Asn Glu Gln
        900                 905

<210> SEQ ID NO 33
<211> LENGTH: 2670
<212> TYPE: DNA
<213> ORGANISM: Artificial Sequence
<220> FEATURE:
<223> OTHER INFORMATION: Nucleotide sequence encoding GFP2-OGOR-Rluc2
      fusion

<400> SEQUENCE: 33
atgtcgggag aattgtggat taccctagtt gacacagcgg acattgtcgg cgtcaccctc        60
accttctgtg tcaacattgt tcttctcgga cttctgaaaa cacgtggaaa aaacttgggc       120
acttataaat atctcatggc gttttttctca gtattctcga ttttttacgc catcatcgag       180
ttcatattac gacctataat gcatattgag aacaccactt tcttttttgat ctcaaggaaa      240 agattcaact actccaccaa acttggaaaa atcaactctg cgttttactg tgcttgtttt       300
gccaccagtt ttgttgtctc aggagttcac tttgtttatc gatattttgc aacttgcaaa      360
ccgaatctac ttcgtttgtt caacttgcca actcttctac tttggccact tggttgcagt      420
gtacccgtga caatgtgggc tagtgtctca tattttttgt atccagatac cgagtacacg      480
gaagcggctg tcaccaatgt actaaataac cactataact ggatcaaaaa ggagaatgta      540
tcgtacattg catacgtcta ttaccaatac gaaaacggag taaggcatat ctacctcaaa      600
aacttgcttg gatgctttgt tcattacttt gtcatgtcga tgacgtttgt tgtgatgttc      660
tactgcggat atgccacgtg gaaaactatg aatgaacaca aggatgtatc tgatagaact      720
atggtgagca agggcgagga gctgttcacc ggggtggtgc ccatcctggt cgagctggac      780
ggcgacgtaa acggccacaa gttcagcgtg tccggcgagg gcgagggcga tgccacctac      840
ggcaagctga ccctgaagtt catctgcacc accggcaagc tgcccgtgcc ctggcccacc      900
ctcgtgacca ccctgagcta cggcgtgcag tgcttcagcc gctaccccga ccacatgaag      960
cagcacgact tcttcaagtc cgccatgccc gaaggctacg tccaggagcg caccatcttc     1020
ttcaaggacg acggcaacta caagacccgc gccgaggtga agttcgaggg cgacaccctg     1080
gtgaaccgca tcgagctgaa gggcatcgac ttcaaggagg acggcaacat cctggggcac     1140
aagctggagt acaactacaa cagccacaac gtctatatca tggccgacaa gcagaagaac     1200
ggcatcaagg tgaacttcaa gatccgccac aacatcgagg acggcagcgt gcagctcgcc     1260
gaccactacc agcagaacac ccccatcggc gacggccccg tgctgctgcc cgacaaccac     1320
tacctgagca cccagtccgc cctgagcaaa gaccccaacg agaagcgcga tcacatggtc     1380
ctgctggagt tcgtgaccgc cgccgggatc actctcggca tggacgagct gtacaagcga     1440
```

```
gcgctacaga aacaactttt caaagcttta gttcttcaga cactcatccc aactatcttc   1500
atgtacgccc caactggagt catgttcatc gcaccgtttt ttgacgtgaa tttgaatgca   1560
aacgccaatt tcattgtgtt ttgctcattt ctgtacccgg gactcgatcc actcattctg   1620
attttgatca ttcgtgattt ccgaagaaca atattcaatt tcttgtgtgg aaagaaaaac   1680
agtgttgatg aatcccgctc gacaacaaga gccaatttgt ctcaagttcc gacgatgacc   1740
agcaaggtgt acgaccccga gcagaggaag aggatgatca ccggccccca gtggtgggcc   1800
aggtgcaagc agatgaacgt gctggacagc ttcatcaact actacgacag cgagaagcac   1860
gccgagaacg ccgtgatctt cctgcacggc aacgccgcta gcagctacct gtggaggcac   1920
gtggtgcccc acatcgagcc cgtggccagg tgcatcatcc ccgatctgat cggcatgggc   1980
aagagcggca gagcggcaa cggcagctac aggctgctgg accactacaa gtacctgacc   2040
gcctggttcg agctcctgaa cctgcccaag aagatcatct tcgtgggcca cgactgggc    2100 gccgccctgg ccttccacta cagctacgag caccaggaca agatcaaggc catcgtgcac   2160
gccgagagcg tggtggacgt gatcgagagc tgggacgagt ggccagacat cgaggaggac   2220
atcgccctga tcaagagcga ggagggcgag aagatggtgc tggagaacaa cttcttcgtg   2280
gagaccgtgc tgcccagcaa gatcatgaga agctggagc cgaggagtt cgccgcctac    2340 ctggagccct tcaaggagaa gggcgaggtg agaagaccca ccctgagctg cccagagag    2400 atcccccctgg tgaagggcgg caagcccgac gtggtgcaga tcgtgagaaa ctacaacgcc   2460
tacctgagag ccagcgacga cctgcccaag atgttcatcg agagcgaccc cggcttcttc   2520
agcaacgcca tcgtggaggg cgccaagaag ttccccaaca ccgagttcgt gaaggtgaag   2580
ggcctgcact tcagccagga ggacgccccc gacgagatgg gcaagtacat caagagcttc   2640
gtggagagag tgctgaagaa cgagcagtaa                                   2670
```

<210> SEQ ID NO 34
<211> LENGTH: 2670
<212> TYPE: DNA
<213> ORGANISM: Artificial Sequence
<220> FEATURE:
<223> OTHER INFORMATION: Nucleotide sequence encoding GFP2-OGOR-RLuc2
    mutant protein

<400> SEQUENCE: 34

```
atgtcgggag aattgtggat taccctagtt gacacagcgg acattgtcgg cgtcaccctc     60
accttctgtg tcaacattgt tcttctcgga cttctgaaaa cacgtggaaa aaacttgggc    120
acttataaat atctcatggc gttttttctca gtattctcga ttttttacgc catcatcgag   180
ttcatattac gacctataat gcatattgag aacaccactt tctttttgat ctcaaggaaa    240
agattcaact actccaccaa acttggaaaa atcaactctg cgttttactg tgcttgtttt    300
gccaccagtt tgttgtgtctc aggagtttat tttgtttatc gatattttgc aacttgcaaa   360
ccgaatctac ttcgtttgtt caacttgcca actcttctac tttggccact tggttgcagt    420
gtacccgtga caatgtgggc tagtgtctca tattttttgt atccagatac cgagtacacg    480
gaagcggctg tcaccaatgt actaaataac cactataact ggatcaaaaa ggagaatgta    540
tcgtacattg catacgtcta ttaccaatac gaaaacggag taaggcatat ctacctcaaa    600
aacttgcttg gatgctttgt tcattacttt gtcatgtcga tgacgtttgt tgtgatgttc    660
tactgcggat atgccacgtg gaaaactatg aatgaacaca aggatgtatc tgatagaact    720
atggtgagca agggcgagga gctgttcacc ggggtggtgc ccatcctggt cgagctggac    780
```

```
ggcgacgtaa acggccacaa gttcagcgtg tccggcgagg gcgagggcga tgccacctac      840
ggcaagctga ccctgaagtt catctgcacc accggcaagc tgcccgtgcc ctggcccacc      900
ctcgtgacca ccctgagcta cggcgtgcag tgcttcagcc gctaccccga ccacatgaag      960
cagcacgact tcttcaagtc cgccatgccc gaaggctacg tccaggagcg caccatcttc     1020
ttcaaggacg acggcaacta caagacccgc gccgaggtga agttcgaggg cgacaccctg     1080
gtgaaccgca tcgagctgaa gggcatcgac ttcaaggagg acggcaacat cctggggcac     1140
aagctggagt acaactacaa cagccacaac gtctatatca tggccgacaa gcagaagaac     1200
ggcatcaagg tgaacttcaa gatccgccac aacatcgagg acggcagcgt gcagctcgcc     1260
gaccactacc agcagaacac ccccatcggc gacggccccg tgctgctgcc cgacaaccac     1320
tacctgagca cccagtccgc cctgagcaaa gaccccaacg agaagcgcga tcacatggtc     1380
ctgctggagt tcgtgaccgc cgccgggatc actctcggca tggacgagct gtacaagcga     1440
gcgctacaga acaacttttt caaagcttta gttcttcaga cactcatccc aactatcttc     1500
atgtacgccc aactggagt catgttcatc gcaccgtttt ttgacgtgaa tttgaatgca      1560
aacgccaatt tcattgtgtt ttgctcattt ctgtacccgg gactcgatcc actcattctg     1620
attttgatca ttcgtgattt ccgaagaaca atattcaatt tcttgtgtgg aaagaaaaac     1680
agtgttgatg aatcccgctc gacaacaaga gccaatttgt ctcaagttcc gacgatgacc     1740
agcaaggtgt acgaccccga gcagaggaag aggatgatca ccggcccca gtggtgggcc      1800 aggtgcaagc agatgaacgt gctggacagc ttcatcaact actacgacag cgagaagcac     1860
gccgagaacg ccgtgatctt cctgcacggc aacgccgcta gcagctacct gtggaggcac     1920
gtggtgcccc acatcgagcc cgtggccagg tgcatcatcc ccgatctgat cggcatgggc     1980
aagagcggca gagcggcaa cggcagctac aggctgctgg accactacaa gtacctgacc      2040
gcctggttcg agctcctgaa cctgcccaag aagatcatct tcgtgggcca cgactgggc      2100 gccgccctgg ccttccacta cagctacgag caccaggaca gatcaaggc catcgtgcac      2160 gccgagagcg tggtggacgt gatcgagagc tgggacgagt ggccagacat cgaggaggac     2220
atcgccctga tcaagagcga ggagggcgag aagatggtgc tggagaacaa cttcttcgtg     2280
gagaccgtgc tgcccagcaa gatcatgaga aagctggagc ccgaggagtt cgccgcctac     2340
ctggagccct tcaaggagaa gggcgaggtg agaagaccca ccctgagctg gcccagagag     2400
atccccctgg tgaagggcgg caagcccgac gtggtgcaga tcgtgagaaa ctacaacgcc     2460
tacctgagag ccagcgacga cctgcccaag atgttcatcg agagcgaccc cggcttcttc     2520
agcaacgcca tcgtggaggg cgccaagaag ttccccaaca ccgagttcgt gaaggtgaag     2580
ggcctgcact tcagccagga ggacgccccc gacgagatgg gcaagtacat caagagcttc     2640
gtggagagag tgctgaagaa cgagcagtaa                                      2670

<210> SEQ ID NO 35
<211> LENGTH: 2714
<212> TYPE: DNA
<213> ORGANISM: Artificial Sequence
<220> FEATURE:
<223> OTHER INFORMATION: Nucleotide sequence encoding GFP2-str-112
      SGSR-RLuc2 mutant protein

<400> SEQUENCE: 35
atgtctgacc gtcattggct cgacatcacc acctactcag accacattgg gtttacgatt       60
tccaccatcg ccaatttcgt tctgatcctt ctgctagtct tccgaccgac caaatcatac      120
```

-continued

```
ggttcataca agtacctgat gatcacattc tgcgtgttca gcctcttta cacctccatt    180
gaaacttttt tgagacctct catccatatc tacgacaata cgatcttcgt gattcagcgc    240
aagagattcc agtactccga gggtaccgct agagccattt catcgaccta ctgcggctgc    300
tacgccatga gcttcaccct gttcgccgtc cactttgtct accgttacta tgcggcttgc    360
aaacccgaca acctccgtta cttccaagga tgctactttg tcgcatgggt attcggagca    420
atggcggtgg cggcgagctg ggggttcgca gcgtttattc tgtacccgga gaccgagagg    480
accaggacgg cgttgataca cgtcatacaa acatcctatg agctggatcc cgagtgggtg    540
ggaaatgttc catatagcta ttggcgcaca gaaaacggag tggaataccct gaatcctcgc    600
aacgtcatcg ggatctttca acacggcgtc atcatgatcc tctccttcgg aacagtcttc    660
tactgcggat tcaacactta taagactttg aacggaagtc tgggggtgtc tgaaaaaaca    720
tccggaatgg tgagcaaggg cgaggagctg ttcaccgggg tggtgcccat cctggtcgag    780
ctggacggcg acgtaaacgg ccacaagttc agcgtgtccg gcgagggcga gggcgatgcc    840
acctacggca agctgaccct gaagttcatc tgcaccaccg gcaagctgcc cgtgccctgg    900
cccacccteg tgaccaccct gagctacggc gtgcagtgct tcagccgcta ccccgaccac    960
atgaagcagc acgacttctt caagtccgcc atgcccgaag gctacgtcca ggagcgcacc   1020
atcttcttca aggacgacgg caactacaag acccgcgccg aggtgaagtt cgagggcgac   1080
accctggtga accgcatcga gctgaagggc atcgacttca aggaggacgg caacatcctg   1140
gggcacaagc tggagtacaa ctacaacagc cacaacgtct atatcatggc cgacaagcag   1200
aagaacggca tcaaggtgaa cttcaagatc cgccacaaca tcgaggacgg cagcgtgcag   1260
ctcgccgacc actaccagca gaacaccccc atcggcgacg gccccgtgct gctgcccgac   1320
aaccactacc tgagcaccca gtccgccctg agcaaagacc ccaacgagaa gcgcgatcac   1380
atggtcctgc tggagttcgt gaccgccgcc gggatcactc tcggcatgga cgagctgtac   1440
aaggtcgaca agaaaatgca cacccaattg ttcaaggcct tggttctaca gactatcatc   1500
cctactacac taatgtacat cccgacaacc atgctctttg tcaccccatt cgttggactc   1560
aacatcggct gttacggcaa catcactact gccaccgtcc atttgtatcc tggaattgac   1620
ccagtcgttt tgatctttat aatccgagac ttccggcaaa cgattttaag accattcaga   1680
tgcttctacc gttcaaatag tgtcgaaaac actgccacca taaggcaata ccagcagagc   1740
agctccaaag gatctagaga attcggtacc atgaccagca aggtgtacga ccccgagcag   1800
aggaagagga tgatcaccgg cccccagtgg tgggccaggt gcaagcagat gaacgtgctg   1860
gacagcttca tcaactacta cgacagcgag aagcacgccg agaacgccgt gatcttcctg   1920
cacggcaacg ccgctagcag ctacctgtgg aggcacgtgg tgccccacat cgagcccgtg   1980
gccaggtgca tcatccccga tctgatcggc atgggcaaga gcggcaagag cggcaacggc   2040
agctacaggc tgctggacca ctacaagtac ctgaccgcct ggttcgagct cctgaacctg   2100
cccaagaaga tcatcttcgt gggccacgac tggggcgccg ccctggcctt ccactacagc   2160
tacgagcacc aggacaagat caaggccatc gtgcacgccg agagcgtggt ggacgtgatc   2220
gagagctggg acgagtggcc agacatcgag gaggacatcg ccctgatcaa gagcgaggag   2280
ggcgagaaga tggtgctgga gaacaacttc ttcgtggaga ccgtgctgcc cagcaagatc   2340
atgagaaagc tggagcccga ggagttcgcg gcctacctgg agcccttcaa ggagaagggc   2400
gaggtgagaa gacccacccct gagctggccc agagagatcc cctggtgaa gggcggcaag   2460
cccgacgtgg tgcagatcgt gagaaactac aacgcctacc tgagagccag cgacgacctg   2520
```

| | |
|---|---|
| cccaagatgt tcatcgagag cgaccccggc ttcttcagca acgccatcgt ggagggcgcc | 2580 |
| aagaagttcc ccaacaccga gttcgtgaag gtgaagggcc tgcacttcag ccaggaggac | 2640 |
| gcccccgacg agatgggcaa gtacatcaag agcttcgtgg agagagtgct gaagaacgag | 2700 |
| cagtaagcgg ccgc | 2714 |

<210> SEQ ID NO 36
<211> LENGTH: 2714
<212> TYPE: DNA
<213> ORGANISM: Artificial Sequence
<220> FEATURE:
<223> OTHER INFORMATION: Nucleotide sequence encoding GFP2-str-113
SGSR-RLuc2 mutant protein

<400> SEQUENCE: 36

| | |
|---|---|
| atgtctgacc gtcattggct cgacatcacc acctactcag accacattgg gtttacgatt | 60 |
| tccaccatcg ccaatttcgt tctgatcctt ctgctagtct tccgaccgac caaatcatac | 120 |
| ggttcataca agtacctgat gatcacattc tgcgtgttca gcctctttta cacctccatt | 180 |
| gaaactttt tgagacctct catccatatc tacgacaata cgatcttcgt gattcagcgc | 240 |
| aagagattcc agtactccga gggtaccgct agagccattt catcgaccta ctgcggctgc | 300 |
| tacgccatga gcttcaccct gttcgccgtc cactttgtct accgttacta tgcggcttgc | 360 |
| aaacccgaca acctccgtta cttccaagga tgctactttg tcgcatgggt attcggagca | 420 |
| atggcggtgg cggcgagctg ggggttcgca gcgtttattc tgtacccgga gaccgagagg | 480 |
| accaggacgc gttgatacac gtcatacaa acatcctatg agctggatcc cgagtgggtg | 540 |
| ggaaatgttc catatagcta ttggcgcaca gaaaacggag tggaatacct gaatcctcgc | 600 |
| aacgtcatcg ggatctttca cacggcgtc atcatgatcc tctccttcgg aacagtcttc | 660 |
| tactgcggat tcaacactta taagactttg aacggaagtc tgggggtgtc tgaaaaaaca | 720 |
| tccggaatgg tgagcaaggg cgaggagctg ttcaccgggg tggtgcccat cctggtcgag | 780 |
| ctggacggcg acgtaaacgg ccacaagttc agcgtgtccg gcgagggcga gggcgatgcc | 840 |
| acctacggca agctgaccct gaagttcatc tgcaccaccg gcaagctgcc cgtgccctgg | 900 |
| cccaccctcg tgaccaccct gagctacggc gtgcagtgct tcagccgcta ccccgaccac | 960 |
| atgaagcagc acgacttctt caagtccgcc atgcccgaag gctacgtcca ggagcgcacc | 1020 |
| atcttcttca aggacgacgg caactacaag acccgcgccg aggtgaagtt cgagggcgac | 1080 |
| accctggtga accgcatcga gctgaagggc atcgacttca aggaggacgg caacatcctg | 1140 |
| gggcacaagc tggagtacaa ctacaacagc cacaacgtct atatcatggc cgacaagcag | 1200 |
| aagaacggca tcaaggtgaa cttcaagatc cgccacaaca tcgaggacgg cagcgtgcag | 1260 |
| ctcgccgacc actaccagca gaacaccccc atcggcgacg gccccgtgct gctgcccgac | 1320 |
| aaccactacc tgagcaccca gtccgccctg agcaaagacc ccaacgagaa gcgcgatcac | 1380 |
| atggtcctgc tggagttcgt gaccgccgcc gggatcactc tcggcatgga cgagctgtac | 1440 |
| aaggtcgaca agaaatgca cacccaattg ttcaaggcct tggttctaca gactatcatc | 1500 |
| cctactacac taatgtacat cccgacaacc atgctctttg tcaccccatt cgttggactc | 1560 |
| aacatcggct gttacggcaa catcactact gccaccgtcc atttgtatcc tggaattgac | 1620 |
| ccagtcgttt tgatctttat aatccgagac ttccggcaaa cgattttaag accattcaga | 1680 |
| tgcttctacc gttcaaatag tgtcgaaaac actgccacca taaggcaata ccagcagagc | 1740 |
| agctccaaag gatctagaga attcggtacc atgaccagca aggtgtacga ccccgagcag | 1800 |

```
aggaagagga tgatcaccgg cccccagtgg tgggccaggt gcaagcagat gaacgtgctg    1860
gacagcttca tcaactacta cgacagcgag aagcacgccg agaacgccgt gatcttcctg    1920
cacggcaacg ccgctagcag ctacctgtgg aggcacgtgg tgccccacat cgagcccgtg    1980
gccaggtgca tcatccccga tctgatcggc atgggcaaga gcggcaagag cggcaacggc    2040
agctacaggc tgctggacca ctacaagtac ctgaccgcct ggttcgagct cctgaacctg    2100
cccaagaaga tcatcttcgt gggccacgac tggggcgccg ccctggcctt ccactacagc    2160
tacgagcacc aggacaagat caaggccatc gtgcacgccg agagcgtggt ggacgtgatc    2220
gagagctggg acgagtggcc agacatcgag gaggacatcg ccctgatcaa gagcgaggag    2280
ggcgagaaga tggtgctgga gaacaacttc ttcgtggaga ccgtgctgcc cagcaagatc    2340
atgagaaagc tggagcccga ggagttcgcc gcctacctgg agcccttcaa ggagaagggc    2400
gaggtgagaa gacccaccct gagctggccc agagagatcc ccctggtgaa gggcggcaag    2460
cccgacgtgg tgcagatcgt gagaaactac aacgcctacc tgagagccag cgacgacctg    2520
cccaagatgt tcatcgagag cgaccccggc ttcttcagca acgccatcgt ggagggcgcc    2580
aagaagttcc ccaacaccga gttcgtgaag gtgaagggcc tgcacttcag ccaggaggac    2640
gcccccgacg agatgggcaa gtacatcaag agcttcgtgg agagagtgct gaagaacgag    2700
cagtaagcgg ccgc                                                      2714

<210> SEQ ID NO 37
<211> LENGTH: 2714
<212> TYPE: DNA
<213> ORGANISM: Artificial Sequence
<220> FEATURE:
<223> OTHER INFORMATION: Nucleotide sequence encoding GFP2-str-114
      SGSR-RLuc2 mutant protein

<400> SEQUENCE: 37
atgtctgacc gtcattggct cgacatcacc acctactcag accacattgg gtttacgatt     60
tccaccatcg ccaatttcgt tctgatcctt ctgctagtct tccgaccgac caaatcatac    120
ggttcataca agtacctgat gatcacattc tgcgtgttca gcctcttttta cacctccatt    180 gaaactttttt tgagacctct catccatatc tacgacaata cgatcttcgt gattcagcgc    240
aagagattcc agtactccga gggtaccgct agagccattt catcgaccta ctgcggctgc    300
tacgccatga gcttcacccct gttcgccgtc cactttgtct accgttacta tgcggcttgc    360
aaacccgaca acctccgtta cttccaagga tgctactttg tcgcatgggt attcggagca    420
atggcggtgg cggcgagctg ggggttcgca gcgtttattc tgtacccgga gaccgagagg    480
accaggacgg cgttgataca cgtcatacaa acatcctatg agctggatcc cgagtgggtg    540
ggaaatgttc catatagcta ttggcgcaca gaaaacggag tggaatacct gaatcctcgc    600
aacgtcatcg ggatctttca acacggcgtc atcatgatcc tctccttcgg aacagtcttc    660
tactgcggat tcaacactta taagactttg aacggaagtc tgggggtgtc tgaaaaaaca    720
tccggaatgg tgagcaaggg cgaggagctg ttcaccgggg tggtgcccat cctggtcgag    780
ctggacggcg acgtaaacgg ccacaagttc agcgtgtccg gcgagggcga gggcgatgcc    840
acctacggca agctgaccct gaagttcatc tgcaccaccg gcaagctgcc cgtgccctgg    900
cccaccctcg tgaccaccct gagctacggc gtgcagtgct tcagccgcta ccccgaccac    960
atgaagcagc acgacttctt caagtccgcc atgcccgaag gctacgtcca ggagcgcacc   1020
atcttcttca aggacgacgg caactacaag acccgcgccg aggtgaagtt cgagggcgac   1080
```

```
accctggtga accgcatcga gctgaagggc atcgacttca aggaggacgg caacatcctg      1140
gggcacaagc tggagtacaa ctacaacagc acaacgtct atatcatggc cgacaagcag      1200
aagaacggca tcaaggtgaa cttcaagatc cgccacaaca tcgaggacgg cagcgtgcag      1260
ctcgccgacc actaccagca gaacaccccc atcggcgacg cccccgtgct gctgcccgac      1320
aaccactacc tgagcaccca gtccgccctg agcaaagacc ccaacgagaa gcgcgatcac      1380
atggtcctgc tggagttcgt gaccgccgcc gggatcactc tcggcatgga cgagctgtac      1440
aaggtcgaca agaaatgca cacccaattg ttcaaggcct tggttctaca gactatcatc      1500
cctactacac taatgtacat cccgacaacc atgctctttg tcaccccatt cgttggactc      1560
aacatcggct gttacggcaa catcactact gccaccgtcc atttgtatcc tggaattgac      1620
ccagtcgttt tgatctttat aatccgagac ttccggcaaa cgattttaag accattcaga      1680
tgcttctacc gttcaaatag tgtcgaaaac actgccacca taaggcaata ccagcagagc      1740
agctccaaag gatctagaga attcggtacc atgaccagca aggtgtacga ccccgagcag      1800
aggaagagga tgatcaccgg cccccagtgg tgggcaggt gcaagcagat gaacgtgctg      1860
gacagcttca tcaactacta cgacagcgag aagcacgccg agaacgccgt gatcttcctg      1920
cacggcaacg ccgctagcag ctacctgtgg aggcacgtgg tgccccacat cgagcccgtg      1980
gccaggtgca tcatccccga tctgatcggc atgggcaaga gcggcaagag cggcaacggc      2040
agctacaggc tgctggacca ctacaagtac ctgaccgcct ggttcgagct cctgaacctg      2100
cccaagaaga tcatcttcgt gggccacgac tggggcgccg ccctggcctt ccactacagc      2160
tacgagcacc aggacaagat caaggccatc gtgcacgccg agagcgtggt ggacgtgatc      2220
gagagctggg acgagtggcc agacatcgag gaggacatcg ccctgatcaa gagcgaggag      2280
ggcgagaaga tggtgctgga gaacaacttc ttcgtggaga ccgtgctgcc cagcaagatc      2340
atgagaaagc tggagcccga ggagttcgcc gcctacctgg agcccttcaa ggagaagggc      2400
gaggtgagaa gacccacccct gagctggccc agagagatcc ccctggtgaa gggcggcaag      2460
cccgacgtgg tgcagatcgt gagaaactac aacgcctacc tgagagccag cgacgacctg      2520
cccaagatgt tcatcgagag cgaccccggc ttcttcagca acgccatcgt ggagggcgcc      2580
aagaagttcc ccaacaccga gttcgtgaag gtgaagggcc tgcacttcag ccaggaggac      2640 gccccccgacg agatgggcaa gtacatcaag agcttcgtgg agagagtgct gaagaacgag      2700
cagtaagcgg ccgc                                                        2714
```

<210> SEQ ID NO 38
<211> LENGTH: 2714
<212> TYPE: DNA
<213> ORGANISM: Artificial Sequence
<220> FEATURE:
<223> OTHER INFORMATION: Nucleotide sequence encoding GFP2-str-113/114
    SGSR-RLuc2 mutant protein

<400> SEQUENCE: 38

```
atgtctgacc gtcattggct cgacatcacc acctactcag accacattgg gtttacgatt      60
tccaccatcg ccaatttcgt tctgatcctt ctgctagtct tccgaccgac caaatcatac      120
ggttcataca agtacctgat gatcacattc tgcgtgttca gcctcttta cacctccatt      180 gaaacttttt tgagacctct catccatatc tacgacaata cgatcttcgt gattcagcgc      240
aagagattcc agtactccga gggtaccgct agagccattt catcgaccta ctgcggctgc      300
tacgccatga gcttcacccct gttcgccgtc cactttgtct accgttacta tgcggcttgc      360
```

```
aaacccgaca acctccgtta cttccaagga tgctactttg tcgcatgggt attcggagca    420
atggcggtgg cggcgagctg gggggttcgca gcgtttattc tgtacccgga gaccgagagg    480
accaggacgg cgttgataca cgtcatacaa acatcctatg agctggatcc cgagtgggtg    540
ggaaatgttc catatagcta ttggcgcaca gaaaacggag tggaataccct gaatcctcgc    600 aacgtcatcg ggatctttca acacggcgtc atcatgatcc tctccttcgg aacagtcttc    660
tactgcggat tcaacactta taagactttg aacggaagtc tggggggtgtc tgaaaaaaca    720 tccggaatgg tgagcaaggg cgaggagctg ttcaccgggg tggtgcccat cctggtcgag    780
ctggacggcg acgtaaacgg ccacaagttc agcgtgtccg gcgagggcga gggcgatgcc    840
acctacggca agctgaccct gaagttcatc tgcaccaccg gcaagctgcc cgtgccctgg    900
cccaccctcg tgaccaccct gagctacggc gtgcagtgct tcagccgcta ccccgaccac    960
atgaagcagc acgacttctt caagtccgcc atgcccgaag gctacgtcca ggagcgcacc   1020
atcttcttca aggacgacgg caactacaag acccgcgccg aggtgaagtt cgagggcgac   1080
accctggtga accgcatcga gctgaagggc atcgacttca aggaggacgg caacatcctg   1140
gggcacaagc tggagtacaa ctacaacagc cacaacgtct atatcatggc cgacaagcag   1200
aagaacggca tcaaggtgaa cttcaagatc cgccacaaca tcgaggacgg cagcgtgcag   1260
ctcgccgacc actaccagca gaacacccccc atcggcgacg gccccgtgct gctgcccgac   1320
aaccactacc tgagcaccca gtccgccctg agcaaagacc ccaacgagaa gcgcgatcac   1380
atggtcctgc tggagttcgt gaccgccgcc gggatcactc tcggcatgga cgagctgtac   1440
aaggtcgaca agaaatgcca cacccaattg ttcaaggcct tggttctaca gactatcatc   1500
cctactacac taatgtacat cccgacaacc atgctctttg tcaccccatt cgttggactc   1560
aacatcggct gttacggcaa catcactact gccaccgtcc atttgtatcc tggaattgac   1620
ccagtcgttt tgatctttat aatccgagac ttccggcaaa cgattttaag accattcaga   1680
tgcttctacc gttcaaatag tgtcgaaaac actgccacca taaggcaata ccagcagagc   1740
agctccaaag gatctagaga attcggtacc atgaccagca aggtgtacga ccccgagcag   1800
aggaagagga tgatcaccgg ccccccagtgg tgggccaggt gcaagcagat gaacgtgctg   1860
gacagcttca tcaactacta cgacagcgag aagcacgccg agaacgccgt gatcttcctg   1920
cacggcaacc ccgctagcag ctacctgtgg aggcacgtgg tgccccacat cgagcccgtg   1980
gccaggtgca tcatccccga tctgatcggc atgggcaaga gcggcaagag cggcaacggc   2040
agctacaggc tgctggacca ctacaagtac ctgaccgcct ggttcgagct cctgaacctg   2100
cccaagaaga tcatcttcgt gggccacgac tggggcgccg ccctggcctt ccactacagc   2160
tacgagcacc aggacaagat caaggccatc gtgcacgccg agagcgtggt ggacgtgatc   2220
gagagctggg acgagtggcc agacatcgag gaggacatcg ccctgatcaa gagcgaggag   2280
ggcgagaaga tggtgctgga gaacaacttc ttcgtggaga ccgtgctgcc cagcaagatc   2340
atgagaaagc tggagcccga ggagttcgcc gcctacctgg agcccttcaa ggagaagggc   2400
gaggtgagaa gacccacccct gagctggccc agagagatcc ccctggtgaa gggcggcaag   2460
cccgacgtgg tgcagatcgt gagaaactac aacgcctacc tgagagccag cgacgacctg   2520
cccaagatgt tcatcgagag cgaccccggc ttcttcagca acgccatcgt ggagggcgcc   2580
aagaagttcc ccaacaccga gttcgtgaag gtgaagggcc tgcacttcag ccaggaggac   2640 gccccccgacg agatgggcaa gtacatcaag agcttcgtgg agagagtgct gaagaacgag   2700
```

| | |
|---|---:|
| cagtaagcgg ccgc | 2714 |

<210> SEQ ID NO 39
<211> LENGTH: 2673
<212> TYPE: DNA
<213> ORGANISM: Artificial Sequence
<220> FEATURE:
<223> OTHER INFORMATION: Nucleotide sequence encoding GFP2-str-115
  SGSR-RLuc2 mutant protein

<400> SEQUENCE: 39

| | |
|---|---:|
| atgactgatc aacactgggt tattatcaca gatattgctg gtccaatcgg attttcaatg | 60 |
| tccattttt caaactctat tcttttgttt ttgatatttt cacattcatc tccaataaaa | 120 |
| ggtccataca aacgaatgct catagtattt tgcatattta ccgtattcta ctcatttgtc | 180 |
| gaagtcatgc ttcagccact aatccatatt tacgacgaca cttttatttt gattcatcga | 240 |
| aagagaatag acttgccaaa atggttaaca cgtttggttc ctactaccta ttgttggtgt | 300 |
| tacgcaatga gttttccctt gtttgcatta caatttttat atagatatgt ggcagtatgc | 360 |
| aaaccgcaat atgttgatct ttttgtcgga tgtcacttt atgcttgggt agttttgatc | 420 |
| ttatcactag ccacgagctg gggactcact gcagctttca tgttcccaca aaccgaccga | 480 |
| acaactgaaa ttttttttgca cataatttat agttcatatg acttggagcc ttattggaca | 540 |
| gattatgttg cttataaata ctttgatact gatgagaata atgtgagatg ggtcaatgtt | 600 |
| cttagttttt tcggtgtcct tcagcacggg attgtaatta ctctaagttt tggcacccct | 660 |
| tattattgtg gcatcaacac gtatctcaaa ataaaaaaac acactggaac atcaaacaga | 720 |
| acttccggaa tggtgagcaa gggcgaggag ctgttcaccg gggtggtgcc catcctggtc | 780 |
| gagctggacg gcgacgtaaa cggccacaag ttcagcgtgt ccggcgaggg cgagggcgat | 840 |
| gccacctacg gcaagctgac cctgaagttc atctgcacca ccggcaagct gcccgtgccc | 900 |
| tggcccaccc tcgtgaccac cctgagctac ggcgtgcagt gcttcagccg ctaccccgac | 960 |
| cacatgaagc agcacgactt cttcaagtcc gccatgcccg aaggctacgt ccaggagcgc | 1020 |
| accatcttct tcaaggacga cggcaactac aagacccgcg ccgaggtgaa gttcgagggc | 1080 |
| gacaccctgg tgaaccgcat cgagctgaag ggcatcgact tcaaggagga cggcaacatc | 1140 |
| ctggggcaca gctggagta caactacaac agccacaacg tctatatcat ggccgacaag | 1200 |
| cagaagaacg gcatcaaggt gaacttcaag atccgccaca acatcgagga cggcagcgtg | 1260 |
| cagctcgccg accactacca gcagaacacc cccatcggcg acggccccgt gctgctgccc | 1320 |
| gacaaccact acctgagcac ccagtccgcc ctgagcaaag accccaacga gaagcgcgat | 1380 |
| cacatggtcc tgctggagtt cgtgaccgcc gccgggatca ctctcggcat ggacgagctg | 1440 |
| tacaaggtcg accgatgtat tcaactacaa ctttttcagag ctctggttgc acagacaatt | 1500 |
| ttaccaatgt tcatgatgta tattcccgtt ggtttcatgt ttgcatgtcc atattttgac | 1560 |
| ttgcaattag gtgcatacac caattatcaa acagtcatgg cacaacttta tccgggaatc | 1620 |
| gacccatttg tgatgctgtt tttgatagat tcttatagaa taacaatatt tggatggtta | 1680 |
| tgtccaagat tgtttatgt aaagccgatg cattccacat acaccctaac ttctagaatg | 1740 |
| accagcaagg tgtacgaccc cgagcagagg aagaggatga tcaccggccc ccagtggtgg | 1800 |
| gccaggtgca agcagatgaa cgtgctggac agcttcatca actactacga cagcgagaag | 1860 |
| cacgccgaga acgccgtgat cttcctgcac ggcaacgccg ctagcagcta cctgtgggag | 1920 |
| cacgtggtgc cccacatcga gccgtggccc aggtgcatca tccccgatct gatcggcatg | 1980 |

| | |
|---|---:|
| ggcaagagcg gcaagagcgg caacggcagc tacaggctgc tggaccacta caagtacctg | 2040 |
| accgcctggt tcgagctcct gaacctgccc aagaagatca tcttcgtggg ccacgactgg | 2100 |
| ggcgccgccc tggccttcca ctacagctac gagcaccagg acaagatcaa ggccatcgtg | 2160 |
| cacgccgaga gcgtggtgga cgtgatcgag agctgggacg agtggccaga catcgaggag | 2220 |
| gacatcgccc tgatcaagag cgaggagggc gagaagatgg tgctggagaa caacttcttc | 2280 |
| gtggagaccg tgctgcccag caagatcatg agaaagctgg agcccgagga gttcgccgcc | 2340 |
| tacctggagc ccttcaagga agggcgag gtgagaagac ccaccctgag ctggcccaga | 2400 |
| gagatccccc tggtgaaggg cggcaagccc gacgtggtgc agatcgtgag aaactacaac | 2460 |
| gcctacctga gagccagcga cgacctgccc aagatgttca tcgagagcga ccccggcttc | 2520 |
| ttcagcaacg ccatcgtgga gggcgccaag aagttccccca acaccgagtt cgtgaaggtg | 2580 |
| aagggcctgc acttcagcca ggaggacgcc cccgacgaga tgggcaagta catcaagagc | 2640 |
| ttcgtggaga gagtgctgaa gaacgagcag taa | 2673 |

<210> SEQ ID NO 40
<211> LENGTH: 2729
<212> TYPE: DNA
<213> ORGANISM: Artificial Sequence
<220> FEATURE:
<223> OTHER INFORMATION: Nucleotide sequence encoding GFP2-str-116
      SGSR-RLuc2 mutant protein

<400> SEQUENCE: 40

| | |
|---|---:|
| atgaccgatc gtcgctgggt cgctattacg gacattgccg gaccgattgg gttcacaatg | 60 |
| tcaattttttt cgaactcggt gctgttatcg ttgatattct caagcagctc tccaattaaa | 120 |
| ggagcttaca aaatatgtt gatagtgttg tgtatattca ctatgttcta ctcttttgtt | 180 |
| gaaataatgc ttcaaccgtt gattcatatt tatgatgaca cgctgttctt gatccaccgg | 240 |
| aaaagatttg acctgtctaa aggaattaca cgtttgatac ctacaacata ttgttggtgt | 300 |
| tatgcaatga gtttctcatt attcgccctc cagtttttgt acagatatgt ggcagtttgc | 360 |
| aaacctcact tagttgtttt ttttactgga tgctatttct attattggtt ggcactcatc | 420 |
| ttatcacttg ctacaagttg ggggcttact gcagctttta tgttcccgca aaccaatcga | 480 |
| acaactgaaa gcttcaacta cgtaataaaa acttcttatg acttagatcc ttattggacg | 540 |
| gattatgttg cctataaata ttttgacacc gatgagaatc atgtgagatg ggtgaatgtt | 600 |
| cttagtttat ttggagtctt gcagcacgga ttagtaatta cgttgagttt tggaacctta | 660 |
| ttctactgtg gaattaaaac ttatctcagc attactgaac atgttggaat gtccagcaag | 720 |
| acctccggaa tggtgagcaa gggcgaggag ctgttcaccg gggtggtgcc catcctggtc | 780 |
| gagctggacg gcgacgtaaa cggccacaag ttcagcgtgt ccggcgaggg cgagggcgat | 840 |
| gccacctacg gcaagctgac cctgaagttc atctgcacca ccggcaagct gcccgtgccc | 900 |
| tggcccaccc tcgtgaccac cctgagctac ggcgtgcagt gcttcagccg ctaccccgac | 960 |
| cacatgaagc agcacgactt cttcaagtcc gccatgcccg aaggctacgt ccaggagcgc | 1020 |
| accatcttct tcaaggacga cggcaactac aagacccgcg ccgaggtgaa gttcgagggc | 1080 |
| gacaccctgg tgaaccgcat cgagctgaag ggcatcgact tcaaggagga cggcaacatc | 1140 |
| ctggggcaca agctggagta caactacaac agccacaacg tctatatcat ggccgacaag | 1200 |
| cagaagaacg gcatcaaggt gaacttcaag atccgccaca acatcgagga cggcagcgtg | 1260 |
| cagctcgccg accactacca gcagaacacc cccatcggcg acggccccgt gctgctgccc | 1320 |

```
gacaaccact acctgagcac ccagtccgcc ctgagcaaag accccaacga gaagcgcgat    1380
cacatggtcc tgctggagtt cgtgaccgcc gccgggatca ctctcggcat ggacgagctg    1440
tacaaggtcg accgaagtct tcaacttcaa ctattccgtg ctttagttgc tcagacatgt    1500
cttccaatgc tcatgatgta catgccaata ggattcatgt tttcttgccc ttactttgat    1560
ttgcaacttg gagcagtcac aaactatcaa accgtcatgg cacagttata cccaggaatc    1620
gacccattta tgttgctatt tcttattaac gcctacagaa agacagtgtt aagcttgatc    1680
tgtcctaatt ttatccagaa aaatatgtt caaacggcaa ctactcgtga tggcacagat    1740
gcctcggcaa caatgaattc tgttaaatct acacagttag gtaccatgac agcaaggtg    1800
tacgaccccg agcagaggaa gaggatgatc accggccccc agtggtgggc caggtgcaag    1860
cagatgaacg tgctggacag cttcatcaac tactacgaca gcgagaagca cgccgagaac    1920
gccgtgatct tcctgcacgg caacgccgct agcagctacc tgtggaggca cgtggtgccc    1980
cacatcgagc ccgtggccag gtgcatcatc cccgatctga tcggcatggg caagagcggc    2040
aagagcggca acggcagcta caggctgctg gaccactaca agtacctgac cgcctggttc    2100
gagctcctga acctgcccaa gaagatcatc ttcgtgggcc acgactgggg cgccgccctg    2160
gccttccact acagctacga gcaccaggac aagatcaagg ccatcgtgca cgccgagagc    2220
gtggtggacg tgatcgagag ctgggacgag tggccagaca tcgaggagga catcgccctg    2280
atcaagagcg aggagggcga gaagatggtg ctggagaaca acttcttcgt ggagaccgtg    2340
ctgcccagca agatcatgag aaagctggag cccgaggagt cgccgcccta cctggagccc    2400
ttcaaggaga agggcgaggt gagaagaccc accctgagct ggcccagaga gatccccctg    2460
gtgaagggcg gcaagcccga cgtggtgcag atcgtgagaa actacaacgc ctacctgaga    2520
gccagcgacg acctgcccaa gatgttcatc gagagcgacc ccggcttctt cagcaacgcc    2580
atcgtggagg gcgccaagaa gttccccaac accgagttcg tgaaggtgaa gggcctgcac    2640
ttcagccagg aggacgcccc cgacgagatg ggcaagtaca tcaagagctt cgtggagaga    2700
gtgctgaaga acgagcagta agcggccgc                                      2729
```

<210> SEQ ID NO 41
<211> LENGTH: 346
<212> TYPE: PRT
<213> ORGANISM: Caenorhabditis elegans

<400> SEQUENCE: 41

```
Met Ser Gly Gln Leu Trp Leu Ala Leu Val Asp Ala Ala Asp Met Val
1               5                  10                  15

Gly Phe Thr Leu Thr Ile Ser Ile Asn Ile Ile Leu Leu Gly Leu Ile
            20                  25                  30

Arg Thr Arg Gly Lys Thr Leu Gly Thr Tyr Lys Tyr Leu Met Ser Phe
        35                  40                  45

Phe Ser Phe Phe Ser Ile Phe Tyr Ala Ile Val Glu Ser Ile Leu Arg
    50                  55                  60

Pro Ile Met His Ile Glu Asn Thr Thr Phe Phe Leu Ile Ser Arg Lys
65                  70                  75                  80

Arg Phe Asp Tyr Ser Thr Arg Leu Gly Lys Ile Asn Ser Ala Phe Tyr
                85                  90                  95

Cys Ala Cys Phe Ala Thr Ser Phe Val Leu Ser Ala Val His Phe Val
            100                 105                 110

Tyr Arg Tyr Phe Ala Ala Cys Lys Pro Asn Leu Leu Arg Leu Phe Asn
        115                 120                 125
```

```
Leu Pro His Leu Leu Leu Trp Pro Leu Met Cys Ser Ile Pro Val Thr
        130                 135                 140

Ala Trp Ala Ser Val Ser Tyr Phe Leu Tyr Pro Asp Thr Glu Tyr Thr
145                 150                 155                 160

Glu Ala Ala Val Thr Tyr Val Leu Lys Thr His Tyr Glu Val Ile Lys
                165                 170                 175

Lys Glu Asn Val Ser Tyr Ile Ala Tyr Val Tyr Tyr Gln Tyr Glu Asn
            180                 185                 190

Gly Glu Arg His Ile Tyr Ile Lys Asn Leu Leu Gly Cys Phe Val His
            195                 200                 205

Tyr Phe Val Met Ser Met Thr Phe Val Val Phe Tyr Cys Gly Phe
        210                 215                 220

Ser Thr Trp Trp Thr Ile Arg Glu His Arg Gly Ala Ser Asp Arg Thr
225                 230                 235                 240

Arg His Leu His Arg Gln Leu Phe Lys Ala Leu Val Phe Gln Thr Leu
                245                 250                 255

Val Pro Ser Ile Phe Met Tyr Ile Pro Thr Gly Val Met Phe Ile Ala
            260                 265                 270

Pro Phe Phe Asp Ile Asn Leu Asn Ala Asn Ala Asn Phe Ile Val Phe
        275                 280                 285

Cys Ser Phe Leu Tyr Pro Gly Leu Asp Pro Leu Ile Leu Ile Phe Ile
    290                 295                 300

Ile Arg Glu Phe Arg Val Thr Ile Leu Asn Ile Ile Arg Gly Asn Glu
305                 310                 315                 320

Arg Gly Asn Ala Val Gly Glu Ala Tyr Ser Thr Ser Arg Ile Lys Ser
                325                 330                 335

Ser Gln Pro Ala Ala Val Asn Leu Ser Gly
            340                 345

<210> SEQ ID NO 42
<211> LENGTH: 341
<212> TYPE: PRT
<213> ORGANISM: Caenorhabditis elegans

<400> SEQUENCE: 42

Met Ser Asp Arg His Trp Leu Asp Ile Thr Thr Tyr Ser Asp His Ile
1               5                   10                  15

Gly Phe Thr Ile Ser Thr Ile Ala Asn Phe Val Leu Ile Leu Leu Leu
            20                  25                  30

Val Phe Arg Pro Thr Lys Ser Tyr Gly Ser Tyr Lys Tyr Leu Met Ile
        35                  40                  45

Thr Phe Cys Val Phe Ser Leu Phe Tyr Thr Ser Ile Glu Thr Phe Leu
    50                  55                  60

Arg Pro Leu Ile His Ile Tyr Asp Asn Thr Ile Phe Val Ile Gln Arg
65                  70                  75                  80

Lys Arg Phe Gln Tyr Ser Glu Gly Thr Ala Arg Ala Ile Ser Ser Thr
                85                  90                  95

Tyr Cys Gly Cys Tyr Ala Met Ser Phe Thr Leu Phe Ala Val His Phe
            100                 105                 110

Val Tyr Arg Tyr Tyr Ala Ala Cys Lys Pro Asp Asn Leu Arg Tyr Phe
        115                 120                 125

Gln Gly Cys Tyr Phe Val Ala Trp Val Phe Gly Ala Met Ala Val Ala
    130                 135                 140

Ala Ser Trp Gly Phe Ala Ala Phe Ile Leu Tyr Pro Glu Thr Glu Arg
```

-continued

```
                145                 150                 155                 160
        Thr Arg Thr Ala Leu Ile His Val Ile Gln Thr Ser Tyr Glu Leu Asp
                    165                 170                 175
        Pro Glu Trp Val Gly Asn Val Pro Tyr Ser Tyr Trp Arg Thr Glu Asn
                    180                 185                 190
        Gly Val Glu Tyr Leu Asn Pro Arg Asn Val Ile Gly Ile Phe Gln His
                    195                 200                 205
        Gly Val Ile Met Ile Leu Ser Phe Gly Thr Val Phe Tyr Cys Gly Phe
                    210                 215                 220
        Asn Thr Tyr Lys Thr Leu Asn Gly Ser Leu Gly Val Ser Glu Lys Thr
        225                 230                 235                 240
        Lys Glu Met His Thr Gln Leu Phe Lys Ala Leu Val Leu Gln Thr Ile
                            245                 250                 255
        Ile Pro Thr Thr Leu Met Tyr Ile Pro Thr Thr Met Leu Phe Val Thr
                        260                 265                 270
        Pro Phe Val Gly Leu Asn Ile Gly Cys Tyr Gly Asn Ile Thr Thr Ala
                    275                 280                 285
        Thr Val His Leu Tyr Pro Gly Ile Asp Pro Val Val Leu Ile Phe Ile
                290                 295                 300
        Ile Arg Asp Phe Arg Gln Thr Ile Leu Arg Pro Phe Arg Cys Phe Tyr
        305                 310                 315                 320
        Arg Ser Asn Ser Val Glu Asn Thr Ala Thr Ile Arg Gln Tyr Gln Gln
                        325                 330                 335
        Ser Ser Ser Lys Gly
                    340
```

<210> SEQ ID NO 43
<211> LENGTH: 351
<212> TYPE: PRT
<213> ORGANISM: Artificial Sequence
<220> FEATURE:
<223> OTHER INFORMATION: str113/114 chimeric protein

<400> SEQUENCE: 43

```
        Met Ser Asp Arg His Trp Leu Asp Ile Thr Thr Tyr Ser Asp His Ile
        1                   5                   10                  15
        Gly Phe Thr Ile Ser Thr Ile Ala Asn Phe Val Leu Ile Leu Leu Leu
                        20                  25                  30
        Val Phe Arg Pro Thr Lys Ser Tyr Gly Ser Tyr Lys Tyr Leu Met Ile
                    35                  40                  45
        Thr Phe Cys Val Phe Ser Leu Phe Tyr Thr Ser Ile Glu Thr Phe Leu
                50                  55                  60
        Arg Pro Leu Ile His Ile Tyr Asp Asn Thr Ile Phe Val Ile Gln Arg
        65                  70                  75                  80
        Lys Arg Phe Gln Tyr Ser Glu Gly Thr Ala Arg Ala Ile Ser Ser Thr
                        85                  90                  95
        Tyr Cys Gly Cys Tyr Ala Met Ser Phe Thr Leu Phe Ala Val His Phe
                    100                 105                 110
        Val Tyr Arg Tyr Tyr Ala Ala Cys Lys Pro Asp Asn Leu Arg Tyr Phe
                    115                 120                 125
        Gln Gly Cys Tyr Phe Val Ala Trp Val Phe Gly Ala Met Ala Val Ala
                    130                 135                 140
        Ala Ser Trp Gly Phe Ala Ala Phe Ile Leu Tyr Pro Glu Thr Glu Arg
        145                 150                 155                 160
        Thr Arg Thr Ala Leu Ile His Val Ile Gln Thr Ser Tyr Glu Leu Asp
```

```
                    165                 170                 175
Pro Glu Trp Val Gly Asn Val Pro Tyr Ser Tyr Trp Arg Thr Glu Asn
                180                 185                 190

Gly Val Glu Tyr Leu Asn Pro Arg Asn Val Ile Gly Ile Phe Gln His
            195                 200                 205

Gly Val Ile Met Ile Leu Ser Phe Gly Thr Val Phe Tyr Cys Gly Phe
        210                 215                 220

Asn Thr Tyr Lys Thr Leu Asn Gly Ser Leu Gly Val Ser Glu Lys Thr
225                 230                 235                 240

Ser Gly Val Asp Lys Glu Met His Thr Gln Leu Phe Lys Ala Leu Val
                245                 250                 255

Leu Gln Thr Ile Ile Pro Thr Thr Leu Met Tyr Ile Pro Thr Thr Met
                260                 265                 270

Leu Phe Val Thr Pro Phe Val Gly Leu Asn Ile Gly Cys Tyr Gly Asn
            275                 280                 285

Ile Thr Thr Ala Thr Val His Leu Tyr Pro Gly Ile Asp Pro Val Val
        290                 295                 300

Leu Ile Phe Ile Ile Arg Asp Phe Arg Gln Thr Ile Leu Arg Pro Phe
305                 310                 315                 320

Arg Cys Phe Tyr Arg Ser Asn Ser Val Glu Asn Thr Ala Thr Ile Arg
                325                 330                 335

Gln Tyr Gln Gln Ser Ser Ser Lys Gly Ser Arg Glu Phe Gly Thr
                340                 345                 350

<210> SEQ ID NO 44
<211> LENGTH: 1041
<212> TYPE: DNA
<213> ORGANISM: Caenorhabditis elegans

<400> SEQUENCE: 44
atgtctggtc aattatggtt ggccctcgtg gatgctgccg atatggtagg attcactctc      60
acgatctcca tcaacatcat tctactgggg ctgattagaa cacgtggaaa aacgttggga     120
acgtacaaat acttgatgag cttcttctcg ttcttctcaa tctttttatgc aatcgttgaa     180 tctattttga gaccaataat gcatatcgaa aacacgacgt tctttctgat ttctcggaaa     240
cgcttcgatt actcaactcg ccttggtaaa atcaactctg ctttctactg tgcttgtttt     300
gccacgagtt ttgtcctgtc tgcggtacac tttgtgtatc ggtactttgc cgcttgcaaa     360
ccgaatctgc tacgcttgtt taaccttccg catcttttac tgtggccttt gatgtgttcg     420
attcctgtga ctgcgtgggc aagtgtttct tacttttttgt acccagacac cgagtacact     480
gaagcagcag ttacatatgt tctgaaaaca cactacgagg tgatcaaaaa agaaaatgta     540
tcttatatcg catacgtata ctatcaatat gaaaatgggg agcgtcacat ctacataaaa     600
aatttgcttg gctgctttgt acactacttc gttatgtcaa tgacatttgt agttgtgttt     660
tactgcggat tttctacatg gtggacgatt cgtgagcatc gtggagcatc tgataggaca     720
cgtcacctgc atagacaatt gtttaaggca cttgtatttc aaaccttgt tccatcaata     780 tttatgtaca tcccaactgg tgtcatgttc atcgctccct ttttcgacat caacctgaat     840
gccaatgcaa acttcatcgt tttttgctca ttctctatc caggtcttga cccactaatt     900 ctcatttta tcattcgcga attcagggtc actatttga atatcatcag aggaaatgag     960
cggggaaatg ctgttggcga agcatactca acttctcgaa taaaatcatc acaacctgca    1020
gctgttaatc tttctggata a                                              1041
```

<210> SEQ ID NO 45
<211> LENGTH: 1026
<212> TYPE: DNA
<213> ORGANISM: Caenorhabditis elegans

<400> SEQUENCE: 45

```
atgtctgacc gtcattggct cgacatcacc acctactcag accacattgg gtttacgatt      60
tccaccatcg ccaatttcgt tctgatcctt ctgctagtct tccgaccgac caaatcatac     120
ggttcataca agtacctgat gatcacattc tgcgtgttca gcctcttta cacctccatt     180
gaaactttt tgagacctct catccatatc tacgacaata cgatcttcgt gattcagcgc     240
aagagattcc agtactccga gggtaccgct agagccattt catcgaccta ctgcggctgc     300
tacgccatga gcttcaccct gttcgccgtc cactttgtct accgttacta tgcggcttgc     360
aaacccgaca acctccgtta cttccaagga tgctactttg tcgcatgggt attcggagca     420
atggcggtgg cggcgagctg ggggttcgca gcgtttattc tgtacccgga gaccgagagg     480
accaggacgg cgttgataca cgtcatacaa acatcctatg agctggatcc cgagtgggtg     540
ggaaatgttc catatagcta ttggcgcaca gaaaacggag tggaataacct gaatcctcgc     600
aacgtcatcg ggatctttca acacggcgtc atcatgatcc tctccttcgg aacagtcttc     660
tactgcggat tcaacactta taagactttg aacggaagtc tgggggtgtc tgaaaaaaca     720
aaagaaatgc acacccaatt gttcaaggcc ttggttctac agactatcat ccctactaca     780
ctaatgtaca tcccgacaac catgctcttt gtcaccccat tcgttggact caacatcggc     840
tgttacggca acatcactac tgccaccgtc catttgtatc ctggaattga cccagtcgtt     900
ttgatcttta atccgaga cttccggcaa acgatttaa gaccattcag atgcttctac     960
cgttcaaata gtgtcgaaaa cactgccacc ataaggcaat accagcagag cagctccaaa    1020
ggataa                                                                1026
```

<210> SEQ ID NO 46
<211> LENGTH: 1056
<212> TYPE: DNA
<213> ORGANISM: Artificial Sequence
<220> FEATURE:
<223> OTHER INFORMATION: str113/114 chimeric protein encoding sequence

<400> SEQUENCE: 46

```
atgtctgacc gtcattggct cgacatcacc acctactcag accacattgg gtttacgatt      60
tccaccatcg ccaatttcgt tctgatcctt ctgctagtct tccgaccgac caaatcatac     120
ggttcataca agtacctgat gatcacattc tgcgtgttca gcctcttta cacctccatt     180
gaaactttt tgagacctct catccatatc tacgacaata cgatcttcgt gattcagcgc     240
aagagattcc agtactccga gggtaccgct agagccattt catcgaccta ctgcggctgc     300
tacgccatga gcttcaccct gttcgccgtc cactttgtct accgttacta tgcggcttgc     360
aaacccgaca acctccgtta cttccaagga tgctactttg tcgcatgggt attcggagca     420
atggcggtgg cggcgagctg ggggttcgca gcgtttattc tgtacccgga gaccgagagg     480
accaggacgg cgttgataca cgtcatacaa acatcctatg agctggatcc cgagtgggtg     540
ggaaatgttc catatagcta ttggcgcaca gaaaacggag tggaataacct gaatcctcgc     600
aacgtcatcg ggatctttca acacggcgtc atcatgatcc tctccttcgg aacagtcttc     660
tactgcggat tcaacactta taagactttg aacggaagtc tgggggtgtc tgaaaaaaca     720
tccggagtcg acaaagaaat gcacacccaa ttgttcaagg ccttggttct acagactatc     780
```

-continued

```
atccctacta cactaatgta catcccgaca accatgctct ttgtcacccc attcgttgga    840
ctcaacatcg gctgttacgg caacatcact actgccaccg tccatttgta tcctggaatt    900
gacccagtcg ttttgatctt tataatccga gacttccggc aaacgattt aagaccattc    960 agatgcttct accgttcaaa tagtgtcgaa aacactgcca ccataaggca ataccagcag   1020
agcagctcca aaggatctag agaattcggt acctaa                              1056
```